US009737537B2

(12) United States Patent
Chen et al.

(10) Patent No.: US 9,737,537 B2
(45) Date of Patent: *Aug. 22, 2017

(54) HETEROCYCLIC RECEPTOR AGONISTS FOR THE TREATMENT OF DIABETES AND METABOLIC DISORDERS

(71) Applicant: CymaBay Therapeutics, Inc., Newark, CA (US)

(72) Inventors: Xin Chen, San Ramon, CA (US); Peng Cheng, Union City, CA (US); L. Edward Clemens, Davis, CA (US); Jeffrey D. Johnson, Moraga, CA (US); Jingyuan Ma, Sunnyvale, CA (US); Alison Murphy, Milpitas, CA (US); Imad Nashashibi, San Jose, CA (US); Christopher J. Rabbat, San Jose, CA (US); Jiangao Song, Sunnyvale, CA (US); Maria E. Wilson, San Francisco, CA (US); Yan Zhu, Foster City, CA (US); Zuchun Zhao, Pleasanton, CA (US)

(73) Assignee: CYMABAY THERAPEUTICS, INC., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/333,416

(22) Filed: Oct. 25, 2016

(65) Prior Publication Data
US 2017/0105993 A1  Apr. 20, 2017

Related U.S. Application Data

(60) Continuation of application No. 14/626,749, filed on Feb. 19, 2015, now abandoned, which is a continuation of application No. 13/612,451, filed on Sep. 12, 2012, now Pat. No. 8,975,258, which is a continuation of application No. 12/619,577, filed on Nov. 16, 2009, now Pat. No. 8,288,384, which is a division of application No. 11/964,461, filed on Dec. 26, 2007, now Pat. No. 7,638,541.

(60) Provisional application No. 60/877,903, filed on Dec. 28, 2006.

(51) Int. Cl.
*A61K 31/506* (2006.01)
*A61K 31/454* (2006.01)

(52) U.S. Cl.
CPC .......... *A61K 31/506* (2013.01); *A61K 31/454* (2013.01)

(58) Field of Classification Search
CPC ..................... A61K 31/506; A61K 31/454
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,778,443 A | 12/1973 | Arya | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,094,987 A | 6/1978 | Hasspacher et al. | |
| 4,673,564 A | 6/1987 | Kawata et al. | |
| 4,894,235 A | 1/1990 | Kohne et al. | |
| 5,013,556 A | 5/1991 | Woodle et al. | |
| 5,340,591 A | 8/1994 | Nakano et al. | |
| 5,420,298 A | 5/1995 | Edwards et al. | |
| 5,456,923 A | 10/1995 | Nakamichi et al. | |
| 5,707,646 A | 1/1998 | Yajima et al. | |
| 5,792,769 A | 8/1998 | Lu et al. | |
| 5,817,667 A | 10/1998 | Chu et al. | |
| 5,817,677 A | 10/1998 | Linz et al. | |
| 5,880,138 A | 3/1999 | Heinz et al. | |
| 5,939,099 A | 8/1999 | Grabowski et al. | |
| 6,015,712 A | 1/2000 | Monia et al. | |
| 6,015,715 A | 1/2000 | Kirschner et al. | |
| 6,020,346 A | 2/2000 | Armour et al. | |
| 6,051,712 A | 4/2000 | Binggeli et al. | |
| 6,150,526 A | 11/2000 | Binggeli et al. | |
| 6,221,660 B1 | 4/2001 | Bonini et al. | |
| 6,255,305 B1 | 7/2001 | Broughton et al. | |
| 6,274,735 B1 | 8/2001 | Lohri et al. | |
| 6,468,756 B1 | 10/2002 | Bonini et al. | |
| 6,506,757 B1 | 1/2003 | Tajima et al. | |
| 6,770,645 B2 | 8/2004 | Denton et al. | |
| 6,784,185 B2 | 8/2004 | Allerton et al. | |
| 6,969,724 B2 | 11/2005 | Barlocco et al. | |
| 7,012,083 B2 | 3/2006 | Gibson et al. | |
| 7,108,991 B2 | 9/2006 | Chen et al. | |
| 7,319,104 B2 | 1/2008 | Cadilla et al. | |
| 7,524,838 B2 | 4/2009 | Genevois-Borella et al. | |
| 7,576,074 B2 | 8/2009 | Rice et al. | |

(Continued)

FOREIGN PATENT DOCUMENTS

| | | |
|---|---|---|
| CN | 1829718 A | 9/2006 |
| CN | 1898235 A | 1/2007 |
| CN | 101616586 A | 12/2009 |
| DE | 27 01 705 A1 | 8/1977 |
| EP | 0 630 887 A1 | 12/1994 |
| EP | 0 755 923 A1 | 1/1997 |
| EP | 0 867 183 A1 | 9/1998 |
| EP | 0 901 786 A2 | 3/1999 |
| EP | 1 092 727 A2 | 4/2001 |
| EP | 1 129 706 A2 | 9/2001 |

(Continued)

OTHER PUBLICATIONS

U.S. Appl. No. 13/032,513, filed Feb. 22, 2011, Chen, et al.

(Continued)

*Primary Examiner* — Craig Ricci
*Assistant Examiner* — Christopher R Stone
(74) *Attorney, Agent, or Firm* — Foley & Lardner LLP

(57) ABSTRACT

Compounds and methods are provided for the treatment of, inter alia, Type II diabetes and other diseases associated with poor glycemic control. The compounds of the invention are orally active.

2 Claims, 5 Drawing Sheets

(56) References Cited

U.S. PATENT DOCUMENTS

| | | |
|---|---|---|
| 7,638,541 B2 | 12/2009 | Chen et al. |
| 7,709,481 B2 | 5/2010 | Keil et al. |
| 7,851,473 B2 | 12/2010 | Matsumoto et al. |
| 8,114,865 B2 | 2/2012 | Bandiera et al. |
| 8,119,778 B2 | 2/2012 | Fischer et al. |
| 8,183,381 B2 | 5/2012 | Ma et al. |
| 8,188,098 B2 | 5/2012 | Erickson et al. |
| 8,227,495 B2 | 7/2012 | Chen et al. |
| 8,277,495 B2 | 10/2012 | Demetriou et al. |
| 8,288,384 B2 | 10/2012 | Chen et al. |
| 8,344,001 B2 | 1/2013 | Hohlweg et al. |
| 8,410,127 B2 | 4/2013 | Song et al. |
| 8,455,491 B2 | 6/2013 | Puech et al. |
| 8,513,264 B2 | 8/2013 | Mark et al. |
| 2002/0099214 A1 | 7/2002 | Gibson et al. |
| 2002/0198223 A1 | 12/2002 | Allerton et al. |
| 2003/0064990 A1 | 4/2003 | Denton et al. |
| 2004/0024218 A1 | 2/2004 | Barlocco et al. |
| 2004/0162278 A1 | 8/2004 | Armour et al. |
| 2004/0220170 A1 | 11/2004 | Atkinson et al. |
| 2005/0165005 A1 | 7/2005 | Genevois-Borella et al. |
| 2006/0135501 A1 | 6/2006 | Knox et al. |
| 2006/0142262 A1 | 6/2006 | Jones et al. |
| 2006/0155128 A1 | 7/2006 | Jones et al. |
| 2006/0206074 A1 | 9/2006 | Bernal et al. |
| 2006/0227281 A1 | 10/2006 | Kang et al. |
| 2007/0129341 A1 | 6/2007 | Kallus et al. |
| 2009/0054475 A1 | 2/2009 | Chen et al. |
| 2009/0137590 A1 | 5/2009 | Ma et al. |
| 2009/0186112 A1 | 7/2009 | Maingueneau |
| 2009/0270404 A1 | 10/2009 | Wilson et al. |
| 2009/0286812 A1 | 11/2009 | Erickson et al. |
| 2010/0087465 A1 | 4/2010 | Chen et al. |
| 2010/0130511 A1 | 5/2010 | Chen et al. |
| 2010/0267721 A1 | 10/2010 | Hohlweg et al. |
| 2011/0046137 A1 | 2/2011 | Beswick et al. |
| 2011/0137032 A1 | 6/2011 | Endo et al. |
| 2011/0152270 A1 | 6/2011 | Song et al. |
| 2011/0160222 A1 | 6/2011 | Chen et al. |
| 2011/0263617 A1 | 10/2011 | Mark et al. |
| 2011/0294836 A1 | 12/2011 | Song et al. |
| 2011/0313160 A1 | 12/2011 | Chen et al. |
| 2011/0318418 A1 | 12/2011 | Mcwherter et al. |
| 2012/0184572 A1 | 7/2012 | Song et al. |
| 2012/0322804 A1 | 12/2012 | Ma et al. |
| 2013/0281691 A1 | 10/2013 | Chen et al. |
| 2013/0310398 A1 | 11/2013 | Mark et al. |
| 2014/0024830 A1 | 1/2014 | Chen et al. |

FOREIGN PATENT DOCUMENTS

| | | |
|---|---|---|
| EP | 1 176 147 A1 | 1/2002 |
| EP | 1 422 228 A1 | 5/2004 |
| EP | 1 500 648 A1 | 1/2005 |
| EP | 1 133 559 B1 | 8/2005 |
| EP | 1 707 202 A1 | 10/2006 |
| EP | 1 584 683 B1 | 7/2007 |
| EP | 1 813 606 A1 | 8/2007 |
| EP | 1 829 863 A1 | 9/2007 |
| EP | 1 852 433 A1 | 11/2007 |
| EP | 2 280 704 B1 | 2/2011 |
| GB | 0 882 813 | 11/1961 |
| GB | 1 422 263 A | 1/1976 |
| JP | 11-500447 | 1/1999 |
| JP | 11-513382 | 11/1999 |
| JP | 2002-514169 | 5/2002 |
| JP | 2002-539192 | 11/2002 |
| JP | 2005-532272 | 10/2005 |
| JP | 2005-330266 | 12/2005 |
| JP | 2006-505509 | 2/2006 |
| JP | 2006-506380 | 2/2006 |
| JP | 2006-518763 | 8/2006 |
| JP | 2006-293353 | 10/2006 |
| JP | 2006-525355 | 11/2006 |
| JP | 2007-045752 | 2/2007 |
| JP | 2007-145828 | 6/2007 |
| JP | 2007-533672 | 11/2007 |
| JP | 2008-526235 | 7/2008 |
| JP | 2008-532647 | 8/2008 |
| JP | 2009-509988 | 3/2009 |
| JP | 2009-541512 | 11/2009 |
| JP | 2009-541518 | 11/2009 |
| JP | 2010-512418 | 4/2010 |
| JP | 2010-514795 | 5/2010 |
| JP | 2010-526793 | 8/2010 |
| JP | 2010-530840 | 9/2010 |
| WO | WO-98/04559 | 2/1998 |
| WO | WO-99/46232 | 9/1999 |
| WO | WO-00/50562 A2 | 8/2000 |
| WO | WO-00/55126 | 9/2000 |
| WO | WO-01/14372 A2 | 3/2001 |
| WO | WO-02/098223 A1 | 5/2002 |
| WO | WO-02/088101 A2 | 11/2002 |
| WO | WO-03/074495 A1 | 9/2003 |
| WO | WO-03/099795 | 12/2003 |
| WO | WO-2004/006846 A2 | 1/2004 |
| WO | WO-2004/037809 A1 | 5/2004 |
| WO | WO-2004/076413 | 9/2004 |
| WO | WO-2004/078413 A1 | 9/2004 |
| WO | WO-2004/089373 A1 | 10/2004 |
| WO | WO-2004/098518 A2 | 11/2004 |
| WO | WO-2004/099154 | 11/2004 |
| WO | WO-2004/113323 A1 | 12/2004 |
| WO | WO-2005/007658 | 1/2005 |
| WO | WO-2005/011654 A2 | 2/2005 |
| WO | WO-2005/061489 A1 | 7/2005 |
| WO | WO-2005/061547 A2 | 7/2005 |
| WO | WO-2005/082089 A2 | 9/2005 |
| WO | WO-2005/116653 | 12/2005 |
| WO | WO-2005/121088 A1 | 12/2005 |
| WO | WO-2006/054652 A1 | 5/2006 |
| WO | WO-2006/069788 A1 | 7/2006 |
| WO | WO-2006/073167 A1 | 7/2006 |
| WO | WO-2006/074057 A2 | 7/2006 |
| WO | WO-2006/076231 A2 | 7/2006 |
| WO | WO-2006/091428 A2 | 8/2006 |
| WO | WO-2006/094763 A1 | 9/2006 |
| WO | WO-2006/124692 A2 | 11/2006 |
| WO | WO-2006/133216 A2 | 12/2006 |
| WO | WO-2006/134487 A1 | 12/2006 |
| WO | WO-2007/003960 A1 | 1/2007 |
| WO | WO-2007/003961 A2 | 1/2007 |
| WO | WO-2007/014290 A2 | 2/2007 |
| WO | WO-2007/023507 A2 | 3/2007 |
| WO | WO-2007/035355 A2 | 3/2007 |
| WO | WO-2007/039177 A2 | 4/2007 |
| WO | WO-2007/120702 | 10/2007 |
| WO | WO-2008/008887 A2 | 1/2008 |
| WO | WO-2008/025800 A1 | 3/2008 |
| WO | WO-2008/070692 A2 | 6/2008 |
| WO | WO-2008/073929 A1 | 6/2008 |
| WO | WO-2008/073936 A1 | 6/2008 |
| WO | WO-2008/074749 | 6/2008 |
| WO | WO-2008/083238 A2 | 7/2008 |
| WO | WO-2008/137436 | 11/2008 |
| WO | WO-2008/138876 | 11/2008 |
| WO | WO-2009/010429 | 1/2009 |
| WO | WO-2009/010761 | 1/2009 |
| WO | WO-2009/014637 | 1/2009 |
| WO | WO-2009/016516 | 2/2009 |
| WO | WO-2009/037394 | 3/2009 |
| WO | WO-2009/070869 A1 | 6/2009 |
| WO | WO-2009/123992 A1 | 10/2009 |
| WO | WO-2010/008739 A2 | 1/2010 |
| WO | WO-2010/013849 A1 | 2/2010 |
| WO | WO-2010/048149 A2 | 4/2010 |
| WO | WO-2011/041154 A1 | 4/2011 |
| WO | WO-2010/029089 A2 | 3/2012 |

OTHER PUBLICATIONS

U.S. Appl. No. 13/449,238, filed Apr. 17, 2012, Xin, et al.
U.S. Appl. No. 13/463,617, filed May 3, 2012, Jingyuan, et al.

(56) References Cited

OTHER PUBLICATIONS

U.S. Appl. No. 13/612,451, filed Sep. 12, 2012, Xin, et al.
"Report of the Expert committee on the diagnosis and classification of diabetes mellitus", Diabetes Care, vol. 26, (Suppl 1): S5-19, (2003).
Annoura, et al., "Synthesis and Biological Evaluation of New 4-Arlypiperidines and 4-Aryl-4-piperidinols: Dual Na+ and Ca2+ Channel Blockers with Reduced Affinity for Dopamine D2 Receptors," Biorganic & Medicinal Chemistry, 10, 2002, pp. 371-383.
Ashcroft & Gribble. "ATP-sensitive K+ Channels and Insulin Secretion: Their Role in Health and Disease," Diabetologia, (1999) 42: 903-19.
Barrett-Conner. "Epidemiology, Obesity, and Non-insulin-dependent Diabetes Mellitus" Epidemiologic Reviews, (1998) 11: 172-81.
Bell & Polonsky. "Diabetes Mellitus and Genetically Programmed Defects in β-cell Function," Nature, (2001) 414: 788-91.
Bighley et al., "Salt Forms of Drugs and Absorption," in Swarbrick, J. and Boylan, J.C., et al., eds. "Encyclopedia of Pharmaceutical Technology." 13 Ed., Marcel Dekker, NY (1996) pp. 453-499.
Blicklé. "Meglitinide Analogues: a Review of Clinical Data Focused on Recent Trials," Diabetes & Metabolism, (2006) 32(2): 113-20.
Blough, et al., "Synthesis and Transporter Binding Properties of 3.beta.-[41(Phenylalkyl,-phenylalkenyl, and -phenylalkynl) phenyl]tropane- 2.beta.-carboxylic Acid Methyl Esters: Evidence of a Remote Phenyl Binding Domain on the Dopamine Transporter," Journal of Medicinal Chemistry, 45:18, 2002, pp. 4029-4037.
Brubaker. "The Glucagon-Like Peptides Pleiotropic Regulators of Nutrient Homeostatsis," Annals of New York Academy of Sciences, (2006) 1070: 10-26.
Byrn et al., "Solid-State Chemistry of Drugs, 11: Hydrates and Solvates," 2nd ed., SSCI, Inc., (1999) 233-247 & 516.
Cannon, J. G., Chapter Nineteen in Burger's Medicinal Chemistry and Drug Discovery, Fifth Edition, vol. I: Principles and Practice, Wiley-Interscience 1995, pp. 783-802.
Cantin et al., "PDE-10A Inhibitors as Insulin Secretagogues," Bioorganic & Medicinal Chemistry Letters, (2007) 17(10): 2869-73.
Castro, et al., "Enhancement of Oral Absorption in Selective 5-HT1D Receptor Agonists: Fluorinated 3[3-(Piperidin-1-yl)propyl]indoles," Journal of Medicinal Chemistry (1998) 41(15): 2667-70.
Cavaghan et al., "Interactions Between Insulin Resistance and Insulin Secretion in the Development of Glucose Intolerance," The Journal of Clinical Investigation, (2000) 106(3): 329-33.
Cavalla et al., "Analgetics Based on the Pyrrolidine Ring. V," Journal of Medicinal Chemistry, (1970) 13(5): 794-800.
Chiasson et al., "The Efficacy of Acarbose in the Treatment of Patients with Non-Insulin-dependent Diabetes Mellitus: A Multicenter Controlled Clinical Trial." Annals of Internal Medicine, (1994) 121(12): 928-35.
Chilean Examination Report dated Jun. 15, 2011 for Chilean Application No. 2042-2008.
Chinese Office Action dated Jan. 14, 2013 in related Chinese Patent Application No. 200980133021.8.
Choi et al., "Alterations in Regulation of Energy Homeostasis in Cyclic Nucleotide Phosphodiesterase 3B-null Mice." Journal of Clinical Investigation, (2006) 116(12): 3240-51.
Coniff et al., "Acarbose: A Review of US Clinical Experience." Clinical Therapy, (1997) 19(1): 16-26.
Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus." American Journal of Medicine, (1995) 98: 443-51.
Crawley et al., "Methoxytetrahydropyrans. A New Series of Selective and Orally Potent 5-Lioxygenase Inhibitors," Journal of Medicinal Chemistry, (1992) 35(14): 2600-9.
Deacon. "Dipeptidyl Peptidase 4 Inhibition with Sitagliptin: a New Therapy for Type 2 Diabetes." Expert Opinion on Investigational Drugs, 16:4, 2007, pp. 533-545.

Deng et al., "A Novel and Efficient Synthesis of 2,5-Substituted 1,2,4-Triazol-3-Ones," Tetrahedron Letters, (2005) 46(46): 7993-6.
Drucker, "The Role of Gut Hormones in Glucose Homeostasis," Journal of Clinical Investigation, (2007) 117(1): 24-32.
Elahi et al., "The Insulinotropic Actions of Glucose-dependent Insulinotropic Polypeptide (GIP) and Glucagon-like Peptide-1 (7-37) in Normal and Diabetic Subjects," Regulatory Peptides, (1994) 61: 63-74.
EP Communication Pursuant to Article 94(3) EPC dated Dec. 9, 2013 in related EP Patent Application No. 09727673.7.
European IPRP dated Oct. 19, 2010 for related European Patent Application No. 09727673.7.
Farilla et al., "Glucagon-Like Peptide 1 Inhibits Cell Apoptosis and Improves Glucose Responsiveness of Freshly Isolated Human Islets," Endocrinology, (2003) 144(12) 5149-58.
Farilla et al., "Glucagon-Like Peptide-1 Promotes Islet Cell Growth and Inhibits Apoptosis in Zucker Diabetic Rats," Endocrinology, 143:11, (2002), pp. 4397-4408.
Filipsson et al., "The Neuropeptide Pituitary Adenylate Cyclase-Activating Polypeptide and Islet Function," Diabetes, (2001) 50(9): 1959-69.
Flier, "Insulin receptors and insulin resistance," Annual Reviews of Medicine, 34, (1983), pp. 145-160.
Freudenrich, et al., "Design of Inhibitors from the Three-dimensional Structure of Alcohol Dehydrogenase. Chemical Synthesis and Enzymic Properties," Journal of the American Chemical Society, 106:11, 1984, pp. 3344-53.Freudenrich et al., "Design of Inhibitors from the Three-dimensional Structure of Alcohol Dehydrogenase. Chemical Synthesis and Enzymic Properties," Journal of the American Chemical Society, (1984) 106(11): 3344-53.
Friedrichsen et al., "Stimulation of Pancreatic β-cell Replication by Incretins Involves Transcriptional Induction of Cyclin D1 via Multiple Signalling Pathways." Journal of Endocrinology, (2006) 188(3): 481-92.
Furman et al., "Modulation of Cyclic Nucleotides and Cyclic Nucleotide Phosphodiesterases in Pancreatic Islet β-cells and Intestinal L-cells as Targets for Treating Diabetes Mellitus," Current Opinions in Investigational Drugs, (2006) 7(10): 898-905.
Gavin, et al. "Report of the Expert Committee on the Diagnosis and Classification of Diabetes Mellitus", Diabetes Care, (2003) 26(Supp 1): S5-S20.
Gilon et al., "Mechanisms and Physiological Significance of the Cholinergic Control of Pancreatic β-Cell Function," Endocrinology Reviews, (2001) 22(5): 565-604.
Gloyn et al., "Insights into the Structure and Regulation of Glucokinase from a Novel Mutation (V62M), Which Causes Maturity-onset Diabetes of the Young." J Biol Chem (2005) 280(14): 14105-14113.
González et al., "Investigational treatments for type 2 diabetes mellitus: exenatide and liraglutide." Expert Opin Investig Drugs (2006) 15(8): 887-895.
Gould et al., "Pyrrolidines. IX. 3-Aryl-3-pyrrolidinols," Journal of Medicinal Chemistry, (1964) 7(1): 60-7.
Gould, P.L., "Salt Selection for Basic Drugs," International Journal Pharmaceutics, 33, 1986, pp. 201-217.
Green et al. "Dipeptidyl peptidase IV (DPP IV) inhibitors: a newly emerging drug class for the treatment of type 2 diabetes." Diabetes Vasc. Dis. Res. (2006), 3:159-165.
Greene, T.W., "Protective Groups in Organic Synthesis," 3rd Edition, John Wiley & Sons, Inc., (1999) 518-23.
Gromada et al., "Glucagon-Like Peptide 1(7-36) Amide Stimulates Exocytosis in Human Pancreatic beta-Cells by Both Proximal and Distal Regulatory Steps in Stimulus-Secretion Coupling." Diabetes (1998) 47(1): 57-65.
Guertin et al., "Small Molecule Glucokinase Activators as Glucose Lowering Agents: A New Paradigm for Diabetes Therapy." Curr Med Chem (2006) 13(15): 1839-1843.
Guillory, J.K., "Generation of Polymorphs, hydrates, Solvates and Amorphous Solids," in "Polymorphism in Pharmaceutical Solids." Brittain, H.G. ed., (1999) 183-220.
Haffner, "Management of Dyslipidemia in Adults With Diabetes." Diabetes Care (1998) 21(1): 160-178.

(56) References Cited

OTHER PUBLICATIONS

Han et al., "The Calcium/Calmodulin-dependent Phosphodiesterase PDE1C Down-regulates Glucose-induced Insulin Secretion." J Biol Chem (1999) 274(32): 22337-22344.
Hansen, "Towards Selective Kir6.2/SUR1 Potassium Channel Openers, Medicinal Chemistry and Therapeutic Perspectives." Curr Med Chem (2006) 13(4): 361-376.
Hansotia et al., "Extrapancreatic incretin receptors modulate glucose homeostasis, body weight, and energy expenditure." J Clin Invest (2007) 117(1): 143-152, Epub Dec. 21, 2006.
Härndahl et al., "Important Role of Phosphodiesterase 3B for the Stimulatory Action of cAMP on Pancreatic β-Cell Exocytosis and Release of Insulin." J Biol Chem (2002) 277(40): 37446-37455.
Hatakeyama et al., "Rapid glucose sensing by protein kinase a for insulin exocytosis in mouse pancreatic islets." J Physiol (2006) 570(Pt 2): 271-282.
Henquin, "Pathways in β-Cell Stimulus-Secretion Coupling as Targets from Therapeutic Insulin Secretagogues." Diabetes (2004) 53(Supp 3): S48-S58.
Holz, "Perspectives in Diabetes Epac: A New cAMP-Binding Protein in Support of Glucagon-Like Peptide-1 Receptor-Mediated Signal Transduction in the Pancreatic R-Cell." Diabetes (2004) 53(1): 5-13.
Hussain et al., "Increased Pancreatic β-Cell Proliferation Mediated by CREB Binding Protein Gene Activation." Mol Cell Biol (2006) 26(20): 7747-7759.
International Search Report and Written Opinion dated Feb. 22, 2010 in related PCT Application No. PCT/US2009/047551.
International Search Report and Written Opinion dated Jan. 26, 2009 in related PCT Application No. PCT/US2008/069714.
International Search Report and Written Opinion dated Jun. 19, 2009 in related PCT Application No. PCT/US2009/038847.
International Search Report and Written Opinion dated May 23, 2008 in related PCT Application No. PCT/US2007/088978.
International Search Report and Written Opinion dated Oct. 29, 2010 in related PCT Application No. PCT/US2010/049486.
International Search Report dated Oct. 10, 2011 in related PCT Application No. PCT/US2011/040972.
International Search Report dated Oct. 6, 2011 in related PCT Application No. PCT/US11/39069.
Iwamoto et al., "Effect of Combination Therapy of Troglitazone and Sulphonylureas in Patients with Type 2 Diabetes Who Were Poorly Controlled by Sulphonylurea Therapy Alone." Diabet Med (1996) 13: 365-370.
Kahn, "The Importance of β-Cell Failure in the Development and Progression of Type 2 Diabetes." J Clin Endicrinol Metab (2001) 86:4047-4058.
Kahn, "The Importance of the β-Cell in the Pathogenesis of Type 2 Diabetes Mellitus." Am J Med (2000) 108 Suppl 6a, 2S-8S.
Kahn, "Type 2 Diabetes: When Insulin Secretion Fails to Compensate for Insulin Resistance." Cell (1998) 92: 593-596.
Kaplan et al., "Cardiovascular diseases" in Health and Human Behavior, (McGraw-Hill, New York 1993): 206-242.
Kashima et al., "Critical Role of cAMP-GEFII Rim2 Complex in Incretin-potentiated Insulin Secretion." J Biol Chem (2001) 276(49): 46046-46053, Epub Oct. 11, 2001.
Kim et al., "(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine: A potent, orally active dipeptidyl peptidase IV inhibitor for the treatment of type 2 diabetes." J. Med. Chem., 2005, 48(1):141-151.
Kim et al., "Exendin-4 induction of cyclin D1 expression in INS-1 β-cells: involvement of cAMP-responsive element." J Endocrinol (2006) 188(3): 623-633.
Knowler et al., "Obesity in the Pima Indians: its magnitude and relationship with diabetes," Am. J. Clin. Nutr. (1991) 53:1543S-1551S.
Kwiterovich, "State-of-the-Art Update and Review: Clinical Trials of Lipid-Lowering Agents." Am J Cardiol (1998) 82(12A): 3U-17U.

Langer, "New Methods of Drug Delivery." Science (1990) 249: 1527-1533.
Le Bourdonnec, B., et al., "Discovery of a series of aminopiperidines as novel iNOS inhibitors," Bioorganic and Medicinal Chemistry Letters, vol. 18, Issue 1, pp. 336-343 (2008).
Le Bourdonnec, et al., "Synthesis and Structure-activity Relationships of a New Series of 2α substitued Trans-4,5-dimethyl-4-(3-hydroxyphenyl)piperidine as μ-selective Opioid Antagonists," Bioorganic and Medicinal Chemistry Letters, (2006) 16(4): 864-8.
Levy et al., "Beta-cell Deterioration Determines the Onset and Rate of Progression of Secondary Dietary Failure in Type 2 Diabetes Mellitus: the 10-year Follow-up of the Belfast Diet Study." Diabetes Med (1998) 15: 290-296.
Li et al., "Glucagon-like Peptide-1 Receptor Signaling Modulates β Cell Apoptosis." J Biol Chem (2003) 278(1): 471-478.
Mahler et al., "Clinical Review 102 Type 2 Diabetes Mellitus: Update on Diagnosis, Pathophysiology, and Treatment." J Clin Endocrinol Metab (1999) 84(4): 1165-1171.
Matschinsky et al., "Perspectives in Diabetes the Network of Glucokinase-Expressing Cells in Glucose Homeostasis and the Potential of Glucokinase Activators for Diabetes Therapy." Diabetes (2006) 55(1): 1-12.
Matschinsky, "Glucokinase, Glucose Homeostasis, and Diabetes Mellitus." Curr Diab Rep (2005) 5(3): 171-176.
Meneilly et al., "The Effect of Glyburide on β-Cell Sensitivity to Glucose-Dependent Insulinotropic Polypeptide." Diabetes Care (1993) 16(1): 110-114.
Miura et al., "Glucagon-like peptide-1 induces a cAMP-dependent increase of [Na+]i associated with insulin secretion in pancreatic β-cells." Am J Physiol Endocrinol Metab (2003) 285, E1001-E1009.
Morissette, et al., "High-throughput Crystallization: Polymorphs, Salt, Co-crystals and Solvates of Pharmaceutical Solids," Advanced Drug Delivery Reviews, 56, 2004, pp. 275-300.
Morissette, et al.,"High-Throughput Crystallization: Polymorphs, Salts, Co-Crystals and Solvates of Pharmaceutical Solids", Advanced Drug Delivery Reviews, vol. 56, p. 275-300 (2004).
Nauck et al., "Preserved Incretin Activity of Glucagon-like Peptide 1 [7-36 Amide] but Not of Synthetic Human Gastric Inhibitory Polypeptide in Patients with type-2 Diabetes Mellitus." J Clin Invest (1993) 91: 301-307.
Patani, G.A. & Lavoie E.J., "Bioisosterism: A Rational Approach in Drug Design," Chemical Reviews, (1996) 96(8): 3147-76.
Prentki et al., "Islet β cell Failure in type 2 dieabetes." J Clin Invest (2006) 116(7): 1802-1812.
Qader et al., "Expression of islet inducible nitric oxide synthase and inhibition of glucose-stimulated insulin release after long-term lipid infusion in the rat is counteracted by PACAP27." Am J Physiol Endocrinol Metab (2007) 292(5): E1447-E1455.
Reaven, "Insulin Resistance and Human DISEASE: a Short History." J Basic & Clin Phys & Pharm (1998) 9: 387-406.
Reimann et al., "Signaling Mechanisms Underlying the Release of Glucagon-Like Peptide 1." Diabetes (2006) 55(Suppl 2): S78-S85.
Rendell, "The Role of Sulphonylureas in the Management of Type 2 Diabetes Mellitus." Drugs (2004) 64(12): 1339-13.58.
Saltiel, "New Perspectives into the Molecular Pathogenesis and Treatment of Type 2 Diabetes." Cell (2001) 104: 517-529.
Sato, et al., "New μ-Opioid Receptor Agonists with Phenoxyacetic Acid Moiety," Chemical & Pharmaceutical Bulletin, (2002) 50(2): 292-7.
Saxena et al., "Genome-Wide Association Analysis Identifies Loci for Type 2 Diabetes and Triglyceride Levels." Science (2007) 316: 1331-1336.
Seino, "ATP-Sensitive Potassium Channels: A Model of Heteromultimeric Potassium Channel/Receptor Assemblies." Annu Rev Physiol (1999) 61: 337-362.
Shibasaki et al., "Interaction of ATP Sensor, cAMP Sensor, Ca2+ Sensor, and Voltage-dependent Ca2+ Channel in Insulin Granule Exocytosis." J Biol Chem (2004) 279(9): 7956-7961.
Shinki Tonyobyoyaku no Kaihatsu Jokyo (Development of Novel Agent for Diabetes), Medicament News, Feb. 15, 2008, No. 1934 (10).

(56) References Cited

OTHER PUBLICATIONS

Shinki Tonyobyoyaku no Kaihatsu Jokyo (Translated as: Development status of novel diabetes drugs), Medicament News, Feb. 15, 2008, No. 1934, (10).
Singer, et al., "Synthesis of SAR of Tolylamine 5-HT6 Antagonists," Bioorganic & Medicinal Chemistry Letters, (2009) 19: 2409-12.
Soga et al., "Lysophosphatidylcholine Enhances Glucose-dependent Insulin Secretion via an Orphan G-protein-coupled Receptor." Biochemical and Biophysical Research Communications (2005) 326(4): 744-751.
Steinthorsdottir et al., "A Variant in CDKAL1 Influences Insulin Response and Risk of Type 2 Diabetes." Nature Genetics (2007) 39(6): 770-775.
Still et al., "Rapid Chromatographic Technique for Preparative Separations with Moderate Resolution." J. Org. Chem., 1978, 43(14):2923-2925.
Supplementary European Search Report dated Mar. 4, 2011 in related European Application No. 07869989.9.
Supplementary Partial European Search Report dated Jul. 25, 2012 in related European Application No. 09798422.3.
Thomas, et al., "Investigation of the N-Substituent Conformation Governing Potency and .mu. Receptor Subtype-Selectivity in (+)-(3R,4R)-Dimethyl-4-(3-hydroxyphenyl)-piperidine Opioid Antagonists," Journal of Medicinal Chemistry, 41:11, 1998, pp. 1980-1990.
Thorens et al., "Cloning and Functional Expression of the Human Islet GLP-1 Receptor: Demonstration that Exendin-4 is an Agonist and Exendin-(9-39) an Antagonist of the Receptor." Diabetes (1993) 42, 1678-1682.
Thorens, "GLUT2 in pancreatic and extra-pancreatic gluco-detection." Mol Membr Biol (2001) 18(4): 265-273.
Turner et al., "Glycemic Control With Diet, Sulfonylurea, Metformin, or Insulin in Patients With Type 2 Diabetes Mellitus: Progressive Requirement for Multiple Therapies (UKPDS 49)." JAMA (1999) 281(21): 2005-2012.
Turner et al., "Insulin resistance, impaired glucose tolerance and non-insulin-dependent diabetes, pathologic mechanisms and treatment: Current status and therapeutic possibilities." Prog Drug Res (1998) 51: 33-94.
U.K. Prospective Diabetes Study Group: "UKPDS 28: A Randomized Trial of Efficacy of Early Addition of Metformin in Sulfonylurea-Treated Type 2 Diabetes," Diabetes Care (1998) 21(1): 87-92.
US Office Action on U.S. Appl. No. 12/414,639 DTD Apr. 12, 2016.
US Office Action on U.S. Appl. No. 14/626,749 DTD Sep. 25, 2015.
Vilsbøll et al., "Reduced Postprandial Concentrations of Intact Biologically Active Glucagon-Like Peptide 1 in Type 2 Diabetic Patients." Diabetes (2001) 50: 609-613.
Vippagunta, et al., "Crystalline Solids," Advanced Drug Delivery Reviews, (2001) 48: 3-26.
Waid, et al., "Constrained Amino Acids, an Approach to the Synthesis of 3-Substituted Prolines," Tetrahedron Letters, (1996) 37(24): 4091-4.
Walz et al., "Early and rapid development of insulin resistance, islet dysfunction and glucose intolerance after high-fat feeding in mice overexpressing phosphodiesterase 3B." J Endocrinol (2006) 189(3): 629-641.
Wu, et al., "Pyrrolidines. VII. 3-Hydroxy-1-Pyrrolidinecarboxylic Acid Esters," Journal of Medicinal Chemistry, 5:4, 1962, pp. 752-62.
Yamada et al., "Cytosolic Ca2+ responses to sub-picomolar and nanomolar PACAP in pancreatic β3-cells are mediated by VPAC2 and PAC1 receptors." Regul Pept (2004) 123(1-3): 147-153.
Zhou et al., "Overexpression of Repressive cAMP Response Element Modulators in High Glucose and Fatty Acid-treated Rat Islets." J Biol Chem (2003) 278(51): 51316-51323.

Tissue map of rat IC-GPCR2

Tissue Map of mouse IC-GPCR2

HETEROCYCLIC RECEPTOR AGONISTS FOR THE TREATMENT OF DIABETES AND METABOLIC DISORDERS

CROSS-REFERENCES TO RELATED APPLICATIONS

This application is a continuation of U.S. patent application Ser. No. 14/626,749 filed on Feb. 19, 2015, which is abandoned, and which is a continuation of U.S. patent application Ser. No. 13/612,451 filed on Dec. 12, 2012, now U.S. Pat. No. 8,975,258, which is a continuation of U.S. patent application Ser. No. 12/619,577 filed on Nov. 16, 2009, now U.S. Pat. No. 8,288,384, which is a divisional of U.S. patent application Ser. No. 11/964,461, filed Dec. 26, 2007, now U.S. Pat. No. 7,638,541, which claims the benefit under 35 U.S.C. 119(e) to U.S. Provisional Application No. 60/877,903 filed on Dec. 28, 2006, the disclosures of each of which are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Diabetes mellitus can be divided into two clinical syndromes, Type I and Type II diabetes mellitus. Type I diabetes, or insulin-dependent diabetes mellitus, is a chronic autoimmune disease characterized by the extensive loss of beta cells in the pancreatic islets of Langerhans (hereinafter referred to as "pancreatic islet cells" or "islet cells"), which produce insulin. As these cells are progressively destroyed, the amount of secreted insulin decreases, eventually leading to hyperglycemia (abnormally high level of glucose in the blood) when the amount secreted drops below the level required for euglycemia (normal blood glucose level). Although the exact trigger for this immune response is not known, patients with Type I diabetes have high levels of antibodies against pancreatic beta cells (hereinafter "beta cells"). However, not all patients with high levels of these antibodies develop Type I diabetes.

Type II diabetes, or non-insulin-dependent diabetes mellitus, develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type II diabetes (Kahn S E, *Am. J. Med.* (2000) 108 Suppl 6a, 2S-8S).

The fasting hyperglycemia that characterizes Type II diabetes occurs as a consequence of the combined lesions of insulin resistance and beta cell dysfunction. The beta cell defect has two components: the first component, an elevation of basal insulin release (occurring in the presence of low, non-stimulatory glucose concentrations), is observed in obese, insulin-resistant pre-diabetic stages as well as in Type II diabetes. The second component is a failure to increase insulin release above the already elevated basal output in response to a hyperglycemic challenge. This lesion is absent in pre-diabetes and appears to define the transition from normo-glycemic insulin-resistant states to frank diabetes. There is currently no cure for diabetes. Conventional treatments for diabetes are very limited, and focus on attempting to control blood glucose levels in order to minimize or delay complications. Current treatments target either insulin resistance (metformin, thiazolidinediones ("TZDs")), or insulin release from the beta cell (sulphonylureas, exanatide). Sulphonylureas, and other compounds that act by depolarizing the beta cell, have the side effect of hypoglycemia since they cause insulin secretion independent of circulating glucose levels. One approved drug, Byetta (exanatide) stimulates insulin secretion only in the presence of high glucose, but is not orally available and must be injected. Januvia (sitagliptin) is another recently approved drug that increases blood levels of incretin hormones, which can increase insulin secretion, reduce glucagon secretion and have other less well characterized effects. However, Januvia and other dipeptidyl peptidases IV inhibitors may also influence the tissue levels of other hormones and peptides, and the long-term consequences of this broader effect have not been fully investigated. There is an unmet need for oral drugs that stimulate insulin secretion in a glucose dependent manner.

Progressive insulin resistance and loss of insulin secreting pancreatic β-cells are primary characteristics of Type II diabetes. Normally, a decline in the insulin sensitivity of muscle and fat is compensated for by increases in insulin secretion from the β-cell. However, loss of β-cell function and mass results in insulin insufficiency and diabetes (Kahn B B, *Cell* 92:593-596, 1998; Cavaghan M K, et al., *J. Clin. Invest.* 106:329-333. 2000; Saltiel A R, *Cell* 104:517-529, 2001; Prentki M and Nolan C J. *J Clin Invest.* 116:1802-1812. (2006); and Kahn S E. *J. Clin. Endocrinol. Metab.* 86:4047-4058, 2001). Hyperglycemia further accelerates the decline in β-cell function (UKPDS Group, J. A. M. A. 281:2005-2012, 1999; Levy J, et al., *Diabetes Med.* 15:290-296, 1998; and Zhou Y P, et al., *J Biol Chem* 278:51316-23, 2003). Several of the genes in which allelic variation is associated with an increased risk of Type II diabetes are expressed selectively in the beta cell (Bell G I and Polonsky K S, *Nature* 414:788-791 (2001); Saxena R, et al., *Science.* (2007) April 26; [Epub ahead of print]; and Valgerdur Steinthorsdottir, et al., *Nature Genetics* (2007) April 26; [Epub ahead of print]).

Insulin secretion from the beta cells of pancreatic islets is elicited by increased levels of blood glucose. Glucose is taken up into the beta cell primarily by the beta cell and liver selective transporter GLUT2 (Thorens B. *Mol Membr Biol.* 2001 October-December; 18(4):265-73). Once inside the cell, glucose is phosphorylated by glucokinase, which is the primary glucose sensor in the beta cell since it catalyzes the irreversible rate limiting step for glucose metabolism (Matschinsky F M. *Curr Diab Rep.* 2005 June; 5(3):171-6). The rate of glucose-6-phosphate production by glucokinase is dependent on the concentration of glucose around the beta cell, and therefore this enzyme allows for a direct relationship between level of glucose in the blood and the overall rate of glucose oxidation by the cell. Mutations in glucokinase produce abnormalities in glucose dependent insulin secretion in humans giving further evidence that this hexokinase family member plays a key role in the islet response to glucose (Gloyn A L, et al., *J Biol Chem.* 2005 Apr. 8;

280(14):14105-13. Epub 2005 Jan. 25). Small molecule activators of glucokinase enhance insulin secretion and may provide a route for therapeutic exploitation of the role of this enzyme (Guertin K R and Grimsby *J. Curr Med Chem.* 2006; 13(15):1839-43; and Matschinsky F M, et al., *Diabetes* 2006 January; 55(1):1-12) in diabetes. Glucose metabolism via glycolysis and mitochondrial oxidative phosphorylation ultimately results in ATP production, and the amount of ATP produced in a beta cell is directly related to the concentration of glucose to which the beta cell is exposed.

Elevated ratios of ATP to ADP that occur in the presence of higher glucose result in the closure of the Kir6.2 channel via interaction with the SUR1 subunit of the channel complex. Closure of these channels on the plasma membrane of the beta cell results in depolarization of the membrane and subsequent activation of voltage dependent calcium channels (VDCCs) (Ashcroft F M, and Gribble F M, *Diabetologia* 42:903-919, 1999; and Seino S, *Anna Rev Physiol.* 61:337-362, 1999). Calcium ion entry as well as release of calcium from intracellular stores triggers exocytosis of insulin granules, resulting is secretion of insulin into the blood stream. Agents which close the Kir6.2 channel such as sulphonylureas and metaglitinides (Rendell M. *Drugs* 2004; 64(12):1339-58; and Blickle J F, *Diabetes Metab.* 2006 April; 32(2):113-20) also cause membrane depolarization, and therefore these agents stimulate insulin secretion in a glucose independent fashion. Potassium channel openers, such as diazoxide, inhibit insulin secretion by preventing elevated ATP/ADP ratios from closing the Kir6.2 channel (Hansen J B. *Curr Med Chem.* 2006; 13(4):361-76). Calcium channel blockers, such as verapamil and nifedipine, can also inhibit insulin secretion (Henquin, J. C. (2004) *Diabetes* 53, S48-S58). Although sulfonylureas and metaglitinides are effective glucose lowering agents in the clinic, they act independently of blood glucose levels. Because they act independently of glucose levels, these drugs may result in hypoglycemia.

Glucose dependent insulin secretion from the beta cell is dependent on numerous neurotransmitters and blood-borne hormones, as well as local, intra-islet factors. CNS activation of the vagal innervation of the islet can lead to the release of small molecules such as acetylcholine and peptides such as vasoactive intestinal polypeptide (VIP), gastrin releasing peptide (GRP) and Pituitary Adenylate Cyclase Activating Peptide (PACAP). Acetylcholine activation of phospholipase C through the $G_{\alpha q}$-coupled GPCR M3 muscarinic receptor leads to release of Ca++ from intracellular stores (Gilon P, and Henquin J C. *Endocr Rev.* 2001 October; 22(5):565-604). Cholinergic agonists also lead to a subtle Na+-dependent plasma membrane depolarization that can work in concert with glucose-initiated depolarization to enhance insulin release (Gilon P, and Henquin J C. *Endocr Rev.* 2001 October; 22(5):565-604). VIP and PACAP each bind to an overlapping set of $G_\alpha$-coupled GPCRs (PAC1, VIPR1, and VIPR2) on the beta cell that lead to stimulation of adenylate cyclase and an increase in intracellular cAMP (Filipsson K, et al., *Diabetes,* 2001 September; 50(9):1959-69; Yamada H, et al., *Regul Pept.* 2004 Dec. 15; 123(1-3): 147-53; and Qader S S, et al., *Am J Physiol Enclocrinol Metab.* 2007 May; 292(5):E1447-55).

Elevation of beta cell cAMP has a substantial potentiating effect on insulin secretion in the presence of stimulatory levels of glucose (see below). Unfortunately, many potentiators of glucose-stimulated insulin secretion also have effects outside of the islet which limit their ability to be used as diabetes therapeutics. For example, the best available selective muscarinic agonists which stimulate insulin secretion also stimulate multiple undesirable responses in multiple tissues (Rhoades R A and Tanner G A, eds. (2003) *Medical Physiology,* 2nd ed. Lippincott, Williams and Wilkins. ISBN 0-7817-1936-4). Likewise, VIP and PACAP receptors are present in multiple organ systems and mediate effects on the reproductive, immune and other diverse systems that make them less attractive as specific enhancers of glucose dependent insulin secretion.

Incretin hormones such as Glucagon-Like Peptide 1 (GLP-1) and Glucose-dependent Insulinotropic Polypeptide (GIP, also known as Gastric Inhibitory Polypeptide) also bind to specific $Galpha_s$-coupled GPCRs receptors on the surface of islet cells, including beta cells, and raise intracellular cAMP (Drucker D J, *J Clin Invest.* 2007 January; 117(1):24-32). Although the receptors for these hormones are present in other cells and tissues, the overall sum of effects of these peptides appear to be beneficial to control of glucose metabolism in the organism (Hansotia T, et al., *J Clin Invest.* 2007 January; 117(1):143-52. Epub 2006 Dec. 21). GIP and GLP-1 are produced and secreted from intestinal K and L cells, respectively, and these peptide hormones are released in response to meals by both direct action of nutrients in the gut lumen and neural stimulation resulting from food ingestion. GIP and GLP-1 have short half-lives in human circulation due to the action of the protease dipeptidyl-peptidase IV (DPP IV), and inhibitors of this protease can lower blood glucose due to their ability to raise the levels of active forms of the incretin peptides. The glucose lowering that can be obtained with DPPIV inhibitors, however, is somewhat limited since these drugs are dependent on the endogenous release of the incretin hormones. Peptides (eg. exanatide (Byetta)) and peptide-conjugates that bind to the GIP or GLP-1 receptors but are resistant to serum protease cleavage can also lower blood glucose substantially (Gonzalez C, et al., *Expert Opin Investig Drugs* 2006 August; 15(8):887-95), but these incretin mimetics must be injected and tend to induce a high rate of nausea and therefore are not ideal therapies for general use in the Type II diabetic population. The clinical success of DPPIV inhibitors and incretin mimetics, though far from ideal, do point to the potential utility of compounds that increase incretin activity in the blood or directly stimulate cAMP in the beta cell. Some studies have indicated that beta cell responsiveness to GIP is diminished in Type II diabetes (Nauck M A, et al., *J. Clin. Invest.* 91:301-307 (1993); and Elahi D, et al., *Regal. Pept.* 51:63-74 (1994)). Restoration of this responsiveness (Meneilly G S, et al., *Diabetes Care.* 1993 January; 16(1):110-4) may be a promising way to improve beta cell function in vivo.

Since increased incretin activity has a positive effect on glucose dependent insulin secretion and perhaps other mechanisms that lead to lower blood glucose, it is also of interest to explore therapeutic approaches to increasing incretin release from intestinal K and L cells. GLP-1 secretion appears to be attenuated in Type II diabetes (Vilsboll T, et al., *Diabetes* 50:609-613), so improving incretin release may ameliorate this component of metabolic dysregulation. Nutrients such as glucose and fat in the gut lumen prompt incretin secretion by interaction with apical receptors (Vilsboll T, et al., *Diabetes* 50:609-613). GLP-1 and GIP release can also result from neural stimulation; acetylcholine and GRP can enhance incretin release in a manner perhaps analogous to the effects of these neurotransmitters on the beta cell in regard to insulin secretion (Brubaker P, *Ann N Y Acad Sci.* 2006 July; 1070:10-26; and Reimann F, et al., *Diabetes* 2006 December; 55 (Supplement 2):S78-S85). Somatostatin, leptin and free fatty acids also appear to modulate incretin secretion (Brubaker P, *Ann N Y Acad Sci.* 2006 July; 1070:10-26; and Reimann, F. et al., *Diabetes.* 2006 December; 55 (Supplement 2):S78-S85). To date, however, there does not appear to be a way to selectively impact these pathways to promote incretin secretion for therapeutic benefit. There is a need for oral drugs that stimulate incretin secretion in the treatment of diabetes.

Incretins can also increase the rate of beta cell proliferation and decrease the apoptotic rates of beta cells in animal models (Farilla L, et al., *Endocrinology* 2002 November; 143(11):4397-408) and human islets in vitro (Farilla L, et al., *Endocrinology* 2003 December; 144(12):5149-58). The net result of these changes is an increase in beta cell number and islet mass, and this should provide for increased insulin secretory capacity, which is another desired aim of antidiabetic therapies. GLP-1 has also been shown to protect islets from the destructive effects of agents such as streptozotocin by blocking apoptosis (Li Y, et al., *J Biol Chem.* 2003 Jan. 3; 278(1):471-8). Cyclin D1, a key regulator of progression through the cell cycle, is up-regulated by GLP-1, and other agents that increase cAMP and PKA activity also have a similar effect (Friedrichsen B N, et al., *J Endocrinol.* 2006 March; 188(3):481-92; and Kim M J, et al., *J Endocrinol.* 2006 March; 188(3):623-33). Increased transcription of the cyclin D1 gene occurs in response to PKA phosphorylation of CREB (cAMP-response element binding) transcription factors (Hussain M A, et al., *Mol Cell Biol.* 2006 October; 26(20):7747-59). There is a need for oral drugs that increase beta cell number and islet mass in the treatment of diabetes.

Beta cell cAMP levels may also be raised by inhibiting the degradation of this second messenger by phosphodiesterases to AMP (Furman B, and Pyne N, *Curr Opin Investig Drugs* 2006 October; 7(10):898-905). There are several different cAMP phosphodiesterases in the beta cell, and many of these have been shown to serve as a brake on glucose-dependent insulin secretion. Inhibitors of cAMP phosphodiesterases have been shown to increase insulin secretion in vitro and in vivo, including PDE1C, PDE3B, PDE10, (Han P, et al., *J Biol Chem.* 1999 Aug. 6; 274(32):22337-44; Harndahl L, et al., *J Biol Chem.* 2002 Oct. 4; 277(40):37446-55; Walz H A, et al., *J Endocrinol.* 2006 June; 189(3):629-41; Choi Y H, et al., *J Clin Invest.* 2006 December; 116(12):3240-51; and Cantin L D, et al., *Bioorg Med Chem Lett.* 2007 May 15; 17(10):2869-73) but so far, no PDEs have been found to have the cell type selectivity necessary to avoid undesirable effects. However, this remains an area of active investigation due to the potential for amplification of the effects of incretins and other agents that stimulate adenylate cyclase.

There appear to be multiple mechanisms by which cAMP elevation in the beta cell can enhance glucose dependent insulin secretion. Classically, many of the intracellular effects of cAMP are mediated by the cAMP-dependent protein kinase (protein kinase A, PKA) (Hatakeyama H, et al., *J Physiol.* 2006 Jan. 15; 570 (Pt 2):271-82). PKA consists of a complex of two regulatory and two catalytic domains; binding of cAMP to the catalytic domains releases the catalytic domains and results in increased protein phosphorylation activity. One of the downstream effects of this kinase activity is enhanced efficiency of insulin exocytosis (Gromada J, et al., Diabetes 1998 January; 47(1):57-65). Another cAMP binding protein is Epac, a guanine nucleotide exchange factor (GEF) (Kashima Y, et al., *J Biol Chem.* 2001 Dec. 7; 276(49):46046-53. Epub 2001 Oct. 11; and Shibasaki T, et al., *J Biol Chem.* 2004 Feb. 27; 279(9):7956-61), which mediates a cAMP-dependent, but PKA-independent, increase in insulin exocytosis. Epac activated by cAMP may also enhance of release of intracellular Ca++ (Holz G G, *Diabetes* 2004 January; 53(1):5-13). The effects of cAMP on insulin secretion are dependent on elevated glucose levels, so raising cAMP in the pancreatic beta cell is an important goal for therapeutics of Type II diabetes.

Agents that raise intracellular cAMP levels in the beta cell increase insulin secretion in a glucose dependent manner (Miura Y and Matsui H, *Am. J. Physiol Endocrinol. Metab* (2003) 285, E1001-E1009). One mechanism for raising cAMP is by the action of G-protein coupled cell surface receptors, which stimulate the enzyme adenylate cyclase to produce more cAMP. The GLP-1 receptor, which is the target of exanatide, is an example of such a receptor (Thorens B, et al., *Diabetes* (1993) 42, 1678-1682). There is a need for oral drugs that increase intracellular levels of cAMP in the treatment of diabetes.

BRIEF SUMMARY OF THE INVENTION

Quite surprisingly, we now find that novel agonists of another G-protein coupled receptor ("GPCR"), IC-GPCR2 is useful in the treatment of diabetes. IC-GPCR2 can also raise intracellular cAMP levels (see In Vitro Activity Table 1 in Biological Example 1). IC-GPCR2 is also referred to as RUP3 and GPR119. Such raised cAMP levels increase insulin secretion in a glucose dependent manner (see Biological Examples 2, 3 and 5) and thus provide a useful treatment for, inter alia, Type II diabetes. The novel agonists described in this invention are orally active (see Biological Examples 3 and 5), providing a significant differentiating feature to exanatide. Additionally, Biological Example 5 provides data on the effect of GPR119 agonists on glucose levels, insulin secretion and weight in diabetic ZDF rats (see FIGS. 3, 4 and 5). Biological Example 6 shows the triglyceride and glucose lowering effects of the GPR119 agonists of the present invention. Biological Example 4 shows the tissue specific expression of GPR119. We have also found that nucleic acid probes corresponding to IC-GPCR2 are highly enriched in pancreatic islets (the majority of which are beta cells), and are not detected in any other tissue examined (see FIGS. 1 and 2). This surprising occurrence means that the novel agonists described in the current invention will be useful in diagnosing diseases effecting pancreatic islets (including beta cells) such as diabetes. Agonists of IC-GPCR2 capable of raising intracellular cAMP levels have now been identified using a cell-based screen (see Biological Example 1).

The present invention provides compounds represented by Formula I:

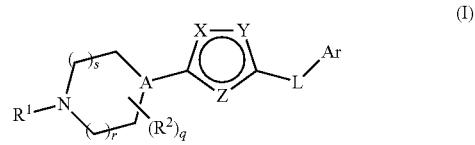

as well as pharmaceutical compositions containing those compounds.

The present invention further provides compounds represented by Formula II:

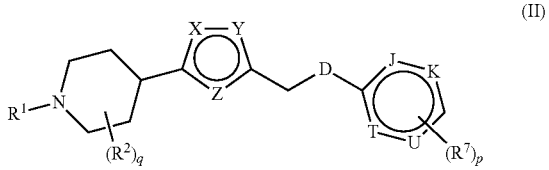

(II)

as well as pharmaceutical compositions containing compounds of Formula II.

Also provided are methods of treating diseases such as Type II diabetes and other diseases and conditions using one or more of these compounds or compositions, as described in further detail below. The invention also provides methods of raising intracellular levels of cyclic AMP (cAMP) by using one or more of the compounds described herein. Further, the compounds may be used to stimulate insulin production and stimulate secretion of insulin, glucagon-like peptide 1 (GLP1), and glucose dependent insulinotropic polypeptide (GIP) in a mammal, in particular a human. Additionally, the compounds described herein are useful in lowering blood glucose when administered to a subject in need of treatment to lower blood glucose. The compounds of the present invention are also useful in lowering blood triglyceride levels in need of such treatment.

In a related aspect, the present invention provides methods of diagnosing a number of diseases and conditions using labeled compounds of Formula I or Formula II.

DETAILED DESCRIPTION OF THE INVENTION

Abbreviations and Definitions

Figure 1:
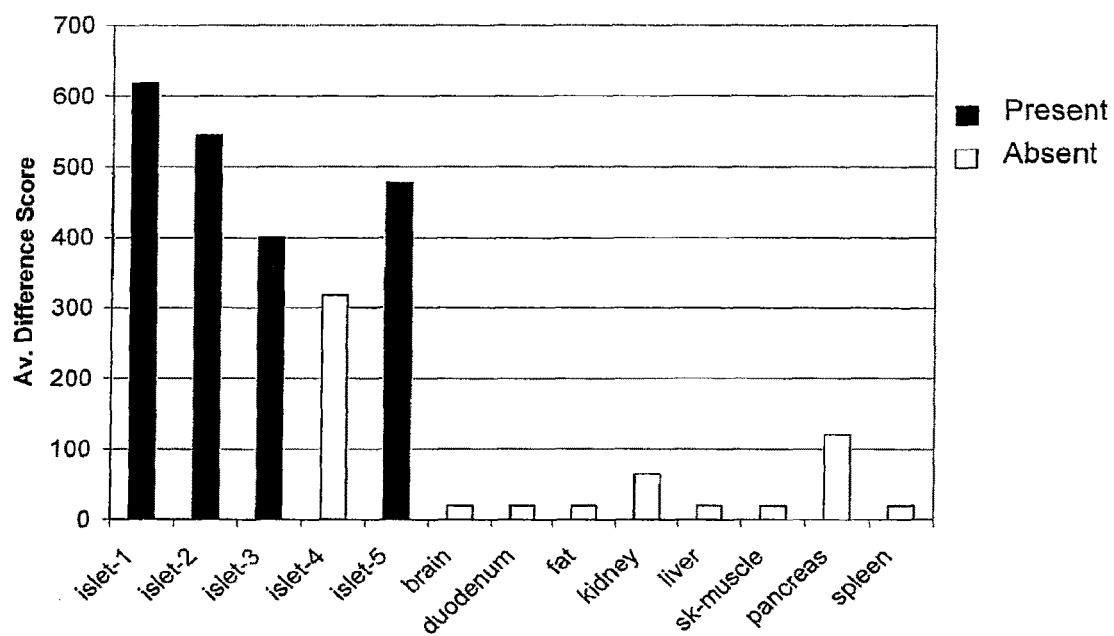
FIG. 1 illustrates rat islet chip hybridization results demonstrating the islet enrichment of IC-GPCR2 mRNA relative to other tissues. Chips were hybridized with equivalent amounts of cRNA from five sets of isolated rat islets, as well as the rat tissues: brain, duodenum, adipose (fat), kidney, liver, skeletal muscle, pancreas and spleen. The "Average Difference" score reflects the relative abundance of the IC-GPCR2 mRNA in each of the tissues. The Affymetrix GeneChip analysis package called the IC-GPCR2 mRNA "Present" in four of five islet samples and "Absent" in each of the other tissues.
Figure 2:
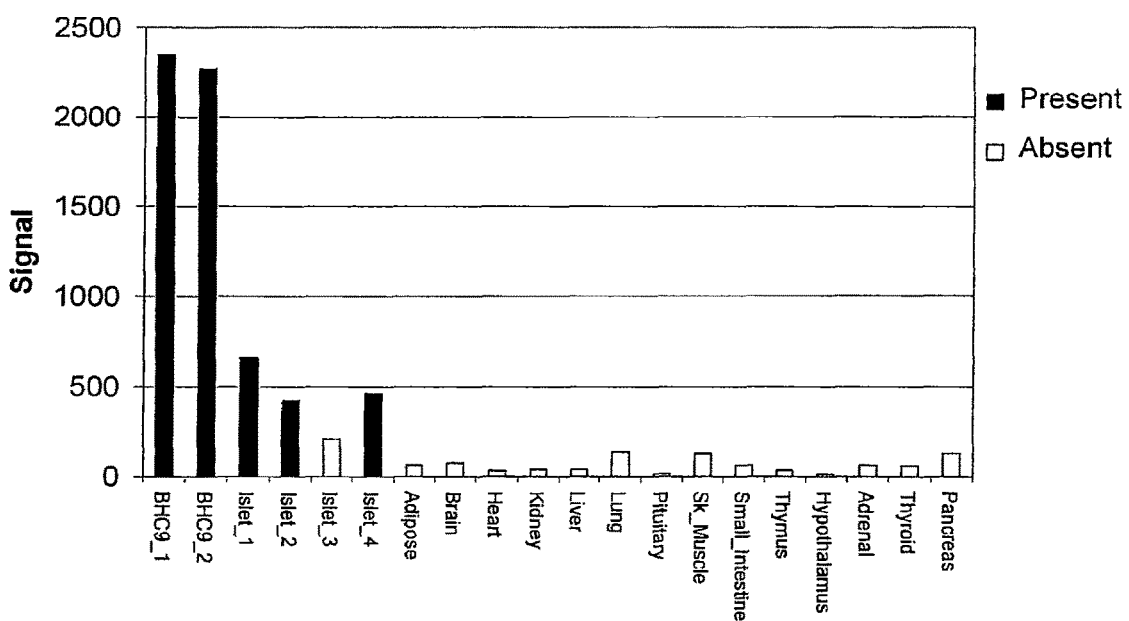
FIG. 2 illustrates mouse islet chip hybridization results demonstrating the islet enrichment of IC-GPCR2 mRNA relative to other tissues. Chips were hybridized with equivalent amounts of cRNA from a pancreatic beta cell line (betaHC9), four sets of isolated mouse islets, as well as the mouse tissues: adipose (fat), brain, heart, kidney, liver, lung, pituitary, skeletal muscle, small intestine, thymus, hypothalamus, adrenal, thyroid and pancreas. The "Signal" score reflects the relative abundance of the IC-GPCR2 mRNA in each of the tissues. The Affymetrix GeneChip analysis package called the IC-GPCR2 mRNA "Present" in betaHC9, and three of four islet samples. The Affymetrix GeneChip analysis package called the IC-GPCR2 mRNA "Absent" in each of the other tissues.

The abbreviations used herein are conventional, unless otherwise defined: AcOH: acetic acid; nBuLi: n-butyllithium; $Cs_2CO_3$: cesium carbonate; $CH_2Cl_2$: dichloromethane; $CH_3MgI$: methyl magnesium iodide; $CuCl_2$: copper chloride; DAST: (diethylamino)sulfur trifluoride; DEAD: diethyl azodicarboxylate; DIBAL: diisobutylaluminum hydride; DIPEA: diisopropylethylamine; DMSO: dimethyl sulfoxide; $Et_3N$: triethylamine; EtOAc: ethyl acetate; $H_2$: hydrogen; HBr: hydrogen bromide; HCl: hydrogen chloride; $H_2O$: water; $H_2O_2$: hydrogen peroxide; HPLC: high performance liquid chromatography; KCN: potassium cyanide; LHMDS: lithium hexamethyldisilazide; $LiAlH_4$: lithium aluminum hydride; LiOH: lithium hydroxide; MeCN: acetonitrile; MeI methyl iodide; MeOH: methanol; $MgSO_4$: magnesium sulfate; $MgCO_3$: magnesium carbonate; MsCl: mesyl chloride; $NaHSO_3$: sodium hydrogen sulfite; mCPBA: meta-chloroperoxybenzoic acid; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium bisulfate; $Na_2SO_4$: sodium sulfate; NBS: N-bromosuccinimide; $NH_4Cl$: ammonium chloride; $NH_4OAc$: ammonium acetate; NMR: nuclear magnetic resonance; Pd/C: palladium on carbon; $PPh_3$: triphenyl phosphine; iPrOH: isopropyl alcohol; $SOCl_2$: thionyl chloride; THF: tetrahydrofuran; TLC: thin layer chromatography.

Unless otherwise stated, the following terms used in the specification and claims have the meanings given below:

"Alkyl" refers to monovalent saturated aliphatic hydrocarbyl groups having from 1 to 10 carbon atoms and, in some embodiments, from 1 to 6 carbon atoms. "$C_{u-v}$alkyl" refers to alkyl groups having from u to v carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5 and, in some embodiments, 1 to 3 or 1 to 2 substituents selected from the group consisting of alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkylidene" or "alkylene" refers to divalent saturated aliphatic hydrocarbyl groups having from 1 to 10 carbon atoms and, in some embodiments, from 1 to 6 carbon atoms. "$(C_{u-v})$alkylene" refers to alkylene groups having from u to v carbon atoms. The alkylidene and alkylene groups include branched and straight chain hydrocarbyl groups. For example "$(C_{1-6})$alkylene" is meant to include methylene, ethylene, propylene, 2-methypropylene, pentylene, and the like.

"Substituted alkylidene" or "substituted alkylene" refers to an alkylidene group having from 1 to 5 and, in some embodiments, 1 to 3 or 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyclo alkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted hetero aryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $(C_{u-v})$alkenyl refers to alkenyl groups having from u to v carbon atoms and is meant to include for example, ethenyl, propenyl, 1,3-butadienyl, and the like.

"Substituted alkenyl" refers to alkenyl groups having from 1 to 3 substituents and, in some embodiments, 1 to 2 substituents, selected from the group consisting of alkoxy, substituted alkoxy, acyl, acylamino, acyloxy, alkyl, substituted alkyl, alkynyl, substituted alkynyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined as herein and with the proviso that any hydroxy or thiol substitution is not attached to an acetylenic carbon atom.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Substituted alkynyl" refers to alkynyl groups having from 1 to 3 substituents and, in some embodiments, from 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, substituted hydrazino, heteroaryl, substituted heteroaryl, heterocyclic and substituted heterocyclic are as defined herein. Acyl includes the "acetyl" group $CH_3C(O)$—.

"Acylamino" refers to the groups —$NR^{20}C(O)H$, —$NR^{20}C(O)$alkyl, —$NR^{20}C(O)$substituted alkyl, —$NR^{20}C(O)$cycloalkyl, —$NR^{20}C(O)$substituted cycloalkyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic wherein $R^{20}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{21}$R$^{22}$ where R$^{21}$ and R$^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclyl, and —SO$_2$-substituted heterocyclyl and wherein R$^{21}$ and R$^{22}$ are optionally joined together with the nitrogen bound thereto to form a heterocyclyl or substituted heterocyclyl group, provided that R$^{21}$ and R$^{22}$ are both not hydrogen, and wherein alkyl, substituted alkyl, alkenyl, substituted alkenyl, alkynyl, substituted alkynyl, cycloalkyl, substituted cycloalkyl, aryl, substituted aryl, hetero aryl, substituted heteroaryl, heterocyclic, and substituted heterocyclic are as defined herein. When R$^{21}$ is hydrogen and R$^{22}$ is alkyl, the substituted amino group is sometimes referred to herein as alkylamino. When R$^{21}$ and R$^{22}$ are alkyl, the substituted amino group is sometimes referred to herein as dialkylamino. When referring to a monosubstituted amino, it is meant that either R$^{21}$ or R$^{22}$ is hydrogen but not both. When referring to a disubstituted amino, it is meant that neither R$^{21}$ nor R$^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, hydroxy, alkoxy, substituted alkoxy, amino, substituted amino, and acylamino, and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{20}$C(O)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{20}$C(S)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocycic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{20}$—SO$_2$NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocycliv, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{25}$)NR$^{23}$R$^{24}$ where R$^{25}$, R$^{23}$, and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and Spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Substituted aryl" refers to aryl groups which are substituted with 1 to 8 and, in some embodiments, 1 to 5, 1 to 3 or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio, and substituted alkylthio, wherein said substituents are defined herein.

"Arylalkyl" or "Aryl(C$_1$-C$_z$)alkyl" refers to the radical —R$^u$R$^v$ where R$^u$ is an alkylene group (having eight or fewer main chain carbon atoms) and R$^v$ is an aryl group as defined herein. Thus, "arylalkyl" refers to groups such as, for example, benzyl, and phenylethyl, and the like. Similarly, "Arylalkenyl" means a radical —R$^u$R$^v$ where R$^u$ is an alkenylene group (an alkylene group having one or two double bonds) and R$^v$ is an aryl group as defined herein, e.g., styrenyl, 3-phenyl-2-propenyl, and the like.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azido" refers to the group —N$_3$.

"Hydrazino" refers to the group —NHNH$_2$.

"Substituted hydrazino" refers to the group —NR$^{26}$NR$^{27}$R$^{28}$ where R$^{26}$, R$^{27}$, and R$^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{27}$ and R$^{28}$ are optionally joined, together with the nitrogen bound thereto to form a heterocyclic or substituted heterocyclic group, provided that R$^{27}$ and R$^{28}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "carbonitrile" refers to the group —CN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{20}$—C(O)O-alkyl, —NR$^{20}$—C(O)O-substituted alkyl, —NR$^{20}$—C(O)O-alkenyl, —NR$^{20}$—C(O)O-substituted alkenyl, —NR$^{20}$—C(O)O-alkynyl, —NR$^{20}$—C(O)O-substituted alkynyl, —NR$^{20}$—C(O)O-aryl, —NR$^{20}$—C(O)O-substituted aryl, —NR$^{20}$—C(O)O-cycloalkyl, —NR$^{20}$—C(O)O-substituted cycloalkyl, —NR$^{20}$—C(O)O-heteroaryl, —NR$^{20}$—C(O)O-substituted heteroaryl, —NR$^{20}$—C(O)O-heterocyclic, and —NR$^{20}$—C(O)O-substituted heterocyclic wherein R$^{20}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cycloalkyl" refers to a saturated or partially saturated cyclic group of from 3 to 14 carbon atoms and no ring heteroatoms and having a single ring or multiple rings including fused, bridged, and Spiro ring systems. For multiple ring systems having aromatic and non-aromatic rings that have no ring heteroatoms, the term "cycloalkyl" applies when the point of attachment is at a non-aromatic carbon atom (e.g., 5,6,7,8-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl. "$C_{u-v}$cycloalkyl" refers to cycloalkyl groups having u to v carbon atoms as ring members. "$C_{u-v}$cycloalkenyl" refers to cycloalkenyl groups having u to v carbon atoms as ring members.

"Cycloalkenyl" refers to a partially saturated cycloalkyl ring having at least one site of >C=C< ring unsaturation.

"Substituted cycloalkyl" refers to a cycloalkyl group, as defined herein, having from 1 to 8, or 1 to 5, or in some embodiments 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are as defined herein. The term "substituted cycloalkyl" includes substituted cycloalkenyl groups.

"Cycloalkyloxy" refers to —O-cycloalkyl wherein cycloalkyl is as defined herein.

"Substituted cycloalkyloxy" refers to —O-(substituted cycloalkyl) wherein substituted cycloalkyl is as defined herein.

"Cycloalkylthio" refers to —S-cycloalkyl wherein substituted cycloalkyl is as defined herein.

"Substituted cycloalkylthio" refers to —S-(substituted cycloalkyl) wherein substituted cycloalkyl is as defined herein.

"Guanidino" refers to the group —NHC(=NH)$NH_2$.

"Substituted guanidino" refers to —$NR^{29}C(=NR^{29})N(R^{29})_2$ where each $R^{29}$ is independently selected from the group consisting of hydrogen, alkyl, substituted alkyl, aryl, substituted aryl, heteroaryl, substituted heteroaryl, heterocyclyl, and substituted heterocyclyl and two $R^{29}$ groups attached to a common guanidino nitrogen atom are optionally joined together with the nitrogen bound thereto to form a heterocyclic or substituted heterocyclic group, provided that at least one $R^{29}$ is not hydrogen, and wherein said substituents are as defined herein.

"Halo" or "halogen" refers to fluoro, chloro, bromo and iodo.

"Haloalkyl" refers to substitution of alkyl groups with 1 to 5 or in some embodiments 1 to 3 halo groups, e.g., —$CH_2Cl$, —$CH_2F$, —$CH_2Br$, —$CFClBr$, —$CH_2CH_2Cl$, —$CH_2CH_2F$, —$CF_3$, —$CH_2CF_3$, —$CH_2CCl_3$, and the like, and further includes those alkyl groups such as perfluoroalkyl in which all hydrogen atoms are replaced by fluorine atoms.

"Haloalkoxy" refers to substitution of alkoxy groups with 1 to 5 or in some embodiments 1 to 3 halo groups, e.g., —$OCH_2Cl$, —$OCH_2F$, —$OCH_2CH_2Br$, —$OCH_2CH_2Cl$, —$OCF_3$, and the like.

"Hydroxy" or "hydroxyl" refers to the group —OH.

"Heteroalkyl" means an alkyl radical as defined herein with one, two or three substituents independently selected from cyano, —$OR^w$, —$NR^xR^y$, and —$S(O)_nR^z$ (where n is an integer from 0 to 2), with the understanding that the point of attachment of the heteroalkyl radical is through a carbon atom of the heteroalkyl radical. $R^w$ is hydrogen, alkyl, cycloalkyl, cycloalkyl-alkyl, aryl, arylalkyl, alkoxycarbonyl, aryloxycarbonyl, carboxamido, or mono- or di-alkylcarbamoyl. $R^x$ is hydrogen, alkyl, cycloalkyl, cycloalkyl-alkyl, aryl or arylalkyl. $R^y$ is hydrogen, alkyl, cycloalkyl, cycloalkyl-alkyl, aryl, arylalkyl, alkoxycarbonyl, aryloxycarbonyl, carboxamido, mono- or di-alkylcarbamoyl or alkylsulfonyl. $R^z$ is hydrogen (provided that n is 0), alkyl, cycloalkyl, cycloalkyl-alkyl, aryl, arylalkyl, amino, monoalkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^w$, $R^x$, $R^y$, and $R^z$ can be further substituted by amino, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —$OR^w$, —$NR^xR^y$, or —$S(O)_nR^z$ portions.

"Heteroaryl" refers to an aromatic group of from 1 to 14 carbon atoms and 1 to 6 heteroatoms selected from the group consisting of oxygen, nitrogen, and sulfur and includes a 5 to 18 member ring or ring system that includes a single ring (e.g., imidazolyl) or multiple rings (e.g., benzimidazol-2-yl and benzimidazol-6-yl). For multiple ring systems, including fused, bridged, and Spiro ring systems having aromatic and non-aromatic rings, the term "heteroaryl" applies if there is at least one ring heteroatom and the point of attachment is at an atom of an aromatic ring (e.g., 1,2,3,4-tetrahydroquinolin-6-yl and 5,6,7,8-tetrahydroquinolin-3-yl). In one embodiment, the nitrogen and/or the sulfur ring atom(s) of the heteroaryl group are optionally oxidized to provide for the N-oxide sulfinyl, or sulfonyl moieties. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

"Substituted heteroaryl" refers to heteroaryl groups that are substituted with from 1 to 8, or in some embodiments 1 to 5, or 1 to 3, or 1 to 2 substituents selected from the group consisting of the substituents defined for substituted aryl.

"Heteroaryloxy" refers to —O-heteroaryl wherein heteroaryl is as defined herein.

"Substituted heteroaryloxy" refers to the group —O-(substituted heteroaryl) wherein heteroaryl is as defined herein.

"Heteroarylthio" refers to the group —S-heteroaryl wherein heteroaryl is as defined herein.

"Substituted heteroarylthio" refers to the group —S-(substituted heteroaryl) wherein heteroaryl is as defined herein.

"Heterocycle" or "heterocyclic" or "heterocyclo" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and Spiro ring systems. For multiple ring systems having aromatic and/or non-aromatic rings, the term "heterocyclic", "heterocycle", "heterocyclo", "heterocycloalkyl" or "heterocyclyl" applies when there is at least one ring heteroatom and the point of attachment is at an atom of a non-aromatic ring (e.g., 1,2,3,4-tetrahydroquinoline-3-yl, 5,6,7,8-tetrahydroquinoline-6-yl, and decahydroquinolin-6-yl). In one embodiment, the nitrogen and/or sulfur atom(s) of the heterocyclic group are optionally oxidized to provide for the N-oxide, sulfinyl, sulfonyl moieties. More specifically the heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

"Substituted heterocycle" or "substituted heterocyclic" or "substituted heterocyclo" or "substituted heterocycloalkyl" or "substituted heterocyclyl" refers to heterocyclic groups, as defined herein, that are substituted with from 1 to 5 or in some embodiments 1 to 3 of the substituents as defined for substituted cycloalkyl.

"Heterocyclyloxy" refers to the group —O-heterocyclyl wherein heterocyclyl is as defined herein.

"Substituted heterocyclyloxy" refers to the group —O-(substituted heterocyclyl) wherein heterocyclyl is as defined herein.

"Heterocyclylthio" refers to the group —S-heterocycyl wherein heterocyclyl is as defined herein.

"Substituted heterocyclylthio" refers to the group —S-(substituted heterocycyl) wherein heterocyclyl is as defined herein.

Examples of heterocycle and heteroaryl groups include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorphinyl), 1,1-dioxothiomorpholinyl, piperidinyl, pyrrolidine, and tetrahydrofuranyl.

"Nitro" refers to the group —$NO_2$.

"Oxo" refers to the atom (=O).

"Oxide" refers to products resulting from the oxidation of one or more heteroatoms. Examples include N-oxides, sulfoxides, and sulfones.

"Spirocycloalkyl" refers to a 3 to 10 member cyclic substituent formed by replacement of two hydrogen atoms at a common carbon atom with an alkylene group having 2 to 9 carbon atoms, as exemplified by the following structure wherein the methylene group shown below attached to bonds marked with wavy lines is substituted with a spirocycloalkyl group:

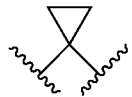

"Sulfonyl" refers to the divalent group —$S(O)_2$—.

"Substituted sulfonyl" refers to the group —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-$SO_2$—, phenyl-$SO_2$—, and 4-methylphenyl-$SO_2$—.

"Sulfonyloxy" refers to the group —$OSO_2$-alkyl, —$OSO_2$-substituted alkyl, —$OSO_2$-alkenyl, —$OSO_2$-substituted alkenyl, —$OSO_2$-cycloalkyl, —$OSO_2$-substituted cycloalkyl, —$OSO_2$-aryl, —$OSO_2$-substituted aryl, —$OSO_2$-heteroaryl, —$OSO_2$-substituted heteroaryl, —$OSO_2$-heterocyclic, —$OSO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiol" refers to the group —SH.

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the atom (=S).

"Thiocyanate" refers to the group —SCN.

"Compound" and "compounds" as used herein refers to a compound encompassed by the generic formulae disclosed herein, any subgenus of those generic formulae, and any forms of the compounds within the generic and subgeneric formulae, such as an oxide, ester, prodrug, pharmaceutically acceptable salt, or solvate. Unless specified otherwise, the term further includes the racemates, stereoisomers, and tautomers of the compound or compounds.

"Racemates" refers to a mixture of enantiomers.

"Solvate" or "solvates" of a compound refer to those compounds, where compounds are as defined above, that are bound to a stoichiometric or non-stoichiometric amount of a solvent. Solvates of a compound includes solvates of all forms of the compound such as the oxide, ester, prodrug, or pharmaceutically acceptable salt of the disclosed generic and subgeneric formulae. Preferred solvents are volatile, non-toxic, and/or acceptable for administration to humans.

"Stereoisomer" or "stereoisomers" refer to compounds that differ in the chirality of one or more stereocenters. Stereoisomers include enantiomers and diastereomers. The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of Advanced Organic Chemistry, 4th edition J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a patient. Prodrugs of a compound of the present invention are prepared by modifying functional groups present in the compound in such a way that the modifications may be cleaved in vivo to release the parent compound, or an active metabolite. For example, prodrugs include compounds wherein a hydroxy, amino, or sulfhydryl group in a compound I is bonded to any group that may be cleaved in vivo to regenerate the free hydroxyl, amino, or sulfhydryl group, respectively. Particularly favored derivatives and prodrugs are those that increase the bioavailability of the compounds of the embodiments when such compounds are administered to a patient (e.g., by allowing an orally administered compound to be more readily absorbed into the blood) or which enhance delivery of the parent compound to a biological compartment (e.g., the brain or lymphatic system) relative to the parent species. Prodrugs include ester, amide, carbamate (e.g., N,N-dimethylaminocarbonyl) forms of hydroxy functional groups of compounds of the invention. Examples of ester prodrugs include formate, acetate, propionate, butyrate, acrylate, and ethylsuccinate derivatives. An general overview of prodrugs is provided in T Higuchi and V Stella, Pro-drugs as Novel Delivery Systems, Vol. 14 of the A.C.S. Symposium Series, and in Edward B Roche, ed., Bioreversible Carriers in Drug Design, American Pharmaceutical Association and Pergamon Press, 1987, both of which are incorporated herein by reference.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium. When the molecule contains a basic functionality, acid addition salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, oxalic acid, 4-toluenesulfonic acid, camphorsulfonic acid, methanesulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts can also be formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like. Pharmaceutically acceptable salts are suitable for administration in a patient and possess desirable pharmacological properties. Suitable salts further include those described in P. Heinrich Stahl, Camille G. Wermuth (Eds.), Handbook of Pharmaceutical Salts Properties, Selection, and Use; 2002.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

"Patient" refers to mammals and includes humans and non-human mammals. Examples of patients include, but are not limited to mice, rats, hamsters, guinea pigs, pigs, rabbits, cats, dogs, goats, sheep, cows, and humans.

The term "mammal" includes, without limitation, humans, domestic animals (e.g., dogs or cats), farm animals (cows, horses, or pigs), and laboratory animals (mice, rats, hamsters, guinea pigs, pigs, rabbits, dogs, or monkeys).

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

"Protecting group" refers to a grouping of atoms that when attached to a reactive group in a molecule masks, reduces or prevents that reactivity. Examples of protecting groups can be found in T. W. Greene and P. G. Wuts, Protective Groups in Organic Chemistry, (Wiley, 2nd ed. 1991) and Harrison and Harrison et al., Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

Turning next to the compositions of the invention, the term "pharmaceutically acceptable carrier or excipient" means a carrier or excipient that is useful in preparing a pharmaceutical composition that is generally safe, possesses acceptable toxicities. Acceptable carriers or excipients include those that are acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes:

(1) preventing or reducing the risk of developing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A preferred embodiment of the invention is treatment of a disease that consists of relieving the disease.

The term "diagnosing" refers to determining the presence or absence of a particular disease or condition. Additionally, the term refers to determining the level or severity of a particular disease or condition, as well as monitoring of the disease or condition to determine its response to a particular therapeutic regimen.

The term "therapeutically effective amount" means the amount of the subject compound that will elicit the biological or medical response of a tissue, system, animal or human that is being sought by the researcher, veterinarian, medical doctor or other clinician.

"A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Patient" refers to mammals and includes humans and non-human mammals. Examples of patients include, but are not limited to mice, rats, hamsters, guinea pigs, pigs, rabbits, cats, dogs, goats, sheep, cows, and humans.

The term "mammal" includes, without limitation, humans, domestic animals (e.g., dogs or cats), farm animals (cows, horses, or pigs), and laboratory animals (mice, rats, hamsters, guinea pigs, pigs, rabbits, dogs, or monkeys).

The term "insulin resistance" can be defined generally as a disorder of glucose metabolism. More specifically, insulin resistance can be defined as the diminished ability of insulin to exert its biological action across a broad range of concentrations producing less than the expected biologic effect (see, e.g., Reaven G M, *J. Basic & Clin. Phys. & Pharm.* (1998) 9:387-406 and Flie J, *Ann Rev. Med.* (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant individuals can progress to a point where a diabetic state is reached.

The term "diabetes mellitus" or "diabetes" means a disease or condition that is generally characterized by metabolic defects in production and utilization of glucose that result in the failure to maintain appropriate blood sugar levels in the body. The result of these defects is elevated blood glucose, referred to as "hyperglycemia." Two major forms of diabetes are Type I diabetes and Type II diabetes. As described above, Type I diabetes is generally the result of an absolute deficiency of insulin, the hormone that regulates glucose utilization. Type II diabetes often occurs in the face of normal, or even elevated levels of insulin and can result from the inability of tissues to respond appropriately to insulin. Most Type II diabetic patients are insulin resistant and have a relative deficiency of insulin, in that insulin secretion can not compensate for the resistance of peripheral tissues to respond to insulin. In addition, many Type II diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in women with no previous history of Type I or Type II diabetes.

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

The term "abdominal obesity" is defined by a cutoff point of waist circumference ≥102 cm in men and ≥80 cm in women, as recommended by the third report of the national cholesterol education program expert panel on detection, evaluation, and treatment of high blood cholesterol in adults (NCEP/ATP Panel III).

The guidelines for diagnosis of Type II diabetes, impaired glucose tolerance, and gestational diabetes have been outlined by the American Diabetes Association (see, e.g., The Expert Committee on the Diagnosis and Classification of Diabetes Mellitus, Diabetes Care, (1999) Vol 2 (Suppl 1):S5-19).

The term "secretagogue" means a substance or compound that stimulates secretion. For example, an insulin secretagogue is a substance or compound that stimulates secretion of insulin.

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications that generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications that generally result from large blood vessel damage. These complications include, e.g., cardiovascular disease and peripheral vascular disease. Cardiovascular disease refers to diseases of blood vessels of the heart. See, e.g., Kaplan R M, et al., "Cardiovascular diseases" in Health and Human Behavior, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels.

The term "modulate" refers to the treating, prevention, suppression, enhancement or induction of a function or condition. For example, compounds can modulate Type II diabetes by increasing insulin in a human, thereby suppressing hyperglycemia.

The term "triglyceride(s)" ("TGs"), as used herein, incorporates its common usage. TGs consist of three fatty acid molecules esterified to a glycerol molecule. TGs serve to store fatty acids that are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL and/or VLDL, and depressed levels of HDL).

The term "hyperlipidemia" includes, but is not limited to, the following:

(1) Familial Hyperchylomicronemia, a rare genetic disorder that causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia is an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine, which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated TG levels (and usually not cholesterol levels) and can often be associated with low plasma HDL levels.

Risk factors for hyperlipidemia include, but are not limited to, the following: (1) disease risk factors, such as a history of Type I diabetes, Type II diabetes, Cushing's syndrome, hypothroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index ("BMI")

greater than 27.8 kg/m² for men and 27.3 kg/m² for women (BMI equals weight (kg)/height (m²). Obesity is linked to a variety of medical conditions including diabetes and hyperlipidemia. Obesity is also a known risk factor for the development of Type II diabetes (See, e.g., Barrett-Conner E, *Epidemol. Rev.* (1989) 11:172-181; and Knowler, et al., *Am. J. Clin. Nutr.* (1991) 53:1543-1551).

The term "pancreas" refers to a gland organ in the digestive and endocrine system of vertebrates, including mammals. The pancreas secretes both digestive enzymes and hormones such as insulin, GLP-1 and GIP as well as other hormones.

The term "islet" or "islet of Langerhans" refers to endocrine cells of the pancreas that are grouped together in islets and secrete insulin and other hormones.

The term "beta cell" refers to cells found in the islet of Langerhans that secrete insulin, amylin, and other hormones.

The term "endocrine cell" refers to cells that secrete hormones into the blood stream. Endocrine cells are found various glands and organ systems of the body including the pancreas, intestines, and other organs.

The term "L cell" refers to gut endocrine cells that produce GLP-1.

The term "K cell" refers to gut endocrine cells that produce GIP.

The term "incretin" refers to a group of hormones that increases insulin secretion in response to food intake. Incretins include GLP-1 and GIP.

The term "insulin" refers to a polypeptide hormone that regulates glucose metabolism. Insulin binds to insulin receptors in insulin sensitive cells and mediates glucose uptake. Insulin is used to treat Type I diabetes and may be used to treat Type II diabetes.

The term "GLP-1" or "glucagon-like peptide" is a peptide hormone primarily produced by L cells. GLP-1 increases insulin secretion, decrease glucagon secretion, increase beta cell mass and insulin gene expression, inhibits acid secretion and gastric emptying in the stomach, and decreases food intake by increasing satiety.

The term "GIP" or "gastric inhibitory peptide" or "glucose dependent insulinotropic polypeptide" refers to a peptide hormone produced primarily by K cells. GIP stimulates insulin secretion. GIP also has significant effects on lipid metabolism.

The term "cAMP" or "cyclic AMP" or "cyclic adenosine monophosphate" refers to an intracellular signaling molecule involved in many biological processes, including glucose and lipid metabolism.

The term "agonist" refers to a compound that binds to a receptor and triggers a response in a cell. An agonist mimics the effect of an endogenous ligand, a hormone for example, and produces a physiological response similar to that produced by the endogenous ligand.

The term "partial agonist" refers to a compound that binds to a receptor and triggers a partial response in a cell. A partial agonist produces only a partial physiological response of the endogenous ligand.

The present invention derives from the discovery of compounds that act as agonists of IC-GPCR2 (SEQ ID NO:1) using a cell-based screen. A stable CHO cell line expressing IC-GPCR2 under the control of the CMV promoter was used and cAMP levels were measured in the cells using a homogeneous time resolved fluorescence assay. With a parental CHO cell line as a control, increased cAMP levels could be measured and compounds identified that, like exanatide, raise cAMP in cells (see In Vitro Activity Table in Biological Example 1). Since elevated intracellular cAMP levels in the beta cell increase insulin secretion in a glucose dependant manner (see Biological Examples 2 and 3), the present invention is useful for the treatment of, inter alia, Type II diabetes and other diseases associated with poor glycemic control. The novel agonists described in this invention are orally active (see Biological Example 3), providing a significant differentiating feature to exanatide. Additionally, the islet specific expression of the receptor for the novel agonists of the present invention (see Biological Example 4) also make the present invention useful for the diagnosis of, inter alia, diabetes and other diseases associated with beta cell health.

Embodiments of the Invention

Compounds

The compounds of the present invention are represented by Formula I:

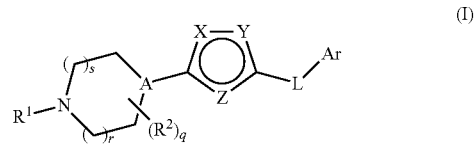

(I)

wherein, the letters X, Y and Z are each independently selected from O, N, N($R^3$), S and C($R^3$) and at least one of X, Y and Z is selected from O, N, N($R^3$) and S. The subscript q is an integer of from 0 to 4; the subscript r is an integer of from 0 to 3; the subscript s is an integer of from 0 to 3, and the sum of r+s is ≤4. The letter A is C($R^4$) or N; L is —(CH$_2$)$_n$— wherein n is an integer of from 2 to 4 and at least one CH$_2$ is replaced by O, N($R^5$), S, S(O) or S(O)$_2$, and any remaining CH$_2$ is optionally substituted with one or two members selected from halogen, $C_{1-4}$ alkyl and $C_{1-4}$ haloalkyl. Ar is a 5- to 10-membered aryl or heteroaryl group, optionally substituted with from one to five $R^6$ substituents.

Turning next to the R groups, $R^1$ is a member selected from $C_{1-10}$ alkyl, $C_{1-10}$ haloalkyl, $C_{3-7}$ cycloalkyl, $C_{2-10}$ alkenyl, $C_{2-10}$ alkynyl, —$X^1$—COR$^a$, —$X^1$—CO$_2$R$^a$, —$X^1$—CONR$^a$R$^b$, —SO$_2$R$^a$, a 4- to 7-membered heterocyclo group, aryl and a 5- to 10-membered heteroaryl group, wherein each of the heterocyclo group and the aryl and the heteroaryl group is optionally substituted with from one to four substituents independently selected from halo, $C_{1-10}$ alkyl, $C_{1-10}$haloalkyl, $C_{3-7}$ cycloalkyl, $C_{2-10}$ alkenyl, $C_{2-10}$ alkynyl, aryl, heteroaryl, CN, NO$_2$, —OR$^a$, —NR$^a$R$^b$, —CO$_2$R$^a$, —CONR$^a$R$^b$, —NR$^a$COR$^b$, —NR$^a$CO$_2$R$^b$, —S(O)$_m$R$^a$, —NR$^a$S(O)$_2$R$^b$, and —SO$_2$NR$^a$R$^b$; and $X^1$ is selected from the group consisting of a bond, —C(O)— and —C(O)—(CH$_2$)$_{1-4}$—, wherein the aliphatic portions of $X^1$ are optionally substituted with one to three members selected from halogen, $C_{1-4}$ alkyl and $C_{1-4}$ haloalkyl.

Each $R^2$ is a member independently selected from halo, $C_{1-8}$ alkyl, $C_{1-8}$ haloalkyl, $C_{3-7}$ cycloalkyl, —COR$^a$, —CO$_2$R$^a$, —CONR$^a$R$^b$, —OR$^a$, —NR$^a$R$^b$, —NR$^a$COR$^b$, —SO$_2$R$^a$ and —SO$_2$NR$^a$R$^b$.

$R^3$ is a member selected from hydrogen, halogen, $C_{1-4}$ alkyl, $C_{1-4}$ haloalkyl, $C_{3-7}$ cycloalkyl, aryl and OR$^a$.

$R^4$ is a member selected from H, halo, $C_{1-6}$ alkyl, OR$^a$ and CN.

$R^5$ is a member selected from —R$^a$, —COR$^a$ and —SO$_2$R$^a$.

Each $R^6$ is independently selected from halo, $C_{1-10}$ alkyl, $C_{1-10}$haloalkyl, $C_{3-7}$ cycloalkyl, $C_{2-10}$ alkenyl, $C_{2-10}$ alkynyl, CN, $NO_2$, $-OR^a$, $-NR^aR^b$, $-COR^a$, $-CO_2R^a$, $-CONR^aR^b$, $-NR^aCOR^b$, $-NR^aCO_2R^b$, $-S(O)_mR^a$, $-NR^aS(O)_mR^b$, $-SO_2NR^aR^b$, a 4- to 7-membered heterocyclo group, aryl and a 5- to 10-membered heteroaryl group, wherein the subscript m is an integer of from 0 to 2 and each of the heterocyclo groups, the aryl and the heteroaryl groups are optionally substituted with from one to four substituents independently selected from halo, oxo, $C_{1-4}$ alkyl, $C_{1-4}$ haloalkyl, $C_{3-7}$ cycloalkyl, CN, $NO_2$, $OR^a$, $-NR^aR^b$, $-CO_2R^a$, $-CONR^aR^b$, $-NR^aCOR^b$, $-NR^aCO_2R^b$, $-S(O)_mR^a$, $-N^aSO_2R^b$, and $-SO_2NR^aR^b$.

For each of the above groups, each $R^a$ and $R^b$ is independently selected from hydrogen, $C_{1-10}$ alkyl, $C_{1-10}$haloalkyl, $C_{3-10}$ cycloalkyl, heterocyclyl, $C_{2-10}$alkenyl, $C_{2-10}$alkynyl, aryl, 5- to 6-membered heteroaryl and aryl$C_{1-4}$alkyl; and wherein the aliphatic portions of each of $R^a$ and $R^b$ is optionally substituted with from one to three members selected from $-OR''$, $-OC(O)N(R'')_2$, $-SR''$, $-S(O)R''$, $-S(O)_2R''$, $-S(O)_2N(R'')_2$, $-NR''S(O)_2R''$, $-C(O)N(R'')_2$, $-C(O)R''$, $-NR''C(O)R''$, $-NR''C(O)N(R'')_2$, $-CO_2R''$, $-NR''CO_2R''$, $-CN$, $-NO_2$, $-N(R'')_2$ and $-NR''S(O)_2N(R'')_2$, wherein each $R''$ is independently hydrogen or an unsubstituted $C_{1-6}$ alkyl; and wherein the aryl and heteroaryl portions are optionally substituted with from one to three members selected from halogen, $-OR'''$, $-OC(O)N(R''')_2$, $-SR'''$, $-S(O)R'''$, $-S(O)_2R'''$, $-S(O)_2N(R''')_2$, $-NR'''S(O)_2R'''$, $-C(O)N(R''')_2$, $-C(O)R'''$, $-NR'''C(O)R'''$, $-NR'''C(O)N(R''')_2$, $-CO_2R'''$, $-NR'''CO_2R'''$, $-CN$, $-NO_2$, $-N(R''')_2$ and $-NR'''S(O)_2N(R''')_2$, wherein each $R'''$ is independently hydrogen or an unsubstituted $C_{1-6}$ alkyl.

The compounds provided herein also include any pharmaceutically acceptable salts of the compounds as well as any isotopically labeled isomers thereof. In general, the compounds useful in the methods described herein are those compound of the formula above, wherein the molecular weight of the compound is less than 1200, more preferably less than about 1000, still more preferably less than about 800 and still more preferably from about 200 to about 600.

The ring having X, Y and Z as ring members will, in one group of embodiments, be a ring in which two of X, Y and Z are independently selected from O, N, $N(R^3)$ and S. In another group of embodiments, the ring is one in which all three of X, Y and Z are independently selected from O, N, $N(R^3)$ and S. One group of preferred rings are represented by the formulae

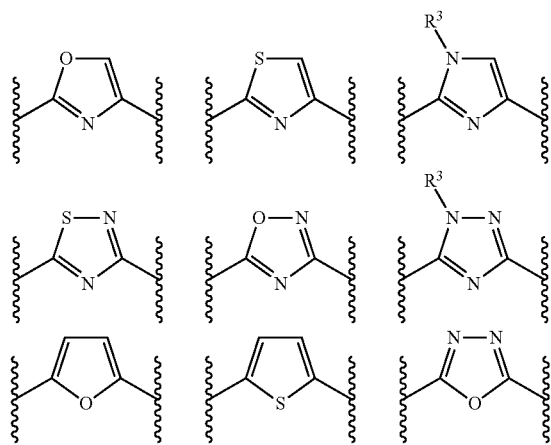

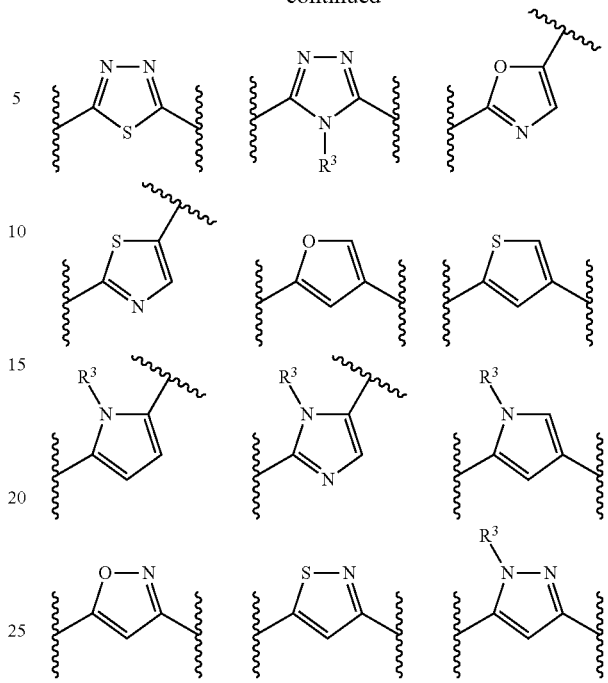

wherein the wavy lines indicate the positions of attachment to either L or to A.

In another group of embodiments, A is $CR^4$.

For each of the above groups of embodiments, an additional set of embodiments are those in which r is 1, s is 0 or 1, q is 0 to 2 and Ar is phenyl, optionally substituted with from 1 to 3 $R^6$ substituents. Still another set of embodiments are those in which r is 1, s is 0 or 1, q is 0 and Ar is selected from the group consisting of pyridyl, pyrimidinyl and pyrazinyl, each of which is optionally substituted with from 1 to 3 $R^6$ substituents. Yet another set of embodiments are those in which r is 1, s is 0 or 1, q is 0 to 2, and n is 2. In still another set of embodiments, r is 1, s is 0 or 1, q is 0 to 2, n is 2 and one $CH_2$ is replaced by O.

In another group of embodiments of Formula I, r is 1; s is 0 or 1; q is 0 to 2; n is 2 and one of $CH_2$ of L is replaced by O, S or $N(R^5)$; A is selected from CH, $C(CH_3)$, CF and C(OH); and the ring having X, Y and Z as ring members is selected from thiazole, oxazole, thiadiazole and oxadiazole. Preferably, Ar is phenyl, optionally substituted with from 1 to 3 $R^6$ substituents. More preferably, Ar is substituted with from 1 to 2 $R^6$ substituents independently selected from the group consisting of halo, $C_{1-10}$ alkyl, $C_{1-10}$haloalkyl, CN, $NO_2$, $-OR^a$, $-NR^aR^b$, $-COR^a$, $-CO_2R^a$, $-CONR^aR^b$, $-NR^aCOR^b$, $-NR^aCO_2R^b$, $-S(O)_mR^a$, $-NR^aS(O)_mR^b$, $-SO_2NR^aR^b$, a 4- to 5-membered heterocyclo group, aryl, and a 5- to 6-membered heteroaryl group. In some embodiments, each $R^6$ is independently selected from the group consisting of halo, $-OR^a$, $-NR^aR^b$, $-NR^aCOR^b$, $-NR^aCO_2R^b$, $-S(O)_mR^a$, $-NR^aS(O)_mR^b$, $-SO_2NR^aR^b$, a 4- to 5-membered heterocyclo group, aryl, and a 5- to 6-membered heteroaryl group. Within each of the groups of embodiments and preferred embodiments, one group of further preferred embodiments are those in which $R^1$ is a 5- to 10-membered heteroaryl group, and is optionally substituted with from one to two substituents independently selected from halo, $C_{1-10}$ alkyl, $C_{1-10}$haloalkyl, $C_{3-7}$ cycloalkyl, $C_{2-10}$alkenyl, $C_{2-10}$ alkynyl, aryl, heteroaryl, CN, $NO_2$, $-OR^a$, $-NR^aR^b$, $-CO_2R^a$, $-CONR^aR^b$, —NR$^a$COR$^b$, —NR$^a$CO$_2$R$^b$, —S(O)$_m$R$^a$, —N$^a$S(O)$_2$R$^b$, and —SO$_2$NR$^a$R$^b$. Still further preferred are those embodiments in which R$^1$ is a pyridine or pyrimidine, and is optionally substituted with from one to two substituents independently selected from halo, C$_{1-10}$ alkyl, C$_{1-10}$ haloalkyl, C$_{3-7}$ cycloalkyl, C$_{2-10}$ alkenyl, C$_{2-10}$ alkynyl, aryl, heteroaryl, CN, NO$_2$, —OR$^a$, —NR$^a$R$^b$, —CO$_2$R$^a$, —CONR$^a$R$^b$, —NR$^a$COR$^b$, —NR$^a$CO$_2$R$^b$, —S(O)$_m$R$^a$, —N$^a$S(O)$_2$R$^b$, and —SO$_2$NR$^a$R$^b$. In still another group of embodiments, R$^1$ is selected from the group consisting of —X$^1$—COR$^a$, —X$^1$—CO$_2$R$^a$, —X$^1$—CONR$^a$R$^b$ and —SO$_2$R$^a$.

In another aspect, this invention provides a compound represented by Formula II.

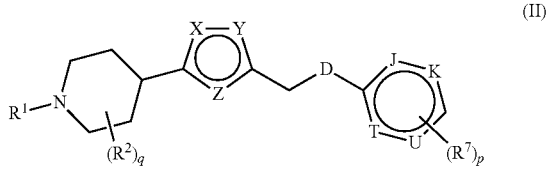

(II)

Wherein the letters X, Y, and Z are each independently selected from the group consisting of O, N, S, and C(R$^3$) and at least one of X, Y, and Z is O, N, NR$^8$, or S; J, K, T, and U are each independently selected from the group consisting of C, and N; the subscript p is an integer of from 0 to 4; and the subscript q is an integer of from 0 to 4.

In Formula II, R$^1$ is a member selected from the group consisting of H, C$_{1-10}$alkyl, C$_{1-10}$substituted alkyl, C$_{3-7}$cycloalkyl, C$_{2-10}$alkenyl, C$_{2-10}$alkynyl, —X$^1$—CO$_2$R$^a$, —X$^1$—CONR$^a$R$^b$, SO$_2$R$^a$, a 4- to 7-membered heterocyclo group, aryl and a 5- to 10-membered heteroaryl group, wherein each of said cycloalkyl group, heterocyclo group, aryl group and heteroaryl group is optionally substituted with from 1 to 4 substituents independently selected from halo, C$_{1-10}$alkyl, C$_{1-10}$substituted alkyl, C$_{3-7}$cycloalkyl, C$_{2-10}$ alkenyl, C$_{2-10}$alkynyl, aryl, heteroaryl, CN, —NR$^a$COR$^b$, —NR$^a$CONR$^a$R$^b$, —NO$_2$, —OR$^a$, —NR$^a$R$^b$, —COR$^a$, —CO$_2$R$^a$, —CONR$^a$R$^b$, —S(O)$_m$R$^a$, —NR$^a$S(O)$_2$R$^b$, and —SO$_2$NR$^a$R$^b$, or optionally R$^a$ and R$^b$ are combined to form a four, five- or six-membered ring, and X$^1$ is selected from the group consisting of a bond, C$_{2-6}$alkene, C$_{2-6}$alkyne, —C(O)—, and —C(O)—(CH$_2$)$_{1-4}$—, wherein the aliphatic portions of X$^1$ are optionally substituted with one to three members selected from halogen, C$_{1-4}$alkyl, C$_{1-4}$substituted alkyl and C$_{1-4}$haloalkyl.

Turning next to R$^2$, each R$^2$ is a member independently selected from the group consisting of halogen, C$_{1-5}$ alkyl, C$_{1-5}$substituted alkyl, C$_{3-7}$cycloalkyl, —COR$^a$, —CO$_2$R$^a$, —CONR$^a$R$^b$, —OR$^a$, —NR$^a$R$^b$, —NR$^a$COR$^b$, —SOR$^a$R$^b$, —SO$_2$R$^a$ and —SO$_2$NR$^a$R$^b$, and wherein when the subscript q is 2 and R$^2$ is alkyl or substituted alkyl, the two R$^2$ members can optionally cyclize to form a ring.

R$^3$ is a member selected from the group consisting of hydrogen, halogen, C$_{1-4}$alkyl, and C$_{1-4}$haloalkyl.

Each R$^7$ of Formula II is independently selected from the group consisting of halo, C$_{1-10}$alkyl, C$_{1-10}$substituted alkyl, C$_{3-7}$cycloalkyl, C$_{2-10}$alkenyl, C$_{2-10}$alkynyl, CN, NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —NR$^a$CONR$^a$R$^b$, —S(O)$_m$R$^a$, —NR$^a$S(O)$_m$R$^b$, —SO$_2$NR$^a$R$^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, C$_{1-4}$ alkyl, C$_{1-4}$ haloalkyl, C$_{3-7}$ cycloalkyl, CN, NO$_2$, —OR$^a$, —NR$^a$R$^b$, —COR$^a$, —CO$_2$R$^a$, —CONR$^a$R$^b$, —NR$^a$COR$^b$, —NR$^a$CO$_2$R$^b$, —NR$^a$CONR$^a$R$^b$, —S(O)$_m$R$^a$, —NR$^a$SO$_2$R$^b$, and —SO$_2$NR$^a$R$^b$ and wherein the subscript m is an integer of from 0 to 2, or optionally R$^a$ and R$^b$ are combined to form a four, five- or six-membered ring.

R$^8$ is a member independently selected from the group consisting of hydrogen, C$_{1-4}$alkyl, and C$_{1-4}$haloalkyl.

For each of the above groups, each R$^a$ and R$^b$ is independently selected from the group consisting of hydrogen, C$_{1-10}$ alkyl, C$_{1-10}$haloalkyl, C$_{3-10}$cycloalkyl, heterocyclyl, C$_{2-10}$alkenyl, C$_{2-10}$alkynyl, aryl, 5- to 6-membered heteroaryl and arylC$_{1-4}$alkyl; and wherein the aliphatic portions of each of said R$^a$ and R$^b$ is optionally substituted with from one to three members selected from the group consisting of halo, —OR'', —OCOR'', —OC(O)N(R'')$_2$, —SR'', —S(O)R'', —S(O)$_2$R'', —S(O)$_2$N(R'')$_2$, —NR''S(O)$_2$R'', —C(O)N(R'')$_2$, —C(O)R'', —NR''C(O)R'', —NR''C(O)N(R'')$_2$, —CO$_2$R'', —NR''CO$_2$R'', —CN, —NO$_2$, —N(R'')$_2$ and —NR''S(O)$_2$N(R'')$_2$, wherein each R'' is independently hydrogen or an unsubstituted C$_{1-6}$ alkyl; and wherein the aryl and heteroaryl portions are optionally substituted with from one to three members selected from halogen, —OR''', —OC(O)N(R''')$_2$, —S(O)R''', —S(O)$_2$R''', —S(O)$_2$N(R''')$_2$, —NR'''S(O)$_2$R''', —C(O)N(R''')$_2$, —C(O)R''', —NR'''C(O) R''', —NR'''C(O)N(R''')$_2$, —CO$_2$R''', —NR'''CO$_2$R''', —CN, —NO$_2$, —N(R''')$_2$ and —NR'''S(O)$_2$N(R''')$_2$, wherein each R''' is independently hydrogen or an unsubstituted C$_{1-6}$ alkyl.

The compounds provided herein also include any pharmaceutically acceptable salts of the compounds as well as any isotopically labeled isomers thereof. In general, the compounds useful in the methods described herein are those compound of the formula above, wherein the molecular weight of the compound is less than 1200, more preferably less than about 1000, still more preferably less than about 800 and still more preferably from about 200 to about 600.

In one embodiment, a preferred R$^1$ group is selected from the group consisting of —X$^1$—COR$^a$, —X$^1$—CONR$^a$R$^b$, SO$_2$R$^a$, aryl, heteroaryl, substituted aryl and substituted heteroaryl. When R$^1$ is an aromatic substituent, R$^1$ is preferably selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl.

When R$^1$ is an aromatic substituent, e.g., aryl or heteroaryl, R$^1$ can be substituted with from one to three substitutents selected from the group consisting of C$_{1-10}$alkyl, C$_{1-10}$haloalkyl, C$_{3-7}$cycloalkyl, aryl, heteroaryl, NO$_2$, —OR$^a$, —NR$^a$R$^b$, —CO$_2$R$^a$, —CONR$^a$R$^b$, —S(O)$_m$R$^a$, —NR$^a$S(O)$_2$R$^b$, and —SO$_2$NR$^a$R$^b$.

In one embodiment, a preferred R$^2$ is a member independently selected from the group consisting of halo, C$_{1-5}$alkyl, C$_{1-5}$haloalkyl, and the subscript q is an integer of from 0 to 2.

In another preferred embodiment, D is O. In compounds of Formula II, when D is O, a preferred R$^1$ group is selected from the group consisting of —X$^1$—COR$^a$, —X$^1$—CO$_2$R$^a$, —X$^1$—CONR$^a$R$^b$, SO$_2$R$^a$, aryl, heteroaryl, substituted aryl and substituted heteroaryl. When R$^1$ is an aromatic substituent, R$^1$ is preferably selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl.

Additionally, when D is O, and $R^1$ is an aromatic substituent, e.g., aryl or heteroaryl, $R^1$ can be substituted with from one to three substituents selected from the group consisting of $C_{1-10}$alkyl, $C_{1-10}$haloalkyl, $C_{3-7}$cycloalkyl, aryl, heteroaryl, $NO_2$, —$OR^a$, —$NR^aR^b$, —$CO_2R^a$, —$CONR^aR^b$, —$S(O)_mR^a$, —$NR^aS(O)_2R^b$, and —$SO_2NR^aR^b$.

Yet another embodiment of this invention is a compound of Formula II wherein J, K, T, and U are all C. In this embodiment, a preferred $R^1$ group is selected from the group consisting of —$X^1$—$COR^a$, —$X^1$—$CO_2R^a$, —$X^1$—$CONR^aR^b$, $SO_2R^a$, aryl, heteroaryl, substituted aryl and substituted heteroaryl. When $R^1$ is an aromatic substituent, $R^1$ is preferably selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl. Further, when J, K, T, and U are all C, and $R^1$ is an aromatic substituent, e.g., aryl or heteroaryl, $R^1$ can be substituted with from one to three substituents selected from the group consisting of $C_{1-10}$alkyl, $C_{1-10}$haloalkyl, $C_{3-7}$cycloalkyl, aryl, heteroaryl, $NO_2$, —$OR^a$, —$NR^aR^b$, —$CO_2R^a$, —$CONR^aR^b$, —$S(O)_mR^a$, —$NR^aS(O)_2R^b$, and —$SO_2NR^aR^b$.

One embodiment of this invention comprises compounds of Formula II wherein the subscript p is an integer of from 1 to 3 and each $R^7$ is independently selected from the group consisting of halo, $C_{1-10}$alkyl, $C_{1-10}$haloalkyl, CN, $NO_2$, —$OR^a$, —$NR^aR^b$, —$COR^a$, —$CO_2R^a$, —$CONR^aR^b$, —$NR^aCOR^b$, —$NR^aCO_2R^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$ haloalkyl, $C_{3-7}$ cycloalkyl, CN, $NO_2$, —$OR^a$, —$CO_2R^a$, —$CONR^aR^b$, —$NR^aCOR^b$, —$NR^aCO_2R^b$, —$S(O)_mR^a$, —$NR^aSO_2R^b$, and —$SO_2NR^aR^b$ and wherein the subscript m is an integer of from 0 to 2.

Yet another aspect of this invention provides compounds of Formula II wherein J, K, T, and U are all C; a preferred $R^1$ group is selected from the group consisting of —$X^1$—$COR^a$, —$X^1$—$CO_2R^a$, —$X^1$—$CONR^aR^b$, $SO_2R^a$, aryl, heteroaryl, substituted aryl and substituted heteroaryl. When $R^1$ is an aromatic substituent, $R^1$ is preferably selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl; and the subscript p is an integer of from 1 to 3 and each $R^7$ is independently selected from the group consisting of halo, $C_{1-10}$alkyl, CN, $NO_2$, —$OR^a$, —$NR^aR^b$, —$COR^a$, —$CO_2R^a$, —$CONR^aR^b$, —$NR^aCOR^b$, —$NR^aCO_2R^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$ haloalkyl, $C_{3-7}$ cycloalkyl, CN, $NO_2$, —$OR^a$, —$NR^aR^b$, —$CO_2R^a$, —$CONR^aR^b$, —$NR^aCOR^b$, —$NR^aCO_2R^b$, —$S(O)_mR^a$, —$NR^aSO_2R^b$, and —$SO_2NR^aR^b$ and wherein the subscript m is an integer of from 0 to 2. Optionally, $R^1$ is substituted with from one to three substituents selected from the group consisting of $C_{1-10}$alkyl, $C_{1-10}$haloalkyl, $C_{3-7}$cycloalkyl, aryl, heteroaryl, $NO_2$, —$OR^a$, —$NR^aR^b$, —$CO_2R^a$, —$CONR^aR^b$, —$S(O)_mR^a$, —$NR^aS(O)_2R^b$, and —$SO_2NR^aR^b$.

A further embodiment of the compounds of the invention are compounds of Formula II, wherein at least one of J, K, T, and U is N. In this embodiment, D is O, S, or $NR^8$.

A preferred embodiment of Formula II provides compounds wherein at least one of J, K, T, and U is N and D is O.

In compounds of Formula II when at least one of J, K, T, and U is N and D is O, a preferred $R^1$ group is selected from the group consisting of —$X^1$—$COR^a$, —$X^1$—$CO_2R^a$, —$X^1$—$CONR^aR^b$, $SO_2R^a$, aryl, heteroaryl, substituted aryl and substituted heteroaryl. When $R^1$ is an aromatic substituent, $R^1$ is preferably selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, substituted imidazolyl, triazolyl, substituted triazolyl, oxazolyl, substituted oxazolyl, thiazolyl, substituted thiazolyl, oxadiazolyl, substituted oxadiazolyl, tetrazolyl, and substituted tetrazolyl; and the subscript p is an integer of from 1 to 3 and each $R^7$ is independently selected from the group consisting of halo, $C_{1-10}$alkyl, $C_{1-10}$haloalkyl, CN, $NO_2$, —$OR^a$, —$NR^aR^b$, —$COR^a$, —$CO_2R^a$, —$CONR^aR^b$, —$NR^aCOR^b$, —$NR^aCO_2R^b$, —$S(O)_mR^a$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$ haloalkyl, $C_{3-7}$ cycloalkyl, CN, $NO_2$, —$OR^a$, —$CO_2R^a$, —$CONR^aR^b$, —$NR^aCOR^b$, —$NR^aCO_2R^b$, —$S(O)_mR^a$, —$NR^aSO_2R^b$, and —$SO_2NR^aR^b$ and wherein the subscript m is an integer of from 0 to 2. Optionally, $R^1$ is substituted with from one to three substituents selected from the group consisting of $C_{1-10}$alkyl, $C_{1-10}$haloalkyl, $C_{3-7}$cycloalkyl, aryl, heteroaryl, $NO_2$, —$OR^a$, —$NR^aR^b$, —$CO_2R^a$, —$CONR^aR^b$, —$S(O)_mR^a$, —$NR^aS(O)_2R^b$, and —$SO_2NR^aR^b$.

One preferred embodiment provides compounds of Formula II wherein when at least one of J, K, T, and U is N and D is O, and $R^1$ is as described in the above paragraph, the subscript p is an integer of from 1 to 3 and each $R^7$ is independently selected from the group consisting of halo, $C_{1-10}$alkyl, $C_{1-10}$haloalkyl, CN, $NO_2$, —$OR^a$, —$NR^aR^b$, —$COR^a$, —$CO_2R^a$, —$CONR^aR^b$, —$NR^aCOR^b$, —$NR^aCO_2R^b$, —$NR^aS(O)_mR^b$, —$SO_2NR^aR^b$, a 4- to 7-membered heterocyclo group, aryl and a 5- to 10-membered heteroaryl group, wherein each of said heterocyclo groups, said aryl and heteroaryl groups are optionally substituted with from one to four substituents independently selected from halo, oxo, $C_{1-4}$ alkyl, $C_{1-4}$haloalkyl, $C_{3-7}$ cycloalkyl, CN, $NO_2$, —$OR^a$, —$NR^aR^b$, —$CO_2R^a$, —$CONR^aR^b$, —$NR^aCOR^b$, —$NR^aCO_2R^b$, —$S(O)_mR^a$, —$NR^aSO_2R^b$, and —$SO_2NR^aR^b$ and wherein the subscript m is an integer of from 0 to 2.

Yet another preferred compound of Formula II provides compounds wherein J, T, and U are all C, and D is O, S, or $NR^8$.

An even more preferred compound of Formula II provides compounds wherein J, T, and U are all C, and D is O.

For compounds of Formula H when J, T, and U are all C, and D is O, the $R^7$ group is a member independently selected from the group consisting of halo, $C_{1-10}$alkyl, $C_{1-10}$ haloalkyl, CN, $NO_2$, —$OR^a$, —$NR^aR^b$, —$COR^a$, —$CO_2R^a$, —$CONR^aR^b$, —$NR^aCOR^b$, —$NR^aCO_2R^b$, —$S(O)_mR^a$, —$NR^aS(O)_mR^b$, —$SO_2NR^aR^b$, a 4- to 5-membered heterocyclo group, and a 5- to 6-membered heteroaryl group and wherein the subscript m is an integer of from 0 to 2. Preferred $R^7$ groups are independently selected from the group consisting of halo, $C_{1-5}$alkyl, $C_{1-5}$haloalkyl, —$SOR^a$, —$SO_2R^a$, and 5-membered heteroaryl group. Even more preferred $R^7$ groups are independently selected from the group consisting of fluoro, chloro, methyl, ethyl, —$CF_3$, —$SO_2CH_3$, imidazolyl, triazolyl, and tetrazolyl and wherein the subscript p is integer of from 1 to 2.

In Formula II, when J, T, and U are all C, and D is O, preferred compounds are compounds wherein the $R^7$ group is a member independently selected from the group consisting of halo, $C_{1-10}$ alkyl, $C_{1-10}$ haloalkyl, CN, $NO_2$, —$NR^aR^b$, —$COR^a$, —$CO_2R^a$, —$CONR^aR^b$, —$NR^aCOR^b$, —$NR^aCO_2R^b$, —$S(O)_mR^a$, —$NR^aS(O)_mR^b$, —$SO_2NR^aR^a$, a 4- to 5-membered heterocyclo group, and a 5- to 6-membered heteroaryl group and wherein the subscript m is an integer of from 0 to 2, and each $R^2$ is a member independently selected from the group consisting of halo, $C_{1-5}$alkyl, $C_{1-5}$haloalkyl, and the subscript q is an integer of from 0 to 2. Preferred $R^7$ groups are independently selected from the group consisting of halo, $C_{1-5}$alkyl, $C_{1-5}$haloalkyl, —$SOR^a$, —$SO_2R^a$, and 5-membered heteroaryl group. Even more preferred $R^7$ groups are independently selected from the group consisting of fluoro, chloro, methyl, ethyl, —$CF_3$, —$SO_2C_{1-3}$alkyl, imidazolyl, triazolyl, and tetrazolyl and wherein the subscript p is integer of from 1 to 2.

Another embodiment of the invention provides compounds of Formula II wherein when J, T, and U are all C, and D is O, the $R^7$ group is a member as described above, and $R^1$ is selected from the group consisting of —$X^1$—$COR^a$, —$X^1CO_2R^a$, —$X^1$—$CONR^aR^b$, $SO_2R^a$, aryl, heteroaryl, substituted aryl and substituted heteroaryl. A Preferred $R^1$ group is selected from the group consisting of is aryl, heteroaryl, substituted aryl and substituted heteroaryl. Even more preferred are compounds wherein $R^1$ is selected from the group consisting of pyridyl, substituted pyridyl, pyrimidinyl, substituted pyrimidinyl, pyrazinyl, substituted pyrazinyl, pyridazinyl, substituted pyridazinyl, phenyl, substituted phenyl, imidazolyl, triazolyl, substituted triazolyl, substituted imidazolyl, oxazolyl, substituted oxazolyl, thiazolyl, substituted thiazolyl, oxadiazolyl, substituted oxadiazolyl, tetrazolyl, and substituted tetrazolyl. Yet even more preferred are compounds wherein $R^1$ is selected from the group consisting of pyrimidinyl, substituted pyrimidinyl, oxadiazolyl, substituted oxadiazolyl, and —$X^1$—$CO_2R^a$ and wherein $X^1$ is a bond.

Additional preferred compounds of the invention are compounds wherein, J, T, and U are all C; and D is O, X is S, Y is C, Z is N; $R^1$ is selected from the group consisting of pyrimidinyl, substituted pyrimidinyl, pyridyl, and substituted pyridyl, each $R^7$ is independently selected from the group consisting of fluoro and tetrazolyl.

In one aspect, this invention provides method of treating a disease or condition selected from the group consisting of Type I diabetes, Type II diabetes and metabolic syndrome. The method comprises administering to a subject in need of such treatment an effective amount of a compound of Formula I or Formula II.

Another aspect of this invention provides methods of stimulating insulin production in a mammal comprising administering an effective amount of a compound of Formula I or Formula II to the mammal. In one aspect the beta cell of the pancreas is stimulated to produce insulin.

Yet another aspect of this invention provides methods of stimulating glucose dependent insulin secretion or production in a mammal comprising administering an effective amount of a compound of Formula I or Formula II to the mammal. In one aspect the beta cell of the pancreas is stimulated to secret insulin.

A further aspect of this invention is a method of lowering blood glucose in a mammal. The method comprises administering an effective amount of a compound of Formula I or Formula II to the mammal. The method further comprises steps to measure blood glucose levels before and after administration of a compound of the invention. Blood glucose levels are easily measured by numerous commercially available glucose monitoring devices that measure blood glucose from samples of blood or urine. Blood glucose can also be measured by commercially available glucometers that do not require blood or urine samples. Biological Example 5 provides methods of measuring glucose levels.

In another embodiment, this invention provides a method of lowering blood triglycerides in a mammal. The method comprises administering an effective amount of a compound of Formula I or Formula II to the mammal. The method further comprises steps to measure blood triglycerides levels before and after administration of a compound of the invention. Blood triglyceride levels are easily measured by numerous commercially available devices that measure blood triglyceride levels from samples of blood. Biological Example 6 provides methods measuring triglyceride levels.

Preparation of Compounds of the Invention

The compounds of the present invention can be prepared in a number of ways familiar to one skilled in the art of organic synthesis. The synthetic route of compounds in the present invention is not limited to the methods outlined below or as provided in the Examples. Individual compounds may require manipulation of the conditions in order to accommodate various functional groups and may require appropriate use of protecting groups. Purification, if necessary, can be accomplished on a silica gel column eluted with the appropriate organic solvent system. Also, reverse phase HPLC or recrystallization may be employed.

One aspect of the present invention provides methods of raising intracellular levels of cyclic AMP (cAMP) in a cell expressing GPR119. The method comprises exposing a cell that expresses GPR119 to a compound as described herein. Cyclic AMP levels are determined by the methods disclosed herein. Preferred cells that express GPR119 are pancreatic cells, islet cells, beta cells, intestinal endocrine cells, and L cells or K cells.

Selected thiazole compounds of Formula I can be prepared using methods generally outlined in Scheme 1.

Scheme 1

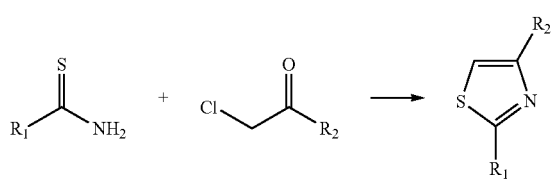

According to Scheme 1, a thioamide can be condensed with a chloromethyl ketone to form a suitable thiazole intermediate. Manipulations of the $R_1$ and $R_2$ groups can be accomplished as provided in the Examples below.

Similarly, oxadiazole compounds of Formula I can be prepared as generally shown in Scheme 2.

Scheme 2

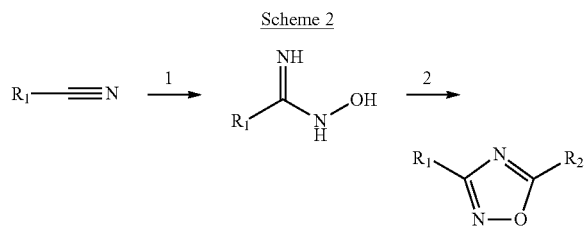

Here, treatment of a suitable nitrile with $NH_2OH$ HCl in the presence of $K_2CO_3$ (step 1) provides the N-hydroxy amidine, which can be converted to an oxadiazole compounds using, for example, $R_2COOH$, isobutylchloroformate, and triethylamine. As above, further manipulation of $R_1$ and $R_2$ can be carried out as provided in the Examples below.

Compositions and Methods of Treatment

In accordance with the present invention, a therapeutically effective amount of a compound of Formula I can be used for the preparation of a pharmaceutical composition useful for treating Type II diabetes and/or lowering the plasma level of glucose. In addition, a therapeutically effective amount of a compound of Formula I can be used for the preparation of a pharmaceutical composition useful for treating other indications that include diabetes as a component, such metabolic syndrome, as well as indications that can be improved as a result of increased insulin production (such as the early stages of Type I diabetes).

The compositions of the invention can include compounds of Formula I and Formula II, pharmaceutically acceptable salts thereof, or a hydrolysable precursor thereof. In general, the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of Type II diabetes.

The compounds of Formula I and Formula II that are used in the methods of the present invention can be incorporated into a variety of formulations for therapeutic administration. More particularly, the compounds of Formula I and Formula II can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, and/or intratracheal administration. Moreover, the compound can be administered in a local rather than systemic manner, in a depot or sustained release formulation. In addition, the compounds can be administered in a liposome.

The compounds of Formula I and Formula II can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. Compounds of Formula I or Formula II can be administered alone, in combination with each other, or they can be used in combination with other known compounds (see Combination Therapy below).

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds of Formula I or Formula II can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide ("DMSO") also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays, animal models, or microdosing of human subjects.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds that exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl, et al., 1975 In: *The Pharmacological Basis of Therapeutics*, Ch. 1).

The amount of active compound that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 100 mg. A more preferred unit dose is between 1 mg to about 20 mg.

Such unit doses can be administered more than once a day, for example 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 20 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

Combination Therapy

As noted above, the compounds of the present invention will, in some instances, be used in combination with other therapeutic agents to bring about a desired effect. Selection of additional agents will, in large part, depend on the desired target therapy (see, e.g., Turner N, et al., *Prog. Drug Res.* (1998) 51:33-94; Haffner S, *Diabetes Care* (1998) 21:160-178; and DeFronzo R, et al. (eds.), *Diabetes Reviews* (1997) Vol. 5 No. 4). A number of studies have investigated the benefits of combination therapies with oral agents (see, e.g., Mahler R, *J. Clin. Endocrinol. Metab.* (1999) 84:1165-71; United Kingdom Prospective Diabetes Study Group: UKPDS 28, *Diabetes Care* (1998) 21:87-92; Bardin C W (ed.), Current Therapy in Endocrinology and Metabolism, 6th Edition (Mosby-Year Book, Inc., St. Louis, Mo. 1997); Chiasson J, et al., *Ann. Intern. Med.* (1994) 121:928-935; Coniff R, et al., *Clin. Ther.* (1997) 19:16-26; Coniff R, et al., *Am. J. Med.* (1995) 98:443-451; and Iwamoto Y, et al., *Diabet. Med.* (1996) 13 365-370; Kwiterovich P, *Am. J. Cardiol* (1998) 82(12A):3U-17U). These studies indicate that diabetes modulation can be further improved by the addition of a second agent to the therapeutic regimen. Combination therapy includes administration of a single pharmaceutical dosage formulation that contains a compound having the general structure of Formula I or Formula II and one or more additional active agents, as well as administration of a compound of Formula I or Formula II and each active agent in its own separate pharmaceutical dosage formulation. For example, a compound of Formula I or Formula II and a DPP-IV inhibitor can be administered to the human subject together in a single oral dosage composition, such as a tablet or capsule, or each agent can be administered in separate oral dosage formulations. Where separate dosage formulations are used, a compound of Formula I or Formula II and one or more additional active agents can be administered at essentially the same time (i.e., concurrently), or at separately staggered times (i.e., sequentially). Combination therapy is understood to include all these regimens.

An example of combination therapy can be seen in modulating (preventing the onset of the symptoms or complications associated with) diabetes (or treating, preventing or reducing the risk of developing, diabetes and its related symptoms, complications, and disorders), wherein the compounds of Formula I or Formula II can be effectively used in combination with, for example, biguanides (such as metformin); thiazolidinediones (such as ciglitazone, pioglitazone, troglitazone, and rosiglitazone); dipeptidyl-peptidase-4 ("DPP-IV") inhibitors (such as vildagliptin and sitagliptin); glucagon like peptide-1 ("GLP-1") receptor agonists (such as exanatide) (or GLP-1 mimetics); PPAR gamma agonists or partial agonists; dual PPAR alpha, PPAR gamma agonists or partial agonists; dual PPAR delta, PPAR gamma agonists or partial agonists; pan PPAR agonists or partial agonists; dehydroepiandrosterone (also referred to as DHEA or its conjugated sulphate ester, DHEA-SO$_4$); anti-glucocorticoids; TNFα inhibitors; α-glucosidase inhibitors (such as acarbose, miglitol, and voglibose); sulfonylureas (such as chlorpropamide, tolbutamide, acetohexamide, tolazamide, glyburide, gliclazide, glynase, glimepiride, and glipizide); pramlintide (a synthetic analog of the human hormone amylin); other insulin secretogogues (such as repaglinide, gliquidone, and nateglinide); insulin (or insulin mimetics); glucagon receptor antagonists; gastric inhibitory peptide ("GIP"); or GIP mimetics; as well as the active agents discussed below for treating obesity, hyperlipidemia, atherosclerosis and/or metabolic syndrome.

Another example of combination therapy can be seen in treating obesity or obesity-related disorders, wherein the compounds of Formula I or Formula II can be effectively used in combination with, for example, phenylpropanolamine, phenteramine; diethylpropion; mazindol; fenfluramine; dexfenfluramine; phentiramine, β-3 adrenoceptor agonist agents; sibutramine; gastrointestinal lipase inhibitors (such as orlistat); and leptins. Other agents used in treating obesity or obesity-related disorders wherein the compounds of Formula I or Formula II can be effectively used in combination with, for example, cannabinoid-1 ("CB-1") receptor antagonists (such as rimonabant); PPAR delta agonists or partial agonists; dual PPAR alpha, PPAR delta agonists or partial agonists; dual PPAR delta, PPAR gamma agonists or partial agonists; pan PPAR agonists or partial agonists; neuropeptide Y; enterostatin; cholecytokinin; bombesin; amylin; histamine $H_3$ receptors; dopamine $D_2$ receptors; melanocyte stimulating hormone; corticotrophin releasing factor; galanin; and gamma amino butyric acid (GABA).

Still another example of combination therapy can be seen in modulating hyperlipidemia (treating hyperlipidemia and its related complications), wherein the compounds of Formula I or Formula II can be effectively used in combination with, for example, statins (such as atorvastatin, fluvastatin, lovastatin, pravastatin, and simvastatin), CETP inhibitors (such as torcetrapib); a cholesterol absorption inhibitor (such as ezetimibe); PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; fenofibric acid derivatives (such as gemfibrozil, clofibrate, fenofibrate, and bezafibrate); bile acid-binding resins (such as colestipol or cholestyramine); nicotinic acid; probucol; betacarotene; vitamin E; or vitamin C.

A further example of combination therapy can be seen in modulating atherosclerosis, wherein a compound of Formula I or Formula II is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin); an HMG-CoA synthase inhibitor; a squalene epoxidase inhibitor; or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrants anion exchange resin, such as cholestyramine, colestipol or dialkylaminoalkyl derivatives of a cross-linked dextran; an LDL receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide); anti-oxidant vitamins, such as vitamin C and E and beta carotene; a beta-blocker; an angiotensin II antagonist; an angiotensin converting enzyme inhibitor; PPAR alpha agonists or partial agonists; PPAR delta agonists or partial agonists; PPAR gamma agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; and a platelet aggregation inhibitor, such as fibrinogen receptor antagonists (i.e., glycoprotein IIb/IIIa fibrinogen receptor antagonists) and aspirin. As noted above, the compounds of Formula I or Formula II can be administered in combination with more than one additional active agent, for example, a combination of a compound of Formula I or Formula II with an HMG-CoA reductase inhibitor (e.g., atorvastatin, fluvastatin, lovastatin, pravastatin, and simvastatin) and aspirin, or a compound of Formula I or Formula II with an HMG-CoA reductase inhibitor and a β blocker.

Additionally, an effective amount of a compound of Formula I or Formula II and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor; an HMG-CoA synthase inhibitor; a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; CETP inhibitors such as torcetrapib; a cholesterol absorption inhibitor such as ezetimibe; PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; niacinamide; a cholesterol absorption inhibitor; a bile acid sequestrant anion exchange resin; a LDL receptor inducer; clofibrate, fenofibrate, and gemfibrozil; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, β-3 adrenergic receptor agonists; sulfonylureas, biguanides, α-glucosidase inhibitors, other insulin secretogogues, and insulin can be used together for the preparation of a pharmaceutical composition useful for the above-described treatments.

An additional example of combination therapy can be seen in modulating metabolic syndrome (or treating metabolic syndrome and its related symptoms, complications and disorders), wherein the compounds of Formula I or Formula II can be effectively used in combination with, for example, the active agents discussed above for modulating or treating diabetes, obesity, hyperlipidemia, atherosclerosis, and/or their respective related symptoms, complications and disorders.

In a further embodiment, a compound of the present invention can be administered in combination with halofenic acid, an ester of halofenic acid, or another prodrug of halofenic acid, preferably with (−)-(4-chlorophenyl)-(3-trifluoromethylphenoxy)-acetic acid 2-acetylaminoethyl ester (metaglidasen).

Methods of Diagnosis and/or Imaging

Compounds of the present invention are also useful in methods of diagnosis and/or imaging. Many direct methods are available to evaluate an agent's biodistribution in the body such as magnetic resonance imaging ("MRI"), positron emission tomography ("PET"), and single photon emission computed tomography ("SPECT"). Each of these methods can detect the distribution of a compound within the body if that compound contains an atom with the appropriate nuclear properties. MRI detects paramagnetic nuclei; PET and SPECT detect the emission of particles from the decay of radionuclei.

Most therapeutic agents are not able to be detected by these techniques without modification. Thus, for PET it is necessary to incorporate an appropriate positron-emitting radionuclide. There are relatively few positron-emitting isotopes that are suitable for labeling a therapeutic agent. The carbon isotope, $^{11}C$, has been used for PET, but has a short half-life of 20.5 minutes. Accordingly, the facilities for synthesis and use are typically near to a cyclotron where the precursor $^{11}C$ starting material is generated. Other isotopes have even shorter half-lives. $^{13}N$ has a half-life of 10 minutes and $^{15}O$ has an even shorter half-life of 2 minutes. The emissions of both are more energetic, however, than those of $^{11}C$ and PET studies have been carried out with these isotopes (see, Clinical Positron Emission Tomography, Mosby Year Book, 1992, K F Hubner, et al., Chapter 2). Another useful isotope, $^{18}F$, has a half-life of 110 minutes. This allows sufficient time for incorporation into a radiolabeled tracer, for purification and for administration into a human or animal subject. $^{18}F$ labeled compounds have been used in studies of glucose metabolism and localization of glucose uptake associated with brain activity. For example, $^{18}F$-L-fluorodopa and other dopamine receptor analogs have also been used in mapping dopamine receptor distribution.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is $^{123}I$, a γ-emitter with a 13.3 hour half life. Compounds labeled with $^{123}I$ can be shipped up to about 1000 miles from the manufacturing site, or the isotope itself can be transported for on-site synthesis. Eighty-five percent of the isotope's emissions are 159 KeV photons, which are readily measured by SPECT instrumentation currently in use. Other halogen isotopes can serve for PET or SPECT imaging, or for conventional tracer labeling. These include [75]Br, [76]Br, [77]Br and [82]Br as having usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs.

In the context of the present invention, methods are provided for diagnosing a disease or condition selected from Type I diabetes and Type II diabetes, the method comprising
(a) administering to a subject having, or at risk for, such a disease or condition an imaging amount of a compound of the invention, wherein the compound is isotopically labeled; and
(b) imaging the subject to determine the number, mass or volume of pancreatic beta cells or islet endocrine cells; or to assess the function of pancreatic beta cells or islet endocrine cells.

Preferably, the compound is labeled with $^{11}$C or [14]C. In other preferred embodiments, the imaging is conducted via PET or SPECT.

Kits

In addition, the present invention provides for kits with unit doses of the compounds of Formula I or Formula II, either in oral or injectable doses. In addition to the containers containing the unit doses will be an informational package insert describing the use and attendant benefits of the drugs in treating Type II diabetes, obesity, hyperlipidemia, atherosclerosis and metabolic syndrome, and/or their respective related symptoms, complications and disorders. Preferred compounds and unit doses are those described herein above.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

EXAMPLES

Experimental Section

General Methods: All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on E. Merck silica gel 60 (240-400 mesh) according to the protocol of Still, Kahn, and Mitra (J. Org. Chem. (1978) 43, 2923). Thin layer chromatography was performed using precoated plates purchased from E. Merck (silica gel 60 $PF_{254}$, 0.25 mm) and spots were visualized with ultraviolet light followed by an appropriate staining reagent.

Nuclear magnetic resonance ("NMR") spectra were recorded on a Varian Inova-400 resonance spectrometer. $^1$H NMR chemical shifts are given in parts per million (δ) downfield from tetramethylsilane ("TMS") using TMS or the residual solvent signal ($CHCl_3$=δ 7.24, DMSO=δ 2.50) as internal standard. $^1$H NMR information is tabulated in the following format: number of protons, multiplicity (s, singlet; d, doublet; t, triplet; q, quartet; m, multiplet), coupling contant(s) (J) in Hertz, and, in selected cases, position assignment. The prefix app is occasionally applied in cases where the true signal multiplicity was unresolved and br indicates the signal in question was broadened.

Preparation of Intermediate 1

4-(4-Chloromethyl-thiazol-2-yl)-piperidine-1-carboxylic acid tert-butyl ester

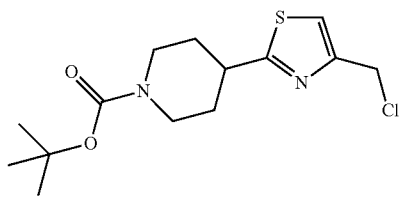 [SMILES: CC(C)(C)OC(=O)N1CCC(c2nc(CCl)cs2)CC1]

To a solution of 4-thiocarbamoyl-piperidine-1-carboxylic acid tert-butyl ester (4.9 g, 20 mmol) in acetone (80 mL) was added 1,3-dichloroacetone (3.3 g, 26 mmol), $MgSO_4$ (3.6 g, 30 mmol) and $MgCO_3$ (1.68 g, 20 mmol). The mixture was heated under reflux overnight, cooled and filtered through celite. The solvent was removed in vacuo and the residue was redissolved with EtOAc (150 mL). The resulting solution was washed successively with 5% $NaHSO_3$, saturated $NaHCO_3$, and brine. After drying ($Na_2SO_4$), the solvent was removed to afford the desired product. $^1$H NMR ($CDCl_3$): δ 7.20 (1H, s), 4.67 (2H, s), 4.20 (2H, br), 3.16 (1H, m), 2.87 (2H, m), 2.09 (2H, m), 1.72 (2H, m), 1.47 (9H, s).

Preparation of Intermediate 2

2-[4-(4-Chloromethyl-thiazol-2-yl)-piperidin-1-yl]-5-ethyl-pyrimidine

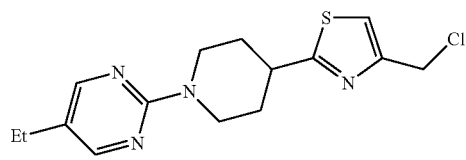 [SMILES: CCc1cnc(N2CCC(c3nc(CCl)cs3)CC2)nc1]

Intermediate 2 was prepared in a manner analogous to Intermediate 1 above.
$^1$H NMR (DMSO-$d_6$): δ 8.45 (2H, d), 7.62 (1H, s), 4.79 (2H, s), 4.61 (2H, m), 3.41 (1H, m), 3.24 (2H, m), 2.52 (2H, q), 2.15 (2H, m), 1.66 (2H, m), 1.17 (3H, m).

Preparation of Intermediate 3

4-[4-(4-Methanesulfonyl-phenoxymethyl)-thiazol-2-yl]-piperidine

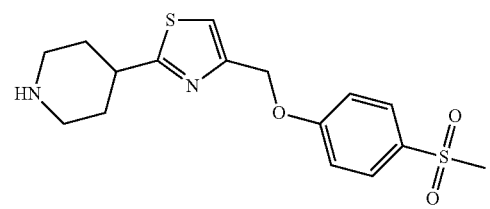 [SMILES: CS(=O)(=O)c1ccc(OCc2csc(C3CCNCC3)n2)cc1]

A solution of 4-[4-(4-Methanesulfonyl-phenoxymethyl)-thiazol-2-yl]-piperidine-1-carboxylic acid tert-butyl ester (615 mg, 1.36 mmol) in methanol (10 mL) was treated with 10 mL of 4N HCl in dioxane. The resulting solution was stirred at room temperature for 30 minutes. Then all the solvents were removed in vacuo to afford the desired product as a HCl salt.

Preparation of Intermediate 4

4-[4-(4-Tetrazol-1-yl-phenoxymethyl)-thiazol-2-yl]-piperidine

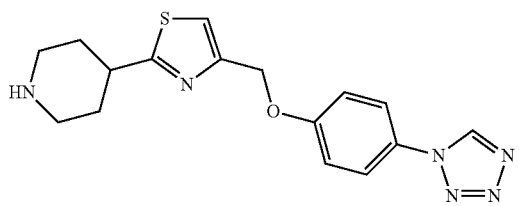 [SMILES: c1cc(-n2cnnn2)ccc1OCc1csc(C2CCNCC2)n1]

Intermediate 4 was prepared in a manner anaolgous to Intermediate 3 above.

$^1$H NMR (DMSO-$d_6$): δ 9.98 (1H, s), 7.82 (2H, m), 7.63 (1H, s), 7.28 (2H, m), 5.19 (2H, s), 3.01 (3H, m), 2.54 (3H, m), 1.92 (2H, m), 1.54 (2H, m).

Preparation of Intermediate 5

4-[4-(2-Fluoro-4-methanesulfonyl-phenoxymethyl)-thiazol-2-yl]-piperidine

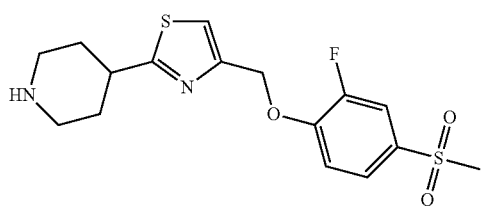 [SMILES: CS(=O)(=O)c1ccc(OCc2csc(C3CCNCC3)n2)c(F)c1]

Intermediate 5 was prepared in a manner analogous to Intermediate 3 above.

Preparation of Intermediate 6

4-[4-(2-Fluoro-4-tetrazol-1-yl-phenoxymethyl)-thiazol-2-yl]-piperidine

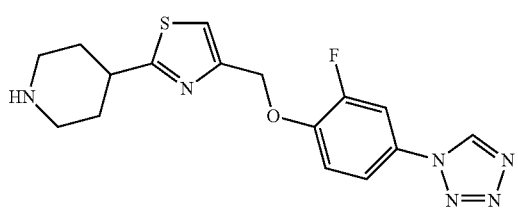 [SMILES: Fc1cc(-n2cnnn2)ccc1OCc1csc(C2CCNCC2)n1]

Intermediate 6 was prepared in a manner analogous to Intermediate 3 above.

Preparation of Intermediate 7

4-[4-(3-Fluoro-4-tetrazol-1-yl-phenoxymethyl)-thiazol-2-yl]-piperidine

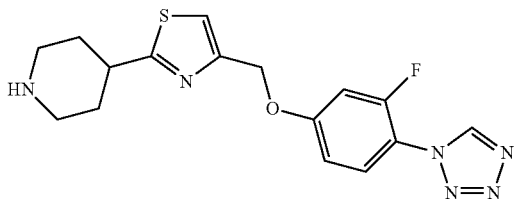 [SMILES: Fc1cc(OCc2csc(C3CCNCC3)n2)ccc1-n1cnnn1]

Intermediate 7 was prepared in a manner analogous to Intermediate 3 above.

Preparation of Intermediate 8

4-[4-(2,6-Difluoro-4-tetrazol-1-yl-phenoxymethyl-thiazol-2-yl]-piperidine

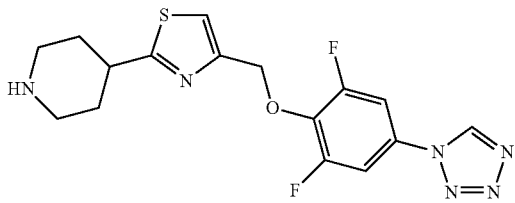 [SMILES: Fc1cc(-n2cnnn2)cc(F)c1OCc1csc(C2CCNCC2)n1]

Intermediate 8 was prepared in a manner analogous to Intermediate 3 above.

Preparation of Intermediate 9

4-[4-(4-Pyrrol-1-yl-phenoxymethyl)-thiazol-2-yl]-piperidine

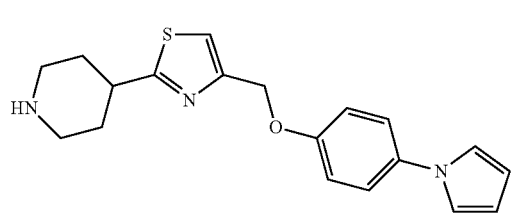 [SMILES: c1ccn(-c2ccc(OCc3csc(C4CCNCC4)n3)cc2)c1]

Intermediate 9 was prepared in a manner analogous to Intermediate 3 above.

Preparation of Intermediate 10

(2-Piperidin-4-yl-thiazol-4-ylmethyl)-(4-tetrazol-1-yl-phenyl)-amine

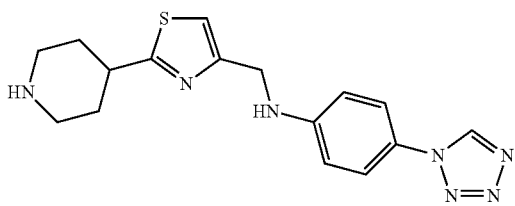 [SMILES: c1cc(-n2cnnn2)ccc1NCc1csc(C2CCNCC2)n1]

Intermediate 10 was prepared in a manner analogous to Intermediate 3 above.

Preparation of Intermediate 11

4-[4-(2-Methyl-4-tetrazol-1-yl-phenoxymethyl)-thiazol-2-yl]-piperidine

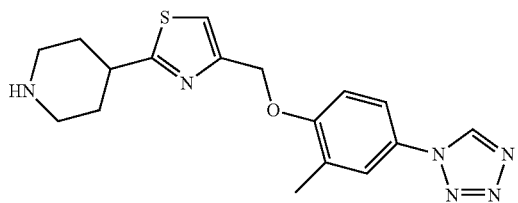

Intermediate 11 was prepared in a manner analogous to Intermediate 3 above.

Preparation of Intermediate 12

4-[4-(2-Isopropyl-5-methyl-4-tetrazol-1-yl-phenoxymethyl)-thiazol-2-yl]-piperidine

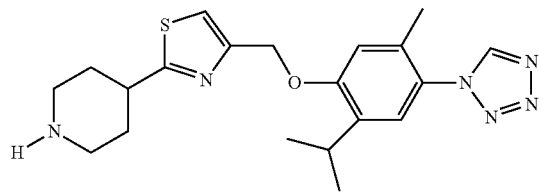 [SMILES: Cc1cc(OCc2csc(C3CCNCC3)n2)c(C(C)C)cc1-n1cnnn1]

Intermediate 12 was prepared in a manner analogous to Intermediate 3 above.

Preparation of Intermediate 13

4-[4-(2-Chloro-4-tetrazol-1-yl-phenoxymethyl)-thiazol-2-yl]-piperidine

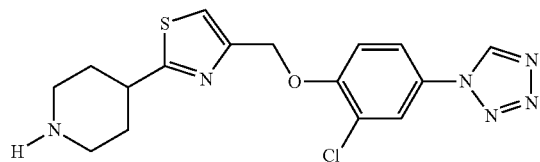 [SMILES: Clc1cc(-n2cnnn2)ccc1OCc1csc(C2CCNCC2)n1]

Intermediate 13 was prepared in a manner analogous to Intermediate 3 above.

Preparation of Intermediate 14

4-(4-Chloromethyl-oxazol-2-yl)-piperidine-1-carboxylic acid tert-butyl ester

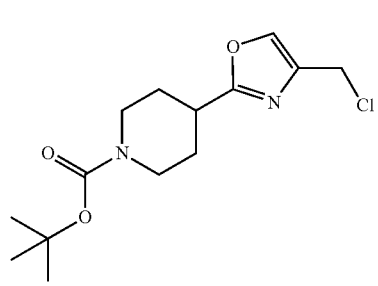 [SMILES: CC(C)(C)OC(=O)N1CCC(c2nc(CCl)co2)CC1]

A mixture of 4-(4-Hydroxymethyl-wxazol-2-yl)-piperidine-1-carboxylic acid tert-butyl ester (800 mg, 2.84 mmol) (obtained by the reduction of 4-(4-Ethoxycarbonyl-oxazol-2-yl)-piperidine-1-carboxylic acid tert-butyl ester which was synthesized according to U.S. Patent Publication No. 2006/0135501 A1), TsCl (812 mg, 4.26 mmol) and triethylamine (1 mL, 752 mg, 7.44 mmol) in dichloromethane (20 mL) was stirred at room temperature for 5 hours. The resulting solution was washed successively with 5% NaHSO$_3$, saturated NaHCO$_3$, and brine. After drying (Na$_2$SO$_4$), the solvent was removed to afford the desired product. $^1$H NMR (CDCl$_3$): δ 7.53 (s, 1H), 4.40 (s, 2H), 4.06 (m, 2H), 2.89 (m, 3H), 1.98 (m, 2H), 1.74 (m, 2H), 1.41 (s, 9H).

Preparation of Intermediate 15

4-[4-(4-Tetrazol-1-yl-phenoxymethyl)-oxazol-2-yl]-piperidine

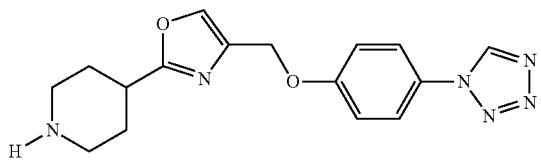 [SMILES: c1cc(-n2cnnn2)ccc1OCc1coc(C2CCNCC2)n1]

Intermediate 15 was prepared in a manner analogous to Intermediate 3 above.

Preparation of Intermediate 16

4-[4-(2-Fluoro-4-tetrazol-1-yl-phenoxymethyl)-oxazol-2-yl]-piperidine

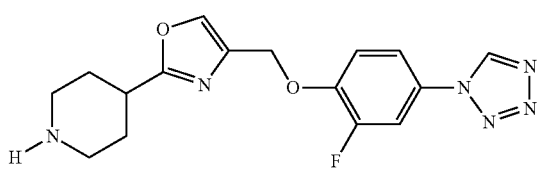 [SMILES: Fc1cc(-n2cnnn2)ccc1OCc1coc(C2CCNCC2)n1]

Intermediate 16 was prepared in a manner analogous to Intermediate 3 above.

Preparation of Intermediate 17

5-(2-Piperidin-4-yl-thiazol-4-ylmethoxy)-2-tetrazol-1-yl-pyridine

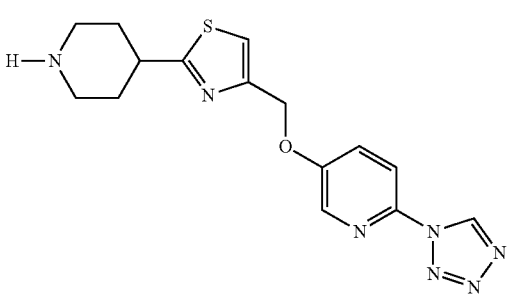 [SMILES: c1cc(-n2cnnn2)ncc1OCc1csc(C2CCNCC2)n1]

Intermediate 17 was prepared in a manner analogous to Intermediate 3 above.

Preparation of Intermediate 18

(6-Fluoro-pyridin-3-yl)-(2-piperidin-4-yl-thiazol-4-ylmethyl-amine

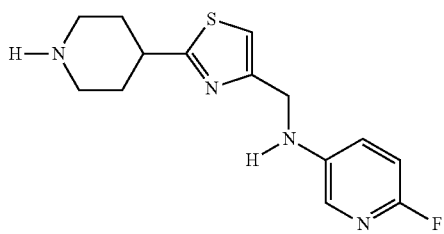 [SMILES: Fc1ccc(NCc2csc(C3CCNCC3)n2)cn1]

Intermediate 18 was prepared in a manner analogous to Intermediate 3 above.

Preparation of Intermediate 19

4-[4-(2,6-Difluoro-4-methanesulfonyl-phenoxymethyl)-thiazol-2-yl]-piperidine

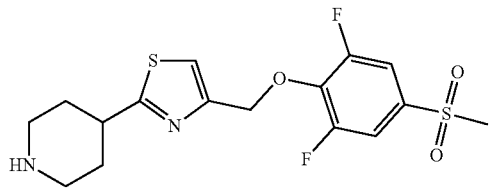 [SMILES: CS(=O)(=O)c1cc(F)c(OCc2csc(C3CCNCC3)n2)c(F)c1]

Intermediate 19 was prepared in a manner analogous to Intermediate 3 above.

Preparation of Intermediate 20

4-[4-(2-Piperidin-4-yl-thiazol-4-ylmethoxy)-phenyl]-morpholine

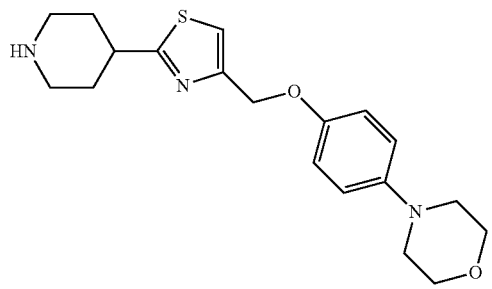 [SMILES: c1cc(N2CCOCC2)ccc1OCc1csc(C2CCNCC2)n1]

Intermediate 20 was prepared in a manner analogous to Intermediate 3 above.

Preparation of Intermediate 21

4-[4-(2-Piperidin-4-yl-thiazol-4-ylmethoxy)-phenyl]-morpholine

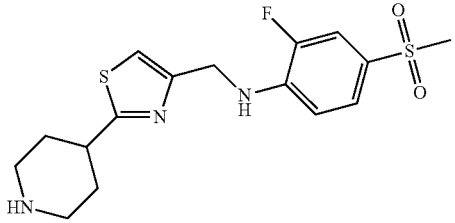 [SMILES: CS(=O)(=O)c1ccc(NCc2csc(C3CCNCC3)n2)c(F)c1]

Intermediate 21 was prepared in a manner analogous to Intermediate 3 above.

Preparation of Intermediate 22

4-(4-Chloromethyl-thiazol-2-yl)-3-methyl-piperidine-1-carboxylic acid tert-butyl ester

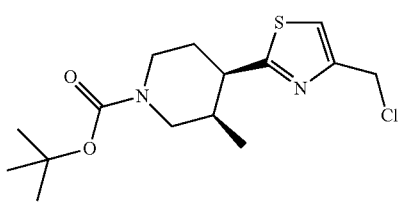 [SMILES: C[C@H]1CN(C(=O)OC(C)(C)C)CC[C@H]1c1nc(CCl)cs1]

Intermediate 22 was prepared in a manner analogous to Intermediate 1 above.

Preparation of Intermediate 23

3-Methyl-4-[4-(4-tetrazol-1-yl-phenoxymethyl)-thiazol-2-yl]-piperidine

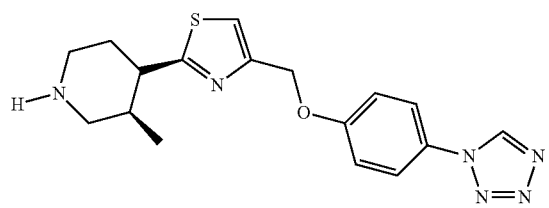

Intermediate 23 was prepared in a manner analogous to Intermediate 3 above.

Preparation of Intermediate 24

4-[4-(2-Fluoro-4-tetrazol-1-yl-phenoxymethyl)-thiazol-2-yl]-3-methyl-piperidine

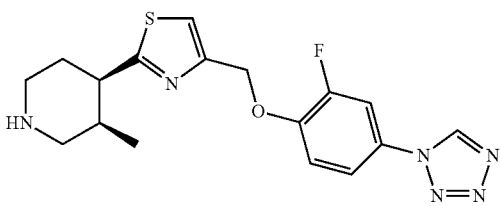 [SMILES: C[C@H]1CNCC[C@H]1c1nc(COc2ccc(-n3cnnn3)cc2F)cs1]

Intermediate 24 was prepared in a manner analogous to Intermediate 3 above.

Preparation of Intermediate 25

4-[4-(4-Methanesulfonyl-benzyloxymethyl)-thiazol-2-yl]-piperidine

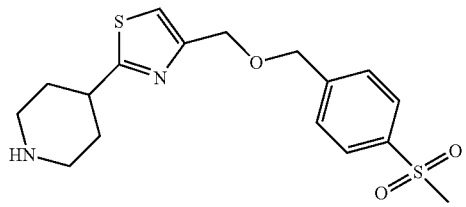 [SMILES: CS(=O)(=O)c1ccc(COCc2csc(C3CCNCC3)n2)cc1]

Intermediate 25 was prepared in a manner analogous to Intermediate 3 above.

Example 1

4-[4-(4-Methanesulfonyl-phenoxymethyl)-thiazol-2-yl]-piperidine-1-carboxylic acid tert-butyl ester

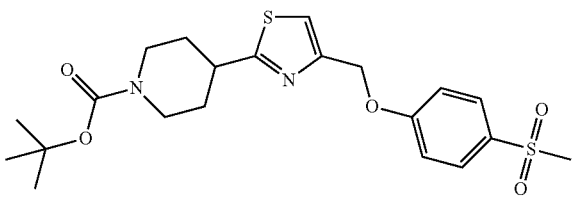

A mixture of 4-(4-Chloromethyl-thiazol-2-yl)-piperidine-1-carboxylic acid tert-butyl ester (Intermediate 1, 463 mg, 1.46 mmol), 4-methanesulfonyl-phenol (252 mg, 1.46 mmol) and $K_2CO_3$ (404 mg, 2.92 mmol) in acetone (25 mL) was heated under reflux overnight. After cooling, the solid was filtered through a pad of celite. The filtrate was concentrated in vacuo. The residue was purified on silica gel (EtOAc-hexanes, 1:1) to afford the desired product. $^1$H NMR (CDCl$_3$): δ 7.88 (2H, d, J=8.8 Hz), 7.23 (1H, s), 7.12 (2H, d, J=8.8 Hz), 5.24 (2H, s), 4.21 (2H, br), 3.17 (1H, m), 3.04 (3H, s), 2.88 (2H, m), 2.11 (2H, m), 1.73 (2H, m), 1.47 (9H, s).

The compounds in Examples 2-19 were synthesized from 4-(4-Chloromethyl-thiazol-2-yl)-piperidine-1-carboxylic acid tert-butyl ester (Intermediate 1), 2-[4-(4-Chloromethyl-thiazol-2-yl)-piperidin-1-yl]-5-ethyl-pyrimidine (Intermediate 2), 4-(4-Chloromethyl-oxazol-2-yl)-piperidine-1-carboxylic acid tert-butyl ester (Intermediate 14) or with the corresponding phenol, thiophenol, amine or aniline in a similar manner to that described in Example 1. One skilled in the art of organic synthesis will appreciate that conditions such as solvent (e.g., DMF, CH$_3$CN); temperature, base (e.g., NEt$_3$, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 2

4-[4-(4-Imidazol-1-yl-phenoxymethyl)-thiazol-2-yl]-piperidine-1-carboxylic acid tert-butyl ester

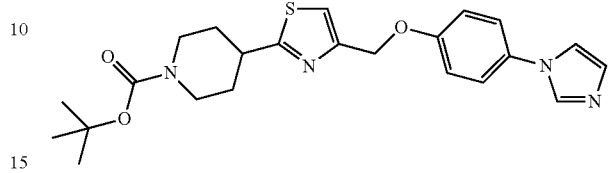

$^1$H NMR (DMSO-d$_6$): δ 8.12 (1H, s), 7.63 (2H, m), 7.54 (2H, d, J=9.2 Hz), 7.15 (2H, d, J=9.2 Hz), 7.05 (1H, s), 5.15 (2H, s), 3.98 (2H, m), 3.21 (1H, m), 2.87 (2H, m), 2.01 (2H, m), 1.52 (2H, m), 1.39 (9H, s).

Example 3

4-[4-(4-Acetylamino-phenoxymethyl)-thiazol-2-yl]-piperidine-1-carboxylic acid tert-butyl ester

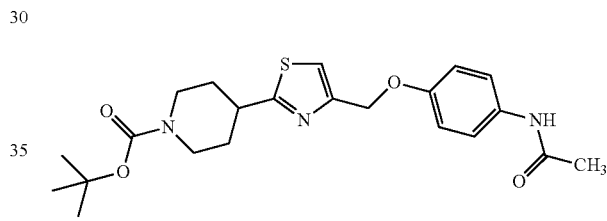

$^1$H NMR (DMSO-d$_6$): δ 9.77 (1H, s), 7.57 (1H, s), 7.45 (2H, d, J=9.0 Hz), 6.94 (2H, d, J=9.0 Hz), 5.04 (2H, s), 3.98 (2H, m), 3.18 (1H, m), 2.82 (2H, m), 2.02 (2H, m), 1.99 (3H, s), 1.51 (2H, m), 1.39 (9H, s).

Example 4

4-[4-(4-Methoxy-benzenesulfonyloxymethyl)-thiazol-2-yl]-piperidine-1-carboxylic acid tert-butyl ester

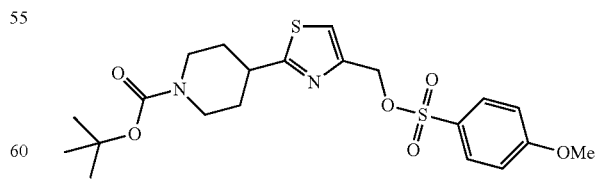

$^1$H NMR (CDCl$_3$): δ 7.60 (2H, d, J=9.0 Hz), 7.24 (1H, s), 6.91 (2H, d, J=9.0 Hz), 4.50 (2H, s), 4.10 (2H, m), 3.85 (3H, s), 2.99 (1H, m), 2.82 (2H, m), 1.89~1.92 (2H, m), 1.53~1.57 (2H, m), 1.46 (9H, s).

Example 5

4-[4-(4-[1,2,4]Triazol-1-yl-phenoxymethyl)-thiazol-2-yl]-piperidine-1-carboxylic acid tert-butyl ester

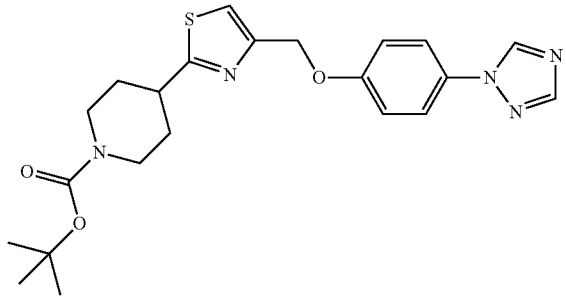 [SMILES: CC(C)(C)OC(=O)N1CCC(c2nc(COc3ccc(-n4cncn4)cc3)cs2)CC1]

$^1$H NMR (CDCl$_3$): δ 8.47 (1H, s), 8.08 (1H, s), 7.58 (2H, d, J=9.2 Hz), 7.24 (1H, s), 7.11 (2H, d, J=9.2 Hz), 5.21 (2H, s), 4.2 (2H, m), 3.18 (1H, m), 2.88 (2H, m), 2.11 (2H, m), 1.74 (2H, m), 1.47 (9H, s).

Example 6

4-{4-[4-(2-Oxo-pyrrolidin-1-yl)-phenoxymethyl]-thiazol-2-yl}-piperidine-1-carboxylic acid tert-butyl ester

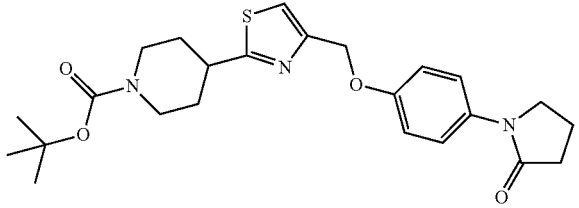 [SMILES: CC(C)(C)OC(=O)N1CCC(c2nc(COc3ccc(N4CCCC4=O)cc3)cs2)CC1]

$^1$H NMR (CDCl$_3$): δ 7.50 (2H, d), 7.20 (1H, s), 6.98 (2H, d), 5.17 (2H, s), 4.20 (2H, br), 3.81 (2H, m), 3.18 (1H, m), 2.88 (2H, m), 2.59 (2H, m), 2.16 (4H, m), 1.73 (2H, m), 1.46 (9H, s).

Example 7

4-[4-(4-Tetrazol-1-yl-phenoxymethyl)-thiazol-2-yl]-piperidine-1-carboxylic acid tert-butyl ester

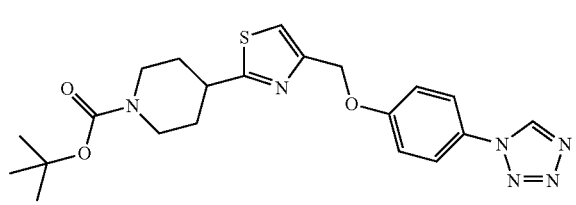 [SMILES: CC(C)(C)OC(=O)N1CCC(c2nc(COc3ccc(-n4cnnn4)cc3)cs2)CC1]

$^1$H NMR (CDCl$_3$): δ 8.94 (1H, s), 7.61 (2H, d), 7.25 (1H, s), 7.19 (2H, d), 5.21 (2H, s), 4.20 (2H, br), 3.20 (1H, m), 2.90 (2H, m), 2.16 (2H, m), 1.77 (2H, m), 1.49 (9H, s).

Example 8

4-[4-(4-Methanesulfonyl-phenylsulfanylmethyl)-thiazol-2-yl]-piperidine-1-carboxylic acid text butyl ester

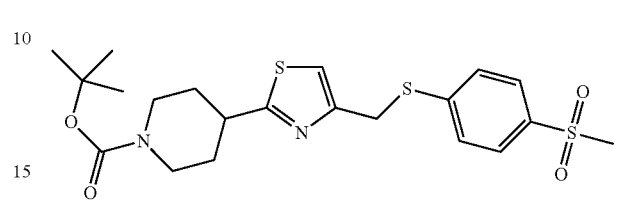

$^1$H NMR (CDCl$_3$): δ 7.7 (2H, d, J=9.0 Hz), 7.36 (2H, d, J=9.0 Hz), 7.00 (1H, s), 4.24 (2H, s), 4.3 (2H, m), 3.05 (1H, m), 2.95 (3H, s), 2.78 (2H, m), 1.99 (2H, m), 1.62 (2H, m), 1.38 (9H, s).

Example 9

4-{2-[1-(5-Ethyl-pyrimidin-2-yl)-piperidin-4-yl]-thiazol-4-ylmethoxy}-benzenesulfonamide

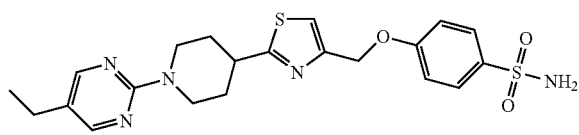 [SMILES: CCc1cnc(N2CCC(c3nc(COc4ccc(S(N)(=O)=O)cc4)cs3)CC2)nc1]

$^1$H NMR (DMSO-d$_6$): δ 8.24 (2H, s), 7.73 (2H, d), 7.64 (1H, s), 7.20 (4H, m), 5.18 (2H, s), 4.67 (2H, m), 3.38 (1H, m), 3.01 (2H, m), 2.47 (2H, m), 2.08 (2H, m), 1.62 (2H, m), 1.53 (3H, m).

Example 10

2-{4-[4-(2,6-Dichloro-4-methanesulfonyl-phenoxymethyl)-thiazol-2-yl]-piperidin-1-yl}-5-ethyl-pyrimidine

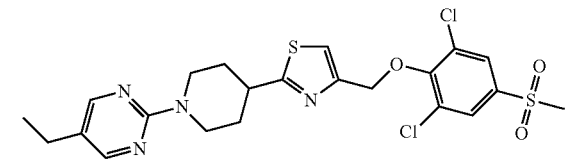 [SMILES: CCc1cnc(N2CCC(c3nc(COc4c(Cl)cc(S(C)(=O)=O)cc4Cl)cs3)CC2)nc1]

$^1$H NMR (DMSO-d$_6$): δ 8.23 (2H, s), 7.99 (2H, s), 7.68 (1H, s), 5.20 (2H, s), 4.64 (2H, m), 3.31 (3H, s), 3.30 (1H, m), 3.0 (2H, m), 2.40 (2H, m), 1.98 (2H, m), 1.54 (2H, m), 1.15 (3H, m).

Example 11

5-Ethyl-2-{4-[4-(3-tetrazol-1-yl-phenoxymethyl)-thiazol-2-yl]piperidin-1-yl}-pyrimidine

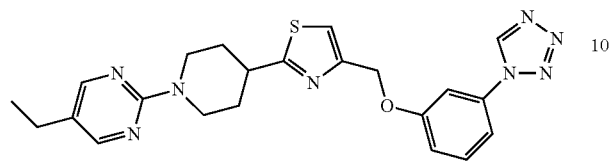

¹H NMR (CDCl₃): δ 9.05 (1H, s), 8.19 (2H, s), 7.55-7.10 (5H, m), 5.24 (2H, s), 4.83 (2H, m), 3.30 (1H, m), 3.04 (2H, m), 2.47 (2H, q, J=7.6 Hz), 2.21 (2H, m), 1.80 (2H, m), 1.19 (3H, t, J=7.6 Hz).

Example 12

5-Ethyl-2-(4-{4-[4-(5-methyl-tetrazol-1-yl)-phenoxymethyl]-thiazol-2-yl}-piperidin-1-yl)-pyrimidine

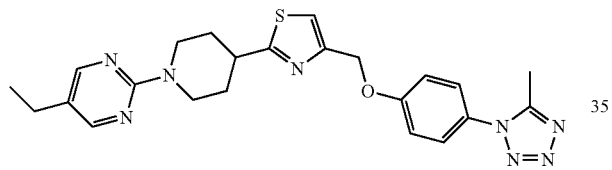

¹H NMR (CDCl₃): δ 8.19 (2H, s), 7.38 (2H, d, J=9.0 Hz), 7.26 (1H, s), 7.17 (2H, d, J=9.0 Hz), 5.24 (2H, s), 4.84 (2H, m), 3.31 (1H, m), 3.05 (2H, m), 2.58 (3H, s), 2.47 (2H, q, J=7.8 Hz), 2.22 (2H, m), 1.82 (2H, m), 1.20 (3H, t, J=7.8 Hz).

Example 13

5-Ethyl-2-{4-[4-(3-methyl-4-methylsulfanyl-phenoxymethyl)-thiazol-2-yl]-piperidin-1-yl}-pyrimidine

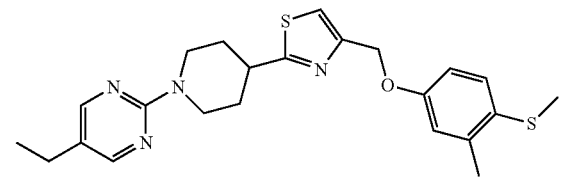 [SMILES: CCc1cnc(N2CCC(c3nc(COc4ccc(SC)c(C)c4)cs3)CC2)nc1]

¹H NMR (DMSO-d₆): δ 8.23 (2H, s), 7.56 (1H, s), 7.16 (1H, m), 6.90 (1H, m), 6.86 (1H, m), 5.06 (2H, s), 4.67 (2H, m), 3.55 (4H, m), 3.01 (2H, m), 2.48 (3H, s), 2.40 (2H, m), 2.09 (2H, m), 1.57 (2H, m), 1.09 (3H, m).

Example 14

5-Ethyl-2-{4-[4-(4-methanesulfonyl-3-methyl-phenoxymethyl)-thiazol-2-yl]-piperidin-1-yl}-pyrimidine

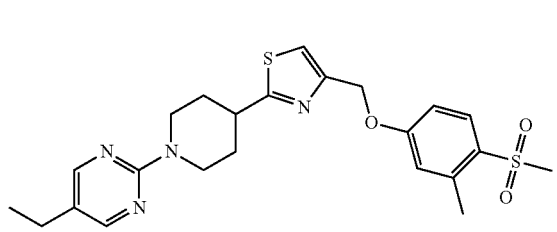 [SMILES: CCc1cnc(N2CCC(c3nc(COc4ccc(S(C)(=O)=O)c(C)c4)cs3)CC2)nc1]

¹H NMR (DMSO-d₆): δ 8.13 (2H, s), 7.91 (1H, m), 7.20 (1H, s), 6.85 (2H, m), 5.14 (2H, s), 4.76 (2H, m), 3.23 (1H, m), 2.98 (3H, s), 2.60 (3H, s), 2.42 (2H, m), 2.15 (2H, m), 1.97 (2H, m), 1.76 (2H, m), 1.13 (3H, m).

Example 15

6-{2-[1-(5-Ethyl-pyrimidin-2-yl)-piperidin-4-yl]-thiazol-4-ylmethoxy}-benzo[1,3]oxathiol-2-one

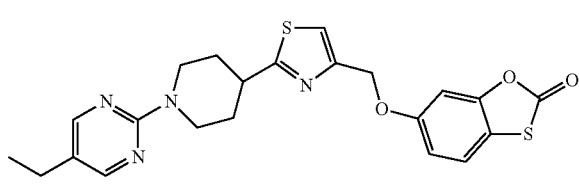 [SMILES: CCc1cnc(N2CCC(c3nc(COc4ccc5sc(=O)oc5c4)cs3)CC2)nc1]

¹H NMR (DMSO-d₆): δ 8.23 (2H, s), 7.64 (1H, m), 7.62 (1H, s), 7.30 (1H, m), 7.03 (1H, m), 5.14 (2H, s), 4.64 (2H, m), 3.31 (1H, m), 3.02 (2H, m), 2.40 (2H, q), 2.09 (2H, m), 1.58 (2H, m), 1.12 (3H, t).

Example 16

5-Ethyl-2-{4-[4-(4-trifluoromethylsulfanyl-phenoxymethyl)-thiazol-2-yl]-piperidin-1-yl}-pyrimidine

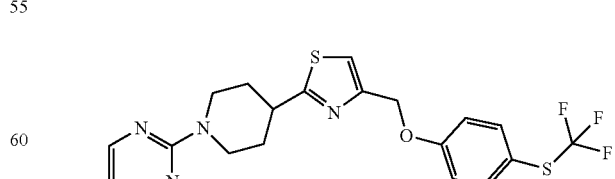

¹H NMR (DMSO-d₆): δ 8.23 (2H, s), 7.63 (3H, m), 7.18 (2H, m), 5.17 (2H, s), 4.67 (2H, m), 3.32 (1H, m), 3.01 (2H, m), 2.40 (2H, q), 2.08 (2H, m), 1.59 (2H, m), 1.13 (3H, t).

Example 17

4-[4-(3-Fluoro-4-tetrazol-1-yl-phenoxymethyl)-thiazol-2-yl]-piperidine-1-carboxylic acid tert-butyl ester

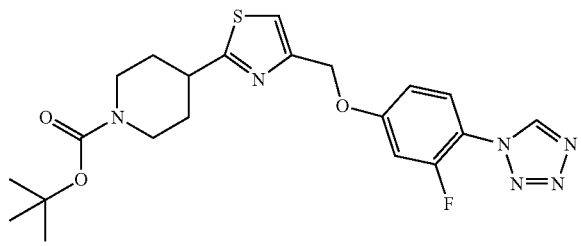 [SMILES: CC(C)(C)OC(=O)N1CCC(c2nc(COc3ccc(-n4cnnn4)c(F)c3)cs2)CC1]

$^1$H NMR (CDCl$_3$): δ 9.04 (1H, s), 7.79 (1H, m), 7.29 (1H, s), 7.01 (2H, m), 5.24 (2H, s), 4.22 (2H, m), 3.19 (1H, m), 2.89 (2H, m), 2.11 (2H, m), 1.74 (2H, m), 1.48 (9H, s).

Example 18

4-[4-(2-Fluoro-4-methanesulfonyl-phenoxymethyl)-thiazol-2-yl]-piperidine-1-carboxylic acid tert-butyl ester

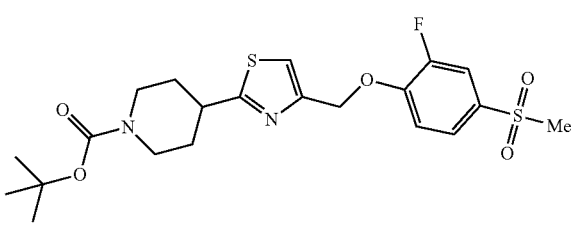 [SMILES: CC(C)(C)OC(=O)N1CCC(c2nc(COc3ccc(S(C)(=O)=O)cc3F)cs2)CC1]

$^1$H NMR (DMSO-d$_6$): δ 7.79 (1H, m), 7.72 (1H, m), 7.70 (1H, s), 7.57 (1H, m), 5.31 (2H, s), 3.99 (2H, m), 3.21 (3H, s), 3.20 (1H, m), 2.85 (2H, m), 2.02 (2H, m), 1.52 (2H, m), 1.39 (9H, s).

Example 19

4-[4-(2-Fluoro-4-tetrazol-1-yl-phenoxymethyl)-thiazol-2-yl]-piperidine-1-carboxylic acid tert-butyl ester

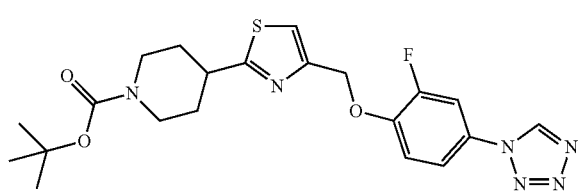 [SMILES: CC(C)(C)OC(=O)N1CCC(c2nc(COc3ccc(-n4cnnn4)cc3F)cs2)CC1]

$^1$H NMR (CDCl$_3$): δ 8.98 (s, 1H), 7.53 (m, 1H), 7.44 (m, 1H), 7.31 (s, 1H), 7.27 (m, 1H), 5.31 (s, 2H), 4.21 (m, 2H), 3.16 (m, 1H), 2.89 (m, 2H), 2.11 (m, 2H), 1.74 (m, 2H), 1.47 (s, 9H).

Example 20

5-Ethyl-2-{4-[4-(4-trifluoromethanesulfinyl-phenoxymethyl)-thiazol-2-yl]-piperidin-1-yl}-pyrimidine

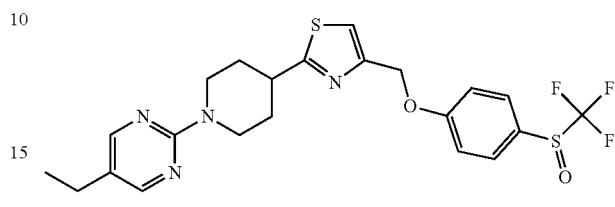

To a solution of 5-Ethyl-2-{4-[4-(4-trifluoromethylsulfanyl-phenoxymethyl)-thiazol-2-yl]-piperidin-1-yl}-pyrimidine (Example 16) in DCM at room temperature was added 3-chloro-benzenecarboperoxoic acid (2 eq.). The reaction was allowed to stir for 1.5 hours and an additional portion of 3-chloro-benzenecarboperoxoic acid (1 eq.) was added to the reaction mixture. The reaction was stirred at room temperature for an additional 4 hours. The organic solution was washed with sodium bicarbonate; the organic layer was isolated, dried over sodium sulfate and filtered. The filtrate was concentrated and the crude product was purified by column chromatography to afford the desired product. $^1$H NMR (DMSO-d$_6$): δ 8.40 (2H, s), 7.58 (2H, d), 7.22 (1H, s), 7.02 (2H, d), 5.17 (2H, s), 3.74 (2H, m), 3.16 (1H, m), 2.96 (2H, m), 2.57 (2H, m), 2.22 (4H, m), 1.24 (3H, m).

Example 21

4-[4-(4-Methanesulfonyl-benzenesulfonylmethyl)-thiazol-2-yl]-piperidine-1-carboxylic acid tert-butyl ester

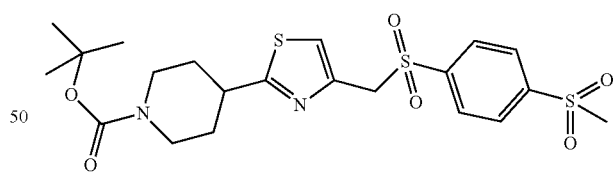

To a solution of 4-[4-(4-Methanesulfonyl-phenylsulfanyl-methyl)-thiazol-2-yl]-piperidine-1-carboxylic acid tert-butyl ester (Example 8, 0.1 g, 0.21 mmol) in CH$_2$Cl$_2$ (5 mL) was added mCPBA (0.11 g, 0.42 mmol) at room temperature. The resulting mixture was stirred at room temperature for 2 hours and was washed with 5% NaHSO$_3$, saturated NaHCO$_3$ and brine. The organic layer was dried with Na$_2$SO$_4$ and the solvent was removed in vacuo. The residue was purified by flash chromatography on silica gel to afford the desired product. $^1$H NMR (CDCl$_3$): δ 8.03 (2H, d, J=9.0 Hz), 7.88 (2H, d, J=9.0 Hz), 7.29 (1H, s), 4.57 (2H, s), 4.10 (2H, m), 3.07 (3H, s), 2.92 (1H, m), 2.75 (2H, m), 1.85 (2H, m), 1.46 (2H, m), 1.44 (9H, s).

Example 22

4-[4-(4-Methanesulfonyl-phenoxymethyl)-thiazol-2-yl]-piperidine-1-carboxylic acid isopropyl ester

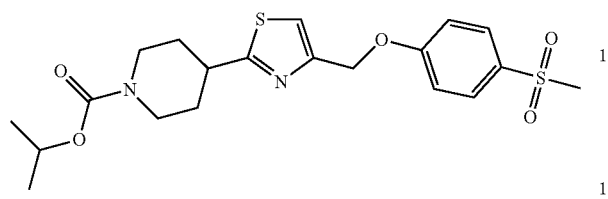

To the HCl salt (Intermediate 3, 43 mg, ~0.12 mmol) of 4-[4-(4-Methanesulfonyl-phenoxymethyl)-thiazol-2-yl]-piperidine was added 3 mL of THF, followed by isopropyl chloroformate (1.0 M solution in toluene, 0.15 mL, 0.15 mmol) and Et$_3$N (0.05 mL). The resulting mixture was stirred at room temperature for 2 hours, and then partitioned between EtOAc and H$_2$O. After concentration of the organic layer in vacuo, the residue was purified by silica gel column chromatography with EtOAc/hexanes (40-70%) to give the desired product. $^1$H NMR (CDCl$_3$): δ 7.86 (2H, d, J=9.0 Hz), 7.23 (1H, s), 7.11 (2H, d, J=9.0 Hz), 5.22 (2H, s), 4.92 (1H, m), 4.24 (2H, m), 3.17 (1H, m), 3.03 (3H, s), 2.90 (2H, m), 2.10 (2H, m), 1.72 (2H, m), 1.23 (6H, d, J=6.4 Hz).

The compounds in Examples 23-46 were synthesized from one of Intermediates 3-13 or Intermediates 15-25 with the corresponding sulfonyl chloride, alkyl chloride, alkyl bromide, chloroformate, acid chloride, carbamyl chloride or isocyanate in a manner similar to that described in Example 22. One skilled in the art of organic synthesis will appreciate that conditions such as solvent (e.g., DMF, CH$_3$CN); temperature, base (e.g., NEt$_3$, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 23

4-[4-(4-Methanesulfonyl-phenoxymethyl)-thiazol-2-yl]-piperidine-1-carboxylic acid benzyl ester

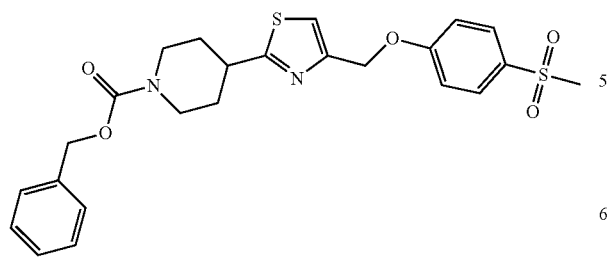

$^1$H NMR (CDCl$_3$): δ 7.87 (2H, d, J=9.2 Hz), 7.31~7.37 (5H, m), 7.23 (1H, s), 7.11 (2H, d, J=9.2 Hz), 5.22 (2H, s), 5.14 (2H, s), 4.29 (2H, m), 3.16~3.22 (1H, m), 3.03 (3H, s), 2.96 (2H, m), 2.12 (2H, m), 1.70~1.80 (2H, m).

Example 24

4-[4-(4-Methanesulfonyl-phenoxymethyl)-thiazol-2-yl]-piperidine-1-carboxylic acid isobutyl ester

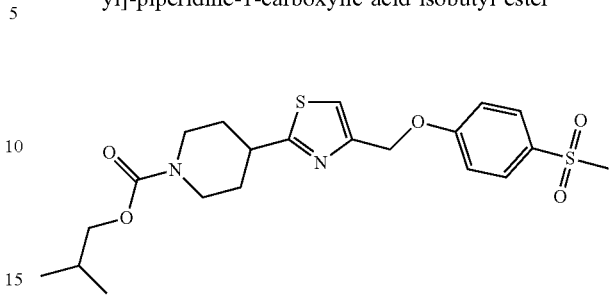

$^1$H NMR (CDCl$_3$): δ 7.87 (2H, d, J=9.0 Hz), 7.23 (1H, s), 7.11 (2H, d, J=9.0 Hz), 5.22 (2H, s), 4.25 (2H, m), 3.87 (2H, d, J=6.6 Hz), 3.17 (1H, m), 3.03 (3H, s), 2.94 (2H, m), 2.12 (2H, m), 1.94 (1H, m), 1.75 (2H, m), 0.93 (6H, d, J=6.6 Hz).

Example 25

4-[4-(4-Methanesulfonyl-phenoxymethyl)-thiazol-2-yl]-piperidine-1-carboxylic acid adamantan-1-yl ester

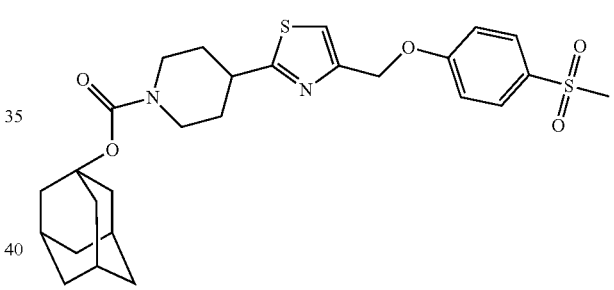

$^1$H NMR (CDCl$_3$): δ 7.89 (2H, d, J=8.8 Hz), 7.24 (1H, s), 7.12 (2H, d, J=8.8 Hz), 5.23 (2H, s), 4.21 (2H, m), 3.12~3.20 (1H, m), 3.03 (3H, s), 2.87 (2H, m), 2.05~2.17 (11H, m), 1.62~1.79 (8H, m).

Example 26

4-[4-(4-Methanesulfonyl-phenoxymethyl)-thiazol-2-yl]-piperidine-1-carboxylic acid methyl ester

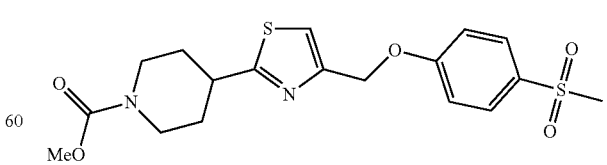

$^1$H NMR (CDCl$_3$): δ 7.87 (2H, d, J=9.0 Hz), 7.23 (1H, s), 7.11 (2H, d, J=9.0 Hz), 5.22 (2H, s), 4.24 (2H, m), 3.71 (3H, s), 3.14~3.17 (1H, m), 3.03 (3H, s), 2.94 (2H, m), 2.12 (2H, m), 1.70~1.80 (2H, m).

Example 27

4-[4-(4-Methanesulfonyl-phenoxymethyl)-thiazol-2-yl]-piperidine-1-carboxylic acid 4-fluoro-phenyl ester

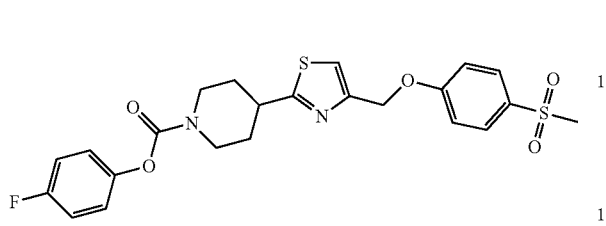

$^1$H NMR (CDCl$_3$): δ 7.88 (2H, d, J=8.8 Hz), 7.12 (2H, d, J=8.8 Hz), 7.01~7.09 (5H, m), 5.24 (2H, s), 4.37 (2H, m), 3.23~3.27 (1H, m), 3.19 (2H, m), 3.04 (3H, 2.20 (2H, m), 1.88 (2H, m).

Example 28

4-[4-(4-Methanesulfonyl-phenoxymethyl)-thiazol-2-yl]-piperidine-1-carboxylic acid 4-methoxy-phenyl ester

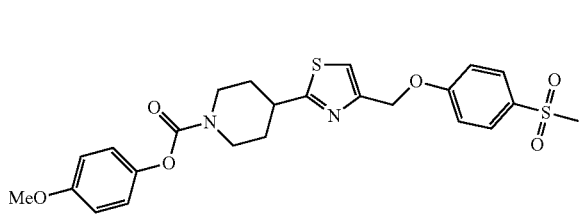 [SMILES: COc1ccc(OC(=O)N2CCC(c3nc(COc4ccc(S(C)(=O)=O)cc4)cs3)CC2)cc1]

$^1$H NMR (CDCl$_3$): δ 7.88 (2H, d, J=8.2 Hz), 7.26 (1H, s), 7.12 (2H, d, J=8.6 Hz), 7.02 (2H, d, J=8.6 Hz), 6.87 (2H, d, J=8.2 Hz), 5.24 (2H, s), 4.38 (2H, m), 3.79 (3H, s), 3.15~3.28 (3H, m), 3.03 (3H, s). 2.19 (2H, m), 1.87 (2H, m).

Example 29

4-[4-(4-Methanesulfonyl-phenoxymethyl)-thiazol-2-yl]-piperidine-1-carboxylic acid naphthalen-1-yl ester

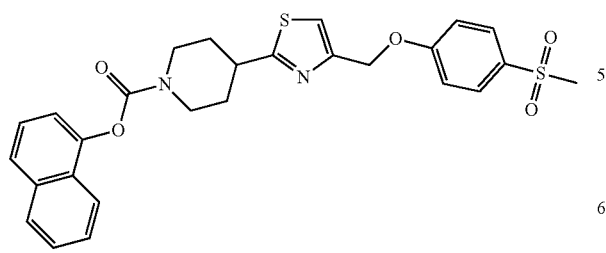

$^1$H NMR (CDCl$_3$): δ 7.88 (4H, m), 7.72 (1H, m), 7.49 (3H, m), 7.29 (2H, m), 7.14 (2H, m), 5.26 (2H, s), 4.64 (1H, m), 4.41 (1H, m), 3.34 (2H, m), 3.12 (1H, m), 3.04 (3H, s), 2.27 (2H, m), 2.00 (2H, m).

Example 30

4-[4-(4-Tetrazol-1-yl-phenoxymethyl)-thiazol-2-yl]-piperidine-1-carboxylic acid isobutyl ester

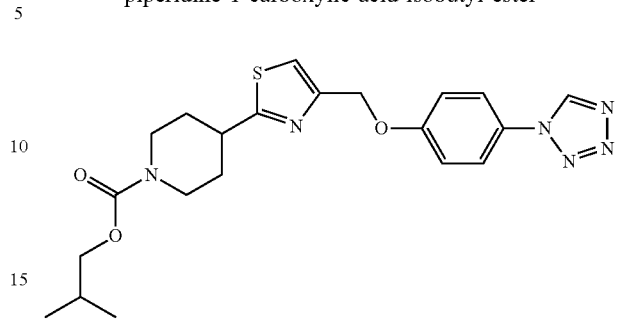

$^1$H NMR (CDCl$_3$): δ 8.94 (1H, s), 7.60 (2H, d), 7.24 (1H, s), 7.14 (2H, d), 5.20 (2H, s), 4.24 (2H, br), 3.85 (2H, d), 3.18 (1H, m), 2.92 (2H, m), 2.11 (2H, m), 1.91 (1H, m), 1.75 (2H, m), 0.91 (6H, d,).

Example 31

4-[4-(4-Tetrazol-1-yl-phenoxymethyl)-thiazol-2-yl]-piperidine-1-carboxylic acid pentyl ester

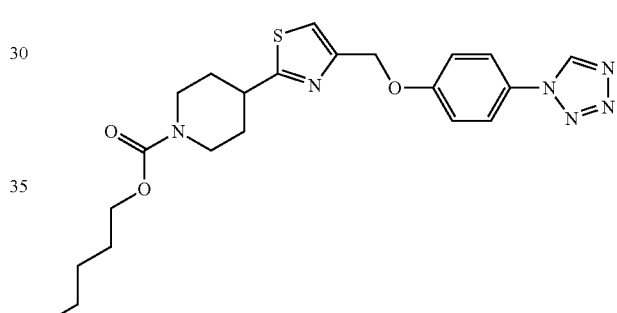

$^1$H NMR (CDCl$_3$): δ 8.94 (1H, s), 7.62 (2H, d, J=9.2 Hz), 7.28 (1H, s), 7.18 (2H, d, J=9.2 Hz), 5.24 (2H, s), 4.27 (2H, br), 4.09 (2H, m), 3.21 (1H, m), 2.94 (2H, m), 2.14 (2H, m), 1.78 (2H, m), 1.65 (2H, m), 1.35 (4H, m), 0.91 (3H, m).

Example 32

4-[4-(4-Tetrazol-1-yl-phenoxymethyl)-thiazol-2-yl]-piperidine-1-carboxylic acid 2-fluoro-ethyl ester

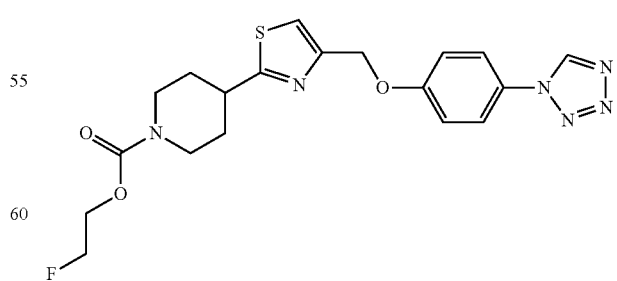

$^1$H NMR (CDCl$_3$): δ 8.97 (1H, s), 7.62 (2H, d, J=9.0 Hz), 7.28 (1H, s), 7.17 (2H, d, J=9.0 Hz), 5.24 (2H, s), 4.70-4.30 (6H, m), 3.22 (1H, m), 2.99 (2H, m), 2.15 (2H, m), 1.78 (2H, m).

Example 33

4-[4-(4-Tetrazol-1-yl-phenoxymethyl)-thiazol-2-yl]-piperidine-1-carboxylic acid butyl ester

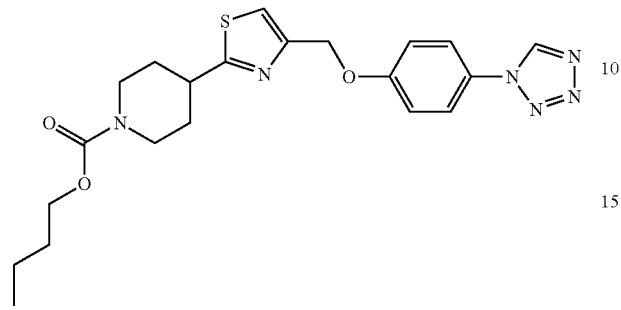

¹H NMR (CDCl₃): δ 9.01 (1H, s), 7.64 (2H, d, J=8.8 Hz), 7.29 (1H, s), 7.17 (2H, d, J=8.8 Hz), 5.24 (2H, s), 4.26 (2H, m), 4.10 (2H, t), 3.21 (1H, m), 2.95 (2H, m), 2.14 (2H, m), 1.78 (2H, m), 1.63 (2H, m), 1.40 (2H, m), 0.95 (3H, t, J=7.4 Hz).

Example 34

4-[4-(4-Tetrazol-1-yl-phenoxymethyl)-thiazol-2-yl]-piperidine-1-carboxylic acid 2,2-dimethyl-propyl ester

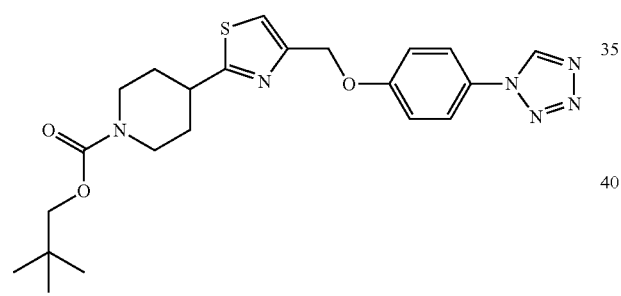

¹H NMR (CDCl₃): δ 9.00 (1H, s), 7.56 (2H, d, J=8.8 Hz), 7.21 (1H, s), 7.08 (2H, d, J=8.8 Hz), 5.14 (2H, s), 4.17 (2H, br), 3.69 (2H, s), 3.13 (1H, m), 2.88 (2H, m), 2.06 (2H, m), 1.73 (2H, m), 0.86 (9H, s).

Example 35

4-[4-(4-Tetrazol-1-yl-phenoxymethyl)-thiazol-2-yl]-piperidine-1-carboxylic acid hexyl ester

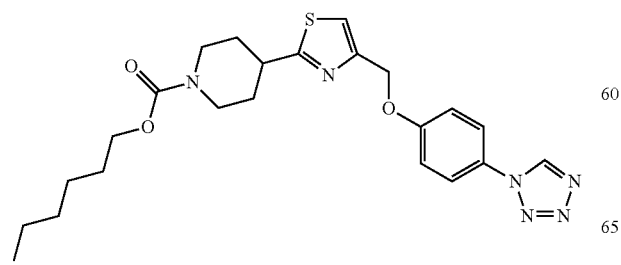

¹H NMR (CDCl₃): δ 9.06 (1H, s), 7.65 (2H, d, J=8.8 Hz), 7.29 (1H, s), 7.18 (2H, d, J=8.8 Hz), 5.24 (2H, s), 4.27 (2H, br), 4.09 (2H, t), 3.21 (1H, m), 2.95 (2H, m), 2.14 (2H, m), 1.78 (2H, m), 1.64 (2H, m), 1.33 (6H, m), 0.89 (3H, m).

Example 36

4-[4-(4-Tetrazol-1-yl-phenoxymethyl)-thiazol-2-yl]-piperidine-1-carboxylic acid 2-ethyl-hexyl ester

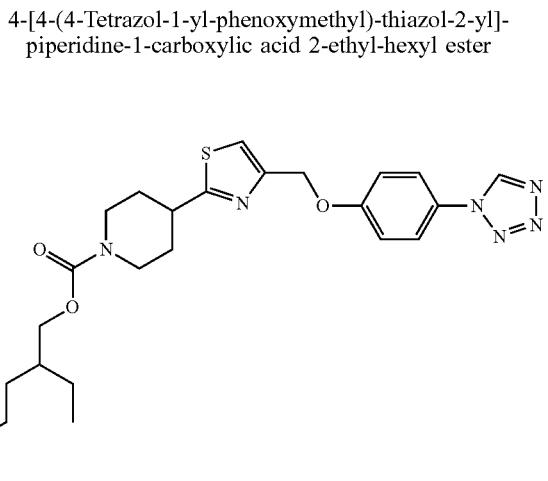

¹H NMR (CDCl₃): δ 8.98 (1H, s), 7.58 (2H, d, J=8.8 Hz), 7.23 (1H, s), 7.10 (2H, d, =8.8 Hz), 5.17 (2H, s), 4.19 (2H, br), 3.95 (2H, m), 3.15 (1H, m), 2.89 (2H, m), 2.07 (2H, m), 1.69 (2H, m), 1.52 (1H, m), 1.35-1.20 (8H, m), 0.90-0.80 (6H, m).

Example 37

4-[4-(4-Tetrazol-1-yl-phenoxymethyl)-thiazol-2-yl]-piperidine-1-carboxylic acid 2-benzyloxy-ethyl ester

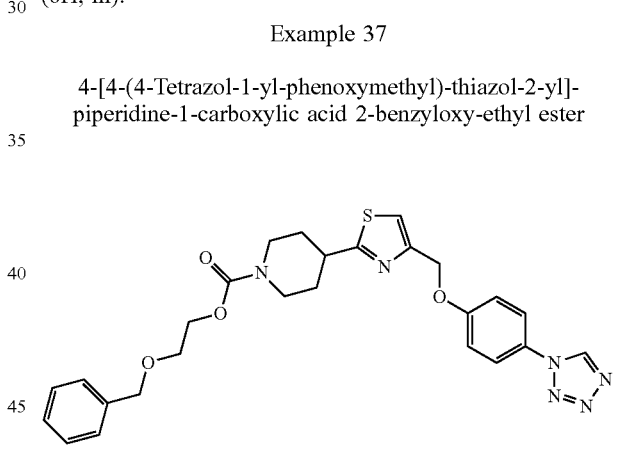

¹H NMR (CDCl₃): δ 8.98 (1H, s), 7.57 (2H, d, J=8.0 Hz), 7.30-7.20 (6H, m), 7.11 (2H, d, J=8.0 Hz), 5.17 (2H, s), 4.52 (2H, s), 4.25-4.20 (4H, m), 3.65 (2H, m), 3.15 (1H, m), 2.91 (2H, m), 2.08 (2H, m), 1.73 (2H, m).

Example 38

4-[4-(4-Tetrazol-1-yl-phenoxymethyl)-thiazol-2-yl]-piperidine-1-carboxylic acid 2-isopropyl-5-methyl-cyclohexyl ester

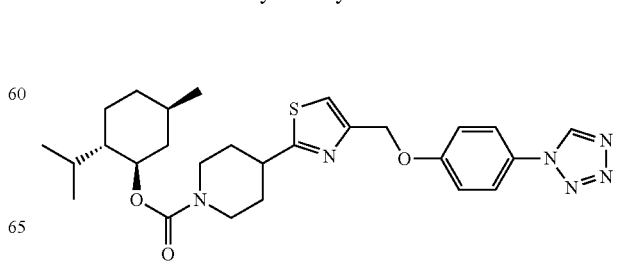

¹H NMR (CDCl₃): δ 8.97 (1H, s), 7.58 (2H, m), 7.23 (1H, s), 7.11 (2H, m), 5.18 (2H, s), 4.21 (2H, br), 3.13 (1H, m), 2.88 (2H, m), 2.05-0.70 (23H, m).

Example 39

Adamantan-1-yl-{4-[4-(4-methanesulfonyl-phenoxymethyl)-thiazol-2-yl]-piperidin-1-yl}-methanone

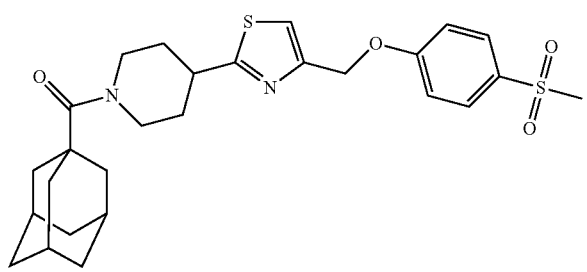 [SMILES: CS(=O)(=O)c1ccc(OCc2csc(C3CCN(C(=O)C45CC6CC(CC(C6)C4)C5)CC3)n2)cc1]

¹H NMR (CDCl₃): δ 7.88 (2H, d, J=8.8 Hz), 7.24 (1H, s), 7.12 (2H, d, J=8.8 Hz), 5.23 (2H, s), 4.61 (2H, m), 3.24~3.30 (1H, m), 3.03 (3H, s), 2.93~3.00 (2H, m), 2.16 (2H, m), 2.02-2.04 (9H, m), 1.70~1.80 (8H, m).

Example 40

{4-[4-(4-Methanesulfonyl-phenoxymethyl)-thiazol-2-yl]-piperidin-1-yl}-pyridin-3-yl-methanone

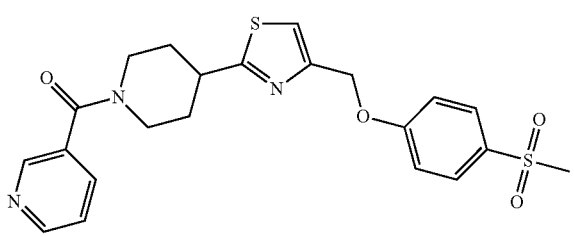 [SMILES: CS(=O)(=O)c1ccc(OCc2csc(C3CCN(C(=O)c4cccnc4)CC3)n2)cc1]

¹H NMR (CDCl₃): δ 8.69 (2H, m), 7.88 (2H, d, J=8.4 Hz), 7.79 (1H, m), 7.38 (1H, m), 7.27 (1H, s), 7.12 (2H, d, J=8.4 Hz), 5.24 (2H, s), 4.79 (2H, br), 3.86 (2H, br), 3.31 (1H, m), 3.04 (3H, s), 2.20 (2H, m), 1.84 (2H, m).

Example 41

3,3-Dimethyl-1-{4-[4-(4-tetrazol-1-yl-phenoxymethyl)-thiazol-2-yl]-piperidin-1-yl}-butan-1-one

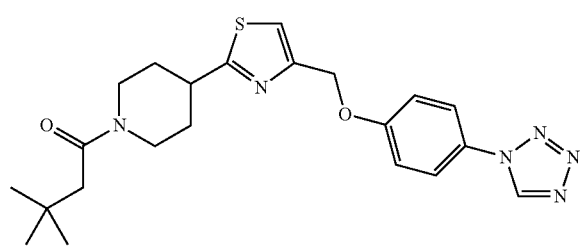 [SMILES: CC(C)(C)CC(=O)N1CCC(c2nc(COc3ccc(-n4cnnn4)cc3)cs2)CC1]

¹H NMR (DMSO-d₆): δ 9.98 (1H, s), 7.81 (2H, d, J=8.8 Hz), 7.66 (1H, s), 7.29 (2H, d, J=8.8 Hz), 5.20 (2H, s), 4.52 (1H, m), 4.10 (1H, m), 3.26 (1H, m), 3.19 (1H, m), 2.70 (1H, m), 2.25 (2H, m), 2.15 (2H, m), 1.50 (2H, m), 0.96 (9H, s).

Example 42

Oxo-{4-[4-(4-tetrazol-1-yl-phenoxymethyl)-thiazol-2-yl]-piperidin-1-yl}-acetic acid methyl ester

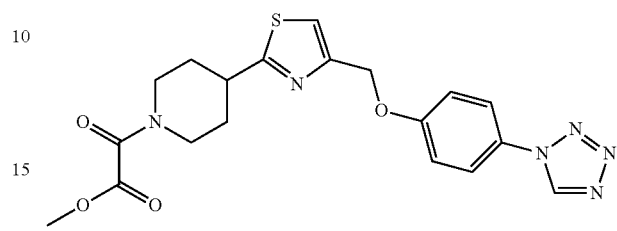

¹H NMR (DMSO-d₆): δ 9.98 (1H, s), 7.81 (2H, d, J=8.8 Hz), 7.68 (1H, s), 7.29 (2H, d, J=8.8 Hz), 5.21 (2H, s), 4.32 (1H, m), 3.80 (3H, s), 3.60 (1H, m), 3.32 (1H, m), 2.94 (2H, m), 2.13 (2H, m), 1.57 (2H, m).

Example 43

3-Oxo-3-{4-[4-(4-tetrazol-1-yl-phenoxymethyl)-thiazol-2-yl]-piperidin-1-yl}-propionic acid ethyl ester

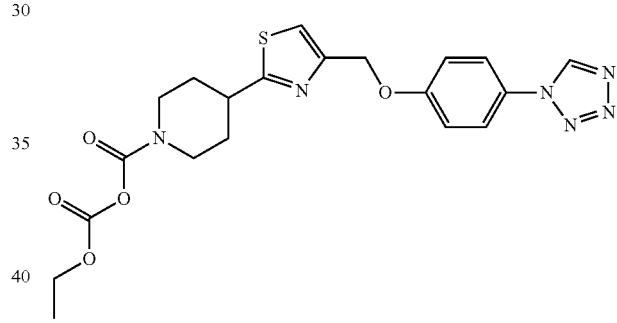

¹H NMR (DMSO-d₆): δ 8.94 (1H, s), 7.61 (2H, m), 7.26 (1H, s), 7.15 (2H, m), 5.20 (2H, s), 4.65 (1H, m), 4.17 (2H, q), 3.87 (1H, m), 3.48 (2H, s), 3.26 (2H, m), 2.81 (1H, m), 2.18 (2H, m), 1.78 (2H, m), 1.27 (3H, t).

Example 44

(4-Methyl-piperazin-1-yl)-{4-[4-(4-tetrazol-1-yl-phenoxymethyl)-thiazol-2-yl]-piperidin-1-yl}-methanone

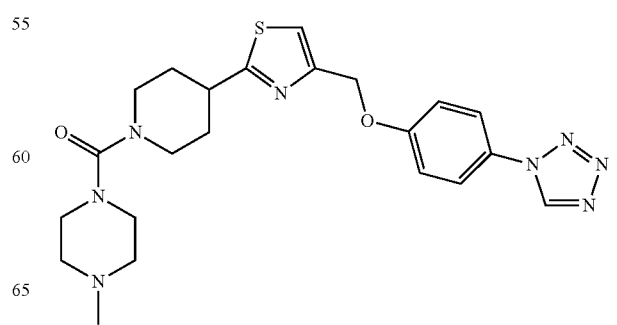

¹H NMR (DMSO-d₆): δ 9.98 (1H, s), 7.81 (2H, d, J=8.9 Hz), 7.64 (1H, s), 7.29 (2H, d), 5.20 (2H, s), 3.29 (2H, m), 3.18 (5H, m), 2.95 (2H, d), 2.61 (3H, s), 2.38 (2H, m), 2.03 (4H, m), 1.65 (2H, m).

Example 45

4-[4-(4-Tetrazol-1-yl-phenoxymethyl)-thiazol-2-yl]-piperidine-1-carboxylic acid diethylamide

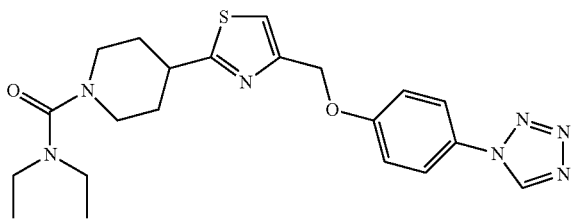 [SMILES: CCN(CC)C(=O)N1CCC(c2nc(COc3ccc(-n4cnnn4)cc3)cs2)CC1]

¹H NMR (DMSO-d₆): δ 9.98 (1H, s), 7.81 (2H, d, J=8.9 Hz), 7.66 (1H, s), 7.29 (2H, d, J=8.9 Hz), 5.20 (2H, s), 3.55 (2H, m), 3.20 (1H, m), 3.14 (4H, q), 2.81 (2H, m), 2.02 (2H, m), 1.64 (2H, m), 1.02 (6H, t, J=6.8 Hz).

Example 46

4-[4-(4-Tetrazol-1-yl-phenoxymethyl)-thiazol-2-yl]-piperidine-1-carboxylic acid ethylamide

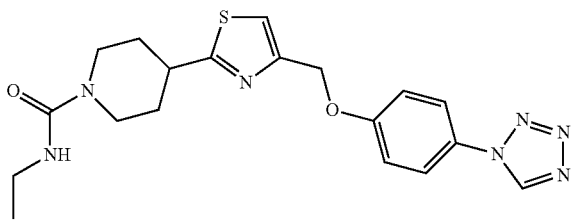 [SMILES: CCNC(=O)N1CCC(c2nc(COc3ccc(-n4cnnn4)cc3)cs2)CC1]

¹H NMR (DMSO-d₆): δ 9.98 (1H, s), 7.81 (2H, d, J=8.9 Hz), 7.65 (1H, s), 7.29 (2H, d, J=8.9 Hz), 6.47 (1H, m), 5.20 (2H, s), 4.01 (2H, d), 3.17 (1H, m), 3.04 (2H, m), 2.78 (2H, m), 1.97 (2H, m), 1.52 (2H, m), 0.99 (3H, t, J=6.8 Hz).

Example 47

2-{4-[4-(4-Methanesulfonyl-phenoxymethyl)-thiazol-2-yl]-piperidin-1-yl}-pyrimidine

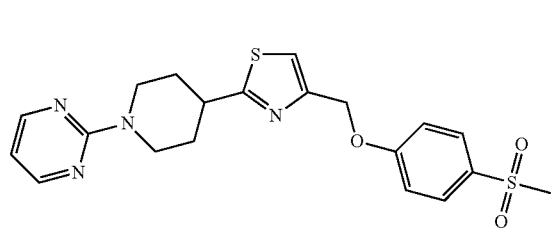 [SMILES: CS(=O)(=O)c1ccc(OCc2csc(C3CCN(c4ncccn4)CC3)n2)cc1]

A mixture of 4-[4-(4-methylsulfonyl-phenoxymethyl)-thiazole-2-yl]-piperidine hydrochloride (100 mg, 0.24 mmol), 2-chloropyrimidine (30 mg, 1.1 eq.) and diisopropylethylamine (122 mg, 4 eq.) in i-PrOH (5 mL) was heated at 90° C. for 1.5 hours. The solvent was removed in vacuo. The residue was purified on silica gel (60% EtOAc in hexanes) to afford the desired product. ¹H NMR (CDCl₃): δ 8.32 (2H, d, J=4.8 Hz), 7.88 (2H, d, J=8.8 Hz), 7.23 (1H, s), 7.12 (2H, d, J=8.8 Hz), 6.49 (1H, t, J=4.8 Hz), 5.24 (2H, s), 4.89 (2H, m), 3.32 (1H, m), 3.06 (2H, m), 3.04 (3H, s), 2.22 (2H, m), 1.81 (2H, m).

The compounds in Examples 48-77 were synthesized from one of Intermediates 3-13 or Intermediates 15-25 with the corresponding substituted 2-chloropyrimidine, 2-iodopyrimidine, 2-chloropyridine, 2-fluoropyridine, 2-methanesulfonyl-pyrimidine, 2-chloropyrazine, 2-chloropyridazine or other suitable heterocycles in a manner similar to that described in Example 47. One skilled in the art of organic synthesis will appreciate that conditions such as solvent (such as DMF, CH₃CN); temperature, base (such as NEt₃, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 48

2-{4-[4-(4-Methanesulfonyl-phenoxymethyl)-thiazol-2-yl]-piperidin-1-yl}-4-methoxy-pyrimidine

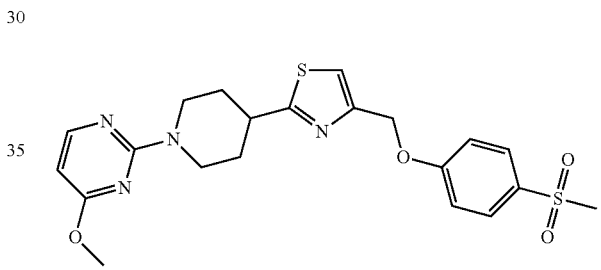

¹H NMR (CDCl₃): δ 8.06 (1H, d, J=6.0 Hz), 7.87 (2H, d, J=8.8 Hz), 7.23 (1H, s), 7.12 (2H, d, J=8.8 Hz), 5.98 (1H, d, J=6.0 Hz), 5.24 (2H, s), 4.88 (2H, m), 3.90 (3H, s), 3.31 (1H, m), 3.04 (5H, m), 2.20 (2H, m), 1.81 (2H, m).

Example 49

2-{4-[4-(4-Methanesulfonyl-phenoxymethyl)-thiazol-2-yl]-piperidin-1-yl}-4-trifluoromethyl-pyrimidine

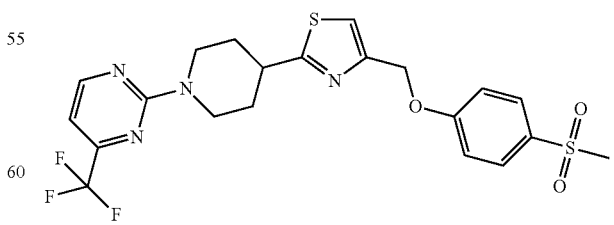

¹H NMR (CDCl₃): δ 8.50 (1H, d, J=4.8 Hz), 7.88 (2H, d, J=8.8 Hz), 7.24 (1H, s), 7.12 (2H, d, J=8.8 Hz), 6.76 (1H, d, J=4.8 Hz), 5.24 (2H, s), 4.92 (2H, m), 3.34 (1H, m), 3.11 (2H, m), 3.04 (3H, s), 2.24 (2H, m), 1.84 (2H, m).

Example 50

2-{4-[4-(4-Methanesulfonyl-phenoxymethyl)-thiazol-2-yl]-piperidin-1-yl}-4,6-dimethyl-pyrimidine

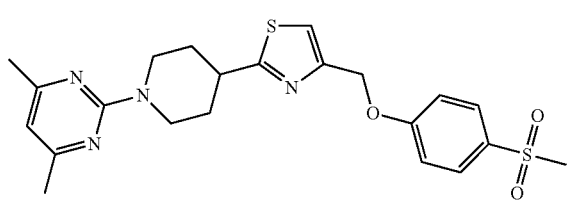

$^1$H NMR (CDCl$_3$): δ 7.88 (2H, d, J=8.4 Hz), 7.22 (1H, s), 7.12 (2H, d, J=8.4 Hz), 6.27 (1H, s), 5.24 (2H, s), 4.96 (2H, m), 3.28 (1H, m), 3.04 (3H, s), 2.99 (2H, m), 2.29 (6H, s), 2.19 (2H, m), 1.80 (2H, m).

Example 51

5-Ethyl-2-{4-[4-(4-methanesulfonyl-phenoxymethyl)-thiazol-2-yl]-piperidin-1-yl}-pyrimidine

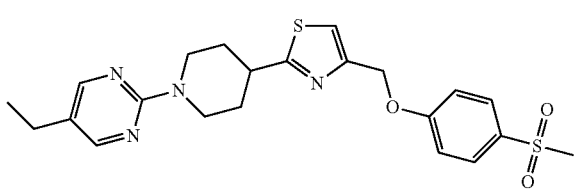 [SMILES: CCc1cnc(N2CCC(c3nc(COc4ccc(S(C)(=O)=O)cc4)cs3)CC2)nc1]

$^1$H NMR (CDCl$_3$): δ 8.19 (2H, s), 7.87 (2H, d, J=8.8 Hz), 7.22 (1H, s), 7.12 (2H, d, J=8.8 Hz), 5.24 (2H, s), 4.84 (2H, m), 3.30 (1H, m), 3.04 (2H, m), 3.03 (3H, s), 2.47 (2H, q, J=7.2 Hz), 2.22 (2H, m), 1.81 (2H, m), 1.20 (3H, t, J=7.2 Hz).

Example 52

5-Ethyl-2-{4-[4-(4-tetrazol-1-yl-phenoxymethyl)-thiazol-2-yl]-piperidin-1-yl}-pyrimidine

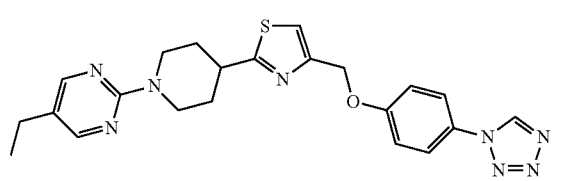 [SMILES: CCc1cnc(N2CCC(c3nc(COc4ccc(-n5cnnn5)cc4)cs3)CC2)nc1]

$^1$H NMR (DMSO-d$_6$): δ 9.98 (1H, s), 8.24 (2H, s), 7.80 (2H, d, J=8.8 Hz), 7.66 (1H, s), 7.28 (2H, d, J=8.8 Hz), 5.20 (2H, s), 4.67 (2H, m), 3.32 (1H, m), 3.01 (2H, m), 2.43 (2H, q, J=7.2 Hz), 2.07 (2H, m), 1.59 (2H, m), 1.11 (3H, t, J=7.2 Hz).

Example 53

5-Fluoro-2-{4-[4-(6-tetrazol-1-yl-pyridin-3-yloxymethyl)-thiazol-2-yl]-piperidin-1-yl}-pyrimidine

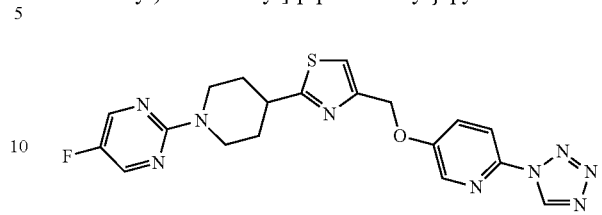

$^1$H NMR (DMSO-d$_6$): δ 10.07 (1H, s), 8.43 (2H, s), 8.41 (1H, d, J=3.2 Hz), 7.98 (1H, d, J=9.2 Hz), 7.86 (1H, dd, J=9.2, 3.2 Hz), 7.71 (1H, s), 5.30 (2H, s), 4.58 (2H, m), 3.31 (1H, m), 3.01 (2H, m), 2.10 (2H, m), 1.59 (2H, m).

Example 54

5-Bromo-2-{4-[4-(4-tetrazol-1-yl-phenoxymethyl)-thiazol-2-yl]-piperidin-1-yl}-pyrimidine

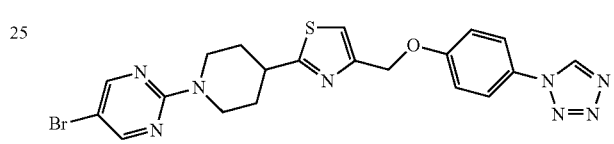

$^1$H NMR (CDCl$_3$): δ 8.90 (1H, s), 8.29 (2H, s), 7.60 (2H, d, J=9.0 Hz), 7.25 (1H, s), 7.16 (2H, d, J=9.0 Hz), 5.23 (2H, s), 4.81 (2H, m), 3.31 (1H, m), 3.06 (2H, m), 2.21 (2H, m), 1.79 (2H, m).

Example 55

5-Fluoro-2-{4-[4-(4-tetrazol-1-yl-phenoxymethyl)-thiazol-2-yl]-piperidin-1-yl}-pyrimidine

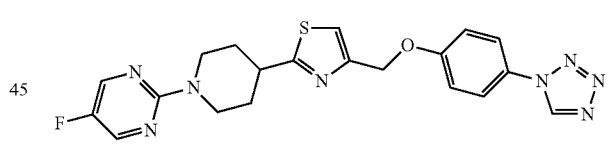

$^1$H NMR (CDCl$_3$): δ 8.91 (1H, s), 8.20 (2H, s), 7.60 (2H, d, J=8.6 Hz), 7.25 (1H, s), 7.16 (2H, d, J=8.6 Hz), 5.23 (2H, s), 4.78 (2H, m), 3.31 (1H, m), 3.06 (2H, m), 2.21 (2H, m), 1.83 (2H, m).

Example 56

4,5-Dichloro-2-{4-[4-(4-tetrazol-1-yl-phenoxymethyl)-thiazol-2-yl]-piperidin-1-yl}-pyrimidine

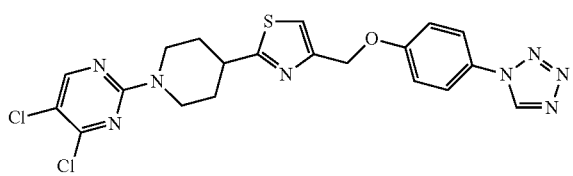 [SMILES: Clc1cnc(N2CCC(c3nc(COc4ccc(-n5cnnn5)cc4)cs3)CC2)nc1Cl]

¹H NMR (CDCl₃): δ 8.91 (1H, s), 8.10 (1H, s), 7.61 (2H, d, J=8.8 Hz), 7.27 (1H, s), 7.16 (2H, d, J=8.8 Hz), 5.23 (2H, s), 4.62 (2H, m), 3.34 (1H, m), 3.18 (2H, m), 2.25 (2H, m), 1.98 (2H, m).

Example 57

4-Chloro-5-methyl-2-{4-[4-(4-tetrazol-1-yl-phenoxymethyl)-thiazol-2-yl]-piperidin-1-yl}-pyrimidine

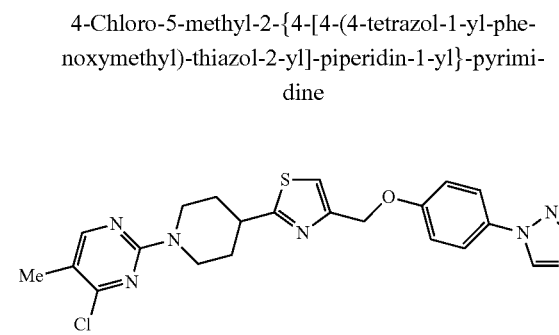

¹H NMR (CDCl₃): δ 8.90 (1H, s), 8.08 (1H, s), 7.60 (2H, d, J=8.8 Hz), 7.24 (1H, s), 7.17 (2H, d, J=8.8 Hz), 5.23 (2H, s), 4.80 (2H, m), 3.30 (1H, m), 3.04 (2H, m), 2.19 (2H, m), 2.16 (3H, s), 1.81 (2H, m).

Example 58

2-Chloro-5-methyl-4-{4-[4-(4-tetrazol-1-yl-phenoxymethyl)-thiazol-2-yl]-piperidin-1-yl}-pyrimidine

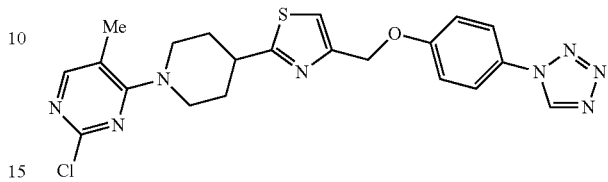

¹H NMR (CDCl₃): δ 8.92 (1H, s), 7.96 (1H, s), 7.60 (2H, d, J=8.8 Hz), 7.27 (1H, s), 7.16 (2H, d, J=8.8 Hz), 5.23 (2H, s), 4.17 (2H, m), 3.31 (1H, m), 3.10 (2H, m), 2.26 (2H, m), 2.21 (3H, s), 1.95 (2H, m).

Example 59

5-(4-Chloro-phenyl)-2-{4-[4-(4-tetrazol-1-yl-phenoxymethyl)-thiazol-2-yl]-piperidin-1-yl}-pyrimidine

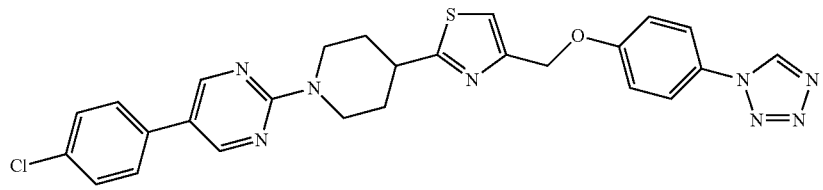 [SMILES: Clc1ccc(-c2cnc(N3CCC(c4nc(COc5ccc(-n6cnnn6)cc5)cs4)CC3)nc2)cc1]

¹H NMR (DMSO-d₆): δ 9.97 (1H, s), 8.71 (2H, s), 7.80 (2H, d, J=8.8 Hz), 7.67 (2H, d, J=8.4 Hz), 7.66 (1H, s), 7.48 (2H, d, J=8.4 Hz), 7.28 (2H, d, J=8.8 Hz), 5.21 (2H, s), 4.76 (2H, m), 3.37 (1H, m), 3.13 (2H, m), 2.12 (2H, m), 1.66 (2H, m).

Example 60

5-Chloro-2-{4-[4-(4-tetrazol-1-yl-phenoxymethyl)-thiazol-2-yl]-piperidin-1-yl}-pyrimidine

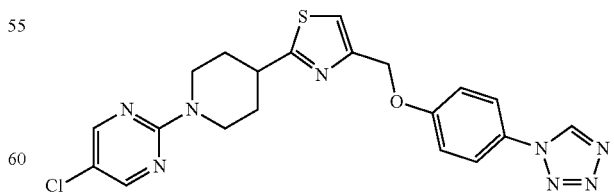

¹H NMR (CDCl₃): δ 8.91 (1H, s), 8.23 (2H, s), 7.61 (2H, d, J=8.8 Hz), 7.26 (1H, s), 7.17 (2H, d, J=8.8 Hz), 5.24 (2H, s), 4.82 (2H, m), 3.32 (1H, m), 3.07 (2H, m), 2.22 (2H, m), 1.81 (2H, m).

Example 61

5-Heptyl-2-{4-[4-(4-methanesulfonyl-phenoxymethyl)-thiazol-2-yl]-piperidin-1-yl}-pyrimidine

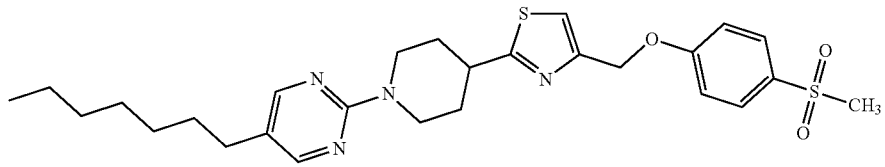 [SMILES: CCCCCCCc1cnc(N2CCC(c3nc(COc4ccc(S(C)(=O)=O)cc4)cs3)CC2)nc1]

$^1$H NMR (CDCl$_3$): δ 8.16 (2H, s), 7.87 (2H, d, J=9.0 Hz), 7.22 (1H, s), 7.12 (2H, d, J=9.0 Hz), 5.24 (2H, s), 4.83 (2H, m), 3.29 (1H, m), 3.04 (2H, m), 3.03 (3H, s), 2.42 (2H, t, J=7.4 Hz), 2.21 (2H, m), 1.80 (2H, m), 1.52 (2H, m), 1.28 (8H, m), 0.89 (3H, t).

Example 62

2-{4-[4-(4-Methanesulfonyl-phenoxymethyl)-thiazol-2-yl]-piperidin-1-yl}-5-pentyl-pyrimidine

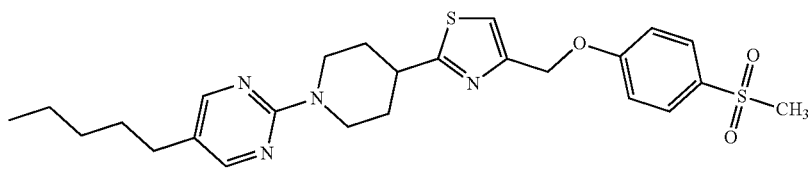 [SMILES: CCCCCc1cnc(N2CCC(c3nc(COc4ccc(S(C)(=O)=O)cc4)cs3)CC2)nc1]

$^1$H NMR (CDCl$_3$): δ 8.16 (2H, s), 7.87 (2H, d, J=8.8 Hz), 7.22 (1H, s), 7.12 (2H, d, J=8.8 Hz), 5.23 (2H, s), 4.83 (2H, m), 3.29 (1H, m), 3.04 (2H, m), 3.03 (3H, s), 2.42 (2H, t, J=7.6 Hz), 2.21 (2H, m), 1.81 (2H, m), 1.56 (2H, m), 1.32 (4H, m), 0.90 (3H, t).

Example 63

5-Heptyl-2-{4-[4-(4-tetrazol-1-yl-phenoxymethyl)-thiazol-2-yl]-piperidin-1-yl}-pyrimidine

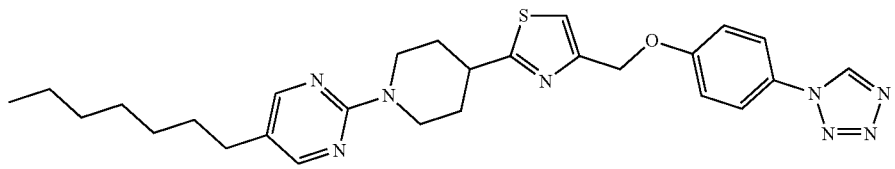 [SMILES: CCCCCCCc1cnc(N2CCC(c3nc(COc4ccc(-n5cnnn5)cc4)cs3)CC2)nc1]

$^1$H NMR (CDCl$_3$): δ 8.90 (1H, s), 8.16 (2H, s), 7.60 (2H, d, J=8.8 Hz), 7.24 (1H, s), 7.17 (2H, d, J=8.8 Hz), 5.23 (2H, s), 4.82 (2H, m), 3.29 (1H, m), 3.04 (2H, m), 2.42 (2H, t), 2.20 (2H, m), 1.80 (2H, m), 1.53 (2H, m), 1.28 (8H, m), 0.87 (3H, t).

Example 64

5-Pentyl-2-{4-[4-(4-tetrazol-1-yl-phenoxymethyl)-thiazol-2-yl]-piperidin-1-yl}-pyrimidine

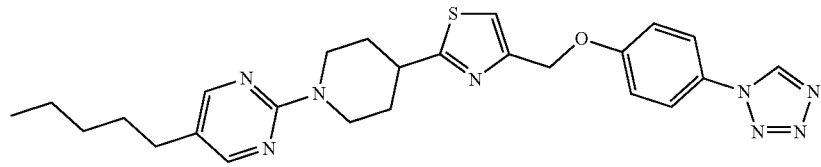 [SMILES: CCCCCc1cnc(N2CCC(c3nc(COc4ccc(-n5cnnn5)cc4)cs3)CC2)nc1]

¹H NMR (CDCl₃): δ 8.90 (1H, s), 8.16 (2H, s), 7.60 (2H, d, J=8.8 Hz), 7.24 (1H, s), 7.17 (2H, d, J=8.8 Hz), 5.23 (2H, s), 4.83 (2H, m), 3.30 (1H, m), 3.04 (2H, m), 2.42 (2H, t), 2.20 (2H, m), 1.80 (2H, m), 1.54 (2H, m), 1.30 (4H, m), 0.89 (3H, t).

Example 65

5-Methyl-2-{4-[4-(4-tetrazol-1-yl-phenoxymethyl)-thiazol-2-yl]-piperidin-1-yl}-pyrimidine

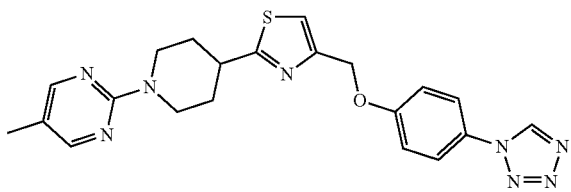 [SMILES: Cc1cnc(N2CCC(c3nc(COc4ccc(-n5cnnn5)cc4)cs3)CC2)nc1]

¹H NMR (CDCl₃): δ 8.94 (1H, s), 8.17 (2H, s), 7.62 (2H, d, J=8.8 Hz), 7.25 (1H, s), 7.17 (2H, d, J=8.8 Hz), 5.24 (2H, s), 4.82 (2H, d), 3.30 (1H, m), 3.04 (2H, m), 2.22 (2H, m), 2.13 (3H, s), 1.81 (2H, m).

Example 66

5-(4-Methoxy-phenyl)-2-{4-[4-(4-tetrazol-1-yl-phenoxymethyl)-thiazol-2-yl]-piperidin-1-yl}-pyrimidine

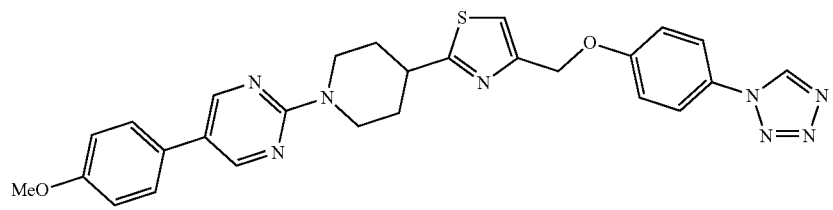 [SMILES: COc1ccc(-c2cnc(N3CCC(c4nc(COc5ccc(-n6cnnn6)cc5)cs4)CC3)nc2)cc1]

¹H NMR (CDCl₃): δ 8.90 (1H, s), 8.52 (s, 2H), 7.61 (2H, d, J=9.0 Hz), 7.41 (2H, d, J=8.6 Hz), 7.25 (1H, s), 7.17 (2H, d, J=9.0 Hz), 6.99 (2H, d, J=8.6 Hz), 5.24 (2H, s), 4.92 (2H, m), 3.85 (3H, s), 3.34 (1H, m), 3.12 (2H, m), 2.25 (2H, m), 1.85 (2H, m).

Example 67

5-Propyl-2-{4-[4-(4-tetrazol-1-yl-phenoxymethyl)-thiazol-2-yl]-piperidin-1-yl}-pyrimidine

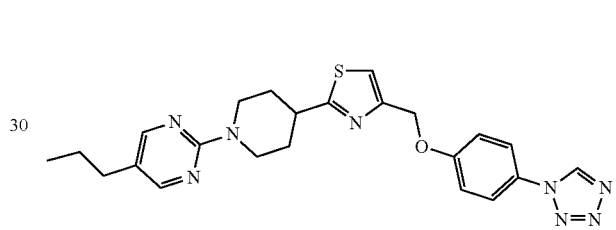

¹H NMR (CDCl₃): δ 8.9 (1H, s), 8.17 (2H, s), 7.61 (2H, d, J=8.8 Hz), 7.24 (1H, s), 7.17 (2H, d, J=8.8 Hz), 5.24 (2H, s), 4.83 (2H, m), 3.31 (1H, m), 3.04 (2H, m), 2.4 (2H, t, J=7.6 Hz), 2.22 (2H, m), 1.81 (2H, m), 1.58 (2H, m), 0.94 (3H, t, J=7.6 Hz).

Example 68

5-Methoxy-2-{4-[4-(4-tetrazol-1-yl-phenoxymethyl)-thiazol-2-yl]-piperidin-1-yl}-pyrimidine

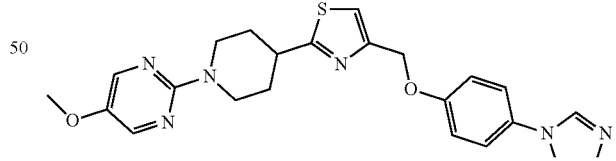

¹H NMR (CDCl₃): δ 8.93 (1H, s), 8.11 (2H, s), 7.61 (2H, d, J=8.8 Hz), 7.25 (1H, s), 7.17 (2H, d, J=8.8 Hz), 5.24 (2H, s), 4.74 (2H, m), 3.81 (3H, s), 3.31 (1H, m), 3.03 (2H, m), 2.22 (2H, m), 1.82 (2H, m).

Example 69

5'-Methyl-4-[4-(4-tetrazol-1-yl-phenoxymethyl)-thiazol-2-yl]-3,4,5,6-tetrahydro-2H-[1,2']bipyridinyl

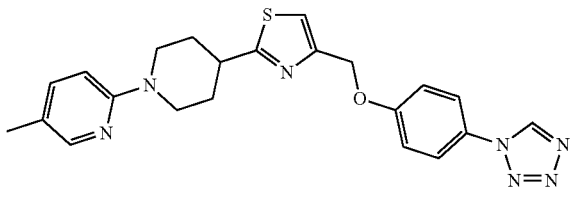

¹H NMR (CDCl₃): δ 8.91 (1H, s), 8.03 (1H, m), 7.61 (2H, m), 7.33 (1H, m), 7.26 (1H, s), 7.18 (2H, m), 6.65 (1H, d, J=8.8 Hz), 5.24 (2H, s), 4.33 (2H, m), 3.25 (1H, m), 2.97 (2H, m), 2.22 (2H, m), 2.21 (3H, s), 1.89 (2H, m).

Example 70

4-[4-(4-Tetrazol-1-yl-phenoxymethyl)-thiazol-2-yl]-5',6"-bis-trifluoromethyl-3,4,5,6-tetrahydro-2H-[1,2';6',2"]terpyridine

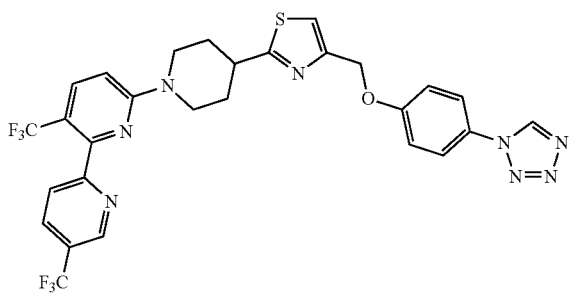 [SMILES: FC(F)(F)c1ccc(-c2nc(N3CCC(c4nc(COc5ccc(-n6cnnn6)cc5)cs4)CC3)ccc2C(F)(F)F)nc1]

¹H NMR (DMSO-d₆): δ 8.81 (1H, m), 8.39 (1H, m), 8.13 (1H, dd, J=8.8, 2.4 Hz), 7.76 (1H, dd, J=8.8, 2.8 Hz), 7.66 (1H, s), 7.59 (2H, m), 7.25 (2H, m), 6.99 (1H, d, J=9 Hz), 6.8 (1H, d, J=9 Hz), 5.19 (2H, s), 4.48 (2H, d), 3.37 (1H, m), 3.10 (2H, m), 2.11 (2H, m), 1.65 (2H, m).

Example 71

4-[4-(4-Tetrazol-1-yl-phenoxymethyl)-thiazol-2-yl]-5'-trifluoromethyl-3,4,5,6-tetrahydro-2H-[1,2']bipyridinyl

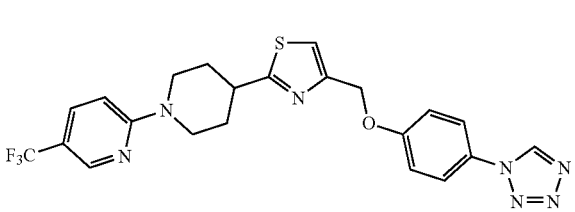 [SMILES: FC(F)(F)c1ccc(N2CCC(c3nc(COc4ccc(-n5cnnn5)cc4)cs3)CC2)nc1]

¹H NMR (DMSO-d₆): δ 9.98 (1H, s), 8.40 (1H, m), 7.81-7.75 (3H, m), 7.66 (1H, s), 7.28 (2H, d), 6.99 (1H, d, J=8.8 Hz), 5.21 (2H, s), 4.48 (2H, d), 3.37 (1H, m), 3.1 (2H, m), 2.12 (2H, m), 1.65 (2H, m).

Example 72

4-[4-(4-Tetrazol-1-yl-phenoxymethyl)-thiazol-2-yl]-3,4,5,6-tetrahydro-2H-[1,2']bipyridinyl-5'-carbaldehyde

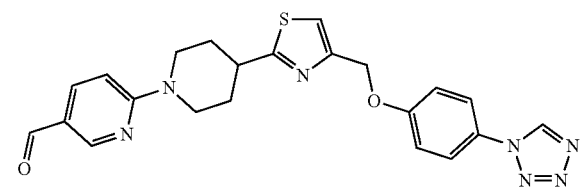 [SMILES: O=Cc1ccc(N2CCC(c3nc(COc4ccc(-n5cnnn5)cc4)cs3)CC2)nc1]

¹H NMR (DMSO-d₆): δ 9.98 (1H, s), 9.72 (1H, s), 8.58 (1H, d, J=2.4 Hz), 7.86 (1H, dd, J=9.2, 2 Hz), 7.8 (2H, d, J=8.4 Hz), 7.67 (1H, s), 7.28 (2H, d, J=8.4 Hz), 6.99 (1H, d, J=8.8 Hz), 5.2 (2H, s), 4.58 (2H, d), 3.41 (1H, m), 3.17 (2H, m), 2.13 (2H, m), 1.65 (2H, m).

Example 73

1-(3-Isopropyl-[1,2,4]oxadiazol-5-yl)-4-[4-(4-methanesulfonyl-phenoxymethyl)-thiazol-2-yl]-piperidine

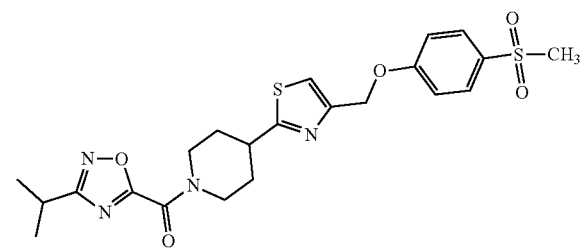 [SMILES: CC(C)c1noc(C(=O)N2CCC(c3nc(COc4ccc(S(C)(=O)=O)cc4)cs3)CC2)n1]

¹H NMR (CDCl₃): δ 7.87 (2H, m), 7.26 (1H, s), 7.11 (2H, m), 5.23 (2H, s), 4.76-4.68 (1H, m), 4.26-4.18 (1H, m), 3.4-3.3 (2H, m), 3.2-3.04 (2H, m), 3.03 (3H, s), 2.32-2.2 (2H, m), 2.00-1.86 (2H, m), 1.36 (6H, d, J=7.2 Hz).

Example 74

2-{4-[4-(4-Methanesulfonyl-phenoxymethyl)-thiazol-2-yl]-piperidin-1-yl}-benzooxazole

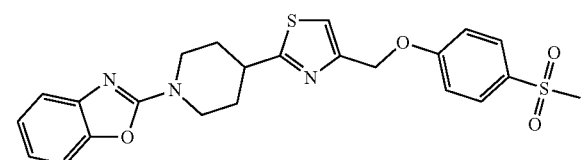

¹H NMR (CDCl₃): δ 7.87 (2H, d, J=8.4 Hz), 7.36 (1H, d, J=7.6 Hz), 7.01~7.19 (6H, m), 5.24 (2H, s), 4.42 (2H, m), 3.30 (3H, m), 3.03 (3H, s), 2.27 (2H, m), 1.95 (2H, m).

Example 75

4-[4-(4-Methanesulfonyl-phenoxymethyl)-thiazol-2-yl]-5'-trifluoromethyl-3,4,5,6-tetrahydro-2H-[1,2']pyridinyl

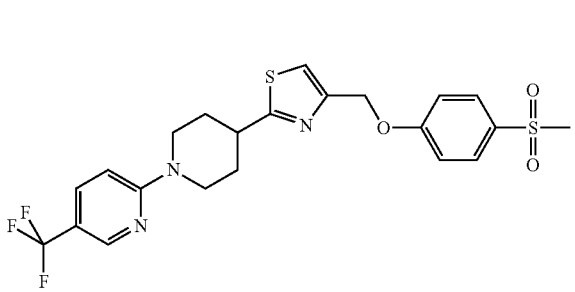 [SMILES: CS(=O)(=O)c1ccc(OCc2csc(C3CCN(c4ccc(C(F)(F)F)cn4)CC3)n2)cc1]

¹H NMR (CDCl₃): δ 8.4 (1H, s), 7.87 (2H, d), 7.63 (1H, m), 7.26 (1H, s), 7.12 (2H, d), 6.69 (1H, d), 5.23 (2H, s), 4.55-4.50 (2H, m), 3.38-3.28 (1H, m), 3.20-3.10 (2H, m), 3.04 (3H, s), 2.30-2.20 (2H, m), 1.90-1.80 (2H, m).

Example 76

5-Ethyl-2-{4-[4-(2-fluoro-4-methanesulfonyl-phenoxymethyl)-thiazol-2-yl]-piperidin-1-yl}-pyrimidine

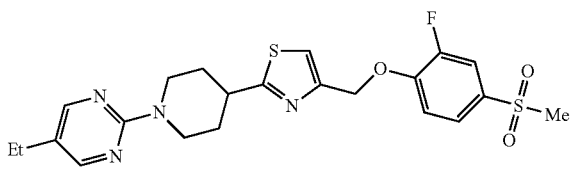 [SMILES: CCc1cnc(N2CCC(c3nc(COc4ccc(S(C)(=O)=O)cc4F)cs3)CC2)nc1]

¹H NMR (CDCl₃): δ 8.18 (2H, s), 7.65~7.70 (2H, m), 7.21~7.26 (2H, m), 5.30 (2H, s), 4.81~4.84 (2H, m), 3.25~3.28 (1H, m), 3.03 (3H, s), 3.00~3.07 (2H, m), 2.44 (2H, q), 2.21 (2H, m), 1.77~1.81 (2H, m), 1.19 (3H, t).

Example 77

5-Ethyl-2-{4-[4-(2-fluoro-4-tetrazol-1-yl-phenoxymethyl)-thiazol-2-yl]-piperidin-1-yl}-pyrimidine

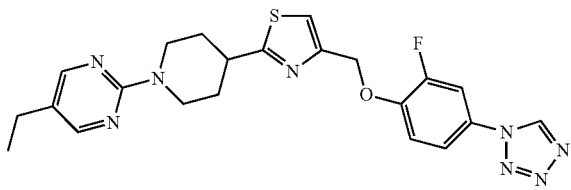 [SMILES: CCc1cnc(N2CCC(c3nc(COc4ccc(-n5cnnn5)cc4F)cs3)CC2)nc1]

¹H NMR (CDCl₃): δ 8.96 (1H, s), 8.19 (2H, s), 7.55-7.25 (4H, m), 5.31 (2H, s), 4.82 (2H, m), 3.30 (1H, m), 3.04 (2H, m), 2.47 (2H, q), 2.23 (2H, m), 1.81 (2H, m), 1.20 (3H, t).

Example 78

4-[4-(4-Methanesulfonyl-phenoxymethyl)-thiazol-2-yl]-4-methyl-piperidine-1-carboxylic acid tert-butyl ester

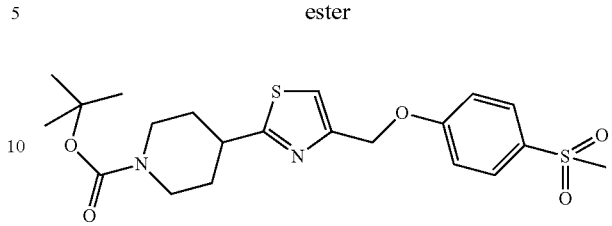

Step 1: 4-Cyano-4-methyl-piperidine-1-carboxylic acid tert-butyl ester

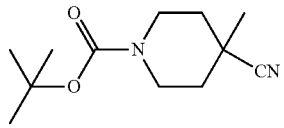 [SMILES: CC1(C#N)CCN(C(=O)OC(C)(C)C)CC1]

To a solution of 4-cyano-piperidine-1-carboxylic acid tert-butyl ester (4.52 g, 20 mmol) in THF (50 mL) was added LHMDS in THF (24 mL, 24 mmol) at 0° C. After stirring at 0° C. for 1 hour, MeI (5.7 g) was added. The reaction mixture was kept at 0° C. for 2 hours, then partitioned between EtOAc and H₂O. After concentration in vacuo, the residue was purified by silica column chromatography with EtOAc/hexanes to give the desired product.

Step 2: 4-Carbamoyl-4-methyl-piperidine-1-carboxylic acid tert-butyl ester

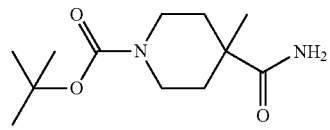 [SMILES: CC(C)(C)OC(=O)N1CCC(C)(C(N)=O)CC1]

To a solution of 4-cyano-4-methyl-piperidine-1-carboxylic acid tert-butyl ester (2.24 g, 10 mmol) in methanol (25 mL) was added DMSO (1 mL), aqueous 1N NaOH (12 mL, 12 mmol) and H₂O₂ (4 mL) at room temperature. The mixture was heated at 50° C. for 3 hours. After cooling to room temperature, the mixture was partitioned between EtOAc and H₂O. The organic layer was washed successively with H₂O and brine. After drying (Na₂SO₄), the solvent was removed to afford the desired product.

Step 3: 4-Methyl-4-thiocarbamoyl-piperidine-1-carboxylic acid tert-butyl ester

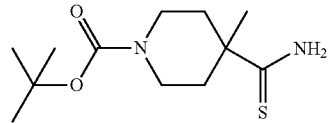

To a solution of 4-carbamoyl-4-methyl-piperidine-1-carboxylic acid tert-butyl ester (2.1 g, 8.7 mmol) in THF (30 mL) was added Lawesson's reagent (3.5 g, 8.7 mmol) at room temperature. The mixture was heated at 50° C. for 3 hours. After cooling to room temperature, the solvent was removed in vacuo and the residue was partitioned between EtOAc and H₂O. The organic layer was washed with saturated NaHCO₃, and brine. After drying (Na₂SO₄), the solvent was removed in vacuo, and the residue was purified by silica column chromatography with EtOAc/hexanes to afford the desired product.

Step 4: 4-(4-Ethoxycarbonyl-thiazol-2-yl)-4-methyl-piperidine-1-carboxylic acid tert-butyl ester

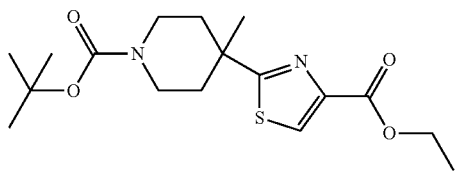 [SMILES: CCOC(=O)c1csc(C2(C)CCN(C(=O)OC(C)(C)C)CC2)n1]

To a solution of 4-methyl-4-thiocarbamoyl-piperidine-1-carboxylic acid tert-butyl ester (1 g, 4 mmol) in EtOH (10 mL) was added ethyl bromopyruvate (0.78 g, 4 mmol) at room temperature. The mixture was heated to refluxing for 3 hours. After cooling to room temperature, the solvent was removed in vacuo. The residue was dissolved in methylene chloride (15 mL), Et₃N (1 mL) and di-tert-butyl dicarbonate (1.3 g) were added to the solution. The mixture was stirred at room temperature overnight. The mixture was washed with H₂O and brine. After drying (Na₂SO₄), the solvent was removed in vacuo, and the residue was purified by silica column chromatography with EtOAc/hexanes to afford the desired product.

Step 5: 4-(4-Hydroxymethyl-thiazol-2-yl)-4-methyl-piperidine-1-carboxylic acid tort-butyl ester

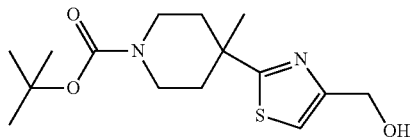 [SMILES: CC(C)(C)OC(=O)N1CCC(C)(c2nc(CO)cs2)CC1]

To a solution of 4-(4-ethoxycarbonyl-thiazol-2-yl)-4-methyl-piperidine-1-carboxylic acid tert-butyl ester (0.6 g, 1.7 mmol) in anhydrous THF (10 mL) was added LiAlH₄ (0.1 g, 2.6 mmol) at 0° C. The mixture was kept at 0° C. for 2 hours and the reaction was quenched with EtOH. The solvent was evaporated and the residue was diluted with EtOAc, washed with 1N NaOH, brine. After drying (Na₂SO₄), the solvent was removed in vacuo, and the residue was purified by silica column chromatography with EtOAc/hexanes to afford the desired product.

Step 6: 4-(4-Methanesulfonyloxymethyl-thiazol-2-yl)-4-methyl-piperidine-1-carboxylic acid tert-butyl ester

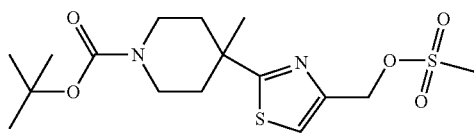 [SMILES: CC(C)(C)OC(=O)N1CCC(C)(c2nc(COS(C)(=O)=O)cs2)CC1]

To a solution of 4-(4-hydroxymethyl-thiazol-2-yl)-4-methyl-piperidine-1-carboxylic acid tert-butyl ester (0.42 g, 1.3 mmol) in methylene chloride (10 mL) was added methanesulfonyl chloride (0.19 g, 1.7 mmol) and triethylamine (0.2 g, 2 mmol) at 0° C. After stirring at 0° C. for 1 hour, the mixture was diluted with EtOAc and washed with H₂O and brine. After drying (Na₂SO₄), the solvent was removed in vacuo, and the residue was purified by silica column chromatography with EtOAc/hexanes to afford the desired product.

Step 7: 4-[4-(4-Methanesulfonyl-phenoxymethyl)-thiazol-2-yl]-4-methyl-piperidine-1-carboxylic acid tert-butyl ester

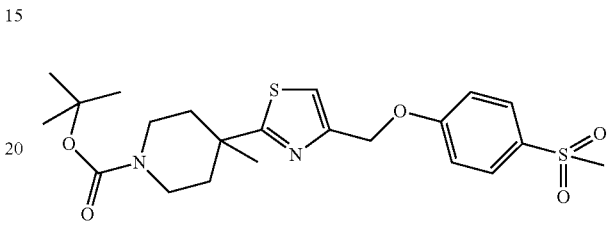

A mixture of 4-(4-methanesulfonyloxymethyl-thiazol-2-yl)-4-methyl-piperidine-1-carboxylic acid tert-butyl ester (0.2 g, 0.5 mmol), 4-methanesulfonyl-phenol (86 mg, 0.5 mmol) and Cs₂CO₃ (170 mg, 0.52 mmol) in acetonitrile (4 mL) was heated at 40° C. overnight. After cooling, the solid was filtered through a pad of celite. The filtrate was concentrated in vacuo. The residue was purified on silica gel (EtOAc-hexanes, 1:1) to afford the desired product. ¹H NMR (CDCl₃): δ 7.83 (2H, m), 7.23 (1H, s), 7.09 (2H, m), 5.2 (2H, s), 3.64-3.54 (2H, m), 3.3~3.24 (2H, m), 2.99 (3H, s), 2.2~2.1 (2H, m), 1.72-1.64 (2H, m), 1.41 (9H, s), 1.36 (3H, s).

Example 79

4-[4-(4-Methanesulfonyl-phenoxymethyl)-5-methyl-thiazol-2-yl]-piperidine-1-carboxylic acid tert-butyl ester

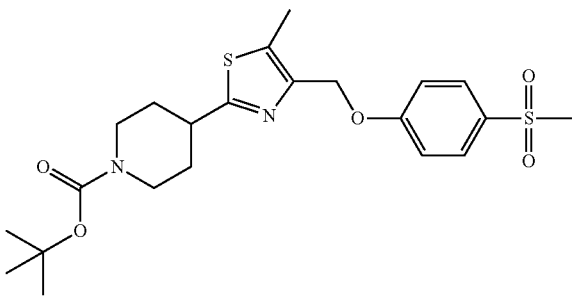 [SMILES: Cc1sc(C2CCN(C(=O)OC(C)(C)C)CC2)nc1COc1ccc(S(C)(=O)=O)cc1]

To a solution of 4-(4-hydroxymethyl-5-methyl-thiazol-2-yl)-piperidine-1-carboxylic acid tort-butyl ester (0.18 g, 0.6 mmol), 4-methanesulfonyl-phenol (0.1 g, 0.6 mmol) and PPh₃ (0.19 g, 0.72 mmol) in THF (5 mL) was added diethylazodicarboxylate (DEAD) (0.22 g, 0.72 mmol) at room temperature. The resulting mixture was stirred at room temperature for 30 minutes. The solvent was removed and the residue was purified by flash chromatography on silica gel to afford the desired product. ¹H NMR (CDCl₃): δ 7.9 (2H, d, J=9 Hz), 7.09 (2H, d, J=9 Hz), 5.2 (2H, s), 4.28-4.10 (2H, m), 3.14-3.04 (1H, m), 3.04 (3H, s), 2.9-2.8 (2H, m), 2.44 (3H, s), 2.1~2 (2H, m), 1.76-1.64 (2H, m), 1.47 (9H, s).

Example 80

4-{4-[1-(4-Methanesulfonyl-phenoxy)-ethyl]-5-methyl-thiazol-2-yl}-piperidine-1-carboxylic acid tert-butyl ester

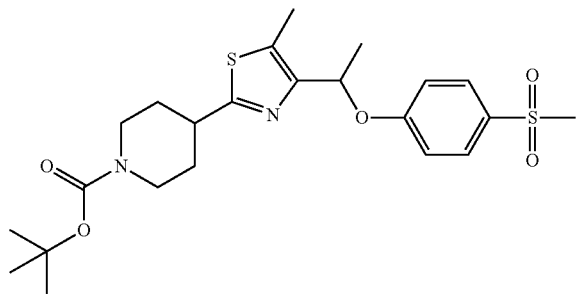 [SMILES: Cc1sc(C2CCN(C(=O)OC(C)(C)C)CC2)nc1C(C)Oc1ccc(S(C)(=O)=O)cc1]

Step 1: 4-[4-(1-Hydroxy-ethyl)-5-methyl-thiazol-2-yl]-piperidine-1-carboxylic acid tert-butyl ester

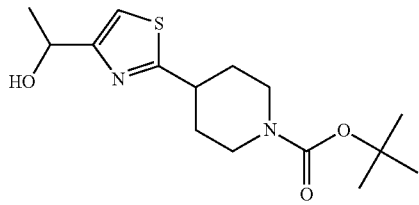 [SMILES: CC(O)c1csc(C2CCN(C(=O)OC(C)(C)C)CC2)n1]

To a solution of 4-(4-formyl-5-methyl-thiazol-2-yl)-piperidine-1-carboxylic acid tert-butyl ester (0.31 g, 1 mmol) in THF (10 mL) was added MeMgI (1 mL, 3 mmol) in Et$_2$O at room temperature. The resulting mixture was stirred at room temperature for 1 hour. The reaction was quenched with saturated aqueous NH$_4$Cl and extracted with EtOAc. The organic layer was washed with H$_2$O and brine. After drying over Na$_2$SO$_4$, the solvent was removed. The residue was purified by flash chromatography on silica gel to afford the desired product.

Step 2: 4-{4-[1-(4-Methanesulfonyl-phenoxy)-ethyl]-5-methyl-thiazol-2-yl}-piperidine-1-carboxylic acid tert-butyl ester

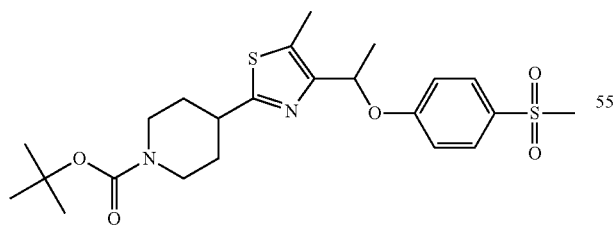

To a solution of 4-[4-(1-Hydroxy-ethyl)-5-methyl-thiazol-2-yl]-piperidine-1-carboxylic acid tert-butyl ester (0.15 g, 0.46 mmol), 4-methanesulfonyl-phenol (0.08 g, 0.46 mmol) and PPh$_3$ (0.14 g, 0.55 mmol) in THF (5 mL) was added DEAD (0.1 g, 0.55 mmol) at room temperature. The resulting mixture was stirred at room temperature for 30 minutes. The solvent was removed. The residue was purified by flash chromatography on silica gel to afford the desired product. $^1$H NMR (CDCl$_3$): δ 7.79 (2H, m), 6.94 (2H, m), 5.59 (1H, q, J=6 Hz), 4.2-4.04 (2H, m), 3.04-2.94 (1H, m), 2.98 (3H, s), 2.86-2.72 (2H, m), 2.39 (3H, s), 2.04-1.96 (2H, m), 1.67 (3H, d, J=6 Hz), 1.66-1.58 (2H, m), 1.42 (9H, s).

Example 81

4-[3-(4-Methanesulfonyl-phenoxymethyl)-[1,2,4]oxadiazol-5-yl]-piperidine-1-carboxylic acid tert-butyl ester

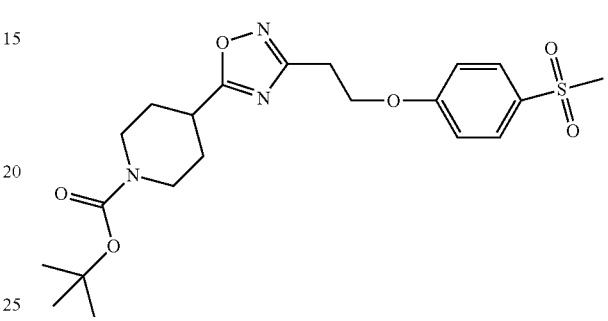

Step 1: N-Hydroxy-2-(4-methanesulfonyl-phenoxy)-acetamidine

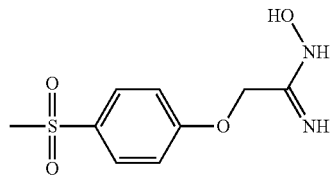 [SMILES: CS(=O)(=O)c1ccc(OCC(=N)NO)cc1]

To a mixture of (4-methanesulfonyl-phenoxy)-acetonitrile (2 g, 9.5 mmol), K$_2$CO$_3$ (1.3 g, 9.5 mmol) in H$_2$O (30 mL) and EtOH (15 mL) was added hydroxylamine hydrogenchloride (1.32 g, 19 mmol). The mixture was heated under reflux overnight, cooled and ethanol was removed in vacuo and the residue was extracted with EtOAc (150 mL). The organic layer was washed successively with H$_2$O and brine. After drying (Na$_2$SO$_4$), the solvent was removed to afford the desired product.

Step 2: 4-[3-(4-Methanesulfonyl-phenoxymethyl)-[1,2,4]oxadiazol-5-yl]-piperidine-1-carboxylic acid tert-butyl ester

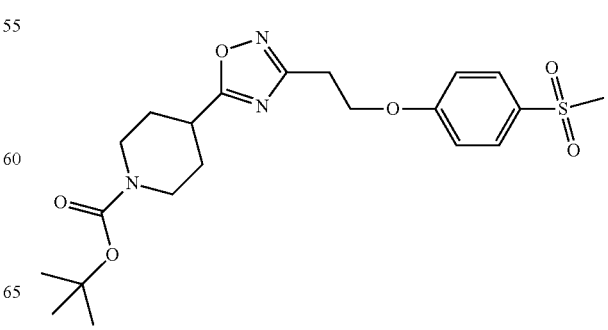

To a solution of piperidine-1,4-dicarboxylic acid mono-tert-butyl ester (2.06 g, 9 mmol), NEt₃ (1.2 g, 12 mmol) in toluene (150 mL) was added isobutylchloroformate (1.23 g, 9 mmol) at 0° C. The mixture was stirred at room temperature for 1.5 hours. N-hydroxy-2-(4-methanesulfonyl-phenoxy)-acetamidine (1.5 g, 6 mmol) was added to the mixture. The mixture was heated under reflux overnight, cooled and the mixture was washed successively with H₂O and brine. After drying (Na₂SO₄), the solvent was removed. The residue was purified by flash chromatography on silica gel to afford the desired product. $^1$H NMR (CDCl₃): δ 7.98 (2H, m), 7.14 (2H, m), 5.24 (2H, s), 4.2-4.05 (2H, m), 3.14 (1H, m), 3.03 (3H, s), 2.95 (2H, m), 2.12~2.04 (2H, m), 1.80 (2H, m), 1.46 (9H, s).

Example 82

4-[5-(4-Methanesulfonyl-phenoxymethyl)-[1,2,4]oxadiazol-3-yl]-piperidine-1-carboxylic acid tert-butyl ester

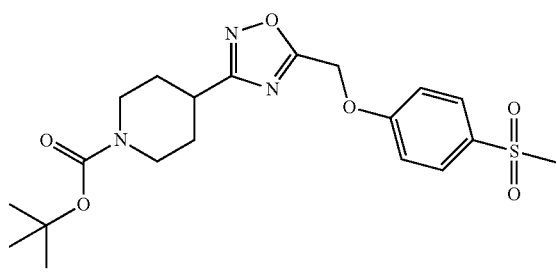 [SMILES: CC(C)(C)OC(=O)N1CCC(c2noc(COc3ccc(S(C)(=O)=O)cc3)n2)CC1]

Step 1:
4-(N-Hydroxycarbamimidoyl)-piperidine-1-carboxylic acid tert-butyl ester

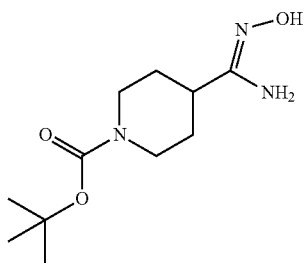 [SMILES: CC(C)(C)OC(=O)N1CCC(/C(N)=N/O)CC1]

To a mixture of 4-cyano-piperidine-1-carboxylic acid tert-butyl ester (6.3 g, 30 mmol), K₂CO₃ (4.2 g, 30 mmol) in H₂O (50 mL) and EtOH (30 mL) was added hydroxylamine hydrogenchloride (4.17 g, 60 mmol). The mixture was heated under reflux overnight, cooled to room temperature and ethanol was removed in vacuo. The residue was extracted with EtOAc (300 mL). The organic layer was washed successively with H₂O and brine. After drying (Na₂SO₄), the solvent was removed to afford the desired product.

Step 2: 4-(5-Hydroxymethyl-[1,2,4]oxadiazol-3-yl)-piperidine-1-carboxylic acid tert-butyl ester

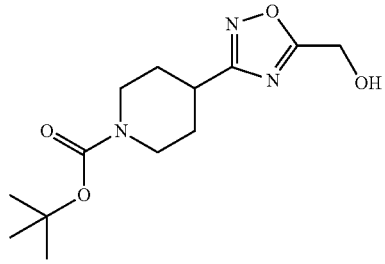 [SMILES: CC(C)(C)OC(=O)N1CCC(c2noc(CO)n2)CC1]

To a solution of hydroxy-acetic acid (1.67 g, 22 mmol), NEt₃ (4.4 g, 44 mmol) in toluene (150 mL) was added isobutylchloroformate (6 g, 44 mmol) at 0° C. The mixture was stirred at room temperature for 1.5 hours. 4-(N-Hydroxycarbamimidoyl)-piperidine-1-carboxylic acid tert-butyl ester (5.35 g, 22 mmol) was added to the mixture. The mixture was heated under reflux overnight, and then cooled to room temperature; the mixture was washed successively with H₂O and brine. After drying (Na₂SO₄), the solvent was removed. The residue was dissolved in THF (20 mL), and aqueous NaOH (10 mL, 10 mmol) was added. The mixture was stirred at room temperature for 2 hours and diluted with EtOAc (50 mL). The organic layer was washed with brine, after drying (Na₂SO₄), the solvent was removed in vacuo, and the residue was purified by silica column chromatography with EtOAc/hexanes to afford the desired product.

Step 3: 4-(5-Methanesulfonyloxymethyl-[1,2,4]oxadiazol-3-yl)-piperidine-1-carboxylic acid tert-butyl ester

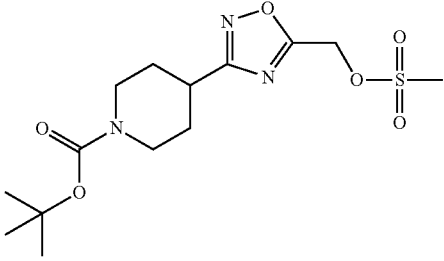 [SMILES: CC(C)(C)OC(=O)N1CCC(c2noc(COS(C)(=O)=O)n2)CC1]

To a solution of 4-(5-hydroxymethyl-[1,2,4]oxadiazol-3-yl)-piperidine-1-carboxylic acid tert-butyl ester (0.2 g, 0.7 mmol) in methylene chloride (5 mL) was added methanesulfonyl chloride (0.1 g, 0.9 mmol) and triethyl amine (0.14 g, 1.4 mmol) at 0° C. After stirred at 0° C. for 1 hour, the mixture was diluted with EtOAc and washed with H₂O, brine. After drying (Na₂SO₄), the solvent was removed in vacuo, and the residue was purified by silica column chromatography with EtOAc/hexanes to afford the desired product Step 4: 4-[5-(4-Methanesulfonyl-phenoxymethyl)-[1,2,4]oxadiazol-3-yl]-piperidine-1-carboxylic acid tert-butyl ester

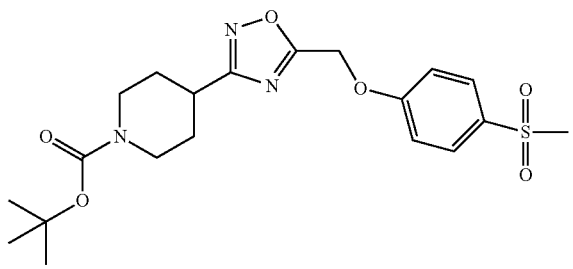 [SMILES: CC(C)(C)OC(=O)N1CCC(c2noc(COc3ccc(S(C)(=O)=O)cc3)n2)CC1]

A mixture of 4-(5-methanesulfonyloxymethyl-[1,2,4]oxadiazol-3-yl)-piperidine-1-carboxylic acid tert-butyl ester (0.12 g, 0.33 mmol), 4-methanesulfonyl-phenol (86 mg, 0.5 mmol) and Cs$_2$CO$_3$ (0.33 g, 1 mmol) in acetonitrile (5 mL) was heated at 50° C. for 2 hours. After cooling, the solid was filtered through a pad of celite. The filtrate was concentrated in vacuo. The residue was purified on silica gel (EtOAc-hexanes, 1:1) to afford the desired product. $^1$H NMR (CDCl$_3$): δ 7.9 (2H, d, J=8.8 Hz), 7.12 (2H, d, J=8.8 Hz), 5.34 (2H, s), 4.2~4.05 (2H, m), 3.03 (3H, s), 3.04~2.85 (3H, m), 2.05~1.96 (2H, m), 1.8~1.7 (2H, m), 1.45 (9H, s).

Example 83

4-(5-Benzyloxymethyl-[1,2,4]oxadiazol-3-yl)-piperidine-1-carboxylic acid tert-butyl ester

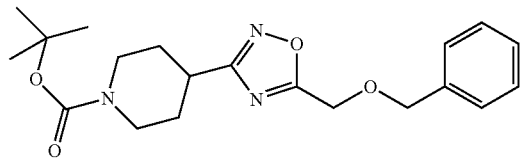 [SMILES: CC(C)(C)OC(=O)N1CCC(c2noc(COCc3ccccc3)n2)CC1]

To a solution of benzyloxy-acetic acid (5 g, 30 mmol), NEt$_3$ (3.6 g, 36 mmol) in toluene (150 mL) was added isobutylchloroformate (4.1 g, 30 mmol) at 0° C. The mixture was stirred at room temperature for 1.5 hours. 4-(N-hydroxycarbamimidoyl)-piperidine-1-carboxylic acid tert-butyl ester (7.3 g, 30 mmol) was added to the mixture. The mixture was heated under reflux overnight, cooled and the mixture was washed successively with H$_2$O and brine. After drying (Na$_2$SO$_4$), the solvent was removed. The residue was purified by flash chromatography on silica gel to afford the desired product. $^1$H NMR (CDCl$_3$): δ 7.4~7.3 (5H, m), 4.7 (2H, s), 4.69 (2H, s), 4.2~4.04 (2H, m), 3.02~2.84 (3H, m), 2.04~1.94 (2H, m), 1.84~1.7 (2H, m), 1.46 (9H, s).

Example 84

5-Ethyl-2-{4-[3-(4-methanesulfonyl-phenoxymethyl)-[1,2,4]oxadiazol-5-yl]-piperidin-1-yl}-pyrimidine

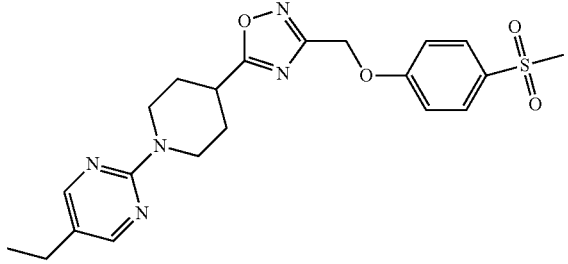 [SMILES: CCc1cnc(N2CCC(c3nc(COc4ccc(S(C)(=O)=O)cc4)no3)CC2)nc1]

To the crude HCl salt (0.18 g, ~0.5 mmol) of 4-[3-(4-methanesulfonyl-phenoxymethyl)-[1,2,4]oxadiazol-5-yl]-piperidine, prepared by treatment of 4-[3-(4-methanesulfonyl-phenoxymethyl)-[1,2,4]oxadiazol-5-yl]-piperidine-1-carboxylic acid tert-butyl ester (Example 81) in dixoane with 4N HCl, was added 2-propanol (3 mL), followed by DIPEA (0.13 g, 1 mmol) and 2-Chloro-5-ethyl-pyrimidine (0.14 g, 1 mmol). The resulting mixture was stirred at 70° C. overnight. After concentration in vacuo, the residue was purified by silica column chromatography with EtOAc/hexanes to afford the desired product. $^1$H NMR (CDCl$_3$): δ 8.18 (2H, s), 7.89 (2H, d, J=8.8 Hz), 7.15 (2H, d, J=8.8 Hz), 5.24 (2H, s), 4.75~4.65 (2H, m), 3.3~3.2 (1H, m), 3.2~3.1 (2H, m), 3.03 (3H, s), 2.47 (2H, q, J=7.6 Hz), 2.22~2.16 (2H, m), 1.96~1.84 (2H, m), 1.19 (3H, t, J=7.6 Hz).

Example 85

4-Hydroxy-4-[4-(4-methylsulfanyl-phenoxymethyl)-thiazol-2-yl]-piperidine-1-carboxylic acid tert-butyl ester

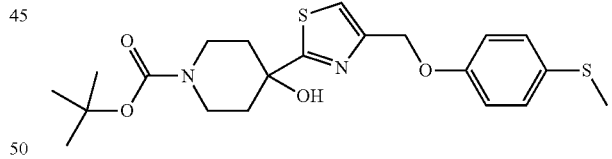

Step 1:
4-(4-Methylsulfanyl-phenoxymethyl)-thiazole

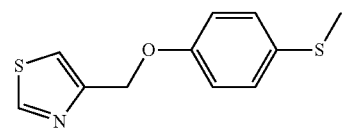

A mixture of 4-chloromethyl thiazole hydrochloride (3.0 g, 17.6 mmol), 4-methylsulfanyl-phenol (2.5 g, 1 eq.) and K$_2$CO$_3$ (6.1 g, 2.5 eq.) in acetone (60 mL) was heated to reflux for 48 hours. After cooling, the solid was filtered off.

The filtrate was evaporated to dryness in vacuo. The crude product was redissolved in diethyl ether. The solution was washed twice with 2N NaOH solution and then with H₂O. After being dried over Na₂SO₄, removal of the solvent afforded the desired product as an off-white solid.

Step 2: 4-Hydroxy-4-[4-(4-methylsulfanyl-phenoxymethyl)-thiazol-2-yl]-piperidine-1-carboxylic acid tert-butyl ester

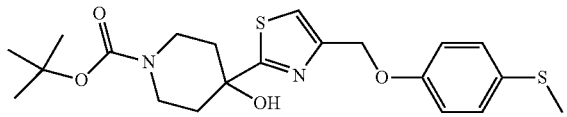 [SMILES: CSc1ccc(OCc2csc(C3(O)CCN(C(=O)OC(C)(C)C)CC3)n2)cc1]

To a stirred solution of 4-(4-methanesulfanyl-phenoxymethyl)-thiazole (3.92 g, 16.5 mmol) in THF (40 mL) at −78° C. was added n-BuLi (1.73 mL, 1.05 eq., 10.0 M in hexanes). The resulting solution was stirred at this temperature for 30 minutes. Then a solution of 1-Boc-4-piperidone (3.30 g, 1 eq.) in THF (20 mL) was added in dropwise. The resulting mixture was stifled for 30 minutes. The reaction was quenched by addition of H₂O (5 mL). Most of the THF was removed in vacuo. The mixture was extracted with EtOAc. The organic layer was separated, washed with brine and dried over Na₂SO₄. After removal of the solvent, the crude product was purified on silica gel (EtOAc:hexanes=2:3) to afford the desired product as a foam. ¹H NMR (CDCl₃): δ 7.27 (2H, d, J=8.8 Hz), 7.26 (1H, s), 6.93 (2H, d, J=8.8 Hz), 5.14 (2H, s), 4.02 (2H, br), 3.27 (2H, br), 2.97 (1H, br), 2.45 (3H, s), 2.11 (2H, m), 1.86 (2H, m), 1.48 (9H, s).

Example 86

4-Hydroxy-4-[4-(4-methanesulfonyl-phenoxymethyl)-thiazol-2-yl]-piperidine-1-carboxylic acid tert-butyl ester

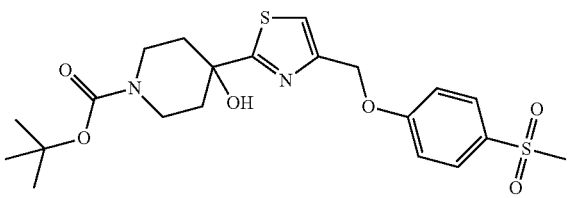 [SMILES: CC(C)(C)OC(=O)N1CCC(O)(c2nc(COc3ccc(S(C)(=O)=O)cc3)cs2)CC1]

To a solution of 4-hydroxy-4-[4-(4-methylsulfanyl-phenoxymethyl)-thiazol-2-yl]-piperidine-1-carboxylic acid tert-butyl ester (Example 85, 6.8 g, 15.6 mmol) in CH₂Cl₂ (150 mL) at room temperature was added m-CPBA (8.4 g, 2.2 eq.) portionwise. The resulting solution was stirred for 30 minutes, then it was washed with 2 N NaOH solution twice and dried over Na₂SO₄. After removal of the solvent, the crude product was purified on silica gel (EtOAc:hexanes=3:2) to afford the desired product as a white foam. ¹H NMR (CDCl₃): δ 7.88 (2H, d, J=8.8 Hz), 7.31 (1H, s), 7.12 (2H, d, J=8.8 Hz), 5.24 (2H, s), 4.03 (2H, br), 3.27 (2H, br), 3.04 (3H, s), 2.13 (2H, m), 1.86 (2H, m), 1.48 (9H, s).

Example 87

4-Fluoro-4-[4-(4-methanesulfonyl-phenoxymethyl)-thiazol-2-yl]-piperidine-1-carboxylic acid tert-butyl ester

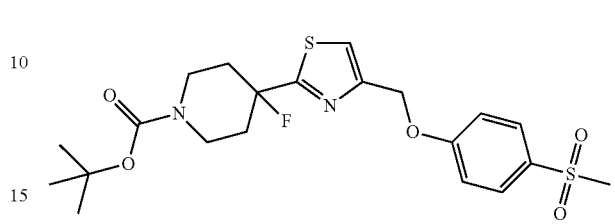

To a solution of 4-hydroxy-4-[4-(4-methanesulfonyl-phenoxymethyl)-thiazol-2-yl]-piperidine-1-carboxylic acid tert-butyl ester (Example 86, 5.29 g, 11.3 mmol) in CH₂Cl₂ (100 mL) at 0° C. was added DAST (1.8 mL, 1.2 eq.). The reaction mixture was stirred for 30 minutes before it was quenched by addition of saturated NaHCO₃ solution (20 mL). The organic phase was separated and dried over Na₂SO₄. After removal of the solvent, the crude product was purified on silica gel (EtOAc:hexanes=2:3) to afford the desired product as a white solid. ¹H NMR (CDCl₃): δ 7.86 (2H, d, J=9.2 Hz), 7.35 (1H, s), 7.10 (2H, d, J=9.2 Hz), 5.22 (2H, s), 4.08 (2H, br), 3.19 (2H, br), 3.02 (3H, s), 2.05~2.32 (4H, m), 1.46 (9H, s).

Example 88

5-Ethyl-2-{4-fluoro-4-[4-(4-methanesulfonyl-phenoxymethyl)-thiazol-2-yl]-piperidin-1-yl}-pyrimidine

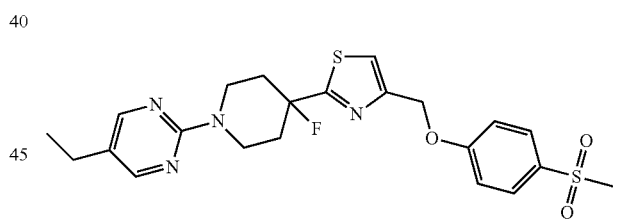

Step 1: 4-Fluoro-4-[4-(4-methanesulfonyl-phenoxymethyl)-thiazol-2-yl]-piperidine hydrochloride

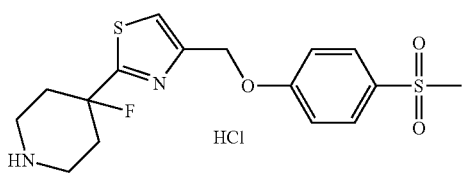 [SMILES: CS(=O)(=O)c1ccc(OCc2csc(C3(F)CCNCC3)n2)cc1 ; Cl]

To a solution of 4-fluoro-4-[4-(4-methanesulfonyl-phenoxymethyl)-thiazol-2-yl]-piperidine-1-carboxylic acid tort-butyl ester (Example 87, 4.24 g, 9.01 mmol) in methanol (50 mL) was added 4 N HCl in dioxane (15 mL). The resulting solution was stirred overnight. The mixture was then evaporated to dryness in vacuo to afford the desired product as a white solid.

Step 2: 5-Ethyl-2-{4-fluoro-4-[4-(4-methanesulfonyl-phenoxymethyl)-thiazol-2-yl]-piperidin-1-yl}-pyrimidine

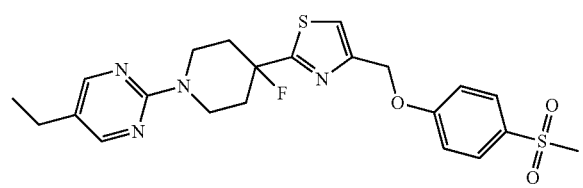 [SMILES: CCc1cnc(N2CCC(F)(c3nc(COc4ccc(S(C)(=O)=O)cc4)cs3)CC2)nc1]

A solution of 4-fluoro-4-[4-(4-methanesulfonyl-phenoxymethyl)-thiazol-2-yl]-piperidine hydrochloride (4.0 g, 9.01 mmol), 2-chloro-5-ethyl-pyrimidine (1.55 g, 1.2 eq.) and DIPEA (4.7 g, 4 eq.) in 2-propanol (30 mL) in a sealed pressure vessel was stirred at 160° C. (oil bath temperature) overnight. After cooling, the solvent was removed in vacuo. The residue was partitioned between water and EtOAc. The organic phase was washed with brine and dried over $Na_2SO_4$. After removal of the solvent, the crude product was purified on silica gel (EtOAc:hexanes=1:1) to afford the desired product as a white solid. $^1H$ NMR ($CDCl_3$): δ 8.19 (2H, s), 7.87 (2H, d, J=9.2 Hz), 7.36 (1H, s), 7.10 (2H, d, J=9.2 Hz), 5.23 (2H, s), 4.69 (2H, m), 3.44 (2H, m), 3.03 (3H, s), 2.48 (2H, q, J=7.6 Hz), 2.15~2.39 (4H, m), 1.21 (3H, t, J=7.6 Hz).

Example 89

4-Fluoro-4-[5-(4-methanesulfonyl-phenoxymethyl)-thiazol-2-yl]-piperidine-1-carboxylic acid tert-butyl ester

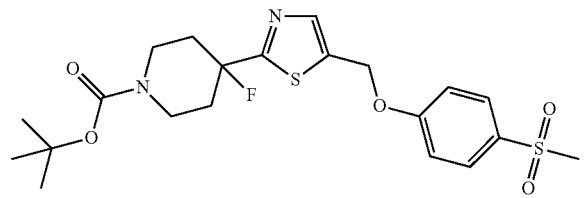 [SMILES: CC(C)(C)OC(=O)N1CCC(F)(c2ncc(COc3ccc(S(C)(=O)=O)cc3)s2)CC1]

Step 1:
4-Hydroxy-4-thiazol-2-yl-piperidine-1-carboxylic acid tert-butyl ester

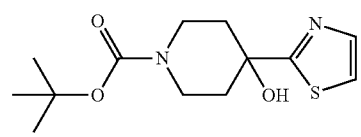 [SMILES: CC(C)(C)OC(=O)N1CCC(O)(c2nccs2)CC1]

To a cooled (−78° C.) and stirred solution of n-BuLi (2.6 mL, 1.05 eq., 10.0 M in hexanes) in dry $Et_2O$ (20 mL) was added dropwise a solution of 2-bromothiazole (4.0 g, 24.4 mmol) in THF (10 mL) over a 10 minute period. After the yellow mixture had been stirred at −78° C. for 30 minutes, a solution of 1-Boc-4-piperidone (4.9 g, 1 eq.) in THF (20 mL) was added slowly. The mixture was then continued to stir for another 30 minutes before the reaction was quenched by addition of water (5 mL). The mixture was warmed to room temperature and extracted with EtOAc. The organic phase was separated, washed with brine and dried over $Na_2SO_4$. After removal of the solvent, the crude product was purified on silica gel (45% EtOAc in hexanes) to afford the desired product as a thick oil.

Step 2:
4-Fluoro-4-thiazol-2-yl-piperidine-1-carboxylic acid tert-butyl ester

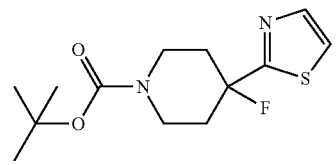 [SMILES: CC(C)(C)OC(=O)N1CCC(F)(c2nccs2)CC1]

To a solution of 4-hydroxy-4-thiazol-2-yl-piperidine-1-carboxylic acid tert-butyl ester (4.36 g, 15.3 mmol) in $CH_2Cl_2$ (50 mL) at 0° C. was added DAST (2.4 mL, 1.2 eq.). The reaction mixture was stirred for 30 minutes before it was quenched by addition of saturated $NaHCO_3$ solution (20 mL). The organic phase was separated and dried over $Na_2SO_4$. After removal of the solvent, the crude product was purified on silica gel (EtOAc:hexanes=1:4) to afford the desired product as a pale yellow oil.

Step 3: 4-Fluoro-4-(5-hydroxymethyl-thiazol-2-yl)-piperidine-1-carboxylic acid tert-butyl ester

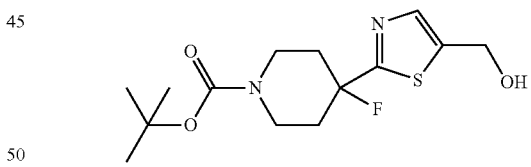

To a cooled (−78° C.) and stirred solution of 4-fluoro-4-thiazol-2-yl-piperidine-1-carboxylic acid tert-butyl ester (3.65 g, 12.7 mmol) in THF (20 mL) was added n-BuLi (1.33 mL, 1.05 eq., 10.0 M in hexanes). The mixture was stirred at this temperature for 30 minutes. Then a suspension of paraformaldehyde (383 mg, 1 eq.) in THF (10 mL) was added in. The resulting mixture was continued to stir at −78° C. for another 30 minutes and gradually warmed to room temperature overnight. The reaction was quenched by addition of water (10 mL). The mixture was extracted with EtOAc. The organic phase was washed with brine and dried over $Na_2SO_4$. After removal of the solvent, the crude product was purified on silica gel (60% EtOAc in hexanes) to afford the desired product as a pale yellow solid.

Step 4: 4-(5-Chloromethyl-thiazol-2-yl)-4-fluoro-piperidine-1-carboxylic acid tert-butyl ester

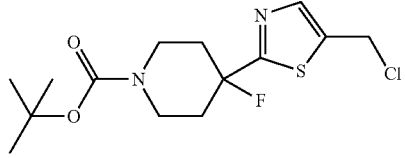 [SMILES: CC(C)(C)OC(=O)N1CCC(F)(c2ncc(CCl)s2)CC1]

To a mixture of 4-fluoro-4-(5-hydroxymethyl-thiazol-2-yl)-piperidine-1-carboxylic acid tert-butyl ester (1.34 g, 4.24 mmol) and pyridine (426 mg, 1.3 eq.) in CH$_2$Cl$_2$ (30 mL) at 0° C. was added MsCl (631 mg, 1.3 eq.). The mixture was warmed to room temperature and stirred overnight. The reaction mixture was washed with saturated NaHCO$_3$ solution and dried over Na$_2$SO$_4$. Removal of the solvent afforded the desired product, which was used directly in the following reaction without further purification.

Step 5: 4-Fluoro-4-[5-(4-methanesulfonyl-phenoxymethyl)-thiazol-2-yl]-piperidine-1-carboxylic acid tert-butyl ester

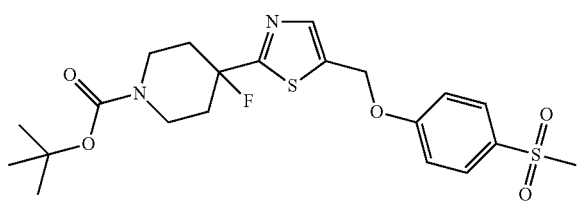 [SMILES: CC(C)(C)OC(=O)N1CCC(F)(c2ncc(COc3ccc(S(C)(=O)=O)cc3)s2)CC1]

A mixture of 4-(5-Chloromethyl-thiazol-2-yl)-4-fluoro-piperidine-1-carboxylic acid tert-butyl ester (1.42 g, 4.24 mmol), 4-methanesulfonyl-phenol (731 mg, 1.0 eq.) and K$_2$CO$_3$ (878 mg, 1.5 eq.) in acetone (30 mL) was heated to reflux overnight. After cooling, the solid was filtered off through a pad of celite. The filtrate was concentrated in vacuo. The crude product was purified on silica gel (EtOAc: hexanes=1:1) to afford the desired product as a white solid. $^1$H NMR (CDCl$_3$): δ 7.86 (2H, d, J=9.2 Hz), 7.35 (1H, s), 7.10 (2H, d, J=9.2 Hz), 5.22 (2H, s), 4.08 (2H, br), 3.19 (2H, br), 3.02 (3H, s), 2.05~2.32 (4H, m), 1.46 (9H, s).

Example 90

5-Ethyl-2-{4-fluoro-4-[5-(4-methanesulfonyl-phenoxymethyl)-thiazol-2-yl]-piperidin-1-yl}-pyrimidine

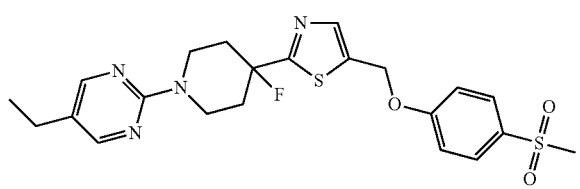 [SMILES: CCc1cnc(N2CCC(F)(c3ncc(COc4ccc(S(C)(=O)=O)cc4)s3)CC2)nc1]

Step 1: 4-Fluoro-4-[5-(4-methanesulfonyl-phenoxymethyl)-thiazol-2-yl]-piperidine hydrochloride

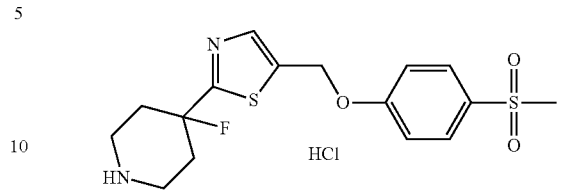

To a solution of 4-fluoro-4-[5-(4-methanesulfonyl-phenoxymethyl)-thiazol-2-yl]-piperidine-1-carboxylic acid tert-butyl ester (Example 89, 1.30 g, 2.76 mmol) in methanol (5 mL) was added 4 N HCl in dioxane (10 mL). The resulting solution was stirred overnight. The mixture was then evaporated to dryness in vacuo to afford the desired product as a white solid.

Step 2: 5-Ethyl-2-{4-fluoro-4-[5-(4-methanesulfonyl-phenoxymethyl)-thiazol-2-yl]-piperidin-1-yl}-pyrimidine

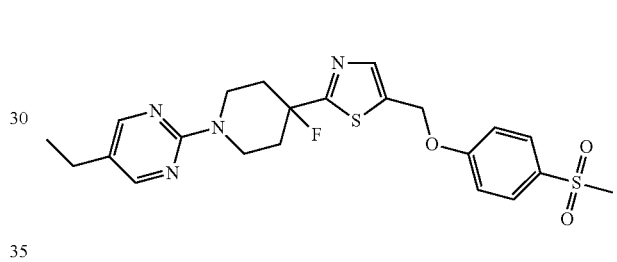

A solution of 4-fluoro-4-[5-(4-methanesulfonyl-phenoxymethyl)-thiazol-2-yl]-piperidine hydrochloride (1.2 g, 2.76 mmol), 2-chloro-5-ethyl-pyrimidine (425 mg, 1.1 eq.) and DIPEA (1.4 g, 4 eq.) in 2-propanol (20 mL) in a sealed pressure vessel was stirred at 160° C. (oil bath temperature) overnight. After cooling, the solvent was removed in vacuo. The residue was partitioned between water and EtOAc. The organic phase was washed with brine and dried over Na$_2$SO$_4$. After removal of the solvent, the crude product was purified on silica gel (EtOAc:hexanes=1:1) to afford the desired product as a white solid. $^1$H NMR (CDCl$_3$): δ 8.19 (2H, s), 7.90 (2H, d, J=8.8 Hz), 7.73 (1H, d), 7.10 (2H, d, 0.1=8.8 Hz), 5.31 (2H, s), 4.67 (2H, m), 3.44 (2H, m), 3.04 (3H, s), 2.48 (2H, q, J=7.6 Hz), 2.13~2.38 (4H, m), 1.20 (3H, t, J=7.6 Hz).

Example 91

4-[4-(4-Methanesulfonyl-phenoxymethyl)-thiazol-2-yl]-piperazine-1-carboxylic acid tert-butyl ester

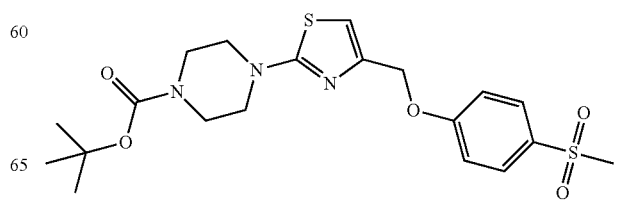

Step 1: 4-(4-Ethoxycarbonyl-thiazol-2-yl)-piperazine-1-carboxylic acid tert-butyl ester

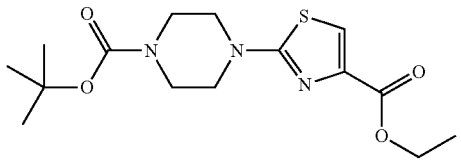 [SMILES: CCOC(=O)c1csc(N2CCN(C(=O)OC(C)(C)C)CC2)n1]

A mixture of 2-bromo-thiazole-4-carboxylic acid ethyl ester (1.4 g, 5.93 mmol), piperazine-1-carboxylic acid tert-butyl ester (1.16 g, 1.05 eq.) and DIPEA (1.15 g, 1.5 eq.) in 1,4-dioxane (20 mL) was heated to reflux overnight. After cooling, the solvent was removed in vacuo. The crude product was purified on silica gel (EtOAc:hexanes=1:4) to afford the desired product as a pale yellow solid.

Step 2: 4-(4-Hydroxymethyl-thiazol-2-yl)-piperazine-1-carboxylic acid tert-butyl ester

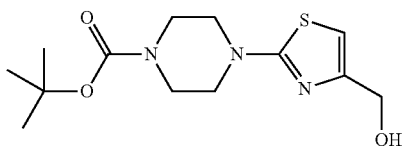 [SMILES: CC(C)(C)OC(=O)N1CCN(c2nc(CO)cs2)CC1]

A solution of 4-(4-ethoxycarbonyl-thiazol-2-yl)-piperazine-1-carboxylic acid tert-butyl ester (1.15 g, 3.37 mmol) in THF (15 mL) at 0° C. was treated with LiAlH$_4$ (128 mg, 1 eq.). The mixture was stirred for 1 hour, then the reaction was quenched with 2 N NaOH solution. The solid was filtered off through a pad of celite and washed with EtOAc (100 mL). The filtrate was washed with water and dried over Na$_2$SO$_4$. Removal of the solvent afforded the desired product as an oil.

Step 3: 4-(4-Chloromethyl-thiazol-2-yl)-piperazine-1-carboxylic acid tert-butyl ester

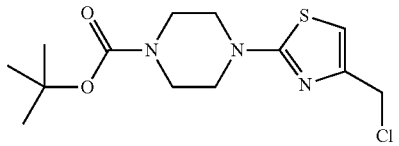 [SMILES: CC(C)(C)OC(=O)N1CCN(c2nc(CCl)cs2)CC1]

To a solution of 4-(4-hydroxymethyl-thiazol-2-yl)-piperazine-1-carboxylic acid tert-butyl ester (848 mg, 2.83 mmol) and DIPEA (550 mg, 1.5 eq.) in CH$_2$Cl$_2$ (10 mL) was added MsCl (285 □L, 1.3 eq.) dropwise. The resulting mixture was stirred overnight. The reaction solution was then concentrated in vacuo. The crude product was purified on silica gel (EtOAc:hexanes=1:4) to afford the desired product as an oil.

Step 4: 4-[4-(4-Methanesulfonyl-phenoxymethyl)-thiazol-2-yl]-piperazine-1-carboxylic acid tert-butyl ester

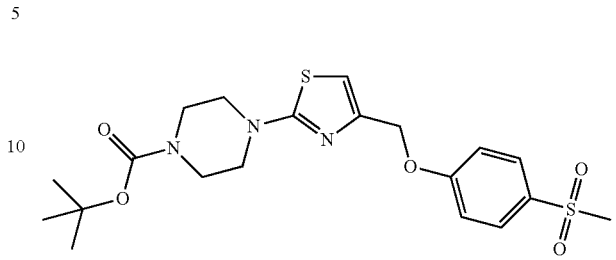

A mixture of 4-(4-Chloromethyl-thiazol-2-yl)-piperazine-1-carboxylic acid tert-butyl ester (700 m g, 2.20 mmol), 4-methanesulfonyl-phenol (417 mg, 1.1 eq.) and K$_2$CO$_3$ (609 mg, 2 eq.) in acetone (30 mL) was heated to reflux overnight. After cooling, the solid was filtered off through a pad of celite. The filtrate was concentrated in vacuo. The crude product was purified on silica gel (EtOAc:hexanes=1: 1) to afford the desired product as an off-white solid. $^1$H NMR (CDCl$_3$): δ 7.87 (2H, d, J=8.8 Hz), 7.12 (2H, d, J=8.8 Hz), 6.59 (1H, s), 5.05 (2H, s), 3.56 (4H, m), 3.48 (4H, m), 3.04 (3H, s), 1.49 (9H, s).

Example 92

1-[4-(4-Methanesulfonyl-phenoxymethyl)-thiazol-2-yl]-4-(2-methyl-propane-1-sulfonyl)-piperazine

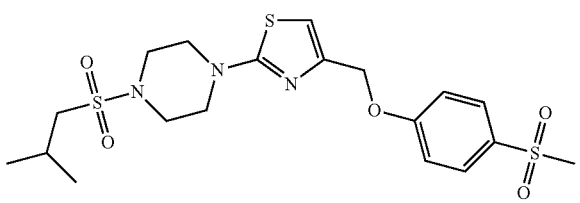 [SMILES: CC(C)CS(=O)(=O)N1CCN(c2nc(COc3ccc(S(C)(=O)=O)cc3)cs2)CC1]

Step 1: 1-[4-(4-Methanesulfonyl-phenoxymethyl)-thiazol-2-yl]-piperazine hydrochloride

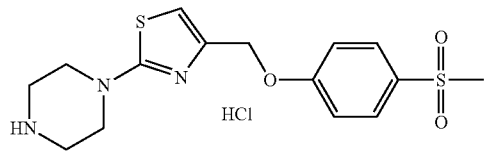 [SMILES: CS(=O)(=O)c1ccc(OCc2csc(N3CCNCC3)n2)cc1 ; Cl]

To a solution of 4-[4-(4-Methanesulfonyl-phenoxymethyl)-thiazol-2-yl]-piperazine-1-carboxylic acid tert-butyl ester (Example 91, 430 mg, 0.95 mmol) in methanol (5 mL) was added 4 N HCl in dioxane (5 mL). The resulting solution was stirred for 30 minutes at room temperature. The mixture was then evaporated to dryness in vacuo to afford the desired product as a pale yellow solid.

Step 2: 1-[4-(4-Methanesulfonyl-phenoxymethyl)-thiazol-2-yl]-4-(2-methyl-propane-1-sulfonyl)-piperazine

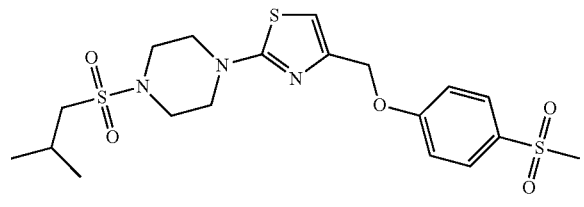 [SMILES: CC(C)CS(=O)(=O)N1CCN(c2nc(COc3ccc(S(C)(=O)=O)cc3)cs2)CC1]

A solution of 1-[4-(4-Methanesulfonyl-phenoxymethyl)-thiazol-2-yl]-piperazine hydrochloride (100 mg, 0.26 mmol) and DIPEA (134 mL, 3 eq.) in CH$_2$Cl$_2$ (5 mL) was added isobutanesulfonyl chloride (41 mL, 1.2 eq.). The mixture was stirred for 1 hour, then the reaction solution was directly purified on silica gel (EtOAc:hexanes=1:1) to afford the desired product as a pale yellow solid. $^1$H NMR (CDCl$_3$): δ 7.87 (2H, d, J=8.8 Hz), 7.12 (2H, d, J=8.8 Hz), 6.62 (1H, s), 5.05 (2H, s), 3.61 (4H, m), 3.39 (4H, m), 3.04 (3H, s), 2.78 (2H, d, J=6.8 Hz), 2.32 (1H, m), 1.12 (6H, d, J=6.8 Hz).

Example 93

4-[4-Methyl-5-(4-tetrazol-1-yl-phenoxymethyl)-thiazol-2-yl]-piperidine-1-carboxylic acid tert-butyl ester

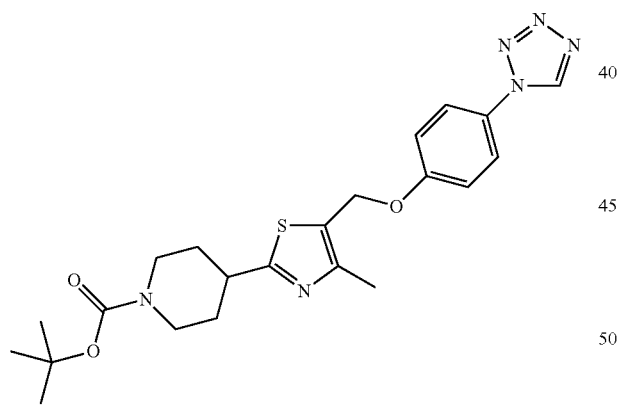

To a solution of 4-(5-Hydroxymethyl-4-methyl-thiazol-2-yl)-piperidine-1-carboxylic acid tert-butyl ester (1.00 g, 3.2 mmol) in THF (6.4 mL) was added, 4-tetrazol-1-yl-phenol (0.52 g, 3.2 mmol), polymer bound triphenylphosphine (3 mmol/g, 1.6 g). To this solution was added ditertierybutylazodicarboxylate (1.1 g, 4.8 mmol), stirred for 4 hours and filtered through a pad of celite. The filtrate was concentrated and purified by silica gel chromatography to provide the desired product. $^1$H NMR (CDCl$_3$): δ 9.01 (1H, s), 7.66 (2H, d), 7.15 (2H, d), 5.21 (2H, s), 4.19 (2H, m), 3.10 (1H, m), 2.86 (2H, m), 2.45 (3H, s), 2.08 (2H, m), 1.72 (2H, m), 1.47 (9H, s).

Example 94

4-{4-[(6-Fluoro-pyridin-3-ylamino)-methyl]-thiazol-2-yl}-piperidine-1-carboxylic acid tert-butyl ester

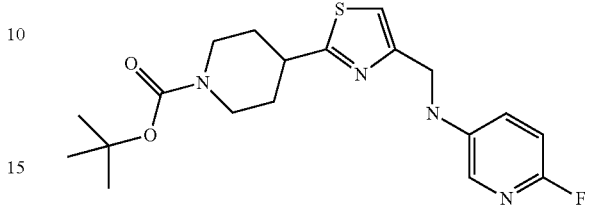

5-amino-2-fluoropyridine (0.476 g, 4.2 mmol) was added to 4-(4-Formyl-thiazol-2-yl)-piperidine-1-carboxylic acid tert-butyl ester (0.84 g, 2.8 mmol) in dry DCM (10 mL). Sodium triacetoxyborohydride (0.9 g, 4.2 mmol) was then added. The reaction was stirred for 3 hours at room temperature under N$_2$. The organic layer was washed with 2M NaOH solution, water, brine, dried (MgSO$_4$), and the solvent was removed in vacuo. The material was purified by silica gel chromatography (DCM/methanol: 10:1 v/v) to give the desired product.
$^1$H NMR (CDCl$_3$): δ 7.59-7.60 (1H, m), 7.06-7.10 (1H, m), 7.02 (1H, s), 6.76 (1H, dd, J=8.8, 3.6 Hz), 4.4 (2H, d), 4.20-4.31 (3H, m), 3.09-3.17 (1H, m), 2.8-2.95 (2H, m), 2.07-2.10 (2H, m), 1.77-1.47, (2H, m), 1.47 (9H, s).

Example 95

1-(3-Isopropyl-[1,2,4]oxadiazol-5-yl)-4-[4-(4-tetrazol-1-yl-phenoxymethyl)-thiazol-2-yl]-piperidine Step 1: 4-[4-(4-Tetrazol-1-yl-phenoxymethyl)-thiazol-2-yl]-piperidine-1-carbonitrile

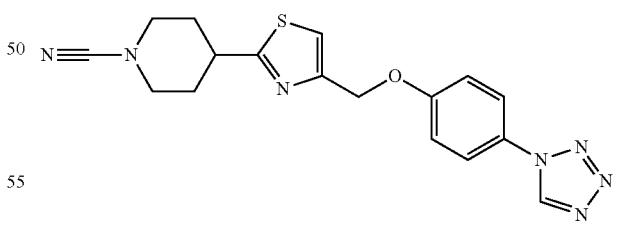

To a mixture of 4-[4-(4-Tetrazol-1-yl-phenoxymethyl)-thiazol-2-yl]-piperidine (1.00 g, 2.92 mmol) and potassium carbonate (1.5 g, 10.9 mmol) in chloroform (25 mL) was added cyanogen bromide (0.371 g, 3.5 mmol). The slurry was refluxed for 48 hours then stirred at room temperature for an additional 48 hours. The reaction was filtered through a pad of celite, concentrated and chromatographed on silica gel (1:1 Hexanes/EtOAc) to afford the desired compound.

Step 2: 1-(3-Isopropyl-[1,2,4]oxadiazol-5-yl)-4-[4-(4-tetrazol-1-yl-phenoxymethyl)-thiazol-2-yl]-piperidine

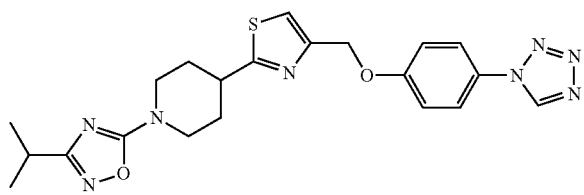 [SMILES: CC(C)c1noc(N2CCC(c3nc(COc4ccc(-n5cnnn5)cc4)cs3)CC2)n1]

To a solution of 4-[4-(4-Tetrazol-1-yl-phenoxymethyl)-thiazol-2-yl]-piperidine-1-carbonitrile (0.450, 1.22 mmol) and N-hydroxy-isobutyramidine (0.150 g, 1.47 mmol) in dry THF (10 mL) was added a 1 M solution of zinc chloride in THF (1.47 mL, 1.47 mmol) over 15 min. The suspension was left to settle for 15 minutes and the white precipitate was collected by filtration and dissolved in 4N HCl in ethanol and water (1:1). The solution was refluxed for 1 hour, cooled and the solid precipitate was filtered off. The filtrate was neutralized by the addition of excess sodium carbonate. The excess was filtered off and the filtrate was diluted with EtOAc. The solution was washed with water, separated, dried (Na$_2$SO$_4$), filtered and concentrated. The residual oil was chromatographed on silica gel (1:1 Hex/EtOAc) to afford the desired compound. $^1$H NMR (CDCl$_3$): δ 8.92 (1H, s), 7.62 (2H, d), 7.28 (1H, s), 7.19 (2H, d), 5.24 (2H, s), 4.26 (2H, m), 3.20 (3H, m), 2.89 (1H, m), 2.26 (2H, m), 1.92 (2H, m), 1.30 (6H, d).

The following three examples were synthesized in similar manner as Example 95 using the required hydroxy amidine and 4-[4-(4-tetrazol-1-yl-phenoxymethyl)-thiazol-2-yl]-piperidine-1-carbonitrile.

Example 96

1-(3-Ethyl-[1,2,4]oxadiazol-5-yl)-4-[4-(4-tetrazol-1-yl-phenoxymethyl)-thiazol-2-yl]-piperidine

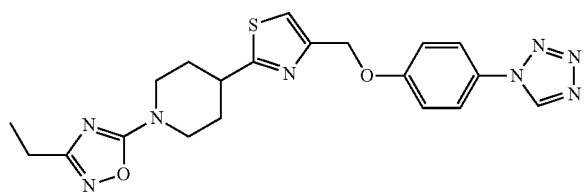 [SMILES: CCc1noc(N2CCC(c3nc(COc4ccc(-n5cnnn5)cc4)cs3)CC2)n1]

$^1$H NMR (CDCl$_3$): δ 8.85 (1H, s), 7.57 (2H, d), 7.28 (1H, s), 7.19 (2H, d), 5.17 (2H, s), 4.22 (2H, m), 3.22 (3H, m), 2.55 (2H, q), 2.17 (2H, m), 1.89 (2H, m), 1.35 (3H, t).

Example 97

1-(3-Cyclopropyl-[1,2,4]oxadiazol-5-yl)-4-[4-(4-tetrazol-1-yl-phenoxymethyl)-thiazol-2-yl]-piperidine

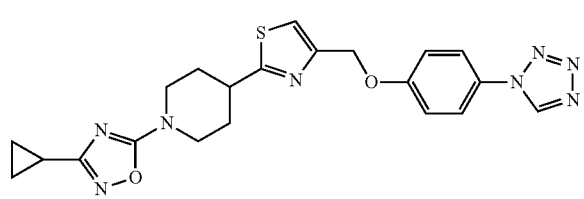 [SMILES: c1cc(-n2cnnn2)ccc1OCc1csc(C2CCN(c3nc(C4CC4)no3)CC2)n1]

$^1$H NMR (CDCl$_3$): δ 8.90 (1H, s), 7.61 (2H, d), 7.27 (1H, s), 7.17 (2H, d), 5.23 (2H, s), 4.22 (2H, m), 3.22 (3H, m), 2.25 (2H, m), 1.88 (3H, m), 0.96 (4H, m).

Example 98

4-[4-(4-Tetrazol-1-yl-phenoxymethyl)-thiazol-2-yl]-1-(3-trifluoromethyl-[1,2,4]oxadiazol-5-yl)-piperidine

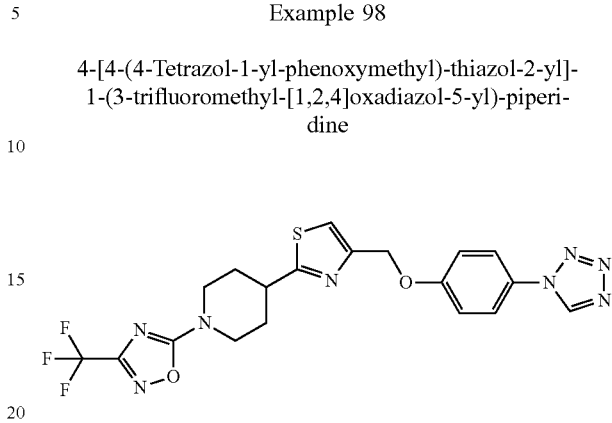

$^1$H NMR (CDCl$_3$): δ 8.92 (1H, s), 7.60 (2H, d), 7.23 (1H, s), 7.16 (2H, d), 5.21 (2H, s), 4.25 (2H, m), 4.15 (2H, m), 3.22 (1H, m), 2.90 (2H, m), 2.18 (2H, m).

Example 99

4-[4-(4-Tetrazol-1-yl-phenoxymethyl)-thiazol-2-yl]-piperidine-1-carboxylic acid amide Step 1: 4-[4-(4-Tetrazol-1-yl-phenoxymethyl)-thiazol-2-yl]-piperidine-1-carbonitrile

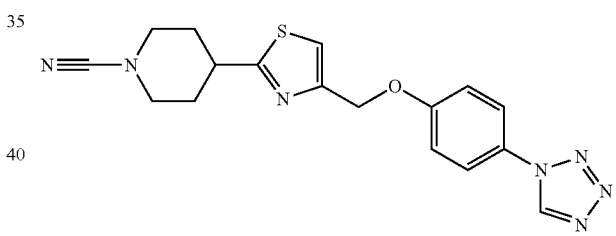

To a mixture of 4-[4-(4-Tetrazol-1-yl-phenoxymethyl)-thiazol-2-yl]-piperidine (1.00 g, 2.92 mmol) and potassium carbonate (1.5 g, 10.9 mmol) in chloroform (25 mL) was added cyanogen bromide (0.371 g, 3.5 mmol). The slung was refluxed for 48 hours then stirred at room temperature for an additional 48 hours. The reaction was filtered through a pad of celite, concentrated and chromatographed on silica gel (1:1 Hexanes/EtOAc) to afford the desired compound.

Step 2: 4-[4-(4-Tetrazol-1-yl-phenoxymethyl)-thiazol-2-yl]-piperidine-1-carboxylic acid amide

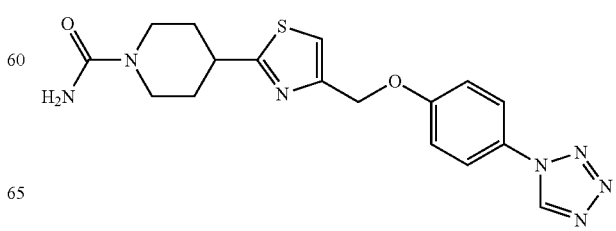

4-[4-(4-Tetrazol-1-yl-phenoxymethyl)-thiazol-2-yl]-piperidine-1-carbonitrile (1.07 g, 2.92 mmol) was dissolved in 4 N HCl in ethanol/water (1:1). The solution was refluxed for 1 hour, cooled and the solid precipitate was filtered off. The filtrate was neutralized by the addition of excess sodium carbonate. The excess sodium carbonate was filtered off and the filtrate was diluted with EtOAc. The solution was washed with water, separated, dried (Na₂SO₄), filtered and concentrated. The residual oil was chromatographed on silica gel (1:1 Hexanes/EtOAc) to afford the desired compound. $^1$H NMR (CDCl₃): δ 8.92 (1H, s), 7.60 (2H, d), 7.23 (1H, s), 7.167 (2H, d), 5.21 (2H, s), 4.25 (2H, m), 4.15 (2H, m), 3.22 (1H, m), 2.90 (2H, m), 2.18 (2H, m).

Example 100

4-[4-(4-Tetrazol-1-yl-phenoxymethyl)-thiazol-2-yl]-piperidine-1-carboxamidine

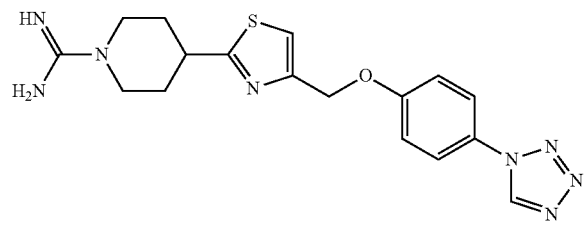 [SMILES: N=C(N)N1CCC(c2nc(COc3ccc(-n4cnnn4)cc3)cs2)CC1]

A mixture of 4-[4-(4-tetrazol-1-yl-phenoxymethyl)-thiazol-2-yl]-piperidine (300 mg, 0.876 mmol), pyrazole-1-carboxamidine hydrochloride (0.128 g, 0.876 mmol.) and triethylamine (0.122 mL, 0.876 mmol) in DMF (2 mL) was stirred at rt for 3 hours. The precipitate was collected by filtration and washed with ether to afford the expected product. $^1$H NMR (DMSO-d₆): δ 10.02 (1H, s), 7.93 (1H, s), 7.82 (2H, m), 7.70 (1H, s), 7.60 (2H, br), 7.28 (2H, m), 5.20 (2H, s), 3.95 (2H, m), 3.38 (1H, m), 3.15 (2H, m), 2.09 (2H, m), 1.66 (2H, m).

Example 101

3-[4-(4-tetrazol-1-yl-phenoxymethyl)-thiazol-2-yl]-azetidine-1-carboxylic acid tert-butyl ester Step 1: 3-(4-chloromethyl-thiazol-2-yl)-azetidine-1-carboxylic acid tert-butyl ester

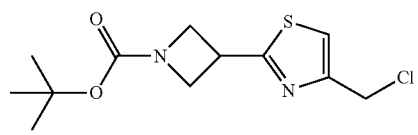 [SMILES: CC(C)(C)OC(=O)N1CC(c2nc(CCl)cs2)C1]

To a solution of 3-Thiocarbamoyl-azetidine-1-carboxylic acid tert-butyl ester (0.800 g, 3.7 mmol) in acetone (15 mL) was added 1,3-dichloroacetone (0.611 g, 4.81 mmol), MgSO₄ (0.67 g, 5.6 mmol) and MgCO₃ (3.12 g, 3.7 mmol). The mixture was heated under reflux overnight, cooled and filtered through celite. The solvent was removed in vacuo and the residue was redissolved with EtOAc (20 mL). The resulting solution was washed successively with 5% NaHSO₃, saturated NaHCO₃, and brine. After drying (Na₂SO₄), the solvent was removed to afford the desired product which was used without further purification.

Step 2: 3-[4-(4-tetrazol-1-yl-phenoxymethyl)-thiazol-2-yl]-azetidine-1-carboxylic acid tert-butyl ester

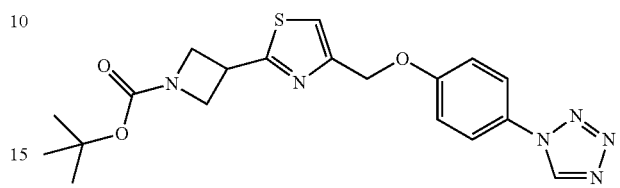

A mixture of 3-(4-chloromethyl-thiazol-2-yl)-azetidine-1-carboxylic acid tert-butyl ester (From Step 1) (386 mg, 1.34 mmol), 4-tetrazol-1-yl-phenol (217 mg, 1.34 mmol), Cs₂CO₃ (655 mg, 2.01 mmol) and KI (22 mg, 0.13 mmol) in acetonitrile (5 mL) was heated under reflux for 4 hours. After cooling, the solid was filtered through a pad of celite. The filtrate was concentrated in vacuo. The residue was purified on silica gel (EtOAc-hexanes, 1:1) to afford the desired product. $^1$H NMR (CDCl₃): δ 8.92 (1H, s), 7.61 (2H, d), 7.32 (1H, s), 7.19 (2H, d), 5.25 (2H, s), 4.39 (2H, m), 4.18 (2H, m), 4.14 (1H, m), 1.46 (9H, s).

Example 102

3-[4-(4-Tetrazol-1-yl-phenoxymethyl)-thiazol-2-yl]-pyrrolidine-1-carboxylic acid tert-butyl ester

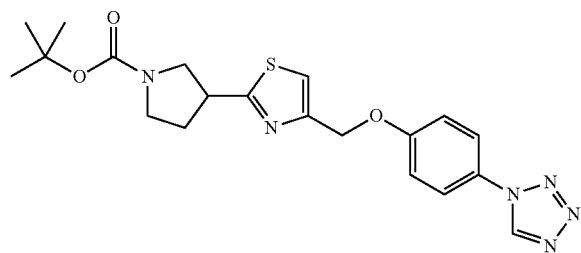 [SMILES: CC(C)(C)OC(=O)N1CCC(c2nc(COc3ccc(-n4cnnn4)cc3)cs2)C1]

Step 1: 3-(4-Chloromethyl-thiazol-2-yl)-pyrrolidine-1-carboxylic acid tert-butyl ester

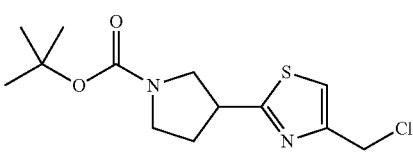 [SMILES: CC(C)(C)OC(=O)N1CCC(c2nc(CCl)cs2)C1]

To a solution of 3-thiocarbamoyl-pyrrolidine-1-carboxylic acid tert-butyl ester (1.06 g, 4.60 mmol) in acetone (25 mL) was added 1,3-dichloroacetone (0.76 g, 5.98 mmol), MgSO₄ (0.83 g, 6.1 mmol) and MgCO₃ (3.87 g, 4.6 mmol). The mixture was heated under reflux overnight, cooled and filtered through celite. The solvent was removed in vacuo and the residue was redissolved with EtOAc (20 mL). The resulting solution was washed successively with 5% NaHSO₃, saturated NaHCO₃, and brine. After drying (Na₂SO₄), the solvent was removed to afford the desired product which was used without further purification.

Step 2: 3-[4-(4-Tetrazol-1-yl-phenoxymethyl)-thiazol-2-yl]-pyrrolidine-1-carboxylic acid tert-butyl ester

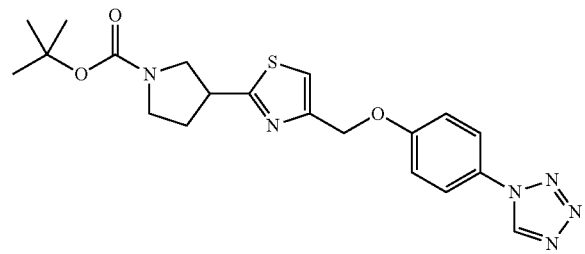 [SMILES: CC(C)(C)OC(=O)N1CCC(c2nc(COc3ccc(-n4cnnn4)cc3)cs2)C1]

A mixture of 3-(4-Chloromethyl-thiazol-2-yl)-pyrrolidine-1-carboxylic acid tert-butyl ester (From Step 1) (775 mg, 2.56 mmol), 4-tetrazol-1-yl-phenol (415 mg, 2.56 mmol), CsCO₃ (1.25 mg, 3.84 mmol) and KI (44 mg, 0.26 mmol) in acetonitrile (20 mL) was heated under reflux overnight After cooling, the solid was filtered through a pad of celite. The filtrate was concentrated in vacuo. The residue was purified on silica gel (EtOAc-hexanes, 1:1) to afford the desired product. ¹H NMR (CDCl₃): δ 8.92 (1H, s), 7.63 (2H, d), 7.27 (1H, s), 7.17 (2H, d), 5.24 (2H, s), 3.87 (1H, m), 3.79 (1H, m), 3.65 (2H, m), 3.45 (1H, m), 2.40 (1H, m), 2.23 (1H, m), 1.47 (9H, s).

Example 103

5-Ethyl-2-{3-[4-(4-tetrazol-1-yl-phenoxymethyl)-thiazol-2-yl]-pyrrolidin-1-yl}-pyrimidine Step 1: 1-[4-(2-Pyrrolidin-3-yl-thiazol-4-yl-methoxy)-phenyl]-1H-tetrazole

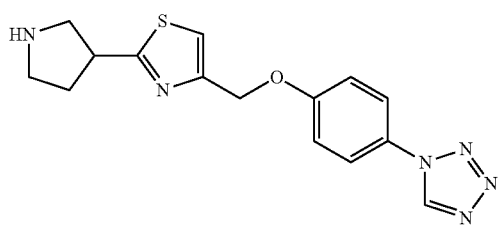 [SMILES: c1cc(-n2cnnn2)ccc1OCc1csc(C2CCNC2)n1]

A solution of 3-[4-(4-Tetrazol-1-yl-phenoxymethyl)-thiazol-2-yl]-pyrrolidine-1-carboxylic acid tert-butyl ester (from Example 102) (411 mg, 0.959 mmol) in dichloromethane (10 mL) and methanol (2 mL) were treated with 1 mL of 4N HCl in dioxane. The resulting solution was stirred at room temperature for 30 minutes. The solvents were removed in vacuo to afford the desired product as an HCl salt.

Step 2: 5-Ethyl-2-{3-[4-(4-tetrazol-1-yl-phenoxymethyl)-thiazol-2-yl]-pyrrolidin-1-yl}-pyrimidine

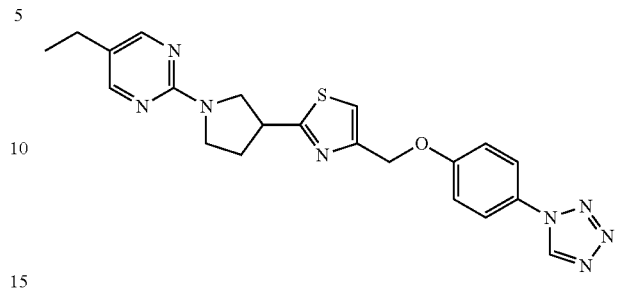

A mixture of 1-[4-(2-Pyrrolidin-3-yl-thiazol-4-yl-methoxy)-phenyl]-1H-tetrazole hydrochloride (From Step 1) (350 mg, 0.959 mmol), 2-chloropyrimidine (0.23 mL, 2.0 eq.) and K₂CO₃ (398 mg, 2.88 mmol) in DMF (5 mL) was heated at 90° C. for 4 hours. Water was added and the solution was extracted with ethyl acetate, separated, dried over sodium sulfate, filtered and concentrated. The residue was purified on silica gel (50:50 EtOAc/hexanes) to afford the desired product. ¹H NMR (CDCl₃): δ 8.91 (1H, s), 8.21 (2H, s), 7.62 (2H, d), 7.27 (1H, s), 7.17 (2H, d), 5.24 (2H, s), 4.12 (1H, m), 3.98 (1H, m), 3.87 (2H, m), 3.69 (1H, m), 2.56 (1H, m), 2.47 (2H, m), 2.37 (1H, m), 1.21 (3H, t).

Example 104

3-[4-(4-Tetrazol-1-yl-phenoxymethyl)-thiazol-2-yl]-piperidine-1-carboxylic acid tert-butyl ester

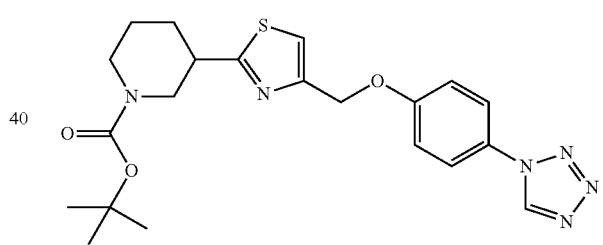

Step 1: 3-(4-Chloromethyl-thiazol-2-yl)-piperidine-1-carboxylic acid tert-butyl ester

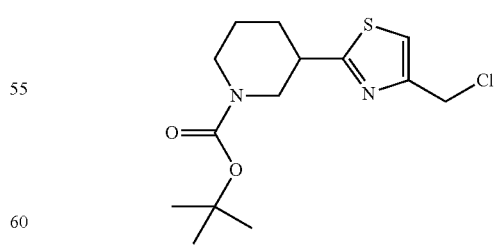

To a solution of 3-Thiocarbamoyl-piperidine-1-carboxylic acid tert-butyl ester (2.2 g, 9.02 mmol) in acetone (45 mL) was added 1,3-dichloroacetone (1.49 g, 11.7 mmol), MgSO₄ (1.63 g, 13.5 mmol) and MgCO₃ (0.76 g, 9.02 mmol). The mixture was heated under reflux overnight, cooled and filtered through celite. The solvent was removed in vacuo and the residue was redissolved with EtOAc (20 mL). The resulting solution was washed successively with 5% NaHSO$_3$, saturated NaHCO$_3$, and brine. After drying (Na$_2$SO$_4$), the solvent was removed to afford the desired product which was used without further purification.

Step 2: 3-[4-(4-Tetrazol-1-yl-phenoxymethyl)-thiazol-2-yl]-piperidine-1-carboxylic acid tert-butyl ester

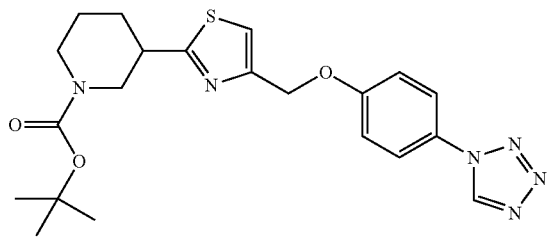 [SMILES: CC(C)(C)OC(=O)N1CCCC(c2nc(COc3ccc(-n4cnnn4)cc3)cs2)C1]

A mixture of 3-(4-Chloromethyl-thiazol-2-yl)-piperidine-1-carboxylic acid tert-butyl ester (From Step 1) (300 mg, 0.946 mmol), 4-tetrazol-1-yl-phenol (155 mg, 0.946 mmol), CsCO$_3$ (467 mg, 1.42 mmol) and KI (16 mg, 0.095 mmol) in acetonitrile (10 mL) was heated under reflux for 4 hours. After cooling, the solid was filtered through a pad of celite. The filtrate was concentrated in vacuo. The residue was purified on silica gel (EtOAc-hexanes, 1:1) to afford the desired product. $^1$H NMR (CDCl$_3$): δ 8.91 (1H, s), 7.63 (2H, d), 7.26 (1H, s), 7.17 (2H, d), 5.24 (2H, s), 4.30 (1H, br), 4.02 (1H, m), 3.20 (1H, m), 3.10 (1H, br), 2.88 (1H, t), 2.21 (1H, m), 1.77 (2H, m), 1.61 (1H, m), 1.47 (9H, s).

Example 105

5-Ethyl-2-{3-[4-(4-tetrazol-1-yl-phenoxymethyl)-thiazol-2-yl]-piperidin-1-yl}-pyrimidine Step 1: 3-[4-(4-Tetrazol-1-yl-phenoxymethyl)-thiazol-2-yl]-piperidine

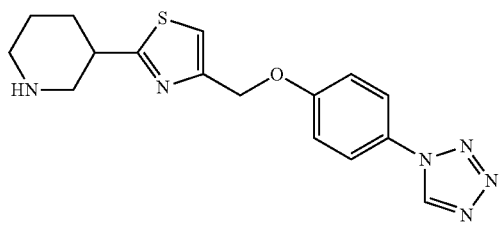 [SMILES: c1cc(-n2cnnn2)ccc1OCc1csc(C2CCCNC2)n1]

A solution of 3-[4-(4-Tetrazol-1-yl-phenoxymethyl)-thiazol-2-yl]-piperidine-1-carboxylic acid tert-butyl ester (500 mg, 1.13 mmol) in dichloromethane (10 mL) and methanol (2 mL) were treated with 2 mL of 4N HCl in dioxane. The resulting solution was stirred at room temperature for 30 minutes. The solvents were removed in vacuo to afford the desired product as an HCl salt.

Step 2: 5-Ethyl-2-{3-[4-(4-tetrazol-1-yl-phenoxymethyl)-thiazol-2-yl]-piperidin-1-yl}-pyrimidine

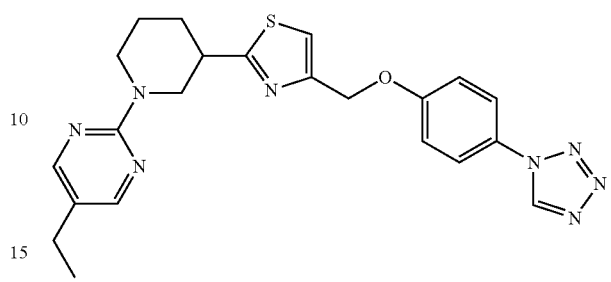

A mixture of 3-[4-(4-Tetrazol-1-yl-phenoxymethyl)-thiazol-2-yl]-piperidine hydrochloride (150 mg, 0.407 mmol), 2-chloropyrimidine (0.074 mL, 2.0 eq.) and NaHCO$_3$ (171 mg, 2.03 mmol) in DMF (5 mL) was heated at 90° C. for 4 hours. Water was added and the solution was extracted with ethyl acetate, separated, dried over sodium sulfate, filtered and concentrated. The residue was purified on silica gel (50:50 EtOAc/hexanes) to afford the desired product. $^1$H NMR (CDCl$_3$): δ 8.91 (1H, s), 8.19 (2H, s), 7.63 (2H, m), 7.26 (1H, s), 7.17 (2H, m), 5.25 (2H, s), 4.97 (1H, m), 4.62 (1H, m), 3.25 (2H, m), 3.07 (1H, m), 2.46 (2H, q), 2.28 (1H, m), 1.88 (2H, m), 1.68 (1H, m), 1.20 (3H, t).

Example 106

4-[4-(4-Methanesulfonyl-benzyloxymethyl)-thiazol-2-yl]-piperidine-1-carboxylic acid tert-butyl ester

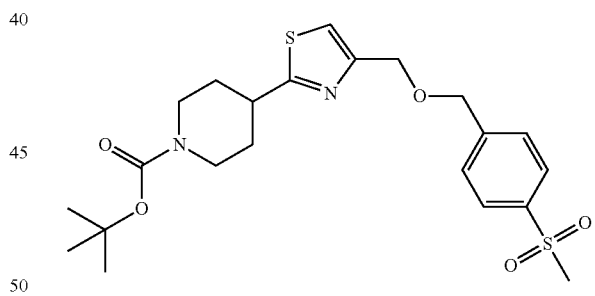

Hydroxybenzyl-4-methylsulfone (1.7 eq.) was dissolved in anhydrous DMF (10 mL), cooled to 0° C. and NaH (2 eq.) was added in one portion. The reaction was allowed to stir at 0° C. for 30 minutes and at room temperature for an additional 30 minutes. 4-(4-Chloromethyl-thiazol-2-yl)-piperidine-1-carboxylic acid tert-butyl ester (Intermediate 1) (0.632 mmol) was added and the reaction was stirred overnight. The reaction was quenched with water and extracted with EtOAc, dried over sodium sulfate, filtered and concentrated under reduced pressure. The residue was purified by silica gel chromatography (EtOAc/hexanes 1:1) to afford the desired product. $^1$H NMR (CDCl$_3$): δ 7.92 (2H, d, J=8.8 Hz), 7.57 (2H, d, J=8.8 Hz), 7.14 (1H, s), 4.71 (2H, s), 4.66 (2H, s), 4.19 (2H, m), 3.13 (1H, m), 3.05 (3H, s), 2.86 (2H, m), 2.09 (2H, m), 1.72 (2H, m), 1.45 (9H, s).

Example 107

2-{4-[4-(4-Tetrazol-1-yl-phenoxymethyl)-thiazol-2-yl]-piperidin-1-yl}-pyrimidin-5-ylamine

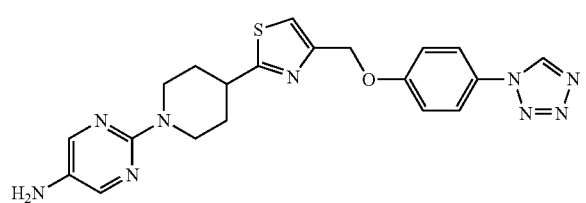 [SMILES: Nc1cnc(N2CCC(c3nc(COc4ccc(-n5cnnn5)cc4)cs3)CC2)nc1]

5-Nitro-2-{4-[4-(4-tetrazol-1-yl-phenoxymethyl)-thiazol-2-yl]-piperidin-1-yl}-pyrimidine (Example 192) (1.07 mmol), ammonium chloride (3 eq.) and iron powder (3 eq.) were suspended in EtOH:THF:H2O (40:20:10) and heated at 100° C. for 5 hours. The hot reaction mixture was filtered through a pad of celite and the filtrate was concentrated. The resulting oil was dissolved in DMF and water and extracted with ethylacetate. The organic layer was washed with water, brine and dried over sodium sulfate. The resulting filtrate was concentrated under reduced pressure. Purification using silica gel chromatography (DCM/MeOH 98:2) provided the expected product. $^1$H NMR (DMSO-$d_6$): δ 9.96 (1H, s), 7.97 (2H, m), 7.90 (2H, m), 7.63 (1H, s), 5.19 (2H, s), 4.44 (2H, m), 3.73 (1H, m), 2.97 (2H, m), 2.20 (2H, m), 1.95 (2H, m).

Example 108

N-(2-{4-[4-(4-Tetrazol-1-yl-phenoxymethyl)-thiazol-2-yl]-piperidin-1-yl}-pyrimidin-5-yl)-acetamide

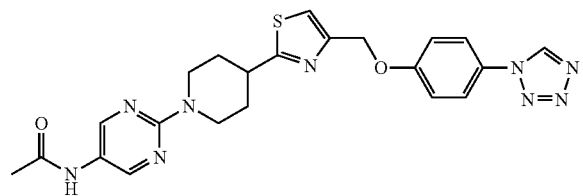 [SMILES: CC(=O)Nc1cnc(N2CCC(c3nc(COc4ccc(-n5cnnn5)cc4)cs3)CC2)nc1]

2-{4-[4-(4-Tetrazol-1-yl-phenoxymethyl)-thiazol-2-yl]-piperidin-1-yl}-pyrimidin-5-ylamine (Example 107) (0.321 mmol) was dissolved in DCM and triethylamine (2 eq.) was added. The reaction was cooled to 0° C., acetylchloride (1 eq.) was added dropwise and the reaction was stirred at room temperature overnight. Water was added and the mixture was extracted with ethyl acetate, dried over sodium sulfate, filtered and concentrated under reduced pressure. Silica gel chromatography of the resulting oil (DCM/MeOH) provided the expected product. $^1$H NMR (CDCl$_3$): δ 8.84 (1H, s), 8.36 (2H, s), 7.55 (2H, m), 7.19 (1H, s), 7.11 (2H, m), 6.94 (1H, s), 5.16 (2H, s), 4.77 (2H, m), 3.25 (1H, m), 3.01 (2H, m), 2.16 (2H, m), 2.15 (3H, s), 1.75 (2H, m).

Example 109

4-[4-(4-Tetrazol-1-yl-phenylcarbamoyl)-thiazol-2-yl]-piperidine-1-carboxylic acid tert-butyl ester

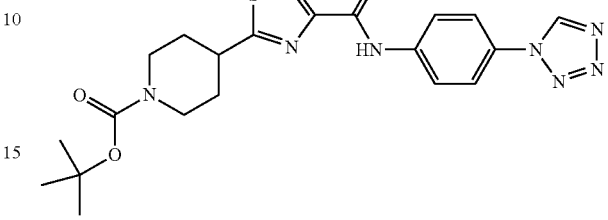

4-(4-Carboxy-thiazol-2-yl)-piperidine-1-carboxylic acid tert-butyl ester (1.28 mmol) was dissolved in anhydrous DMF (20 mL). To the solution was added triethylamine (4 eq.) and O-(Benzotriazol-1-yl)-N,N,N',N'-tetramethyluronium tetrafluoroborate (TBTU) (1.5 eq.). The reaction was allowed to stir at room temperature for 5 minutes before 4-tetrazol-1-yl-phenylamine (1.2 eq.) was added. The reaction was stirred overnight, quenched with water, extracted with ethylacetate, washed with brine, dried over sodium sulfate and filtered. The organic filtrate was concentrated in vacuo and the residual oil was purified by column chromatography (EtOAC/Hex) furnishing the expected product. $^1$H NMR (CDCl$_3$): δ 9.37 (1H, s), 9.02 (1H, s), 8.14 (1H, s), 7.96 (2H, d), 7.72 (2H, d), 4.23 (2H, m), 3.20 (1H, m), 2.91 (2H, m), 2.14 (2H, m), 1.79 (2H, m), 1.45 (9H, s).

Example 110

4-[4-(4-Trifluoromethanesulfonyl-phenoxymethyl)-thiazol-2-yl]-piperidine-1-carboxylic acid tert-butyl ester

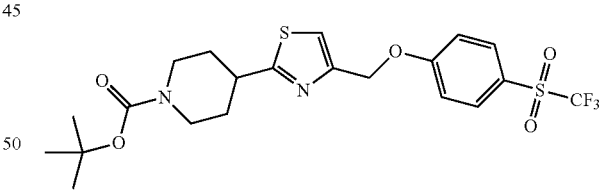

To a solution of [4-(4-Trifluoromethanesulfanyl-phenoxymethyl)-thiazol-2-yl]-piperidine-1-carboxylic acid tert-butyl ester (Example 134) (1.12 mmol) in DCM (20 mL) at room temperature was added 3-chloro-benzenecarboperoxoic acid (2 eq.). The reaction was allowed to stir for 1.5 hours and an additional portion of 3-chloro-benzenecarboperoxoic acid (1 eq.) was added to the reaction mixture. The reaction was stirred at room temperature for an additional 4 hours. The organic solution was washed with sodium bicarbonate, the organic layer was isolated, dried over sodium sulfate and filtered. The filtrate was concentrated and the crude product was purified by column chromatography to afford both the expected sulfone and sulfoxide products.

Sulfone: ¹H NMR (DMSO-d₆): δ 8.05 (2H, d, J=8.6 Hz), 7.70 (1H, s), 7.44 (2H, d, J=8.6 Hz), 5.32 (2H, s), 3.98 (2H, m), 3.19 (1H, m), 2.86 (2H, m), 2.02 (2H, m), 1.56 (2H, m), 1.38 (9H, s).

Example 111

4-[4-(4-Trifluoromethanesulfinyl-phenoxymethyl)-thiazol-2-yl]-piperidine-1-carboxylic acid tert-butyl ester

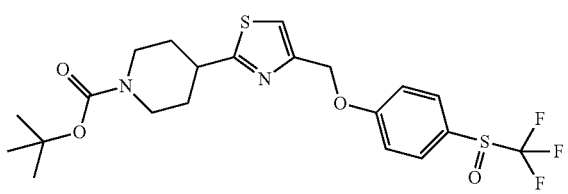 [SMILES: CC(C)(C)OC(=O)N1CCC(c2nc(COc3ccc(S(=O)C(F)(F)F)cc3)cs2)CC1]

This compound was isolated from the reaction mixture of the previous example. ¹H NMR (DMSO-d₆): δ 8.02 (2H, d, J=8.6 Hz), 7.75 (1H, s), 7.32 (2H, d, J=8.6 Hz), 5.31 (2H, s), 3.96 (2H, m), 3.20 (1H, m), 2.85 (2H, m), 2.02 (2H, m), 1.50 (2H, m), 1.38 (9H, s).

Example 112-145 were synthesized from 4-(4-Chloromethyl-thiazol-2-yl)-piperidine-1-carboxylic acid tert-butyl ester (Intermediate 1), 2-[4-(4-Chloromethyl-thiazol-2-yl)-piperidin-1-yl]-5-ethyl-pyrimidine (Intermediate 2) or 4-(4-Chloromethyl-oxazol-2-yl)-piperidine-1-carboxylic acid tert-butyl ester (Intermediate 14) with the corresponding phenol, thiophenol, amine or aniline in a similar manner to that described in Example 1. One skilled in the art of organic synthesis will appreciate that conditions such as solvent (such as DMF, CH₃CN); temperature, base (such as NEt₃, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 112

4-[4-(2,6-Difluoro-4-tetrazol-1-yl-phenoxymethyl)-thiazol-2-yl]-piperidine-1-carboxylic acid tert-butyl ester

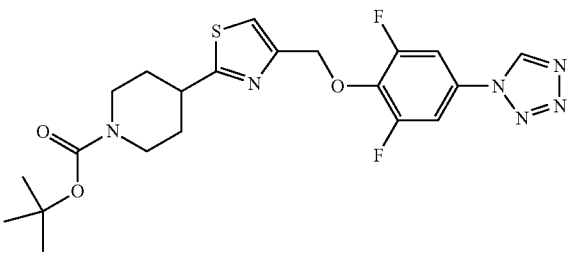 [SMILES: CC(C)(C)OC(=O)N1CCC(c2nc(COc3c(F)cc(-n4cnnn4)cc3F)cs2)CC1]

¹H NMR (CDCl₃): δ 8.98 (1H, s), 7.34 (2H, m), 7.30 (1H, s), 5.36 (2H, s), 4.19 (2H, m), 3.15 (1H, m), 2.87 (2H, m), 2.07 (2H, m), 1.70 (2H, m), 1.47 (9H, s).

Example 113

4-[4-(4-Pyrrol-1-yl-phenoxymethyl)-thiazol-2-yl]-piperidine-1-carboxylic acid tert-butyl ester

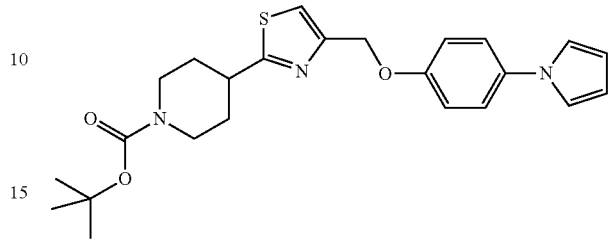

¹H NMR (CDCl₃): δ 7.24 (3H, m), 7.01 (4H, m), 6.31 (2H, m), 5.17 (2H, s), 4.21 (2H, m), 3.14 (1H, m), 2.87 (2H, m), 2.01 (2H, m), 1.74 (2H, m), 1.47 (9H, s).

Example 114

4-{4-[(4-Tetrazol-1-yl-phenylamino)-methyl]-thiazol-2-yl}-piperidine-1-carboxylic acid tert-butyl ester

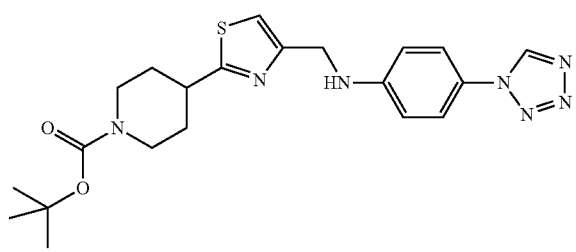 [SMILES: CC(C)(C)OC(=O)N1CCC(c2nc(CNc3ccc(-n4cnnn4)cc3)cs2)CC1]

¹H NMR (CDCl₃): δ 8.85 (1H, s), 7.40 (2H, m), 7.01 (1H, s), 6.72 (2H, m), 4.76 (1H, s), 4.44 (2H, s), 4.15 (2H, m), 3.08 (1H, m), 2.83 (2H, m), 2.04 (2H, m), 1.66 (2H, m), 1.43 (9H, s).

Example 115

2-{4-[4-(3-Chloro-4-tetrazol-1-yl-phenoxymethyl)-thiazol-2-yl]-piperidin-1-yl}-5-ethyl-pyrimidine

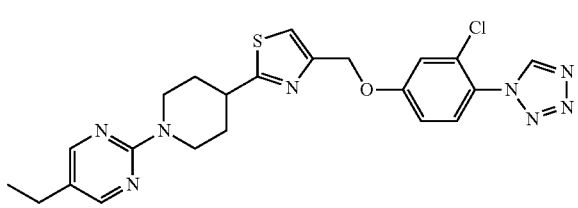 [SMILES: CCc1cnc(N2CCC(c3nc(COc4ccc(-n5cnnn5)c(Cl)c4)cs3)CC2)nc1]

¹H NMR (CDCl₃): δ 8.93 (1H, s), 8.18 (2H, s), 7.48 (1H, m), 7.25 (1H, s), 7.08 (2H, m), 5.22 (2H, s), 4.82 (2H, m), 3.29 (1H, m), 3.04 (2H, m), 2.46 (2H, q), 2.21 (2H, m), 1.80 (2H, m), 1.18 (3H, t).

Example 116

N-(4-{2-[1-(5-Ethyl-pyrimidin-2-yl)-piperidin-4-yl]-thiazol-4-ylmethoxy}-phenyl)-formamide

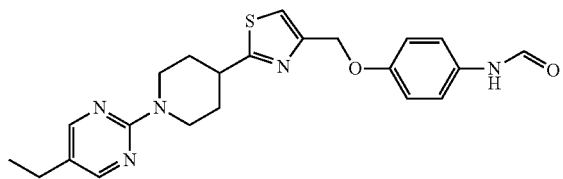 [SMILES: CCc1cnc(N2CCC(c3nc(COc4ccc(NC=O)cc4)cs3)CC2)nc1]

¹H NMR (CDCl₃): δ 8.55-8.30 (1H, m), 8.18 (2H, s), 7.50-6.90 (6H, m), 5.14 (2H, s), 4.83 (2H, m), 3.29 (1H, m), 3.03 (2H, m), 2.46 (2H, q), 2.20 (2H, m), 1.80 (2H, m), 1.19 (3H, t).

Example 117

N-(4-{2-[1-(5-Ethyl-pyrimidin-2-yl)-piperidin-4-yl]-thiazol-4-ylmethoxy}-phenyl)-methanesulfonamide

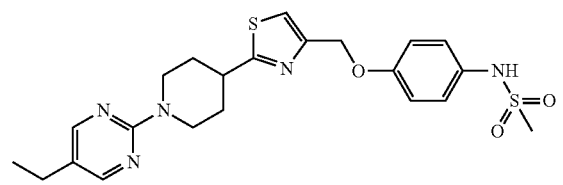 [SMILES: CCc1cnc(N2CCC(c3nc(COc4ccc(NS(C)(=O)=O)cc4)cs3)CC2)nc1]

¹H NMR (CDCl₃): δ 8.20 (s, 2H), 7.21 (m, 3H), 6.95 (m, 2H), 5.13 (s, 2H), 4.81 (m, 2H), 3.29 (m, 1H), 3.06 (m, 2H), 2.94 (s, 3H), 2.47 (q, 2H), 2.20 (m, 2H), 1.81 (m, 2H), 1.19 (t, 3H).

Example 118

4-[4-(2-Methyl-4-tetrazol-1-yl-phenoxymethyl)-thiazol-2-yl]-piperidine-1-carboxylic acid tert-butyl ester

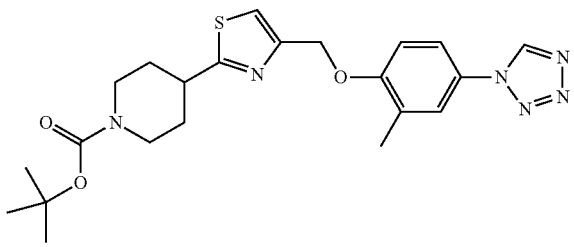 [SMILES: Cc1cc(-n2cnnn2)ccc1OCc1csc(C2CCN(C(=O)OC(C)(C)C)CC2)n1]

¹H NMR (CDCl₃): δ 8.89 (1H, s), 7.48 (1H, s), 7.43 (1H, m), 7.25 (1H, m), 7.05 (1H, m), 5.27 (2H, s), 4.27 (2H, m), 3.18 (1H, m), 2.89 (2H, m), 2.37 (3H, s), 2.21 (2H, m), 1.74 (2H, m), 1.47 (9H, s).

Example 119

5-Ethyl-2-{4-[4-(4-tetrazol-1-yl-2-trifluoromethyl-phenoxymethyl)-thiazol-2-yl]-piperidin-1-yl}-pyrimidine

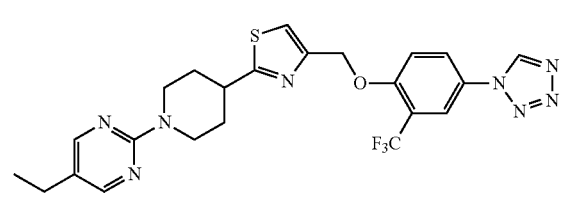

¹H NMR (CDCl₃): δ 8.97 (1H, s), 8.18 (2H, s), 7.92 (1H, m), 7.84 (1H, m), 7.33 (1H, m), 7.26 (1H, s), 5.38 (2H, s), 4.81 (2H, m), 3.27 (1H, m), 3.05 (2H, m), 2.46 (2H, q), 2.19 (2H, m), 1.79 (2H, m), 1.19 (3H, t).

Example 120

2-{4-[4-(2-Chloro-4-tetrazol-1-yl-phenoxymethyl)-thiazol-2-yl]-piperidin-1-yl}-5-ethyl-pyrimidine

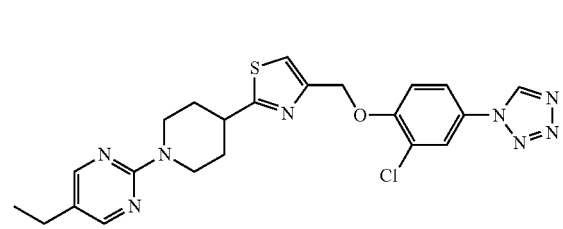 [SMILES: CCc1cnc(N2CCC(c3nc(COc4ccc(-n5cnnn5)cc4Cl)cs3)CC2)nc1]

¹H NMR (acetone-d₆), δ 9.68 (1H, s), 8.24 (2H, s), 8.01 (1H, s), 7.86 (1H, m), 7.60 (1H, m), 7.59 (1H, s), 5.40 (2H, s), 4.82 (2H, m), 3.36 (1H, m), 3.08 (2H, m), 2.48 (2H, q), 2.17 (2H, m), 1.75 (2H, m), 1.18 (3H, t).

Example 121

4-[4-(4-Tetrazol-1-yl-phenoxymethyl)-oxazol-2-yl]-piperidine-1-carboxylic acid tert-butyl ester

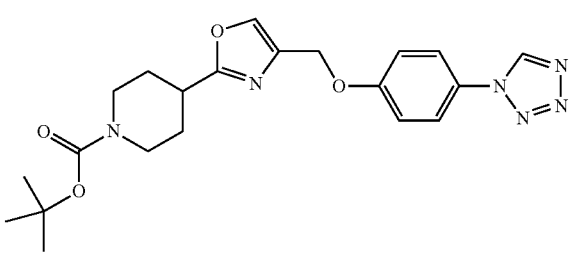 [SMILES: CC(C)(C)OC(=O)N1CCC(c2nc(COc3ccc(-n4cnnn4)cc3)co2)CC1]

¹H NMR (CDCl₃): δ 8.94 (1H, s), 7.65 (1H, s), 7.60 (2H, m), 7.13 (2H, m), 5.01 (2H, s), 4.08 (2H, m), 2.94 (3H, m), 2.03 (2H, m), 1.75 (2H, m), 1.43 (9H, s).

Example 122

4-[4-(2-Fluoro-4-tetrazol-1-yl-phenoxymethyl)-oxazol-2-yl]-piperidine-1-carboxylic acid tert-butyl ester

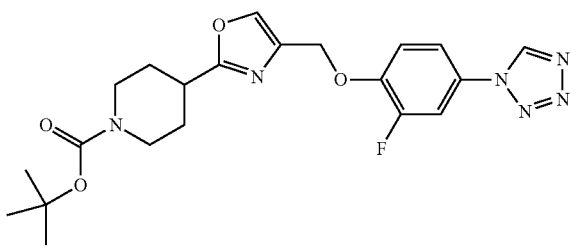

$^1$H NMR (CDCl$_3$): δ 8.88 (1H, s), 7.62 (1H, s), 7.45 (1H, m), 7.36 (1H, m), 7.23 (1H, m), 5.05 (2H, s), 4.04 (2H, m), 2.85 (3H, m), 1.97 (2H, m), 1.71 (2H, m), 1.40 (9H, s).

Example 123

5-Ethyl-2-{4-[4-(4-methanesulfonyl-phenoxymethyl)-oxazol-2-yl]-piperidin-1-yl}-pyrimidine

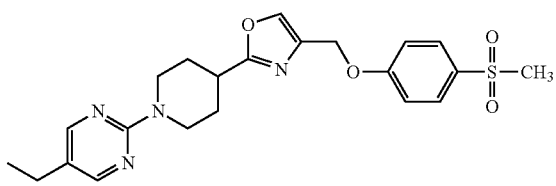 [SMILES: CCc1cnc(N2CCC(c3nc(COc4ccc(S(C)(=O)=O)cc4)co3)CC2)nc1]

$^1$H NMR (CDCl$_3$): δ 8.16 (2H, s), 7.84 (2H, m), 7.63 (1H, s), 7.08 (2H, m), 5.02 (2H, s), 4.67 (2H, m), 3.08 (3H, m), 3.01 (3H, s), 2.44 (2H, q), 2.12 (2H, m), 1.84 (2H, m), 1.17 (3H, t).

Example 124

4-[4-(2,6-Difluoro-4-propionyl-phenoxymethyl)-thiazol-2-yl]-piperidine-1-carboxylic acid tert-butyl ester

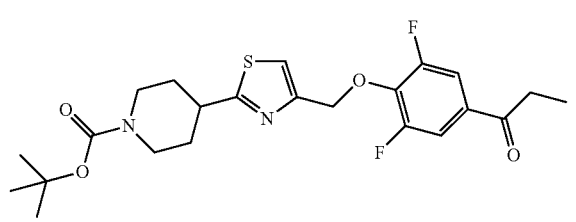 [SMILES: CCC(=O)c1cc(F)c(OCc2csc(C3CCN(C(=O)OC(C)(C)C)CC3)n2)c(F)c1]

$^1$H NMR (CDCl$_3$): δ 7.51 (2H, d), 7.27 (1H, s), 5.37 (2H, s), 4.18 (2H, m), 3.14 (1H, m), 2.92 (2H, q, J=7.4 Hz), 2.88 (2H, m), 2.07 (2H, m), 1.71 (2H, m), 1.47 (9H, s), 1.21 (3H, t, J=7.4 Hz).

Example 125

4-[4-(4-Acetyl-2-fluoro-phenoxymethyl)-thiazol-2-yl]-piperidine-1-carboxylic acid tert-butyl ester

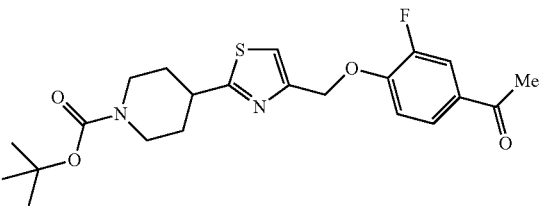 [SMILES: CC(=O)c1ccc(OCc2csc(C3CCN(C(=O)OC(C)(C)C)CC3)n2)c(F)c1]

$^1$H NMR (CDCl$_3$): δ 7.70~7.72 (2H, m), 7.28 (1H, s), 7.09~7.13 (1H, m), 5.30 (2H, s), 4.20 (2H, m), 3.17 (1H, m), 2.88 (2H, m), 2.55 (3H, s), 2.10 (2H, m), 1.72 (2H, m), 1.47 (9H, s).

Example 126

4-[4-(4-Cyano-2-fluoro-phenoxymethyl)-thiazol-2-yl]-piperidine-1-carboxylic acid tert-butyl ester

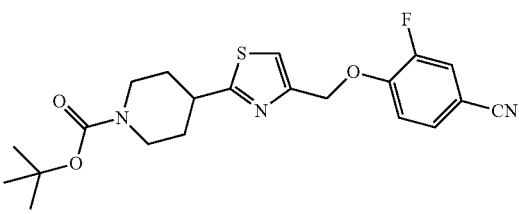 [SMILES: CC(C)(C)OC(=O)N1CCC(c2nc(COc3ccc(C#N)cc3F)cs2)CC1]

$^1$H NMR (CDCl$_3$): δ 7.37-7.42 (2H, m), 7.27 (1H, s), 7.13~7.17 (1H, m), 5.28 (2H, s), 4.20 (2H, m), 3.15 (1H, m), 2.89 (2H, m), 2.09 (2H, m), 1.72 (2H, m), 1.47 (9H, s).

Example 127

4-[4-(6-Tetrazol-1-yl-pyridin-3-yloxymethyl)-thiazol-2-yl]-piperidine-1-carboxylic acid tert-butyl ester

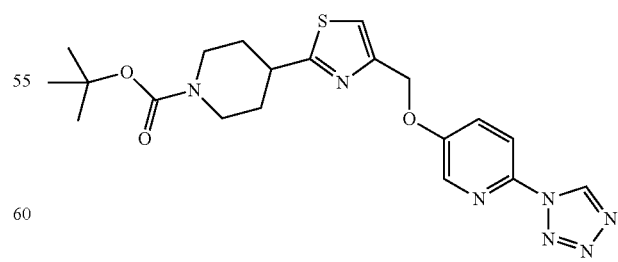

$^1$H NMR (CDCl$_3$): δ 9.41 (1H, s), 8.27 (1H, d), 8.01 (1H, d), 7.58 (1H, dd), 7.28 (1H, s), 5.27 (2H, s), 4.20 (2H, m), 3.14-3.20 (1H, m), 2.87 (2H, m), 2.09-2.12 (2H, m), 1.68-1.78 (2H, m), 1.46 (9H, s)

Example 128

4-[4-(4-[1,2,3]Triazol-1-yl-phenoxymethyl)-thiazol-2-yl]-piperidine-1-carboxylic acid tert-butyl ester

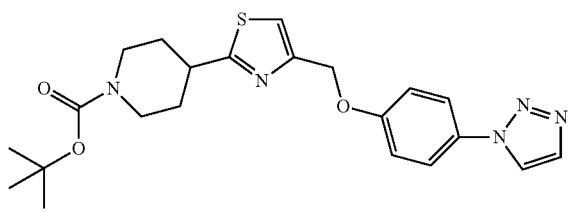 [SMILES: CC(C)(C)OC(=O)N1CCC(c2nc(COc3ccc(-n4ccnn4)cc3)cs2)CC1]

¹H NMR (CDCl₃): δ 7.92 (1H, s), 7.84 (1H, s), 7.65 (2H, d), 7.25 (1H, s), 7.11 (2H, d), 5.22 (2H, s), 4.21 (2H, br), 3.18 (1H, m), 2.88 (2H, br), 2.12 (2H, m), 1.75 (2H, m), 1.47 (9H, s).

Example 129

4-[4-(4-Ethoxycarbonyl-phenoxymethyl)-thiazol-2-yl]-piperidine-1-carboxylic acid tert-butyl ester

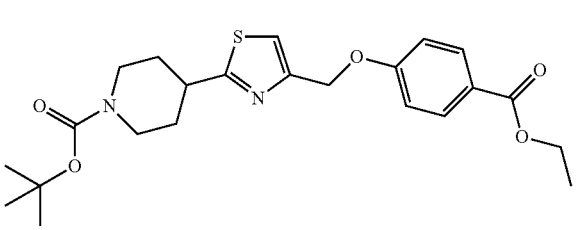 [SMILES: CCOC(=O)c1ccc(OCc2csc(C3CCN(C(=O)OC(C)(C)C)CC3)n2)cc1]

¹H NMR (CDCl₃): δ 8.01 (2H, d), 7.23 (1H, s), 7.01 (2H, d), 5.22 (2H, s), 4.36 (2H, q), 4.22 (2H, br), 3.17 (1H, m), 2.87 (2H, br), 2.12 (2H, m), 1.75 (2H, m), 1.47 (9H, s), 1.39 (2H, t).

Example 130

4-[4-(4-tert-Butoxycarbonylamino-phenoxymethyl)-thiazol-2-yl]-piperidine-1-carboxylic acid tert-butyl ester

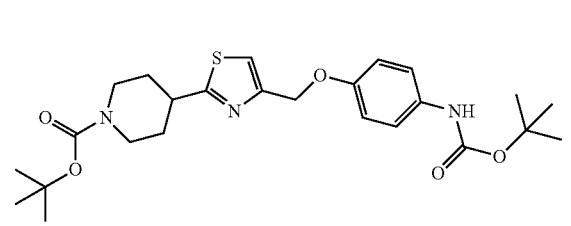 [SMILES: CC(C)(C)OC(=O)Nc1ccc(OCc2csc(C3CCN(C(=O)OC(C)(C)C)CC3)n2)cc1]

¹H NMR (CDCl₃): δ 7.28 (2H, d), 7.19 (1H, s), 6.92 (2H, d), 6.40 (1H, s), 5.12 (2H, s), 4.22 (2H, br), 3.17 (1H, m), 2.87 (2H, br), 2.12 (2H, m), 1.75 (2H, m), 1.50 (9H, s), 1.47 (9H, s).

Example 131

4-[4-(4-Carboxy-phenoxymethyl)-thiazol-2-yl]-piperidine-1-carboxylic acid tert-butyl ester

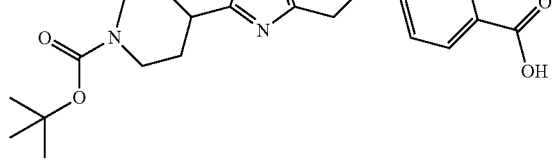

¹H NMR (DMSO-d₆): δ 7.86 (2H, d), 7.64 (1H, s), 7.10 (2H, d), 5.17 (2H, s), 3.96 (2H, m), 3.18 (1H, m), 2.87 (2H, br), 1.96 (2H, m), 1.49 (2H, m), 1.38 (9H, s).

Example 132

4-[4-(2,6-Difluoro-4-methanesulfonyl-phenoxymethyl)-thiazol-2-yl]-piperidine-1-carboxylic acid tert-butyl ester

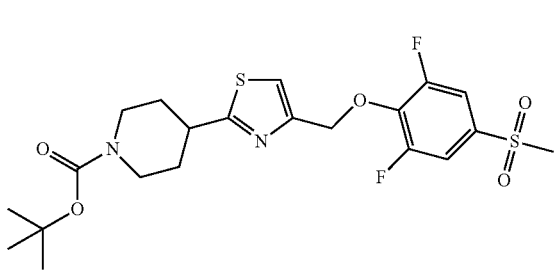 [SMILES: CC(C)(C)OC(=O)N1CCC(c2nc(COc3c(F)cc(S(C)(=O)=O)cc3F)cs2)CC1]

¹H NMR (CDCl₃): δ 7.42 (2H, d), 7.21 (1H, s), 5.25 (2H, s), 4.12 (2H, br), 3.17 (1H, m), 3.00 (3H, s), 2.87 (2H, br), 1.98 (2H, m), 1.71 (2H, m).

Example 133

4-[4-(4-Morpholin-4-yl-phenoxymethyl)-thiazol-2-yl]-piperidine-1-carboxylic acid tert-butyl ester

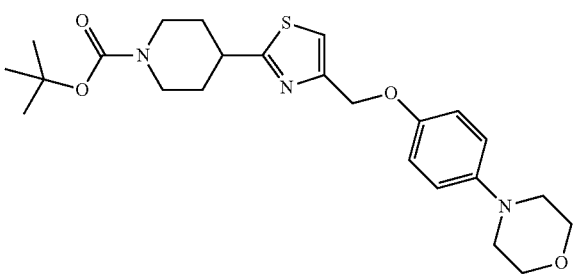 [SMILES: CC(C)(C)OC(=O)N1CCC(c2nc(COc3ccc(N4CCOCC4)cc3)cs2)CC1]

¹H NMR (CDCl₃): δ 7.19 (1H, s), 6.92 (4H, m), 5.12 (2H, s), 4.20 (2H, br), 3.85 (4H, br), 3.16 (1H, m), 3.07 (4H, m), 2.86 (2H, m), 2.10 (2H, m), 1.72 (2H, m), 1.47 (9H, s).

Example 134

4-[4-(4-Trifluoromethylsulfanyl-phenoxymethyl)-thiazol-2-yl]-piperidine-1-carboxylic acid tert-butyl ester

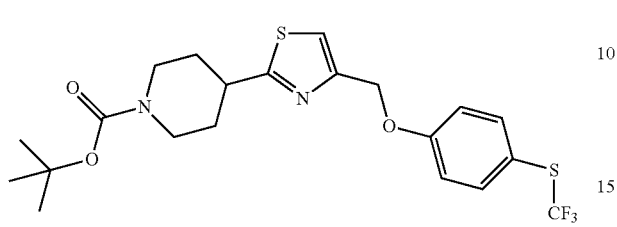

$^1$H NMR (DMSO-d$_6$): δ 7.64 (1H, s), 7.63 (2H, d, J=8.6 Hz), 7.17 (2H, d, J=8.6 Hz), 5.17 (2H, s), 3.99 (2H, m), 3.18 (1H, m), 2.83 (2H, m), 2.01 (2H, m), 1.52 (2H, m), 1.38 (9H, s).

Example 135

4-[4-(4-Benzyloxy-phenoxymethyl)-thiazol-2-yl]-piperidine-1-carboxylic acid tert-butyl ester

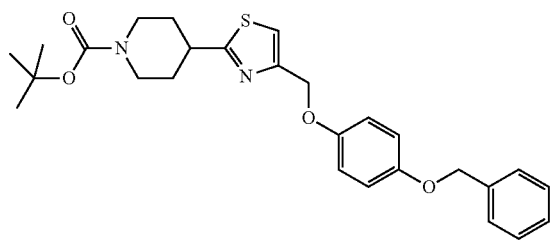 [SMILES: CC(C)(C)OC(=O)N1CCC(c2nc(COc3ccc(OCc4ccccc4)cc3)cs2)CC1]

$^1$H NMR (DMSO-d$_6$): δ 7.55 (1H, s), 7.41 (5H, m), 6.92 (4H, m), 5.12 (4H, s), 3.98 (2H, m), 3.20 (1H, m), 2.84 (2H, m), 2.01 (2H, m), 1.52 (2H, m), 1.38 (9H, s).

Example 136

4-[4-(2-Acetylamino-4-methanesulfonyl-phenoxymethyl)-thiazol-2-yl]-piperidine-1-carboxylic acid tert-butyl ester

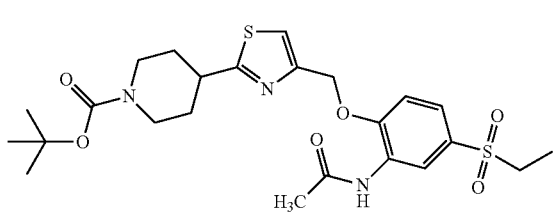 [SMILES: CCS(=O)(=O)c1ccc(OCc2csc(C3CCN(C(=O)OC(C)(C)C)CC3)n2)c(NC(C)=O)c1]

$^1$H NMR (CDCl$_3$): δ 8.81 (1H, s), 7.97 (1H, s), 7.53 (1H, d), 7.25 (1H, s), 7.09 (1H, d), 5.24 (2H, s), 4.16 (2H, m), 3.10 (3H, m), 2.83 (2H, m), 2.16 (3H, m), 2.04 (2H, d), 1.66 (2H, m), 1.40 (9H, s), 1.19 (3H, t).

Example 137

4-(4-Phenoxymethyl-thiazol-2-yl)-piperidine-1-carboxylic acid tert-butyl ester

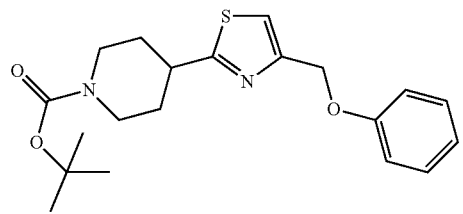 [SMILES: CC(C)(C)OC(=O)N1CCC(c2nc(COc3ccccc3)cs2)CC1]

$^1$H NMR (CDCl$_3$): δ 7.28 (2H, m), 7.19 (1H, s), 6.93 (3H, m), 5.14 (2H, s), 4.19 (2H, s), 3.15 (1H, m), 2.85 (2H, m), 2.07 (2H, d), 1.67 (2H, m), 1.45 (9H, s).

Example 138

4-{4-[(4-Methanesulfonyl-phenylamino)-methyl]-thiazol-2-yl}-piperidine-1-carboxylic acid tert-butyl ester

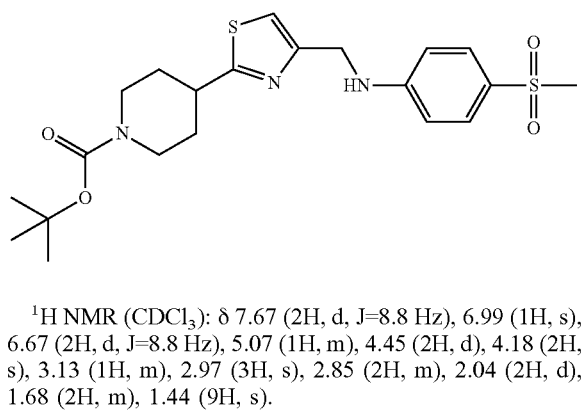

$^1$H NMR (CDCl$_3$): δ 7.67 (2H, d, J=8.8 Hz), 6.99 (1H, s), 6.67 (2H, d, J=8.8 Hz), 5.07 (1H, m), 4.45 (2H, d), 4.18 (2H, s), 3.13 (1H, m), 2.97 (3H, s), 2.85 (2H, m), 2.04 (2H, d), 1.68 (2H, m), 1.44 (9H, s).

Example 139

4-{4-[(2-Fluoro-4-methanesulfonyl-phenylamino)-methyl]-thiazol-2-yl}-piperidine-1-carboxylic acid isopropyl ester

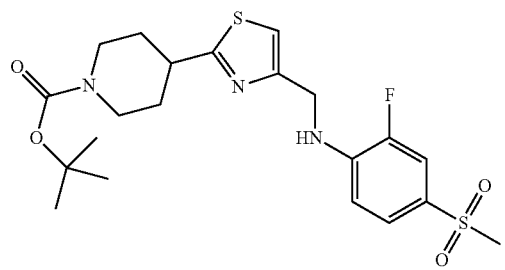 [SMILES: CC(C)(C)OC(=O)N1CCC(c2nc(CNc3ccc(S(C)(=O)=O)cc3F)cs2)CC1]

$^1$H NMR (CDCl$_3$): δ 7.55 (2H, m), 7.05 (1H, s), 6.76 (1H, m), 5.12 (1H, m), 4.52 (2H, d), 4.19 (2H, m), 3.13 (1H, m), 3.05 (3H, s), 2.86 (2H, m), 2.10 (2H, m), 1.76 (2H, m), 1.46 (9H, s).

Example 140

4-[4-(4-Bromo-phenoxymethyl)-thiazol-2-yl]-piperidine-1-carboxylic acid tert-butyl ester

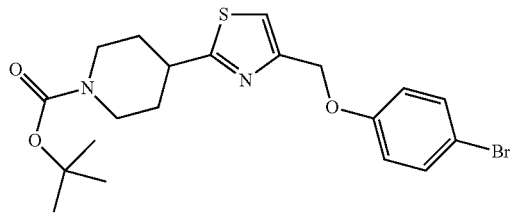 [SMILES: CC(C)(C)OC(=O)N1CCC(c2nc(COc3ccc(Br)cc3)cs2)CC1]

$^1$H NMR (CDCl$_3$): δ 7.36 (2H, m), 7.17 (1H, s), 6.82 (2H, m), 5.10 (2H, s), 4.18 (2H, s), 3.13 (1H, m), 2.85 (2H, m), 2.09 (2H, d), 1.75 (2H, m), 1.43 (9H, s).

Example 141

{2-[1-(5-Ethyl-pyrimidin-2-yl)-piperidin-4-yl]-thiazol-4-ylmethyl}-(2-fluoro-4-methanesulfonyl-phenyl)-amine

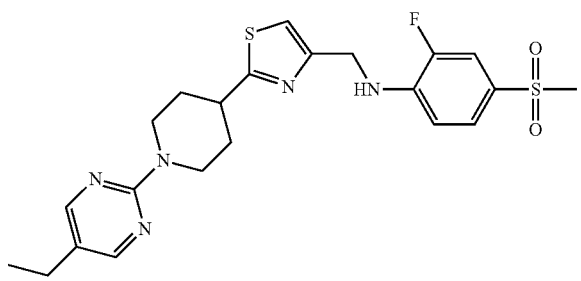 [SMILES: CCc1cnc(N2CCC(c3nc(CNc4ccc(S(C)(=O)=O)cc4F)cs3)CC2)nc1]

$^1$H NMR (CDCl$_3$): δ 8.16 (2H, s), 7.52 (2H, m), 7.01 (1H, s), 6.74 (1H, m), 5.15 (1H, m), 4.83 (2H, m), 4.51 (2H, d), 3.26 (1H, m), 3.02 (5H, m), 2.46 (2H, m), 2.19 (2H, m), 1.78 (2H, m), 1.19 (3H, t).

Example 142

4-{4-[(4-Methanesulfonyl-benzylamino)-methyl]-thiazol-2-yl}-piperidine-1-carboxylic acid tert-butyl ester

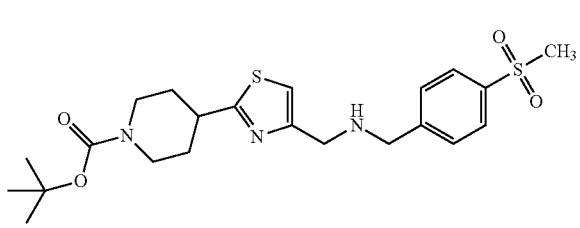 [SMILES: CC(C)(C)OC(=O)N1CCC(c2nc(CNCc3ccc(S(C)(=O)=O)cc3)cs2)CC1]

$^1$H NMR (CDCl$_3$): δ 7.85 (2H, d, J=8.8 Hz), 7.53 (2H, d, J=8.8 Hz), 6.95 (1H, s), 4.14 (2H, s), 3.87 (2H, s), 3.83 (2H, s), 3.11 (1H, m), 3.04 (3H, s), 2.86 (2H, m), 2.07 (3H, m), 1.67 (2H, m), 1.42 (9H, s).

Example 143

4-(4-{[1-(4-Methanesulfonyl-phenyl)-ethylamino]-methyl}-thiazol-2-yl)-piperidine-1-carboxylic acid tert-butyl ester

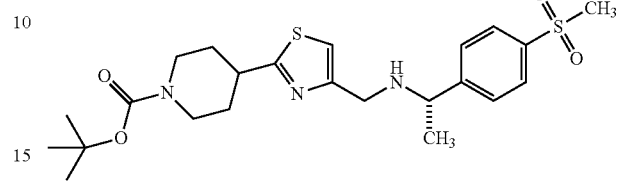

$^1$H NMR (CDCl$_3$): δ 7.87 (2H, d, J=8.8 Hz), 7.56 (2H, d, J=8.8 Hz), 6.87 (1H, s), 4.22 (2H, m), 3.90 (1H, s), 3.66 (2H, m), 3.09 (1H, m), 3.04 (3H, s), 2.82 (3H, m), 2.02 (2H, m), 1.71 (2H, m), 1.40 (9H, s), 1.29 (3H, d).

Example 144

3-Methyl-4-[4-(4-tetrazol-1-yl-phenoxymethyl)-thiazol-2-yl]-piperidine-1-carboxylic acid tert-butyl ester

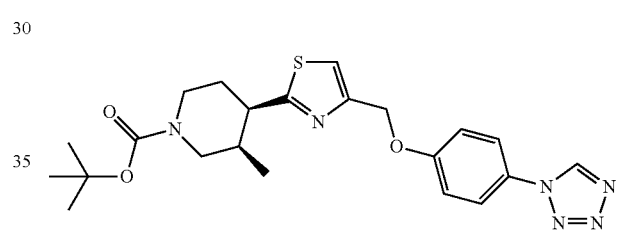

$^1$H NMR (CDCl$_3$): δ 8.93 (1H, s), 7.61 (2H, m), 7.25 (1H, m), 7.12 (2H, m), 5.22 (2H, m), 4.2 (1H, m), 3.95 (1H, m), 3.33 (1H, m), 3.13 (1H, m), 2.8 (1H, m), 2.34 (1H, m), 2.04 (1H, m), 1.89 (1H, m), 1.45 (9H, s), 0.85 (3H, m).

Example 145

4-[4-(2-Fluoro-4-tetrazol-1-yl-phenoxymethyl)-thiazol-2-yl]-3-methyl-piperidine-1-carboxylic acid tert-butyl ester

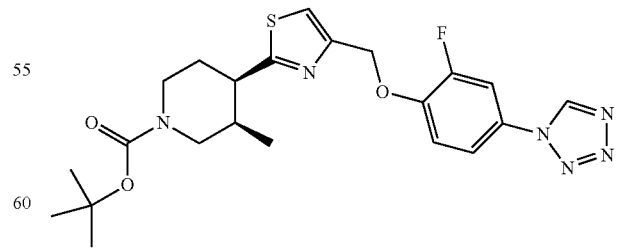

$^1$H NMR (CDCl$_3$): δ 9.07 (1H, s), 7.51 (1H, m), 7.41 (1H, m), 7.23 (2H, m), 5.25 (2H, s), 4.16 (1H, m), 3.88 (1H, m), 3.34 (1H, m), 3.09 (1H, m), 2.8 (1H, m), 2.26 (1H, m), 1.96 (1H, m), 1.83 (1H, m), 1.39 (9H, s), 0.76 (3H, m).

Examples 146-157 were synthesized from one of Intermediates 3-13 or Intermediates 15-25 with the corresponding sulfonyl chloride, alkyl chloride, alkyl bromide, chloroformate, acid chloride, carbamyl chloride or isocyanate in a manner similar to that described in Example 22. One skilled in the art of organic synthesis will appreciate that conditions such as solvent (e.g., DMF, CH₃CN); temperature, base (e.g., NEt₃, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 146

4-[4-(2-Fluoro-4-tetrazol-1-yl-phenoxymethyl)-thiazol-2-yl]-piperidine-1-carboxylic acid allyl ester

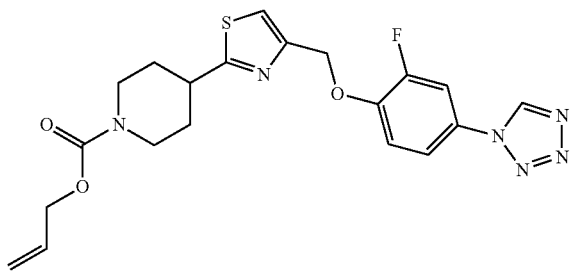 [SMILES: C=CCOC(=O)N1CCC(c2nc(COc3ccc(-n4cnnn4)cc3F)cs2)CC1]

¹H NMR (CDCl₃), δ 9.00 (1H, s), 7.54 (1H, m), 7.45 (1H, m), 7.29 (2H, m), 5.95 (1H, m), 5.30 (3H, m), 5.22 (1H, m), 4.61 (2H, m), 4.28 (2H, m), 3.20 (1H, m), 2.98 (2H, m), 2.14 (2H, m), 1.78 (2H, m).

Example 147

4-[4-(4-Tetrazol-1-yl-phenoxymethyl)-thiazol-2-yl]-piperidine-1-carboxylic acid cyclohexyl ester

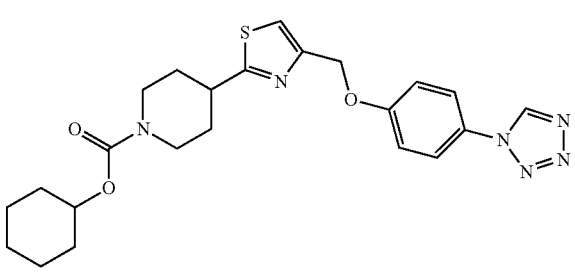 [SMILES: O=C(OC1CCCCC1)N1CCC(c2nc(COc3ccc(-n4cnnn4)cc3)cs2)CC1]

¹H NMR (CDCl₃): δ 8.91 (1H, s), 7.60 (2H, m), 7.25 (1H, s), 7.16 (2H, m), 5.22 (2H, s), 4.68 (1H, m), 4.36 (2H, m), 3.19 (1H, m), 2.91 (2H, m), 2.12 (2H, m), 1.88 (6H, m), 1.40 (6H, m).

Example 148

4-[4-(2-Fluoro-4-methanesulfonyl-phenoxymethyl)-thiazol-2-yl]-piperidine-1-carboxylic acid isopropyl ester ¹H NMR (CDCl₃): δ 7.64~7.70 (2H, m), 7.20~7.26 (2H, m), 5.29 (2H, s), 4.89~4.95 (1H, m), 4.24 (2H, m), 3.13-3.19 (1H, m), 3.03 (3H, s), 2.86~2.93 (2H, m), 2.11 (2H, m), 1.69-1.78 (2H, m), 1.23 (6H, d, J=6.4 Hz).

Example 149

1-Isopropyl-4-[4-(4-tetrazol-1-yl-phenoxymethyl)-thiazol-2-yl]-piperidine

¹H NMR (DMSO-d₆): δ 9.98 (1H, s), 7.79 (2H, d, =8.8 Hz), 7.63 (1H, s), 7.28 (2H, d, J=8.8 Hz), 5.19 (2H, s), 2.91 (1H, m), 2.82 (2H, m), 2.68 (1H, m), 2.20 (2H, m), 2.01 (2H, m), 1.63 (2H, m), 0.94 (6H, d, J=6.4 Hz).

Example 150

1-Propyl-4-[4-(4-tetrazol-1-yl-phenoxymethyl)-thiazol-2-yl]-piperidine

¹H NMR (DMSO-d₆): δ 9.97 (1H, s), 7.80 (2H, d, J=8.8 Hz), 7.64 (1H, s), 7.28 (2H, d, J=8.8 Hz), 5.20 (2H, s), 2.94 (1H, m), 2.88 (2H, m), 2.22 (2H, t, J=7.2 Hz), 1.99 (4H, m), 1.64 (2H, m), 1.41 (2H, m), 0.83 (3H, t, J=7.2 Hz).

Example 151

3,3-Dimethyl-1-{4-[4-(4-tetrazol-1-yl-phenoxymethyl)-thiazol-2-yl]-piperidin-1-yl}-butan-2-one

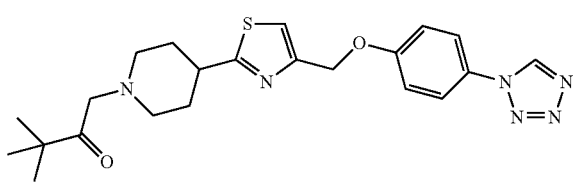 [SMILES: CC(C)(C)C(=O)CN1CCC(c2nc(COc3ccc(-n4cnnn4)cc3)cs2)CC1]

¹H NMR (DMSO-d₆): δ 9.98 (1H, s), 7.80 (2H, d, J=8.8 Hz), 7.64 (1H, s), 7.28 (2H, d, J=8.8 Hz), 5.20 (2H, s), 3.41 (2H, s), 2.95 (1H, m), 2.82 (2H, m), 2.18 (2H, m), 1.98 (2H, m), 1.69 (2H, m), 1.07 (9H, s).

Example 152

1-Butyl-4-[4-(4-tetrazol-1-yl-phenoxymethyl)-thiazol-2-yl]-piperidine

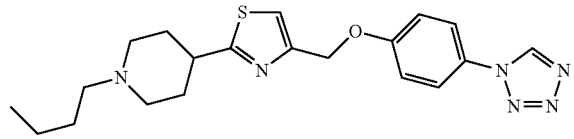 [SMILES: CCCCN1CCC(c2nc(COc3ccc(-n4cnnn4)cc3)cs2)CC1]

¹H NMR (DMSO-d₆): δ 9.97 (1H, s), 7.80 (2H, d, J=8.8 Hz), 7.64 (1H, s), 7.28 (2H, d, J=8.8 Hz), 5.20 (2H, s), 2.94 (1H, m), 2.88 (2H, m), 2.26 (2H, t, J=6.8 Hz), 1.98 (4H, m), 1.66 (2H, m), 1.39 (2H, m), 1.26 (2H, m), 0.86 (3H, t, J=7.2 Hz).

Example 153

2-{4-[4-(4-Tetrazol-1-yl-phenoxymethyl)-thiazol-2-yl]-piperidin-1-yl}-1-(4-trifluoromethoxy-phenyl)-ethanone

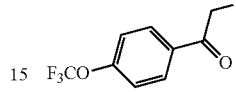

¹H NMR (DMSO-d₆): δ 9.97 (1H, s), 8.14 (2H, d, J=6.4 Hz), 8.02 (2H, d, J=6.4 Hz), 7.80 (2H, d, J=8.8 Hz), 7.64 (1H, s), 7.28 (2H, d, J=8.8 Hz), 5.20 (2H, s), 3.84 (2H, s), 2.98 (1H, m), 2.93 (2H, m), 2.38 (2H, m), 2.00 (2H, m), 1.68 (2H, m).

Example 154

1-Methanesulfonyl-4-[4-(4-tetrazol-1-yl-phenoxymethyl)-thiazol-2-yl]-piperidine

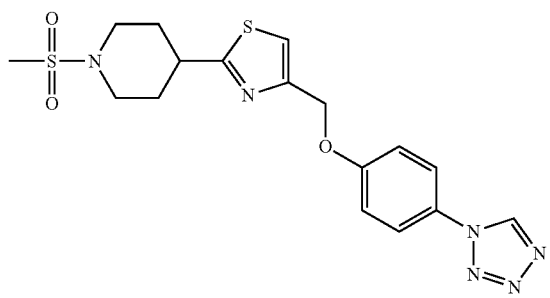 [SMILES: CS(=O)(=O)N1CCC(c2nc(COc3ccc(-n4cnnn4)cc3)cs2)CC1]

¹H NMR (DMSO-d₆): δ 9.98 (1H, s), 7.81 (2H, d, J=8.8 Hz), 7.69 (1H, s), 7.29 (2H, d, J=8.8 Hz), 5.21 (2H, s), 3.60-3.63 (2H, m), 3.32 (3H, s), 3.12-3.18 (1H, m), 2.83-2.90 (2H, m), 2.14-2.17 (2H, m), 1.71 (2H, m).

Example 155

4-[4-(4-Tetrazol-1-yl-phenoxymethyl)-thiazol-2-yl]-piperidine-1-carboxylic acid heptyl ester

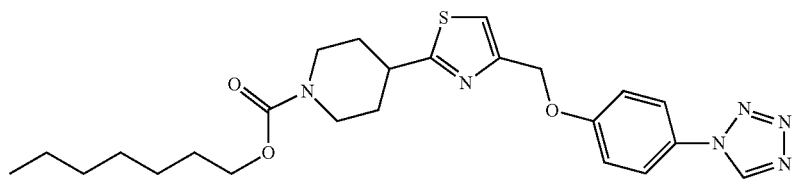 [SMILES: CCCCCCCOC(=O)N1CCC(c2nc(COc3ccc(-n4cnnn4)cc3)cs2)CC1]

¹H NMR (CDCl₃): δ 8.91 (1H, s), 7.60 (2H, d), 7.25 (1H, s), 7.19 (2H, d), 5.24 (2H, s), 4.26 (2H, br), 4.09 (2H, t), 3.20 (1H, m), 2.94 (2H, m), 2.16 (2H, m), 1.77 (2H, m), 1.60 (2H, m), 1.32 (8H, m), 0.90 (3H, t).

Example 156

4-[4-(4-Tetrazol-1-yl-phenoxymethyl)-thiazol-2-yl]-1-(toluene-4-sulfonyl)-piperidine

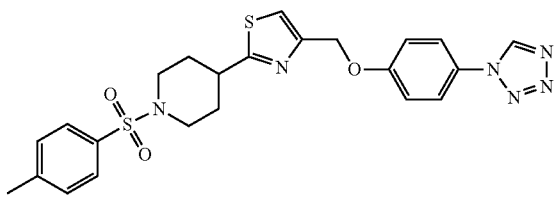 [SMILES: Cc1ccc(S(=O)(=O)N2CCC(c3nc(COc4ccc(-n5cnnn5)cc4)cs3)CC2)cc1]

¹H NMR (CDCl₃): δ 8.91 (1H, s), 7.67 (2H, d, J=8.8 Hz), 7.59 (2H, d, J=8.8 Hz), 7.35 (2H, d, J=8.8 Hz), 7.25 (1H, s), 7.15 (2H, m), 5.19 (2H, s), 3.91 (2H, d), 2.95 (1H, m), 2.44 (3H, s), 2.37 (2H, m), 2.17 (2H, d), 1.94 (2H, m).

Example 157

2-tert-Butoxy-1-{4-[4-(4-tetrazol-1-yl-phenoxymethyl)-thiazol-2-yl]-piperidin-1-yl}-ethanone

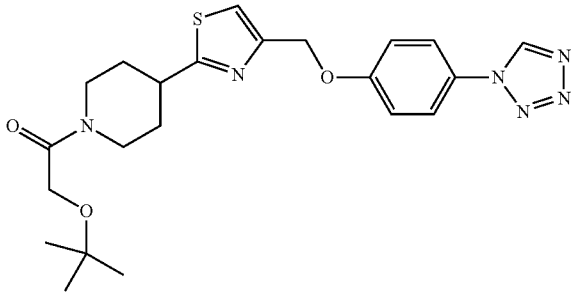 [SMILES: CC(C)(C)OCC(=O)N1CCC(c2nc(COc3ccc(-n4cnnn4)cc3)cs2)CC1]

¹H NMR (DMSO-d₆): δ 9.99 (1H, s), 7.81 (2H, m), 7.26 (2H, m), 5.20 (2H, s), 4.36 (1H, m), 3.97 (3H, m), 3.28 (1H, m), 3.12 (1H, m), 2.71 (1H, m), 2.04 (2H, m), 1.67 (1H, m), 1.46 (1H, m), 1.13 (9H, s).

Examples 158-205 were synthesized from one of Intermediates 3-13 or Intermediates 15-25 with the corresponding 2-chloropyrimidine, 2-iodopyrimidine, 2-chloropyridine, 2-fluoropyridine, 2-methanesulfonyl-pyrimidine, 2-chloropyrazine, 2-chloropyridazine or other suitable heterocycles in a manner similar to that described in Example 47. One skilled in the art of organic synthesis will appreciate that conditions such as solvent (such as DMF, CH₃CN); temperature, base (such as NEt₃, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 158

5-Ethyl-2-{4-[4-(3-fluoro-4-tetrazol-1-yl-phenoxymethyl)-thiazol-2-yl]-piperidin-1-yl}-pyrimidine

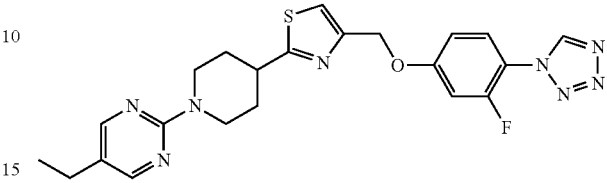

¹H NMR (CDCl₃): δ 9.04 (1H, s), 8.19 (2H, s), 7.78 (1H, m), 7.28 (1H, s), 6.70 (2H, m), 5.23 (2H, s), 4.83 (2H, m), 3.31 (1H, m), 3.05 (2H, m), 2.47 (2H, q), 2.21 (2H, m), 1.81 (2H, m), 1.20 (3H, t).

Example 159

2-{4-[4-(2,6-Difluoro-4-tetrazol-1-yl-phenoxymethyl)-thiazol-2-yl]-piperidin-1-yl}-5-ethyl-pyrimidine

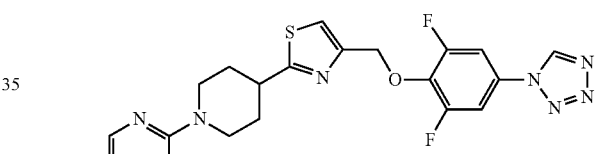

¹H NMR (CDCl₃): δ 8.95 (1H, s), 8.17 (2H, s), 7.34 (2H, m), 7.28 (1H, s), 5.35 (2H, s), 4.76 (2H, m), 3.27 (1H, m), 3.04 (2H, m), 2.46 (2H, q), 2.16 (2H, m), 1.76 (2H, m), 1.19 (3H, t).

Example 160

5-Ethyl-2-{4-[4-(4-pyrrol-1-yl-phenoxymethyl)-thiazol-2-yl]-piperidin-1-yl}-pyrimidine

¹H NMR (CDCl₃): δ 8.18 (2H, s), 7.29 (2H, m), 7.20 (1H, s), 6.99 (4H, m), 6.31 (2H, m), 5.17 (2H, s), 4.84 (2H, m), 3.28 (1H, m), 3.03 (2H, m), 2.46 (2H, q), 2.21 (2H, m), 1.81 (2H, m), 1.19 (3H, t).

Example 161

{2-[1-(5-Ethyl-pyrimidin-2-yl)-piperidin-4-yl]-thiazol-4-ylmethyl}-(4-tetrazol-1-yl-phenyl)-amine

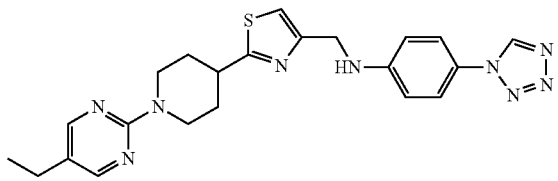

$^1$H NMR (CDCl$_3$): δ 8.83 (1H, s), 8.16 (2H, s), 7.41 (2H, m), 7.02 (1H, s), 6.74 (2H, m), 4.82 (1H, s), 4.79 2H, s), 4.45 (2H, m), 3.25 (1H, m), 3.01 (2H, m), 2.44 (2H, q), 2.17 (2H, m), 1.77 (2H, m), 1.11 (3H, t).

Example 162

2-{4-[4-(2-Fluoro-4-tetrazol-1-yl-phenoxymethyl)-thiazol-2-yl]-piperidin-1-yl}-5-isopropyl-pyrimidine

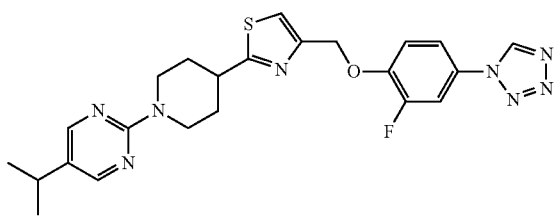 [SMILES: CC(C)c1cnc(N2CCC(c3nc(COc4ccc(-n5cnnn5)cc4F)cs3)CC2)nc1]

$^1$H NMR (CDCl$_3$): δ 8.92 (1H, s), 8.21 (2H, s), 7.51 (1H, m), 7.40 (1H, m), 7.29 (1H, s), 7.26 (1H, m), 5.30 (2H, s), 4.82 (2H, m), 3.28 (1H, m), 3.04 (2H, m), 2.77 (1H, m), 2.20 (2H, m), 1.80 (2H, m), 1.23 (6H, d).

Example 163

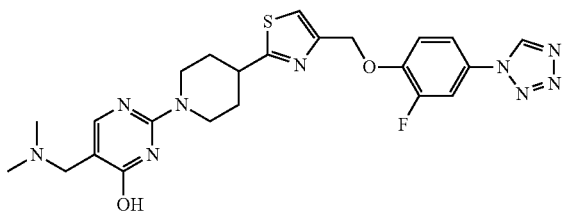 [SMILES: CN(C)Cc1cnc(N2CCC(c3nc(COc4ccc(-n5cnnn5)cc4F)cs3)CC2)nc1O]

$^1$H NMR (CDCl$_3$): δ 8.97 (1H, s), 7.80 (1H, s), 7.50 (1H, m), 7.40 (1H, m), 7.27 (1H, s), 7.24 (1H, m), 5.27 (2H, s), 4.42 (4H, m), 3.24 (1H, m), 3.04 (9H, m), 2.16 (2H, m), 1.88 (2H, m).

Example 164

5-Ethyl-2-{4-[4-(2-methyl-4-tetrazol-1-yl-phenoxymethyl)-thiazol-2-yl]-piperidin-1-yl}-pyrimidine

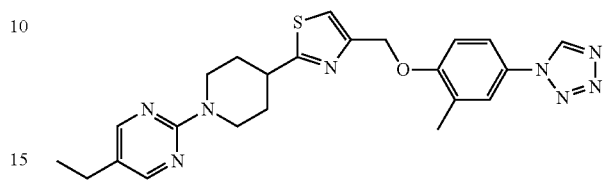

$^1$H NMR (CDCl$_3$): δ 8.88 (1H, s), 8.19 (2H, s), 7.48 (1H, s), 7.44 (1H, m), 7.24 (1H, m), 7.05 (1H, m), 5.26 (2H, s), 4.83 (2H, m), 3.27 (1H, m), 3.05 (2H, m), 2.47 (2H, q), 2.37 (3H, s), 2.22 (2H, m), 1.81 (2H, m), 1.19 (3H, t).

Example 165

5-Chloro-2-{4-[4-(2-chloro-4-tetrazol-1-yl-phenoxymethyl)-thiazol-2-yl]-piperidin-1-yl}-pyrimidine

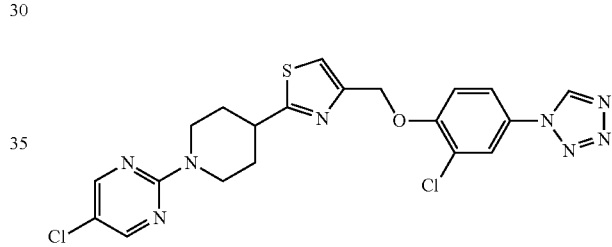

$^1$H NMR (acetone-d$_6$), δ 9.68 (1H, s), 8.33 (2H, s), 8.01 (1H, s), 7.86 (1H, m), 7.60 (1H, m), 7.59 (1H, s), 5.40 (2H, s), 4.78 (2H, m), 3.40 (1H, m), 3.16 (2H, m), 2.20 (2H, m), 1.77 (2H, m).

Example 166

2-{4-[4-(2-Chloro-4-tetrazol-1-yl-phenoxymethyl)-thiazol-2-yl]-piperidin-1-yl}-5-trifluoromethyl-pyrimidine

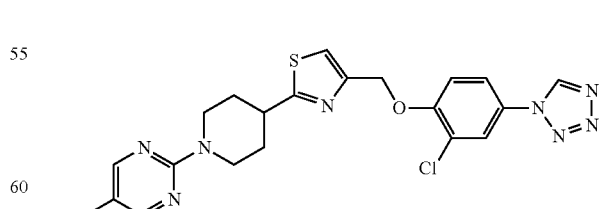

$^1$H NMR (acetone-d$_6$), δ 9.68 (1H, s), 8.62 (2H, s), 8.01 (1H, s), 7.86 (1H, m), 7.61 (1H, s), 7.60 (1H, m), 5.41 (2H, s), 4.92 (2H, m), 3.46 (1H, m), 3.27 (2H, m), 2.25 (2H, m), 1.80 (2H, m).

Example 167

2-{4-[4-(2-Isopropyl-5-methyl-4-tetrazol-1-yl-phenoxymethyl)-thiazol-2-yl]-piperidin-1-yl}-5-trifluoromethyl-pyrimidine

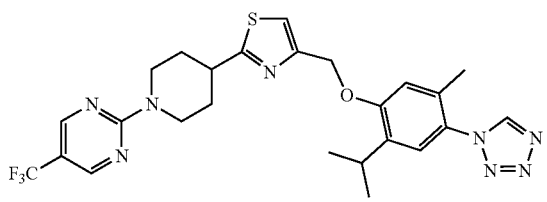 [SMILES: Cc1cc(OCc2csc(C3CCN(c4ncc(C(F)(F)F)cn4)CC3)n2)c(C(C)C)cc1-n1cnnn1]

¹H NMR (CDCl₃): δ 8.73 (1H, s), 8.46 (2H, s), 7.22 (1H, s), 7.10 (1H, s), 6.90 (1H, s), 5.24 (2H, s), 4.93 (2H, m), 3.35 (2H, m), 3.17 (2H, m), 2.23 (2H, m), 2.09 (3H, s), 1.82 (2H, m), 1.20 (6H, d).

Example 168

5-Chloro-2-{4-[4-(2-isopropyl-5-methyl-4-tetrazol-1-yl-phenoxymethyl)-thiazol-2-yl]-piperidin-1-yl}-pyrimidine

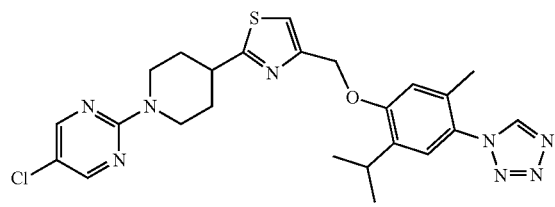 [SMILES: Cc1cc(OCc2csc(C3CCN(c4ncc(Cl)cn4)CC3)n2)c(C(C)C)cc1-n1cnnn1]

¹H NMR (CDCl₃): δ 8.73 (1H, s), 8.20 (2H, s), 7.21 (1H, s), 7.09 (1H, s), 6.90 (1H, s), 5.24 (2H, s), 4.78 (2H, m), 3.35 (1H, m), 3.28 (1H, m), 3.07 (2H, m), 2.19 (2H, m), 2.09 (3H, s), 1.79 (2H, m), 1.20 (6H, d).

Example 169

5-Ethyl-2-{4-[4-(4-tetrazol-1-yl-phenoxymethyl)-oxazol-2-yl]-piperidin-1-yl}-pyrimidine

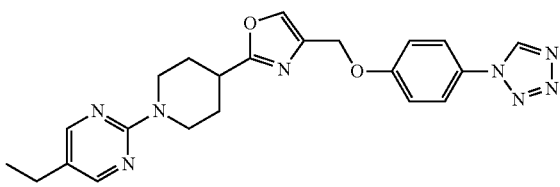 [SMILES: CCc1cnc(N2CCC(c3nc(COc4ccc(-n5cnnn5)cc4)co3)CC2)nc1]

¹H NMR (CDCl₃): δ 8.91 (1H, s), 8.18 (2H, s), 7.65 (1H, s), 7.60 (2H, m), 7.15 (2H, m), 5.03 (2H, s), 4.69 (2H, m), 3.10 (3H, m), 2.44 (2H, q), 2.14 (2H, m), 1.86 (2H, m), 1.19 (3H, t).

Example 170

5-Ethyl-2-{4-[4-(2-fluoro-4-tetrazol-1-yl-phenoxymethyl)-oxazol-2-yl]-piperidin-1-yl}-pyrimidine

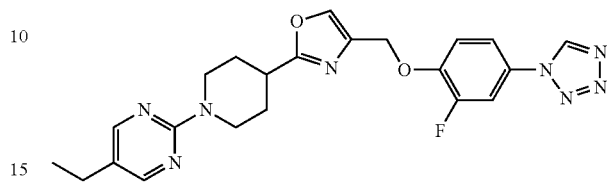

¹H NMR (CDCl₃): δ 8.93 (1H, s), 8.17 (2H, s), 7.67 (1H, s), 7.50 (1H, m), 7.41 (1H, m), 7.29 (1H, m), 5.11 (2H, s), 4.67 (2H, m), 3.08 (3H, m), 2.45 (2H, q), 2.12 (2H, m), 1.84 (2H, m), 1.18 (3H, t).

Example 171

2-{4-[4-(2-Fluoro-4-tetrazol-1-yl-phenoxymethyl)-thiazol-2-yl]-piperidin-1-yl}-5-trifluoromethyl-pyrimidine

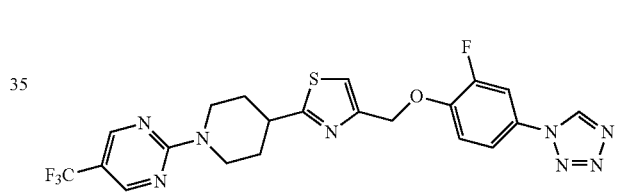

¹H NMR (CDCl₃): δ 8.91 (1H, s), 8.49 (2H, s), 7.52 (1H, d, J=7.6 Hz), 7.41 (1H, d, J=7.6 Hz), 7.32 (1H, s), 7.29 (1H, m), 5.32 (2H, s), 4.95 (2H, m), 3.37 (1H, m), 3.15 (2H, m), 2.24 (2H, m), 1.81 (2H, m).

Example 172

5-Decyl-2-{4-[4-(4-tetrazol-1-yl-phenoxymethyl)-thiazol-2-yl]-piperidin-1-yl}-pyrimidine

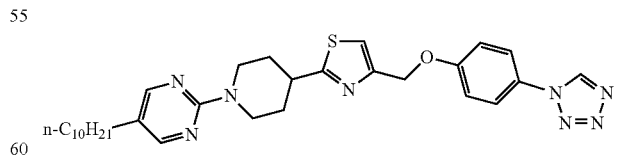

¹H NMR (DMSO-d₆): δ 9.97 (1H, s), 8.21 (2H, s), 7.80 (2H, d, J=8.8 Hz), 7.65 (1H, s), 7.28 (2H, d, J=8.8 Hz), 5.20 (2H, s), 4.66 (2H, m), 3.32 (1H, m), 3.01 (2H, m), 2.37 (2H, m), 2.09 (2H, m), 1.60 (2H, m), 1.45 (2H, m), 1.21 (14H, m), 0.82 (3H, m).

Example 173

6-Methyl-2-{4-[4-(4-tetrazol-1-yl-phenoxymethyl)-thiazol-2-yl]-piperidin-1-yl}-pyrimidine-4-carboxylic acid methyl ester

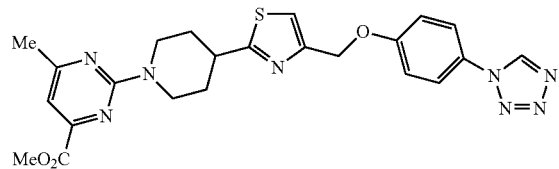 [SMILES: COC(=O)c1cc(C)nc(N2CCC(c3nc(COc4ccc(-n5cnnn5)cc4)cs3)CC2)n1]

$^1$H NMR (DMSO-d$_6$): δ 9.97 (1H, s), 7.80 (2H, d, J=8.8 Hz), 7.66 (1H, s), 7.28 (2H, d, J=8.8 Hz), 7.01 (1H, s), 5.21 (2H, s), 4.76 (2H, m), 3.84 (3H, s), 3.33 (1H, m), 3.06 (2H, m), 2.36 (3H, s), 2.14 (2H, m), 1.61 (2H, m).

Example 174

4-Chloro-2-{4-[4-(4-tetrazol-1-yl-phenoxymethyl)-thiazol-2-yl]-piperidin-1-yl}-pyrimidine

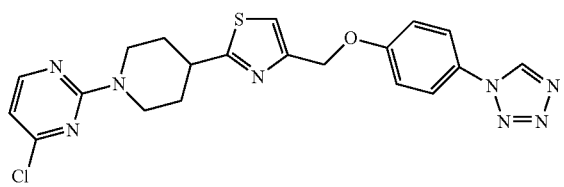 [SMILES: Clc1ccnc(N2CCC(c3nc(COc4ccc(-n5cnnn5)cc4)cs3)CC2)n1]

$^1$H NMR (CDCl$_3$): δ 8.91 (1H, s), 8.15 (1H, d, J=5.2 Hz), 7.60 (2H, d, J=8.8 Hz), 7.25 (1H, s), 7.16 (2H, d, J=8.8 Hz), 6.49 (1H, d, J=5.2 Hz), 5.22 (2H, s), 4.85 (2H, m), 3.30 (1H, m), 3.07 (2H, m), 2.21 (2H, m), 1.80 (2H, m).

Example 175

2-Chloro-4-{4-[4-(4-tetrazol-1-yl-phenoxymethyl)-thiazol-2-yl]-piperidin-1-yl}-pyrimidine

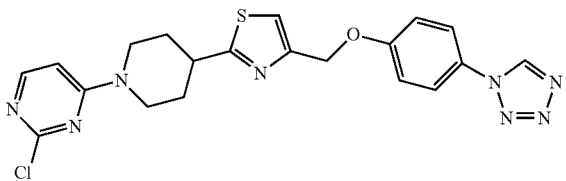 [SMILES: Clc1nccc(N2CCC(c3nc(COc4ccc(-n5cnnn5)cc4)cs3)CC2)n1]

$^1$H NMR (CDCl$_3$): δ 8.90 (1H, s), 8.05 (1H, d, J=6.4 Hz), 7.61 (2H, d, J=8.8 Hz), 7.28 (1H, s), 7.17 (2H, d, J=8.8 Hz), 6.46 (1H, d, J=6.4 Hz), 5.23 (2H, s), 4.45 (2H, m), 3.35 (1H, m), 3.15 (2H, m), 2.27 (2H, m), 1.85 (2H, m).

Example 176

6-Methyl-2-{4-[4-(4-tetrazol-1-yl-phenoxymethyl)-thiazol-2-yl]-piperidin-1-yl}-pyrimidine-4-carboxylic acid

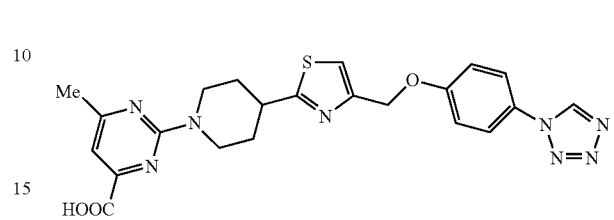

$^1$H NMR (DMSO-d$_6$): δ 13.3 (1H, br), 9.97 (1H, s), 7.80 (2H, d, J=8.8 Hz), 7.66 (1H, s), 7.28 (2H, d, J=8.8 Hz), 6.98 (1H, s), 5.21 (2H, s), 4.79 (2H, m), 3.34 (1H, m), 3.05 (2H, m), 2.35 (3H, s), 2.13 (2H, m), 1.62 (2H, m).

Example 177

5-Chloro-4,6-difluoro-2-{4-[4-(4-tetrazol-1-yl-phenoxymethyl)-thiazol-2-yl]-piperidin-1-yl}-pyrimidine

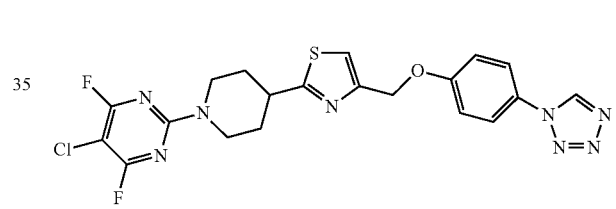

$^1$H NMR (CDCl$_3$): δ 8.91 (1H, s), 7.61 (2H, d, J=8.8 Hz), 7.27 (1H, s), 7.16 (2H, d, J=8.8 Hz), 5.23 (2H, s), 4.69 (2H, m), 3.32 (1H, m), 3.10 (2H, m), 2.23 (2H, m), 1.80 (2H, m).

Example 178

4-Fluoro-2-{4-[4-(4-tetrazol-1-yl-phenoxymethyl)-thiazol-2-yl]-piperidin-1-yl}-pyrimidine

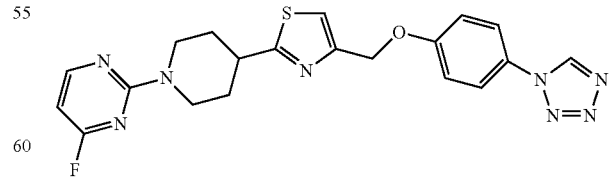

$^1$H NMR (DMSO-d$_6$): δ 9.97 (1H, s), 8.41 (1H, m), 7.80 (2H, d, J=8.0 Hz), 7.66 (1H, s), 7.28 (2H, d, J=8.0 Hz), 6.34 (1H, m), 5.20 (2H, s), 4.60 (2H, m), 3.32 (1H, m), 3.10 (2H, m), 2.11 (2H, m), 1.61 (2H, m).

Example 179

2-Fluoro-4-{4-[4-(4-tetrazol-1-yl-phenoxymethyl)-thiazol-2-yl]-piperidin-1-yl}-pyrimidine

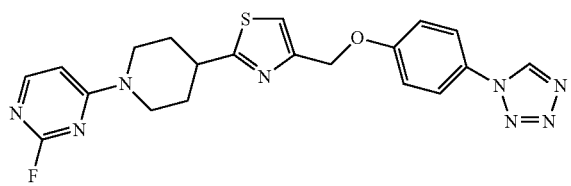

¹H NMR (DMSO-d₆): δ 9.98 (1H, s), 8.08 (1H, m), 7.80 (2H, d, J=9.2 Hz), 7.67 (1H, s), 7.28 (2H, d, J=9.2 Hz), 6.84 (1H, m), 5.20 (2H, s), 4.40 (2H, m), 3.40 (1H, m), 3.14 (2H, m), 2.13 (2H, m), 1.63 (2H, m).

Example 180

2-{4-[4-(4-Tetrazol-1-yl-phenoxymethyl)-thiazol-2-yl]-piperidin-1-yl}-thiazole-5-carboxylic acid ethyl ester

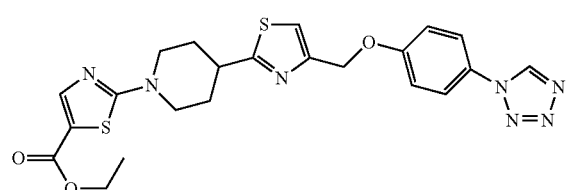

¹H NMR (DMSO-d₆): δ 9.97 (1H, s), 7.84 (1H, m), 7.80 (2H, d, J=9.0 Hz), 7.68 (1H, s), 7.28 (2H, d, J=9.0 Hz), 5.21 (2H, s), 4.19 (2H, t, J=7.20 Hz), 4.03 (2H, m), 3.35 (3H, m), 2.15 (2H, m), 1.75 (2H, m), 1.23 (3H, t, J=7.20 Hz).

Example 181

4-Imidazol-1-yl-6-{4-[4-(4-tetrazol-1-yl-phenoxymethyl)-thiazol-2-yl]-piperidin-1-yl}-pyrimidine

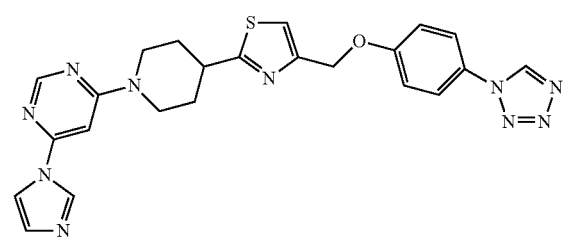 [SMILES: c1cn(-c2cc(N3CCC(c4nc(COc5ccc(-n6cnnn6)cc5)cs4)CC3)ncn2)cn1]

¹H NMR (DMSO-d₆): δ 9.98 (1H, s), 8.59 (1H, s), 8.43 (1H, s), 8.01 (1H, d, J=1.2 Hz), 7.81 (2H, d, J=8.8 Hz), 7.67 (1H, s), 7.27 (2H, d, J=8.8 Hz), 7.14 (1H, s), 7.10 (1H, d, J=1.2 Hz), 5.20 (2H, s), 4.61 (2H, m), 3.40 (1H, m), 3.15 (2H, m), 2.15 (2H, m), 1.66 (2H, m).

Example 182

5-Ethyl-2-{4-[4-(6-tetrazol-1-yl-pyridin-3-yloxymethyl)-thiazol-2-yl]-piperidin-1-yl}-pyrimidine

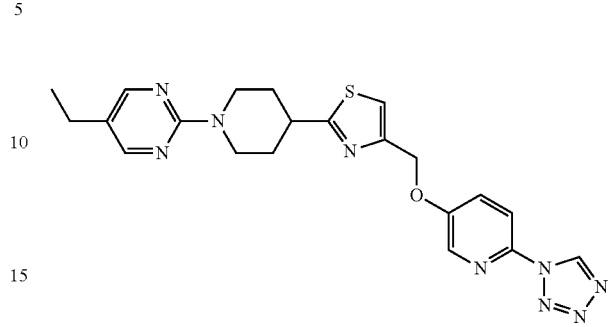

¹H NMR (CDCl₃): δ 9.44 (1H, s), 8.28 (1H, d, J=3.0 Hz), 8.2 (2H, s), 8.02, (1H, d, J=8.8 Hz), 7.58 (1H, dd, J=8.8 Hz, 3.0 Hz), 7.27 (1H, s), 5.27 (2H, s), 4.82-4.85 (2H, m), 3.22-3.35 (1H, m), 3.0-3.1, (2H, m), 2.47 (2H, q, J=7.2 Hz), 2.2-2.23 (2H, m), 1.76-1.86 (2H, m), 1.19 (3H, t, J=7.2 Hz).

Example 183

5-Methyl-2-{4-[4-(6-tetrazol-1-yl-pyridin-3-yloxymethyl)-thiazol-2-yl]-piperidin-1-yl}-pyrimidine

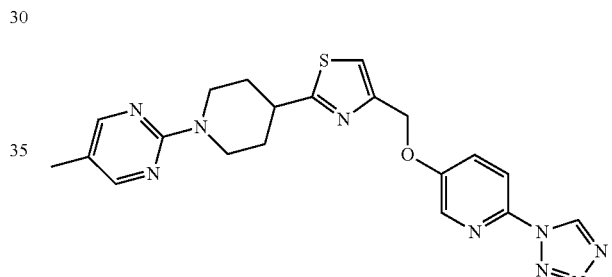

¹H NMR (DMSO-d₆): δ 10.07 (1H, s), 8.42 (1H, d, J=3.0 Hz), 8.21 (2H, s), 7.99 (1H, d, J=9.2 Hz), 7.86 (1H, dd, J=9.2 Hz, 3.0 Hz), 7.70 (1H, s), 5.30 (2H, s), 4.62 (2H, m), 3.56-3.60 (1H, m), 2.98-3.04 (2H, m), 2.06 (3H, s), 1.72-1.76 (2H, m), 1.59 (2H, m).

Example 184

5-Chloro-2-{4-[4-(6-tetrazol-1-yl-pyridin-3-yloxymethyl)-thiazol-2-yl]-piperidin-1-yl}-pyrimidine

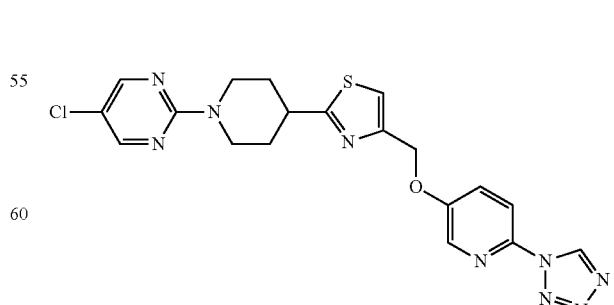

¹H NMR (CDCl₃) δ 9.44 (1H, s), 8.28 (1H, d, J=3.0 Hz), 8.23 (2H, s), 8.02 (1H, d, J=9.0 Hz), 7.58 (1H, dd, J=9.0 Hz, 3.0 Hz), 7.28 (1H, s), 5.27 (2H, s), 4.8-4.83 (2H, m), 3.22-3.38 (1H, m), 3.04-3.11 (2H, m), 2.20-2.23 (2H, m), 1.80 (2H, m)

Example 185

2-{4-[4-(6-Tetrazol-1-yl-pyridin-3-yloxymethyl)-thiazol-2-yl]-piperidin-1-yl}-5-trifluoromethyl-pyrimidine

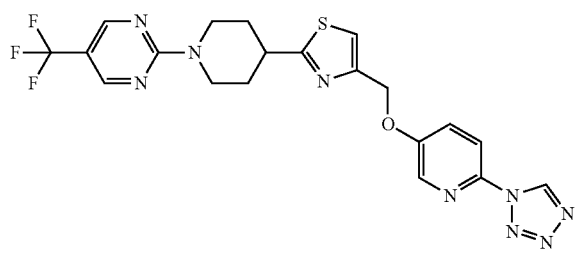 [SMILES: FC(F)(F)c1cnc(N2CCC(c3nc(COc4ccc(-n5cnnn5)nc4)cs3)CC2)nc1]

$^1$H NMR (DMSO-d$_6$): δ 10.07 (1H, s), 8.68 (2H, s), 8.42 (1H, d, J=3.0 Hz), 7.99 (1H, d, J=9.2 Hz), 7.86 (1H, dd, J=9.2 Hz, 3.0 Hz), 7.72 (1H, s), 5.73 (2H, s), 4.74-4.77 (2H, m), 3.37-3.43 (1H, m), 3.15-3.21 (2H, m), 2.12-2.16 (2H, m), 1.59-1.68 (2H, m).

Example 186

3-Chloro-6-{4-[4-(4-tetrazol-1-yl-phenoxymethyl)-thiazol-2-yl]-piperidin-1-yl}-pyridazine

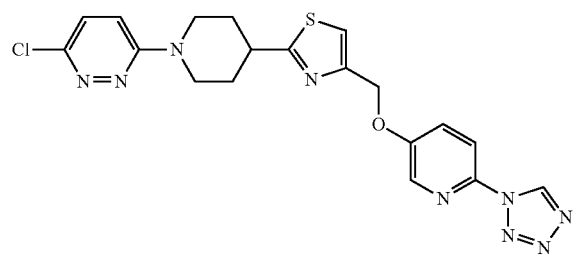 [SMILES: Clc1ccc(N2CCC(c3nc(COc4ccc(-n5cnnn5)nc4)cs3)CC2)nn1]

$^1$H NMR (CDCl$_3$): δ 8.91 (1H, s), 7.61 (2H, d, J=9.0 Hz), 7.26 (1H, s), 7.22 (1H, d, J=9.6 Hz), 7.17 (2H, d, J=9.0 Hz), 6.95 (1H, d, J=9.6 Hz), 5.23 (2H, s), 4.43-4.47 (2H, m), 3.31-3.37 (1H, m), 3.12-3.19 (2H, m), 2.25-2.28 (2H, m), 1.90 (2H, m).

Example 187

2-Tetrazol-1-yl-5-{4-[4-(4-tetrazol-1-yl-phenoxymethyl)-thiazol-2-yl]-piperidin-1-yl}-pyrazine

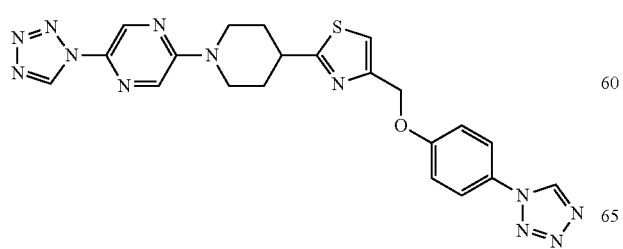

$^1$H NMR (DMSO-d$_6$): δ 9.97 (2H, s), 8.67 (1H, s), 8.37 (1H, s), 7.80 (2H, d, J=8.8 Hz), 7.67 (1H, s), 7.28 (2H, d, J=8.8 Hz), 5.21 (2H, s), 4.50-4.53 (2H, m), 3.38-3.44 (1H, m), 3.17-3.23 (2H, m), 2.15-2.18 (2H, m), 1.69-1.77 (2H, m).

Example 188

{2-[1-(5-Ethyl-pyrimidin-2-yl)-piperidin-4-yl]-thiazol-4-ylmethyl}-(6-fluoro-pyridin-3-yl)-amine

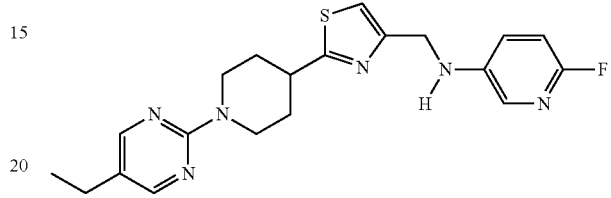

$^1$H NMR (CDCl$_3$): δ 8.19 (2H, s), 7.58-7.62 (1H, m), 7.05-7.10 (1H, m), 7.01 (1H, s), 6.75 (1H, dd, J=8.4 Hz, 2.8 Hz), 4.81-4.85 (2H, m), 4.40 (2H, d, J=5.2 Hz), 4.29 (1H, br s), 3.23-3.29 (1H, m), 3.00-3.06 (2H, m), 2.47 (2H, q, J=7.6 Hz), 2.18-2.20 (2H, m), 1.79 (2H, m), 1.20 (3H, t, J=7.6 Hz).

Example 189

2-{4-[4-(2,6-Difluoro-4-methanesulfonyl-phenoxymethyl)-thiazol-2-yl]-piperidin-1-yl}-5-ethyl-pyrimidine

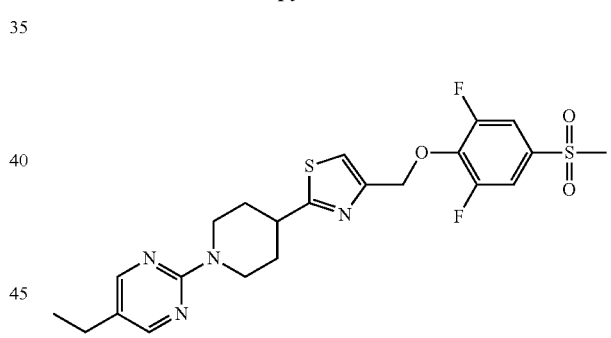

$^1$H NMR (CDCl$_3$): δ 8.19 (2H, s), 7.51 (2H, d), 7.25 (1H, s), 5.40 (2H, s), 4.82 (2H, m), 3.30 (1H, m), 3.06 (3H, s), 3.03 (2H, m), 2.48 (2H, q), 2.15 (2H, m), 1.74 (2H, m), 1.20 (3H, t).

Example 190

5-Butyl-2-{4-[4-(4-tetrazol-1-yl-phenoxymethyl)-thiazol-2-yl]-piperidin-1-yl}-pyrimidine

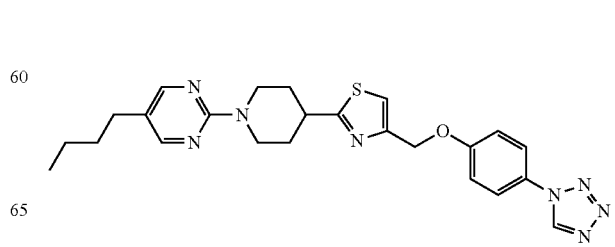

¹H NMR (CDCl₃): δ 8.92 (1H, s), 8.17 (2H, s), 7.62 (2H, m), 7.25 (1H, s), 7.17 (2H, m), 5.24 (2H, s), 4.83 (2H, m), 3.30 (1H, m), 3.04 (2H, m), 2.42 (2H, t), 2.23 (2H, m), 1.84 (2H, m), 1.52 (2H, m), 1.34 (2H, m), 0.92 (3H, m).

Example 191

4-(4-{2-[1-(5-Ethyl-pyrimidin-2-yl)-piperidin-4-yl]-thiazol-4-ylmethoxy}-phenyl)-morpholine

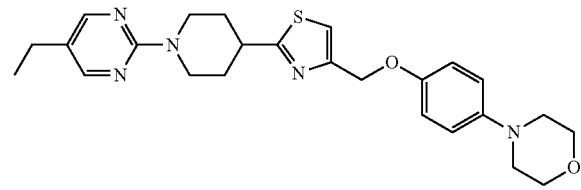 [SMILES: CCc1cnc(N2CCC(c3nc(COc4ccc(N5CCOCC5)cc4)cs3)CC2)nc1]

¹H NMR (CDCl₃): δ 8.18 (2H, s), 7.19 (1H, s), 6.92 (4H, m), 5.12 (2H, s), 4.84 (2H, m), 3.86 (4H, br), 3.30 (1H, m), 3.05 (6H, m), 2.46 (2H, q), 2.21 (2H, m), 1.78 (2H, m), 1.19 (3H, t).

Example 192

5-Nitro-2-{4-[4-(4-tetrazol-1-yl-phenoxymethyl)-thiazol-2-yl]-piperidin-1-yl}-pyrimidine

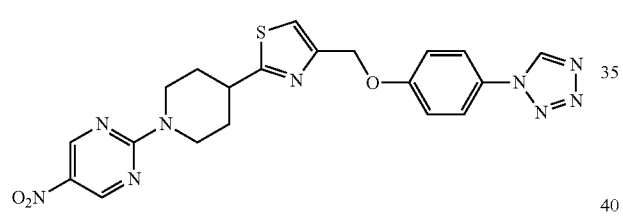

¹H NMR (DMSO-d₆): δ 9.91 (1H, s), 9.11 (2H, s), 7.83 (2H, d, J=8.8 Hz), 7.68 (1H, s), 7.25 (2H, d, J=8.8 Hz), 5.22 (2H, s), 4.81 (2H, m), 3.39 (1H, m), 3.31 (2H, m), 2.23 (2H, s), 1.68 (2H, m).

Example 193

3'-Chloro-4-[4-(4-tetrazol-1-yl-phenoxymethyl)-thiazol-2-yl]-5'-trifluoromethyl-3,4,5,6-tetrahydro-2H-[1,2']bipyridinyl

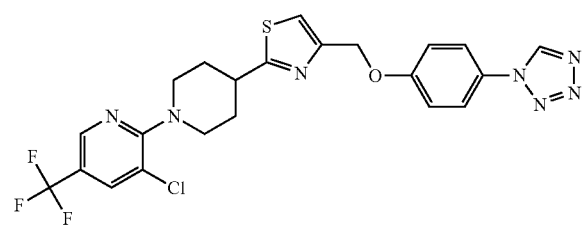 [SMILES: FC(F)(F)c1cnc(N2CCC(c3nc(COc4ccc(-n5cnnn5)cc4)cs3)CC2)c(Cl)c1]

¹H NMR (CDCl₃): δ 8.91 (1H, s), 8.39 (1H, s), 7.76 (1H, s), 7.61 (2H, m), 7.25 (1H, s), 7.18 (2H, m), 5.24 (2H, s), 4.16 (2H, m), 3.26 (1H, m), 3.06 (2H, m), 2.25 (2H, m), 2.01 (2H, m).

Example 194

3'-Chloro-4-[4-(2-fluoro-4-tetrazol-1-yl-phenoxymethyl)-thiazol-2-yl]-5'-trifluoromethyl-3,4,5,6-tetrahydro-2H-[1,2']bipyridinyl

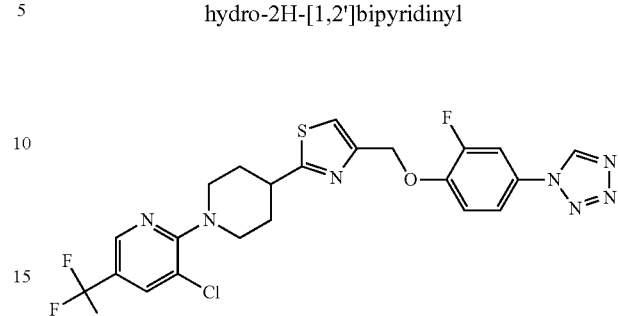

¹H NMR (CDCl₃): δ 8.94 (1H, s), 8.38 (1H, s), 7.75 (1H, s), 7.53 (1H, m), 7.40 (1H, m), 7.31 (1H, s), 7.25 (1H, m), 5.31 (2H, s), 4.15 (2H, d), 3.25 (1H, m), 3.09 (2H, m), 2.23 (2H, d), 1.99 (2H, m).

Example 195

5-Chloro-2-{4-[4-(2-fluoro-4-tetrazol-1-yl-phenoxymethyl)-thiazol-2-yl]-piperidin-1-yl}-pyrimidine

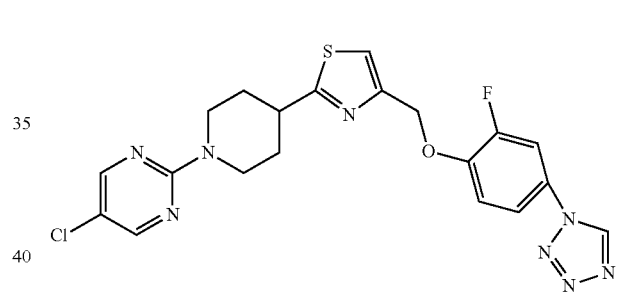

¹H NMR (CDCl₃): δ 8.96 (1H, s), 8.20 (2H, s), 7.52 (1H, m), 7.40 (1H, m), 7.28 (1H, s), 7.25 (1H, m), 5.28 (2H, s), 4.78 (2H, m), 3.30 (1H, m), 3.07 (2H, m), 2.20 (2H, m), 1.79 (2H, m).

Example 196

3',5'-Dichloro-4-[4-(4-tetrazol-1-yl-phenoxymethyl)-thiazol-2-yl]-3,4,5,6-tetrahydro-2H-[1,2']bipyridinyl

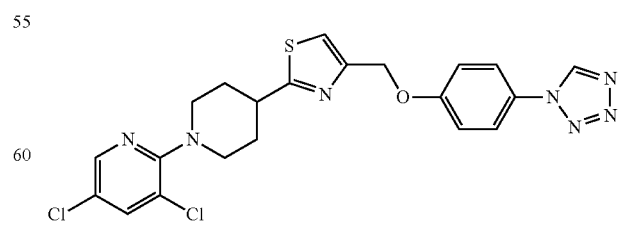

¹H NMR (DMSO-d₆): δ 9.98 (1H, s), 8.26 (1H, s), 8.03 (1H, s), 7.81 (2H, d), 7.67 (1H, s), 7.29 (2H, d), 5.21 (2H, s), 3.79 (2H, m), 3.24 (1H, m), 2.97 (2H, m), 2.14 (2H, m), 1.84 (2H, m).

Example 197

3'-Chloro-4-[4-(4-tetrazol-1-yl-phenoxymethyl)-thiazol-2-yl]-3,4,5,6-tetrahydro-2H-[1,2']bipyridinyl-5'-carboxylic acid ethyl ester

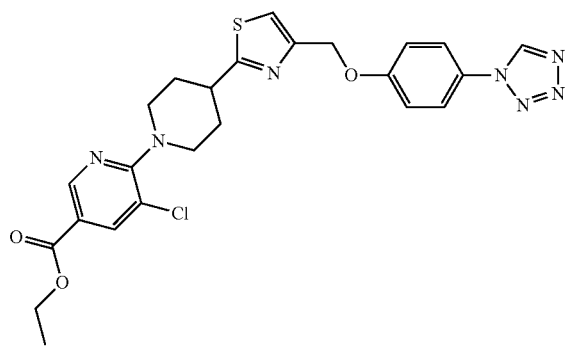 [SMILES: CCOC(=O)c1cnc(N2CCC(c3nc(COc4ccc(-n5cnnn5)cc4)cs3)CC2)c(Cl)c1]

$^1$H NMR (CDCl$_3$): δ 8.92 (1H, s), 8.74 (1H, s), 8.11 (1H, s), 7.61 (2H, d), 7.25 (1H, s), 7.17 (2H, d), 5.23 (2H, s), 4.37 (2H, m), 4.22 (2H, m), 3.31 (1H, m), 3.08 (2H, m) 2.26 (2H, m), 1.98 (2H, m), 1.38 (3H, m).

Example 198

5'-Chloro-4-[4-(4-tetrazol-1-yl-phenoxymethyl)-thiazol-2-yl]-3,4,5,6-tetrahydro-2H-[1,2']bipyridinyl-3'-carboxylic acid methyl ester

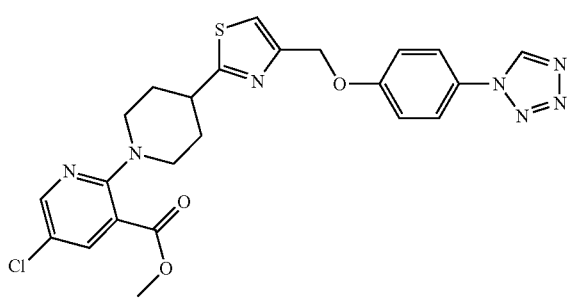 [SMILES: COC(=O)c1cc(Cl)cnc1N1CCC(c2nc(COc3ccc(-n4cnnn4)cc3)cs2)CC1]

$^1$H NMR (CDCl$_3$): δ 8.91 (1H, s), 8.20 (1H, s), 7.99 (1H, s), 7.61 (2H, d), 7.25 (1H, s), 7.16 (2H, d), 5.21 (2H, s), 3.91 (2H, m), 3.88 (3H, s), 3.28 (1H, m), 3.08 (2H, m), 2.20 (2H, m), 1.93 (2H, m).

Example 199

5-Ethyl-2-{3-methyl-4-[4-(4-tetrazol-1-yl-phenoxymethyl)-thiazol-2-yl]-piperidin-1-yl}-pyrimidine

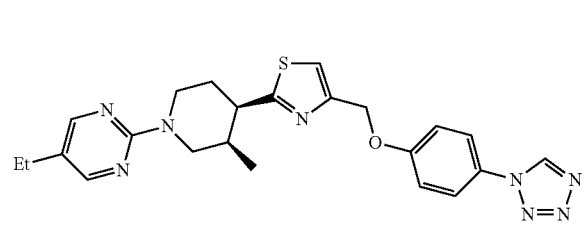 [SMILES: CCc1cnc(N2CC[C@@H](c3nc(COc4ccc(-n5cnnn5)cc4)cs3)[C@@H](C)C2)nc1]

$^1$H NMR (CDCl$_3$): δ 8.90 (1H, s), 8.18 (2H), 7.60 (2H, m), 7.25 (1H, s), 7.17 (2H, m), 5.26 (2H), 4.89-4.51 (2H, m), 3.49-3.20 (2H, m), 2.92 (1H, m), 2.65-2.45 (1H, m), 2.45 (2H, m), 2.17-1.81 (2H, m), 1.20 (3H, m), 0.82-0.92 (3H).

Example 200

5-Ethyl-2-{4-[4-(2-fluoro-4-tetrazol-1-yl-phenoxymethyl)-thiazol-2-yl]-3-methyl-piperidin-1-yl}-pyrimidine

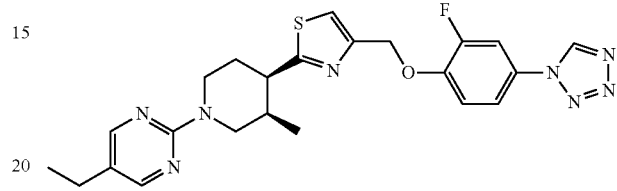

$^1$H NMR (CDCl$_3$): δ 8.93 (1H, s), 8.17 (2H), 7.52-7.25 (4H, m), 5.32 (2H), 4.84-4.46 (2H, m), 3.47-3.22 (2H, m), 2.91 (1H, m), 2.62-2.43 (1H, m), 2.42 (2H, m), 2.07 (2H, m), 1.18 (3H, m), 0.90-0.79 (3H, m).

Example 201

5-Chloro-2-{4-[4-(2-fluoro-4-tetrazol-1-yl-phenoxymethyl)-thiazol-2-yl]-3-methyl-piperidin-1-yl}-pyrimidine

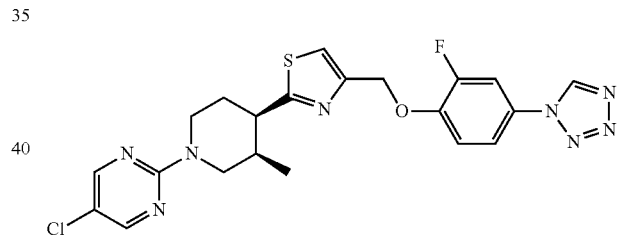

$^1$H NMR (CDCl$_3$): δ 8.93 (1H, s), 8.19 (2H), 7.52-7.25 (4H, m), 5.29 (2H), 4.82-4.51 (2H, m), 3.46-3.21 (2H, m), 2.95 (1H, m), 2.64-2.42 (1H, m), 2.02 (2H, m), 0.90-0.78 (3H, m).

Example 202

2-{4-[4-(2-Fluoro-4-tetrazol-1-yl-phenoxymethyl)-thiazol-2-yl]-3-methyl-piperidin-1-yl}-5-trifluoromethyl-pyrimidine

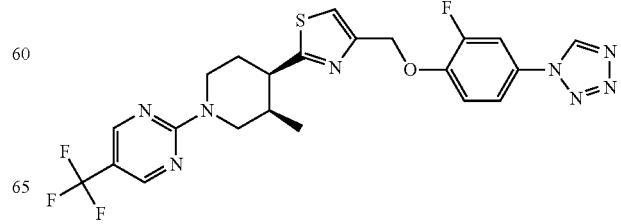

¹H NMR (CDCl₃): δ 8.94 (1H, s), 8.47 (2H), 7.53-7.27 (4H, m), 5.34 (2H), 5.02-4.62 (2H, m), 3.52-2.97 (3H, m), 2.73-2.47 (1H, m), 2.17-2.01 (2H, m), 0.94-0.78 (3H, m).

Example 203

5-Ethyl-2-{4-[4-(4-methanesulfonyl-benzyloxymethyl)-thiazol-2-yl]-piperidin-1-yl}-pyrimidine

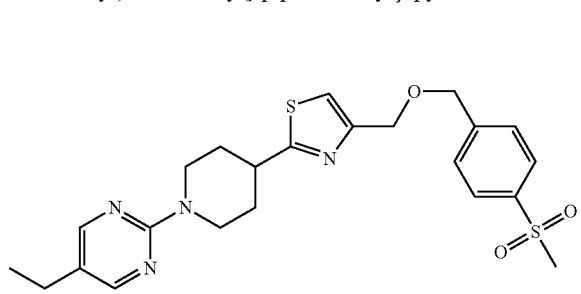

¹H NMR (CDCl₃): δ 8.17 (2H, s), 7.92 (2H, d, J=8.8 Hz), 7.58 (2H, d, J=8.8 Hz), 7.13 (1H, s), 4.83 (2H, m), 4.71 (2H, s), 4.66 (2H, s), 3.27 (1H, m), 3.03 (3H, s), 2.98 (2H, m), 2.46 (2H, m), 2.19 (2H, m), 1.76 (2H, m), 1.19 (3H, m).

Example 204

5-Fluoro-2-{4-[4-(2-fluoro-4-tetrazol-1-yl-phenoxymethyl)-thiazol-2-yl]-piperidin-1-yl}-pyrimidine

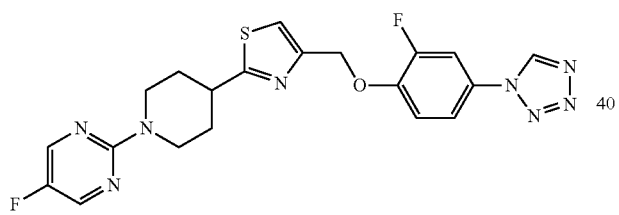

¹H NMR (CDCl₃): δ 8.91 (1H, s), 8.21 (2H, s), 7.52 (1H, m), 7.41 (1H, m), 7.27 (1H, m), 7.25 (1H, s), 5.31 (2H, s), 4.76 (2H, m), 3.28 (1H, m), 3.06 (2H, m), 2.20 (2H, m), 1.81 (2H, m).

Example 205

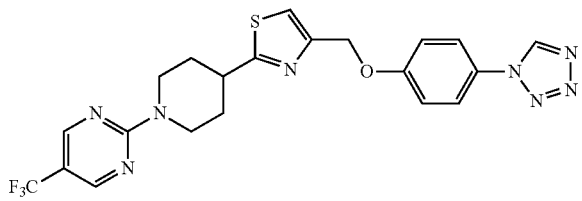 [SMILES: FC(F)(F)c1cnc(N2CCC(c3nc(COc4ccc(-n5cnnn5)cc4)cs3)CC2)nc1]

¹H NMR (CDCl₃): δ 8.91 (1H, s), 8.49 (2H, s), 7.61 (2H, d), 7.27 (1H, s), 7.17 (2H, d), 5.24 (2H, s), 4.96 (2H, m), 3.38 (1H, m), 3.14 (2H, m), 2.26 (2H, m), 1.82 (2H, m).

Example 206

4-(4-{[(4-Methanesulfonyl-phenyl)-methyl-amino]-methyl}-thiazol-2-yl)-piperidine-1-carboxylic acid tert-butyl ester

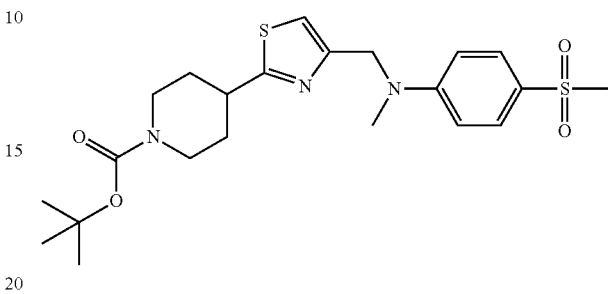

4-{4-[(4-Methanesulfonyl-phenylamino)-methyl]-thiazol-2-yl}-piperidine-1-carboxylic acid tert-butyl ester (Example 138) (0.10 mmol) was dissolved in DMF (2 mL) and NaH (2 eq.) was added in a single portion at room temperature. The reaction was stirred for 30 minutes and methyliodide (10 eq.) was added. After stirring for 3 hours, the reaction was quenched with water and extracted with EtOAc. The organic layer was washed with brine, dried over sodium sulfate, filtered and concentrated in vacuo. Purification of the residue by silica gel chromatography (Hexanes/EtOAc 1:1) provided the expected product. ¹H NMR (CDCl₃): δ 7.73 (2H, m), 6.78 (2H, m), 6.76 (1H, s), 4.70 (2H, s), 4.20 (2H, br), 3.19 (3H, s), 3.12 (1H, m), 3.01 (3H, s), 2.87 (2H, m), 2.07 (2H, m), 1.80 (2H, m), 1.47 (9H, s).

Example 207

{2-[1-(5-Ethyl-pyrimidin-2-yl)-piperidin-4-yl]-thiazol-4-ylmethyl}-(2-fluoro-4-methanesulfonyl-phenyl)-methyl-amine

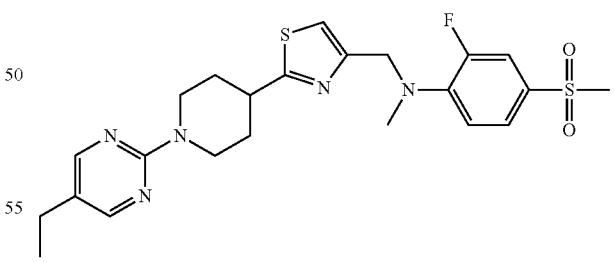

Example 207 was synthesized in a manner analogous to Example 206 utilizing {2-[1-(5-Ethyl-pyrimidin-2-yl)-piperidin-4-yl]-thiazol-4-ylmethyl}-(2-fluoro-4-methanesulfonyl-phenyl)-amine (Example 141) as the starting material. ¹H NMR (CDCl₃): δ 8.19 (2H, s), 7.47-7.57 (2H, m), 6.94 (1H, s), 6.91 (1H, m), 4.80 (2H, m), 4.62 (2H, s), 3.24 (1H, m), 3.09 (3H, s), 3.03 (3H, s), 3.00 (2H, m), 2.47 (2H, m), 2.17 (2H, m), 1.74 (2H, m), 1.19 (3H, t).

Example 208

4-[4-(2-Methylsulfanyl-pyrimidin-5-yloxymethyl)-thiazol-2-yl]-piperidine-1-carboxylic acid tert-butyl ester

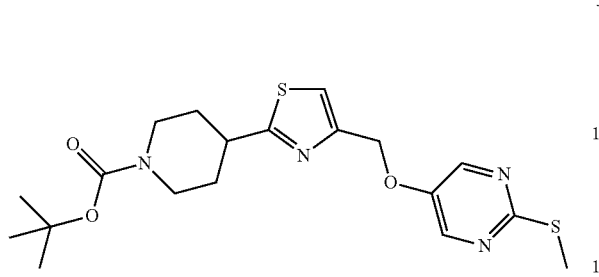

Example 208 was prepared from 4-(4-Chloromethyl-thiazol-2-yl)-piperidine-1-carboxylic acid tert-butyl ester (Intermediate 1) and 2-Methylsulfanyl-pyrimidin-5-ol in a manner similar to that described in Example 1. $^1$H NMR (CDCl$_3$): δ 8.35 (2H, s), 7.23 (1H, s), 5.19 (2H, s), 4.22 (2H, m), 3.16 (1H, m), 2.87 (2H, m), 2.55 (3H, s), 2.10 (2H, m), 1.71 (2H, m), 1.46 (9H, s).

Example 209

4-[4-(4-Tetrazol-1-yl-phenoxymethyl)-thiazol-2-yl]-piperidine-1-carboxylic acid allyl ester

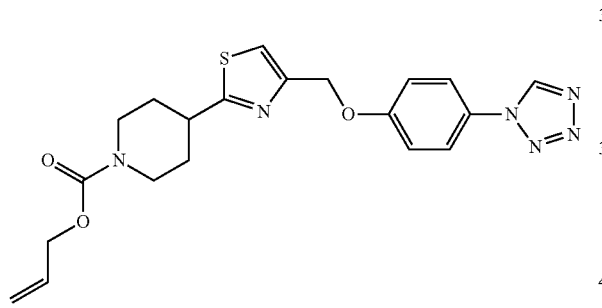

Example 209 was prepared from 4-[4-(4-Tetrazol-1-yl-phenoxymethyl)-thiazol-2-yl]-piperidine (Intermediate 4) and allyl chloroformate in a manner similar to that described in Example 22. $^1$H NMR (CDCl$_3$): δ 8.96 (1H, s), 7.63 (2H, m), 7.20 (1H, s), 7.18 (2H, m), 5.96 (1H, m), 5.31 (1H, m), 5.22 (3H, m), 4.61 (2H, m), 4.29 (2H, m), 3.21 (1H, m), 2.97 (2H, m), 2.15 (2H, m), 1.78 (2H, m).

Example 210

2-{4-[4-Methyl-5-(4-tetrazol-1-yl-phenoxymethyl)-thiazol-2-yl]-piperidin-1-yl}-5-trifluoromethyl-pyrimidine

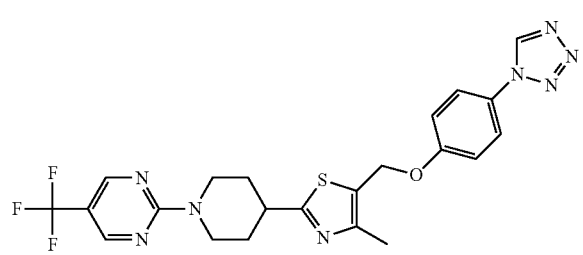 [SMILES: Cc1nc(C2CCN(c3ncc(C(F)(F)F)cn3)CC2)sc1COc1ccc(-n2cnnn2)cc1]

Step 1: 4-[4-Methyl-5-(4-tetrazol-1-yl-phenoxymethyl)-thiazol-2-yl]-piperidine

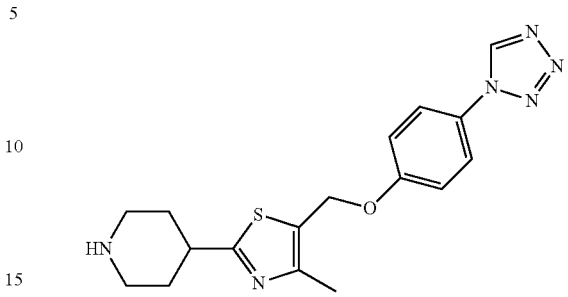

A solution of 4-[4-Methyl-5-(4-tetrazol-1-yl-phenoxymethyl)-thiazol-2-yl]-piperidine-1-carboxylic acid tert-butyl ester (Example 93) (500 mg, 1.10 mmol) in dichloromethane (5 mL) was treated with 1.5 mL of 4N HCl in dioxane. The resulting solution was stirred at room temperature for 5 hours and all the solvent were removed in vacuo to afford the desired product as an HCl salt.

Step 2: 2-{4-[4-Methyl-5-(4-tetrazol-1-yl-phenoxymethyl)-thiazol-2-yl]-piperidin-1-yl}-5-trifluoromethyl-pyrimidine

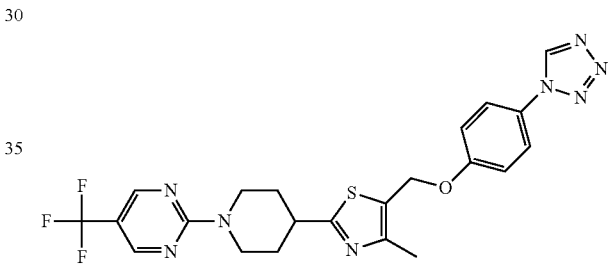

This compound was prepared from 4-[4-Methyl-5-(4-tetrazol-1-yl-phenoxymethyl)-thiazol-2-yl]-piperidine hydrochloride in a similar manner as described in Example 47. $^1$H NMR (CDCl$_3$): δ 8.94 (1H, s), 8.49 (2H, s), 7.64 (2H, m), 7.14 (2H, m), 5.20 (2H, s), 4.95 (2H, m), 3.27 (1H, m), 3.13 (2H, m), 2.46 (3H, s), 2.21 (2H, m), 1.77 (2H, m).

Biological Example 1

Stimulation of cAMP

The compounds of the present invention were evaluated in an assay demonstrating agonism of IC-GPCR2. This assay was developed using a stable cell line expressing IC-GPCR2, generated as follows. IC-GPCR2 (SEQ ID NO:1) was cloned into Gateway pDEST 40vector (Invitrogen), using the Gateway cloning system (invitrogen) according to the manufacturer's instructions. A stable cell line was generated by transfecting a 10cm plate of CHO cells (source) with 8ug of this construct using Transit-CHO transfection kit (Minis). CHO cells were plated the day prior to transfection at a density of 3,000,000 cells/plate. Clones were selected using the antibiotic G418 at 500ug/ml. 23 clones were picked and assayed for the expression of the receptor by measuring changes in intracellular cAMP levels in response to an IC-GPCR2 agonist.

To measure cAMP activity in response to IC-GPCR2 agonist, the clones were plated in 96 well plates at 17500 cells per well. On the day after plating, cells were incubated with the IC-CPCR2 agonist at 10 uM for 30 minutes in Ham's F12 Media (Gibco) with 0.04% DMSO. cAMP was measured using the cAMP dynamic kit from Cis Bio (Bedford, Mass.) according to the manufacturer's instructions. Briefly, cells were lysed, and cAMP levels determined by competitive immunoassay using D2 labeled cAMP, and europium cryptate tagged anti cAMP antibody. When in close proximity, the D2 and europium cryptate undergo fluorescence resonance energy transfer (FRET), which is measured as a fluorescence ratio (665 nm/620 nm). Unlabelled cAMP in the cell lysate competed with the D2 labeled cAMP for the europium crypate labeled antibody. The resulting decrease in FRET signal corresponded to intracellular cAMP levels. Fluorescence was read on a BMG Labtech PHERAstar, software version 1.50.

The clone with the greatest response to IC-GPCR2 agonist was selected for the screening assay.

Determination of Activity of Compounds

Compounds were dissolved in 100% DMSO to a concentration of 10 uM to provide stock solutions. To determine activity against IC-GPCR2, compounds were incubated with IC-GPCR2 stably expressing cells (described above), at 6-8 concentrations ranging from 0.00003 to 10 micromolar, in 96 well plates, in 50 ul of Hams F12 media for 30 minutes. Cells were plated at 17500 cells per well 1 day before running the assay. All compounds were also screened against the parental CHO cells. cAMP was measured using the cAMP dynamic kit from Cis Bio (Bedford, Mass.), according to the manufacturer's instructions. Briefly, cells were lysed and cAMP levels determined by competitive immunoassay using D2 labeled cAMP, and europium cryptate tagged anti cAMP antibody. When in close proximity, the D2 and europium cryptate undergo fluorescence resonance energy transfer (FRET), which is measured as a fluorescence ratio (665 nm/620 nm). Unlabelled cAMP in the cell lysate competed with the D2 labeled cAMP for the europium crypate labeled antibody. The resulting decrease in FRET signal corresponded to intracellular cAMP levels.

Activities of compounds disclosed in Table 1 and Table 2 below are expressed as the % change in FRET signal from DMSO control. "*" no activity observed when tested at 10 micromolar but no higher concentrations were tested. NT indicates the compound was not tested at the indicated concentration.

TABLE 1

| Example # | Activity at 10 uM |
|---|---|
| 1 | 69 |
| 2 | 50 |
| 3 | 63 |
| 4 | NT |
| 5 | 60 |
| 6 | 68 |
| 7 | 64 |
| 8 | 56 |
| 9 | 54 |
| 10 | NT |
| 11 | 34 |
| 12 | 70 |
| 13 | 94 |
| 14 | 84 |
| 15 | 55 |
| 16 | 56 |
| 17 | 69 |
| 18 | 72 |
| 19 | 76 |
| 20 | 27 |

TABLE 1-continued

| Example # | Activity at 10 uM |
|---|---|
| 21 | 23 |
| 22 | 62 |
| 23 | 37 |
| 24 | 58 |
| 25 | 23 |
| 26 | 58 |
| 27 | 63 |
| 28 | 62 |
| 29 | 51 |
| 30 | 73 |
| 31 | 88 |
| 32 | 88 |
| 33 | 77 |
| 34 | 70 |
| 35 | 64 |
| 36 | 95 |
| 37 | 80 |
| 38 | 39 |
| 39 | 9 |
| 40 | 21 |
| 41 | 75 |
| 42 | 67 |
| 43 | 47 |
| 44 | 53 |
| 45 | 84 |
| 46 | 30 |
| 47 | 51 |
| 48 | NT |
| 49 | NT |
| 50 | NT |
| 51 | 57 |
| 52 | 67 |
| 53 | NT |
| 54 | 58 |
| 55 | 66 |
| 56 | NT |
| 57 | 7 |
| 58 | NT |
| 59 | 70 |
| 60 | 60 |
| 61 | NT |
| 62 | NT |
| 63 | NT |
| 64 | NT |
| 65 | NT |
| 66 | 57 |
| 67 | NT |
| 68 | 53 |
| 69 | 74 |
| 70 | 20 |
| 71 | 88 |
| 72 | 78 |
| 73 | 29 |
| 74 | 17 |
| 75 | NT |
| 76 | 74 |
| 77 | NT |
| 78 | 43 |
| 79 | NT |
| 80 | NT |
| 81 | 59 |
| 82 | NT |
| 83 | 27 |
| 84 | 59 |
| 85 | NT |
| 86 | 49 |
| 87 | 62 |
| 88 | 49 |
| 89 | NT |
| 90 | 64 |
| 91 | 28 |
| 92 | 14 |

TABLE 2

| Example # | Activity at 10 uM |
|---|---|
| 93 | NT |
| 94 | 48 |
| 95 | 63 |
| 96 | 79 |
| 97 | 52 |
| 98 | 78 |
| 99 | 67 |
| 100 | NT |
| 101 | 44 |
| 102 | 49 |
| 103 | 79 |
| 104 | 76 |
| 105 | 52 |
| 106 | 71 |
| 107 | 53 |
| 108 | NT |
| 109 | 38 |
| 110 | 51 |
| 111 | 68 |
| 112 | 57 |
| 113 | 60 |
| 114 | 68 |
| 115 | 67 |
| 116 | 74 |
| 117 | 65 |
| 118 | 64 |
| 119 | 53 |
| 120 | 73 |
| 121 | 75 |
| 122 | 76 |
| 123 | 72 |
| 124 | 80 |
| 125 | 78 |
| 126 | 87 |
| 127 | NT |
| 128 | 57 |
| 129 | 43 |
| 130 | 53 |
| 131 | 24 |
| 132 | 70 |
| 133 | 61 |
| 134 | 68 |
| 135 | 66 |
| 136 | * |
| 137 | 35 |
| 138 | 64 |
| 139 | NT |
| 140 | 62 |
| 141 | 64 |
| 142 | 78 |
| 143 | 63 |
| 144 | 81 |
| 145 | 73 |
| 146 | NT |
| 147 | 56 |
| 148 | 74 |
| 149 | NT |
| 150 | 32 |
| 151 | 54 |
| 152 | 68 |
| 153 | 44 |
| 154 | 66 |
| 155 | 73 |
| 156 | 6 |
| 157 | 57 |
| 158 | NT |
| 159 | 78 |
| 160 | 77 |
| 161 | 79 |
| 162 | 79 |
| 163 | NT |
| 164 | 68 |
| 165 | 71 |
| 166 | 74 |
| 167 | NT |
| 168 | NT |
| 169 | 85 |
| 170 | 75 |
| 171 | 76 |
| 172 | NT |
| 173 | 75 |
| 174 | NT |
| 175 | NT |
| 176 | 43 |
| 177 | NT |
| 178 | 39 |
| 179 | NT |
| 180 | 59 |
| 181 | NT |
| 182 | 78 |
| 183 | 78 |
| 184 | 69 |
| 185 | 83 |
| 186 | 80 |
| 187 | 75 |
| 188 | 69 |
| 189 | 76 |
| 190 | 77 |
| 191 | 74 |
| 192 | 74 |
| 193 | 35 |
| 194 | 29 |
| 195 | 68 |
| 196 | 19 |
| 197 | * |
| 198 | 15 |
| 199 | 78 |
| 200 | 82 |
| 201 | 87 |
| 202 | 83 |
| 203 | 76 |
| 204 | NT |
| 205 | 75 |
| 206 | NT |
| 207 | NT |
| 208 | NT |
| 209 | NT |
| 210 | NT |

Biological Example 2

Insulin Secretion (Islet Perifusion)

To determine the effect of IC-GPCR2 agonists on insulin secretion from islets, islets from Sprague Dawley rats were isolated. 200-250 g Sprague Dawley rats (Charles River laboratories) were maintained on regular chow (Purina 5001). Before the procedure, rats were anesthetized with intra peritoneal injection of pentobarbital at 200 mg/kg. The bile duct was clamped where it enters the duodenum, then a catheter was placed in the bile duct between the liver and the pancreas. The pancreas was infused through the catheter with a solution of 0.75 mg/ml collagenase P (Roche) in HBSS buffer (Biowhitaker) supplemented with 0.1% glucose and 0.02% BSA. The pancreas was then excised from the rat and placed in 5 ml of the collagenase P solution in a 37° C. waterbath for 8 minutes. After 8 minutes the digested pancreas was shaken vigorously by hand for 30 seconds. The resulting digest was washed four times in the HBSS buffer, then applied to a discontinuous ficoll gradient. To make the gradient, the digest was resuspended in 7.5 ml of ficoll DL400 solution (Sigma) density 1.108, in a 15 ml tube. Three 2 ml layers of ficoll solution of decreasing density (1.096, 1.069, 1.037) were then added to the tube to create a density gradient. The gradient was centrifuged at 1500 rpm for 15 minutes after which islets were picked from the top two layers. Islets were washed four times in HBSS buffer, then cultured in RPMI 1640 media (Gibco) supplemented with 1% fetal bovine serum. The following day, 25 sizematched islets were placed in a perifusion chamber and exposed to Krebs Ringer Buffer (KRB; 119 mM NaCl, 4.7 mM KCl, 25 mM NaHCO$_3$, 2.5 mM CaCl$_2$, 1.2 mM MgSO$_4$, 1.2 mM KH2PO$_4$) at a rate of 1 ml/minute, using a Cellex Acu-sys S perifusion culture system. The islets were exposed to KRB containing glucose at 2 mM for 30 minutes, followed with buffer containing 16 mM glucose for 30 minutes, then returned to 2 mM glucose for a further 30 minutes, in the presence of 1 uM of the IC-GPCR2 agonist or vehicle (DMSO). Perifusate was collected at 1 minute intervals using a fraction collector, and assayed for insulin using an ELISA kit (Mercodia Ultrasensitive Rat Insulin ELISA Kit, ALPCO). Insulin secretion rate in response to glucose was plotted against time, and the AUC of the curve determined in order to quantify the insulin secretory response to 16 mM glucose during the 30 minute perifusion. Statistical significance of differences in AUC between treated and untreated islets were determined by paired Student's t-test.

The table below shows the fold stimulation of insulin secretion induced by each of the tested IC-GPCR2 agonists at 16 mM glucose. The tested compounds were selected as examples from the exemplified compounds. These results demonstrate that the IC-GPCR2 agonists stimulate insulin secretion in response to glucose.

| Compound | Fold stimulation of insulin secretion at 16 mM glucose | Significance (p value) |
|---|---|---|
| Agonist 1 | 1.66 | 0.01 |
| Agonist 2 | 1.78 | 0.04 |

Biological Example 3

Oral Glucose Tolerance 8-10 week old male C57/6J mice (Harlan) were maintained on regular chow diet (Purina 5001). The day of the experiment mice were fasted for 6 hours, then randomized into groups (n=8) to receive the tested IC-GPCR2 agonist at doses ranging from 3-30 mg/kg or the vehicle (1% CMC, 2% TWEEN 80). Compounds were delivered orally via gavage at 10 ml/kg. Blood glucose levels were measured by glucometer (Ascensia Elite XL, Bayer) at time 0, before administration of compound. Blood glucose was measured again after 30 minutes, and then the mice were dosed orally with 2 g/kg glucose at 10 ml/kg. Blood glucose measurements were taken 15, 30, 60, 90 and 120 minutes after glucose administration, by glucometer (Ascensia Elite XL, Bayer).

Glucose levels were plotted against time and the incremental area under the curve (AUC) of the glucose excursion was determined from T0 to T120 using GraphPad Prism 5.0. Outliers were determined at each time point of the OGTT and for the AUC values using Tukey's box plot outlier test. Animals with any outlying points were excluded from the analysis, and statistical significance of differences in AUC between compound treatment and vehicle was determined by non-parametric Kruskal-Wallis test with Dunn's post test. Differences with a p-value ≤0.05 were considered significant.

Tables 3 and 4 below show the mean percentage inhibition of the glucose excursion. At 30 mg/kg and 3 mg/kg. The values in Tables 3 and 4 that are marked with an asterisk (*) are significant. These results demonstrate that the IC-GPCR2 agonists can lower blood glucose in response to an oral glucose challenge.

TABLE 3

| | % reduction in AUC at 30 mg/kg |
|---|---|
| Agonist 2 | 47.6* |
| Agonist 3 | None |
| Agonist 4 | 33.0* |
| Agonist 5 | 39.3 |
| Agonist 6 | None |
| Agonist 8 | 32.6 |
| Agonist 9 | 13.9 |
| Agonist 10 | 57.8* |
| Agonist 11 | 49.5* |
| Agonist 12 | 23.7 |
| Agonist 13 | 22.7 |
| Agonist 14 | 44.7* |
| Agonist 15 | 18.5 |
| Agonist 16 | 26.9 |

TABLE 4

| | % reduction in AUC at 3 mg/kg |
|---|---|
| Agonist 10 | 51.5* |
| Agonist 17 | 29.3 |
| Agonist 18 | 23.7 |
| Agonist 19 | 2.5 |
| Agonist 20 | 29.4 |

Biological Example 4

Tissue Specific Expression

RNA was extracted from isolated rat and mouse islets, and used to prepare double stranded cDNA using standard techniques (see Sambrook et al., Molecular Cloning, A Laboratory Manual (3rd ed. 2001); Current Protocols in Molecular Biology (Ausubel et al., eds., 1994)). The cDNA was cloned into the pZL1 vector (Invitrogen) and the 3' ends of individual clones were sequenced in multiple rounds of sequencing reactions. Sequence data representing approximately 12,000 independent clones were used to construct oligonucleotide probes synthesized on a GENECHIP® (Affymetrix Inc., Santa Clara, Calif.), producing mouse and rat islet chips. RNA from five rat islet preparations (each preparation from a different mouse), and preparations from a panel of rat tissues, were hybridized to the rat chips. Expression data was analyzed with the Affymetrix MAS 4.0 algorithm to give relative gene expression values as average difference scores, and presence/absence calls. RNA from two preparations from a mouse beta cell line BHC-9, four mouse islet preparations (each preparation from a different mouse), and preparations from a panel of mouse tissues, were hybridized to the mouse chips. Expression data was analyzed with the Affymetrix MAS 5.0 algorithm to give relative gene expression values as signal, and presence/absence calls.

FIGS. 1 (rat) and 2 (mouse) show the tissue specific expression of the receptor for the novel agonists of the present invention, showing tissue specificity to pancreatic islet cells (including the beta cells therein).

(SEQ. ID NO: 1)
atggaatcatattctcatttggagtgatccttgctgtcctggcctccctc atcattgctactaacacactagtggctgtggctgtgctgctgttgatcca

```
                                                  -continued
caagaatgatggtgtcagtctctgcttcaccttgaatctggctgtggctg acaccttgattggtgtggccatctctggcctactcacagaccagctctcc agccatctcggcccacacagaagaccctgtgcagcctgcggatggcattt gtcacttcctccgcagctgcctctgtcctcacggtcatgctgatcacctt tgacaggtaccttgccatcaagcagcccttccgctacttgaagatcatga gtgggttcgtggccggggcctgcattgccgggagtggttagtgtcttacc tcattggcncctcccactcggaatccccatgttccagcagactgcctaca aagggcagtgcagcttctttgctgtatttcaccctcacttcgtgctgacc ctctcctgcgttggcttcttcccagccatgctcctctttgtcttatctac tgcgacatgctcaagattgcctccatgcacagccagcagattcgaaagat ggaacatgcaggagccatggctggaggttatcgatcccacggactccca gcgacttcaaagctctccgtactgtgtctgttctcattgggagctttgac tatcctggaccccaccttatcactggcattgtgcaggtggcctgccagg agtgtcacctctacctagtgctggaacggtacctgtggctgctcggcgtg ggcaactccctgctcaacccactcatctatgcctattggcagaaggaggt gcgactgcagctctaccacatggccctaggagtgaagaaggtgctcacct cattcctcctctttctcttggccaggaattgtggcccagagaggcccagg gaaagttcctgtcacatcgtcactatctccagctcagagtttgatggcta a (SEQ. ID NO: 2)
MESSFSFGVILAVLASLIIATNTLVAVAVLLLIHKNDGVSLCFTLNLAVA

DTLIGVAISGLLTDQLSSPSRPTQKTLCSLRMAFVTSSAAASVLTVMLIT

FDRYLAIKQPFRYLKIMSGFVAGACIAGLWLVSYLIGFLPLGIPMFQQTA

YKGQCSFFAVFHPHFVLTLSCVGFFPAMLLFVFFYCDMLKIASMHSQQIR

KMEHAGAMAGGYRSPRTPSDFKALRTVSVLIGSFALSWTPFLITGIVQVA

CQECHLYLVLERYLWLLGVGNSLLNPLIYAYWQKEVRLQLYHMALGVKKV

LTSFLLFLLARNCGPERPRESSCHIVTISSSEFDG
```

Biological Example 5

Improvement of Glucose Levels, Insulin Levels, and Weight in High-Fat Fed Female ZDF Rats The ZDF rat is a leptin receptor deficient model of obesity, hyperphagia and insulin resistance. Animals develop diabetes due to pancreatic islet failure in the face of insulin resistance. The males develop diabetes spontaneously between 9 and 11 weeks of age, whereas the females remain non-diabetic unless placed on a high fat diet. This diet makes the animals more insulin resistant, and the increased demand for insulin is believed to precipitate islet failure. The female ZDF rats usually become diabetic within 2 weeks of being placed on a high fat diet (Corsetti et al; 2000).

Five week old female ZDF rats were obtained and were acclimatized for 9 days. The rats were then sorted into 8 study groups based on body weight, insulin levels and glucose levels. One group was maintained on regular chow, and the other 7 were placed on a high-fat diet. Drug or vehicle treatment was initiated concurrently with the diet. Statistical significance of observed differences was assessed by two way ANOVA with Bonferroni post test. Analysis was performed with GraphPad Prism 5.0.

Agonist 2 was dosed orally by gavage in 1% carboxymethylcellulose, 2% Tween 80 (vehicle). Agonist 2 was administered at 10, 30, and 100 mg/kg. Blood samples were collected from the tail vein under non-fasting conditions on days 0, 7, 14, 21 and 35. Blood samples were collected after 16 h overnight fast on day 28. Glucose was measured using a glucometer (Ascensia Elite XL, Bayer); insulin was measured using the Mercodia Ultrasensitive Rat Insulin ELISA kit (ALPCO). Insulin, glucose and levels were compared to those of vehicle treated animals to determine efficacy, and statistical significance of differences determined by one way ANOVA.

Fed Plasma Glucose Levels

Figure 3:
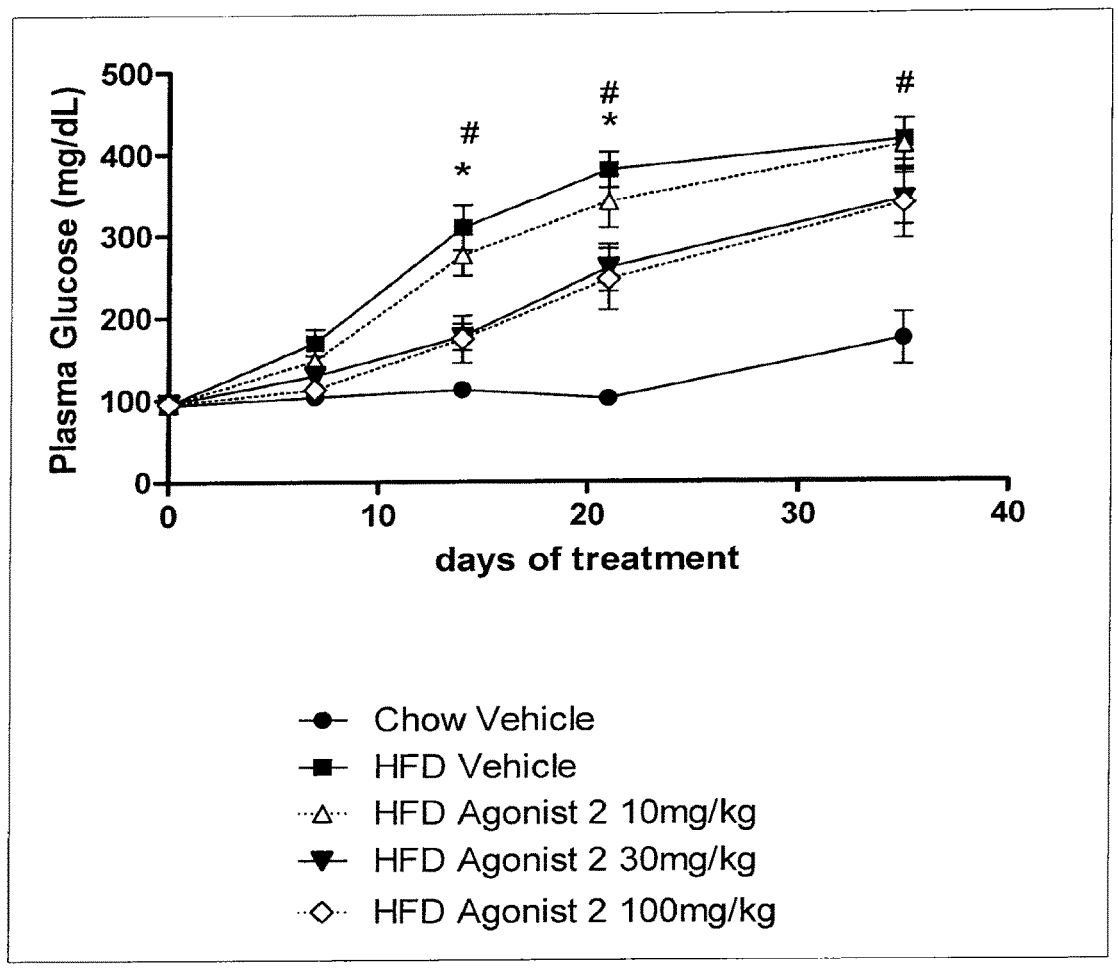
FIG. 3 shows the changes in fed plasma glucose levels of female ZDF rats on a high fat diet. * p≤0.05 agonist 2 at 30 mg/kg and 100 mg/kg vs. high fat diet (HFD) vehicle. #p≤0.05 HFD vs. chow control, by 2 way ANOVA with Bonferroni post test. The experiment was performed as described in Biological Example 5.

FIG. 3 shows the fed plasma glucose levels of the animals during the course of the study. High fat fed female ZDF rats showed a progressive increase in fed plasma glucose levels during the 35 days of the study. Animals on the chow diet showed only a slight increase in fed plasma glucose levels over the course of the study. Animals treated with Agonist 2 showed an increase in plasma glucose during the study, but when treated with 30 and 100 mg/kg of agonist 2, the treated animals had statistically significantly lower plasma glucose than controls at all time points tested. Animals treated with 10 mg/kg agonist 2 showed lower plasma glucose levels than vehicle treated high fat fed control animals but did not reach a statistical significance of $p \leq 0.05$.

Fed Plasma Insulin Levels

Figure 4:
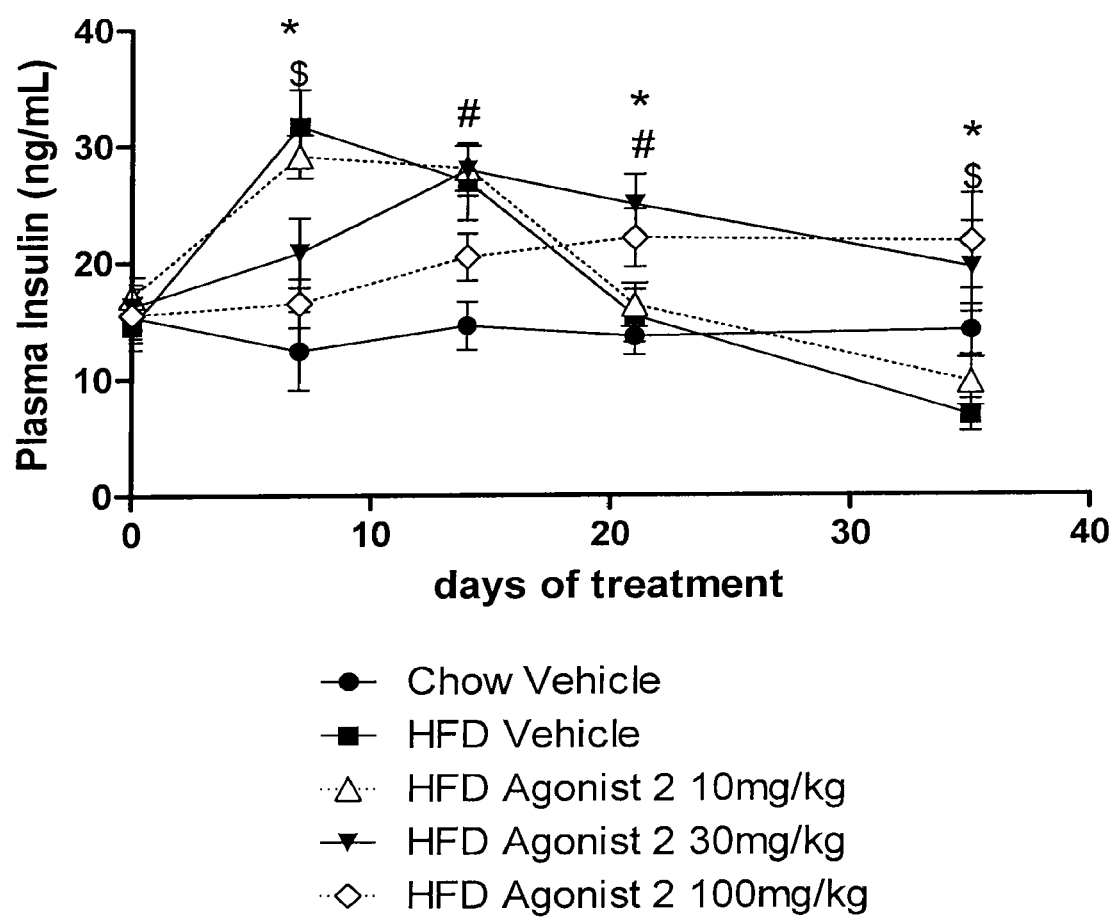
FIG. 4 shows the changes in fed plasma insulin levels of female ZDF rats on a high fat diet. *p≤0.05 agonist 2 at 30 mg/kg vs. high fat diet (HFD) vehicle, #p≤0.05 agonist 2 at 100 mg/kg vs. HFD vehicle, $ p≤0.05 HFD vehicle vs Chow vehicle, by 2 way ANOVA with Bonferroni post test. The experiment was performed as described in Biological Example 5.

FIG. 4 shows the fed plasma insulin levels during the course of the study. After 7 days of high-fat feeding, the vehicle treated group showed elevated fasting insulin levels compared to the chow fed group. Animals treated with 30 and 100 mg/kg agonist 2 had significantly lower insulin levels than the vehicle group after 7 days. After 14 days on a high fat diet, the vehicle treated animals still had increased insulin levels compared to chow fed controls, but the levels were lower than at 7 days. Animals treated with agonist 2 at 10, 30 and 100 mg/kg were not significantly different from vehicle treatment at 14 days. By day 21 of high-fat feeding, insulin levels in vehicle treated animals had dropped back to levels similar to those seen in chow fed controls, whereas insulin levels in animals treated with 30 mg/kg and 100 mg/kg agonist were significantly greater. By day 35 of high fat feeding, insulin levels in the vehicle group had fallen to levels lower than observed in the chow fed group, whereas the insulin levels in the groups treated with 30 mg/kg and 100 mg/kg agonist 2 were significantly greater than in untreated animals. Animals treated with 10 mg/kg agonist 2 did not have insulin levels significantly different from vehicle treated animals at any time point measured in the study.

Effect of 28 Days of Treatment with Agonist 2 on Fasting Plasma Glucose and Insulin Levels in High Fat Fed Female ZDF Rats.

Figure 5:
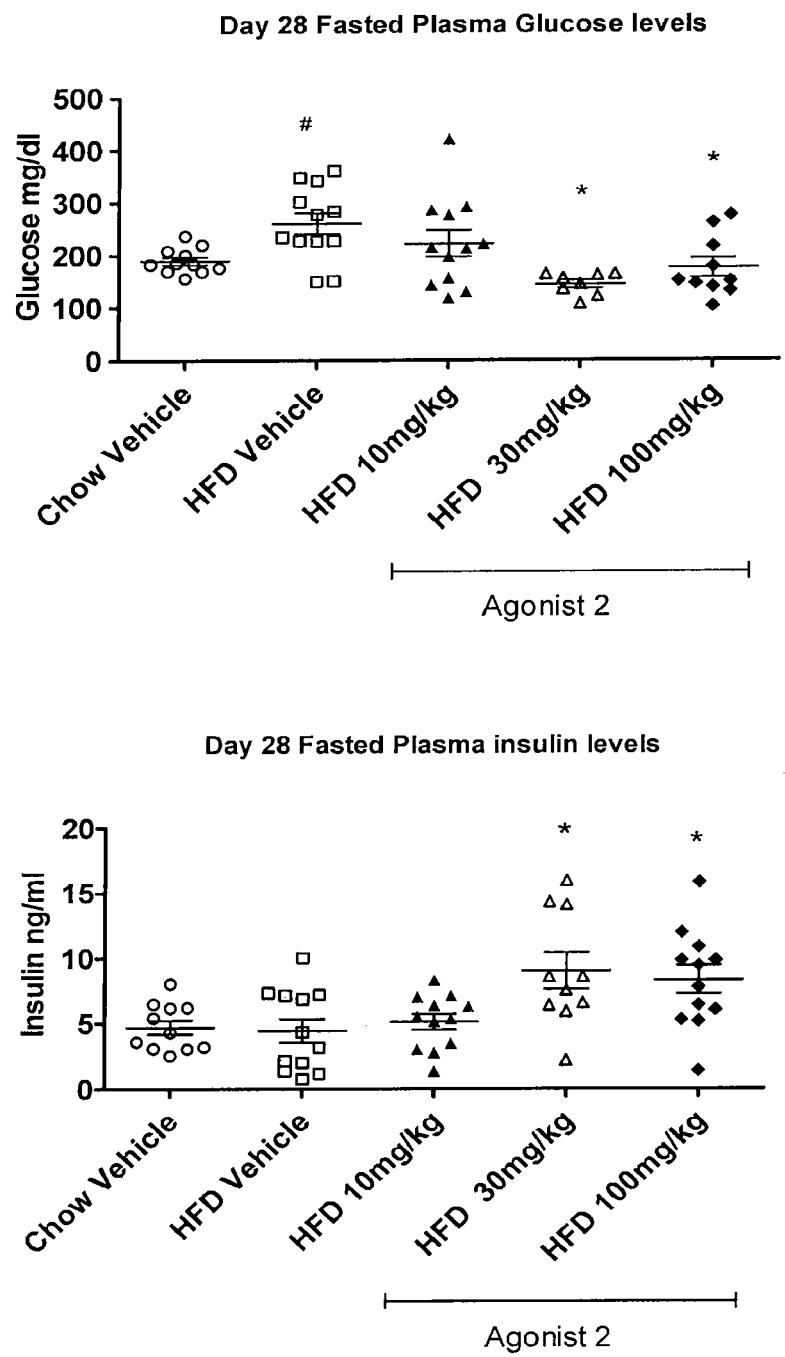
FIG. 5 shows the effect of 28 days of treatment with agonist 2 on fasting plasma glucose and insulin levels in female ZDF rats on high fat diets. * p≤0.05 treatment vs. high fat diet (HFD) vehicle, #p≤0.05 HFD vehicle vs. Chow vehicle, by one way ANOVA with Dunnet's post test. The experiment was performed as described in Biological Example 5.

After 28 days of high-fat feeding, fasted plasma glucose and insulin levels were assessed. The data is provided in FIG. 5. Vehicle treated animals on the high fat diet had significantly elevated fasting plasma glucose compared to chow fed controls. Animals treated with 30 and 100 mg/kg agonist 2 had fasting plasma glucose levels that were significantly lower than vehicle, and similar to chow fed controls. Vehicle treated animals on the high fat diet had similar fasting insulin levels to chow fed controls. Insulin levels in animals treated with agonist 2 at 30 and 100 mg/kg were significantly elevated compared to the vehicle group. This reflects the effect of the high fat diet to increase insulin resistance in these animals. In the absence of drug treatment the islets are unable to continue to compensate for the insulin resistance, and insulin levels fall. Treatment with 30 and 100 mg/kg agonist 2 allows the islets to continue making the insulin required to maintain glucose control in the face of insulin resistance.

The changes in insulin levels seen in the vehicle group on the high-fat diet reflect the etiology of diabetes development in this model. The animals become more insulin resistant due to the high fat diet, and the islets are initially able to compensate for the increased insulin resistance by increasing the output of insulin. This is reflected in higher plasma insulin levels at day 7 and day 14 of the study. After day 14, insulin levels begin to decline as a result of the islet failure inherent to the female ZDF rats. This decline in insulin levels coincides with an increase in plasma glucose as shown in FIG. 3. Treatment with 30 and 100 mg/kg agonist 2 attenuates the initial increase in insulin secretion and prevents the subsequent decline.

Biological Example 6

Improvement in Triglyceride Levels in Female ZDF Rats

Female ZDF rats (Charles River laboratories) were obtained at 6 weeks of age and acclimatized for 1 week before being placed on a high fat diet (RD 13004, Research Diets). Rats were divided into control (n=10) and treatment groups (n=10). Compounds (agonist 2 and agonist 10) were administered to the rats by daily gavage in 1% CMC, 2% TWEEN 80. Agonist 2 was administered at 30 and 100 mg/kg, agonist 10 at 30 mg/kg. Fed triglyceride levels were measured at day 28 and fed glucose levels were measured at day 32. Glucose was also measured after overnight fast on day 35. Glucose was measured using a glucometer (Ascensia Elite XL, Bayer); insulin was measured using the Mercodia Ultrasensitive Rat Insulin ELISA kit (ALPCO). Triglycerides were measured using a Serum Triglyceride Determination Kit (Sigma TR0100). Insulin, glucose and triglyceride levels were compared to those of vehicle treated animals to determine efficacy, and statistical significance of differences determined by one way ANOVA.

Table 5 below shows the percentage change in fed triglyceride levels at day 28, in fed glucose levels at day 32 and in fasted glucose levels at day 35 in drug treated vs. vehicle treated animals.

A significant reduction in fed triglyceride level was observed after 28 days of treatment with 100 mg/kg agonist 2 and with 30 mg/kg agonist 10 compared to vehicle treated animals. A significant reduction of fed plasma glucose was observed after 32 days of treatment with 100 mg/kg agonist 2 and with 30 mg/kg agonist 10 compared to vehicle treated animals. A significant reduction in fasted plasma glucose was observed after 35 days of treatment with 100 mg/kg agonist 2 and with 30 mg/kg agonist 10 compared to vehicle treated animals.

TABLE 5

| Treatment | % Decrease from vehicle group | | |
|---|---|---|---|
|  | Fed plasma glucose | Fasted plasma glucose | Fed plasma TG |
| Agonist 2 30 mg/kg | 22 | 30 | 19 |
| Agonist 2 100 mg/kg | 56* | 52* | 34* |
| Agonist 10 30 mg/kg | 40* | 52* | 44* |

* $p \le 0.01$, by one way ANOVA.

Biological Example 7

Incretin Measurement

The effect of IC-GPCR2 agonists on the secretion of Glucagon-like peptide-1 (GLP-1) and GIP in C57/6J mice are determined as follows.

8-10 week old male C57/6J mice (Harlan) are maintained on a regular chow diet (Purina 5001). On the day of the experiment mice are fasted for 6 hours then randomized into groups (n=8). All groups are treated with the DPPIV inhibitor sitagliptin at 100 mg/kg to prevent degradation of active GLP-1. IC-GPCR-2 agonist compounds are dosed at concentrations ranging from 0.3-300 mg/kg in 1% CMC, 2% TWEEN 80 at −30 minutes. Sitagliptin is administered in the same dosing solution. Oral glucose at 2 g/kg is administered at 0 minutes. At 10 minutes after glucose administration, animals are anesthetized with pentobarbital (40 mg/ml in 10% ethanol) and blood collected by heart puncture in microtainer tubes (BD) with potassium EDTA. For GLP-1 assay, the collection tubes also contain a DPP-IV inhibitor provided in the GLP-1 assay kit.

Insulin is measured using the Mercodia mouse Insulin ELISA Kit (ALPCO) according to the manufacturer's instructions. Bioactive GLP-1 is measured using Glucagon-like peptide-1 (active) ELISA assay kit (Linco) according to the manufacturer's instructions. GIP is measured using rat/mouse GIP total ELISA assay kit (Linco), according to the manufacturer's instructions.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A method of increasing a level of cyclic AMP, insulin, or incretin in a patient in need thereof, comprising administering to the patient a DPP-IV inhibitor selected from the group consisting of sitagliptin and vildagliptin, and a compound selected from the group consisting of

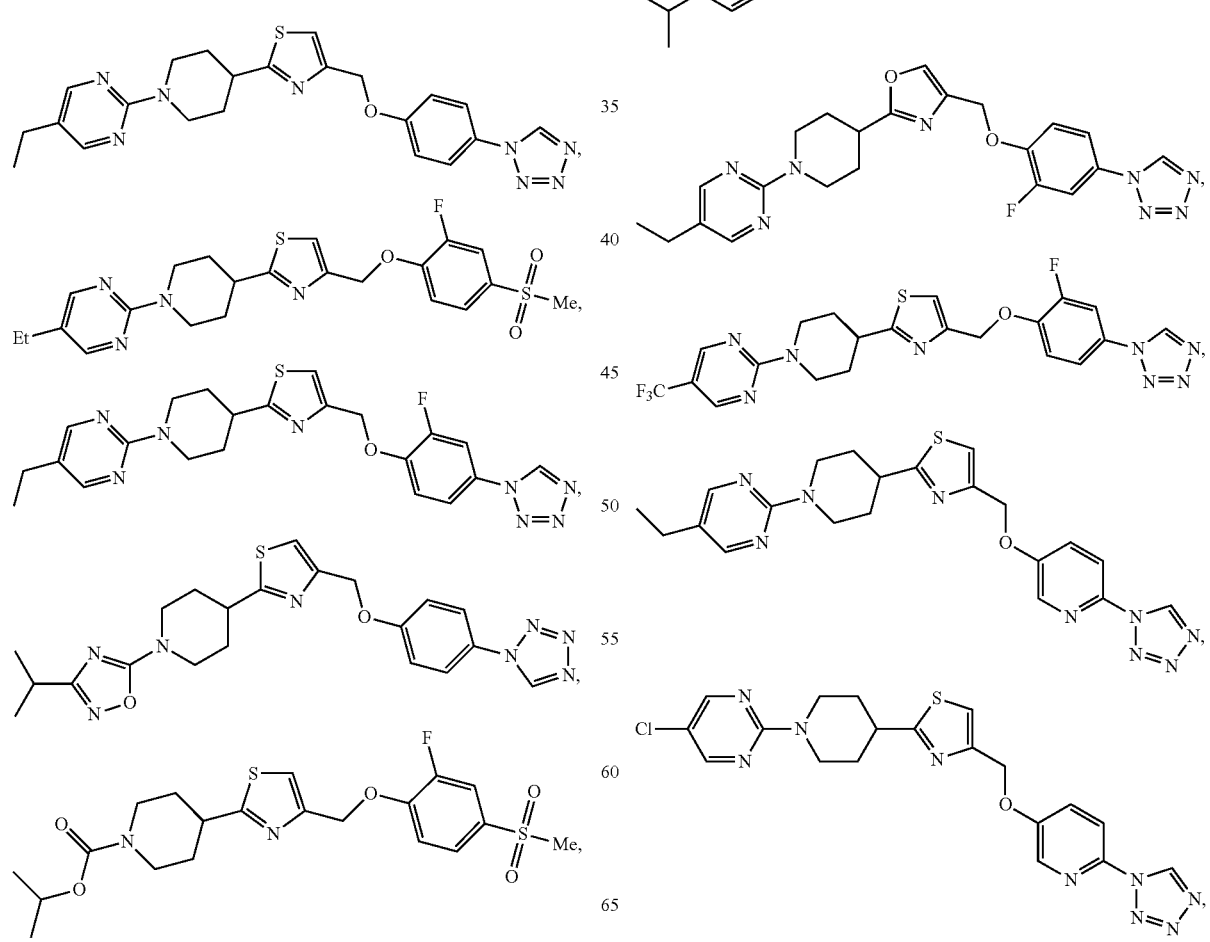

-continued
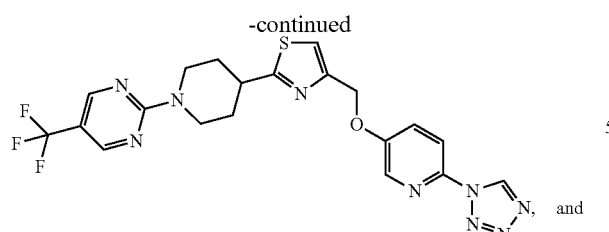
and
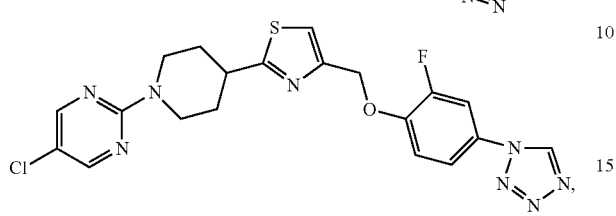
or a pharmaceutically acceptable salt thereof.
2. The method of claim 1 wherein said compound of Formula (I) is
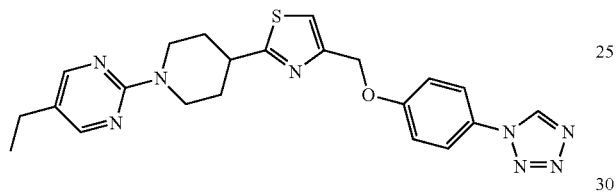
or a pharmaceutically acceptable salt thereof.
* * * * *

SEQUENCE LISTING

<160> NUMBER OF SEQ ID NOS: 2

<210> SEQ ID NO 1
<211> LENGTH: 1008
<212> TYPE: DNA
<213> ORGANISM: Homo sapiens
<220> FEATURE:
<223> OTHER INFORMATION: G-protein couped receptor (GPCR) IC-GPCR2,
      GPR119, RUP3

<400> SEQUENCE: 1
atggaatcat ctttctcatt tggagtgatc cttgctgtcc tggcctccct catcattgct        60
actaacacac tagtggctgt ggctgtgctg ctgttgatcc acaagaatga tggtgtcagt       120

```
ctctgcttca ccttgaatct ggctgtggct gacaccttga ttggtgtggc catctctggc    180
ctactcacag accagctctc cagcccttct cggcccacac agaagaccct gtgcagcctg    240
cggatggcat ttgtcacttc ctccgcagct gcctctgtcc tcacggtcat gctgatcacc    300
tttgacaggt accttgccat caagcagccc ttccgctact tgaagatcat gagtgggttc    360
gtggccgggg cctgcattgc cgggctgtgg ttagtgtctt acctcattgg cttcctccca    420
ctcggaatcc ccatgttcca gcagactgcc tacaaagggc agtgcagctt ctttgctgta    480
tttcaccctc acttcgtgct gaccctctcc tgcgttggct tcttcccagc catgctcctc    540
tttgtcttct tctactgcga catgctcaag attgcctcca tgcacagcca gcagattcga    600
aagatggaac atgcaggagc catggctgga ggttatcgat ccccacggac tcccagcgac    660
ttcaaagctc tccgtactgt gtctgttctc attgggagct tgctctatc ctggaccccc    720 ttccttatca ctggcattgt gcaggtggcc tgccaggagt gtcacctcta cctagtgctg    780
gaacggtacc tgtggctgct cggcgtgggc aactccctgc tcaacccact catctatgcc    840
tattggcaga aggaggtgcg actgcagctc taccacatgg ccctaggagt gaagaaggtg    900
ctcacctcat tcctcctctt tctcttggcc aggaattgtg gcccagagag gcccagggaa    960
agttcctgtc acatcgtcac tatctccagc tcagagtttg atggctaa               1008

<210> SEQ ID NO 2
<211> LENGTH: 335
<212> TYPE: PRT
<213> ORGANISM: Homo sapiens
<220> FEATURE:
<223> OTHER INFORMATION: G-protein couped receptor (GPCR) IC-GPCR2,
      GPR119, RUP3

<400> SEQUENCE: 2

Met Glu Ser Ser Phe Ser Phe Gly Val Ile Leu Ala Val Leu Ala Ser
 1               5                  10                  15

Leu Ile Ile Ala Thr Asn Thr Leu Val Ala Val Ala Val Leu Leu Leu
            20                  25                  30

Ile His Lys Asn Asp Gly Val Ser Leu Cys Phe Thr Leu Asn Leu Ala
        35                  40                  45

Val Ala Asp Thr Leu Ile Gly Val Ala Ile Ser Gly Leu Leu Thr Asp
    50                  55                  60

Gln Leu Ser Ser Pro Ser Arg Pro Thr Gln Lys Thr Leu Cys Ser Leu
65                  70                  75                  80

Arg Met Ala Phe Val Thr Ser Ser Ala Ala Ser Val Leu Thr Val
                85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
        115                 120                 125

Leu Trp Leu Val Ser Tyr Leu Ile Gly Phe Leu Pro Leu Gly Ile Pro
    130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Phe Tyr Cys Asp Met Leu Lys Ile Ala
            180                 185                 190

Ser Met His Ser Gln Gln Ile Arg Lys Met Glu His Ala Gly Ala Met
        195                 200                 205
```

-continued

| | |
|---|---|
| Ala Gly Gly Tyr Arg Ser Pro Arg Thr Pro Ser Asp Phe Lys Ala Leu | |
| 210 215 220 | |
| Arg Thr Val Ser Val Leu Ile Gly Ser Phe Ala Leu Ser Trp Thr Pro | |
| 225 230 235 240 | |
| Phe Leu Ile Thr Gly Ile Val Gln Val Ala Cys Gln Glu Cys His Leu | |
| 245 250 255 | |
| Tyr Leu Val Leu Glu Arg Tyr Leu Trp Leu Leu Gly Val Gly Asn Ser | |
| 260 265 270 | |
| Leu Leu Asn Pro Leu Ile Tyr Ala Tyr Trp Gln Lys Glu Val Arg Leu | |
| 275 280 285 | |
| Gln Leu Tyr His Met Ala Leu Gly Val Lys Lys Val Leu Thr Ser Phe | |
| 290 295 300 | |
| Leu Leu Phe Leu Leu Ala Arg Asn Cys Gly Pro Glu Arg Pro Arg Glu | |
| 305 310 315 320 | |
| Ser Ser Cys His Ile Val Thr Ile Ser Ser Ser Glu Phe Asp Gly | |
| 325 330 335 | |